US008236795B2

(12) United States Patent
Sun et al.

(10) Patent No.: US 8,236,795 B2
(45) Date of Patent: *Aug. 7, 2012

(54) IL-12 MODULATORY COMPOUNDS

(75) Inventors: Lijun Sun, Harvard, MA (US); Elena Kostik, Arlington, MA (US); Teresa Przewloka, Tewksbury, MA (US); Howard P. Ng, Belmont, MA (US); Dinesh Chimmanamada, Waltham, MA (US); Zachary Demko, Somerville, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/731,056

(22) Filed: Mar. 24, 2010

(65) Prior Publication Data

US 2010/0256132 A1    Oct. 7, 2010

Related U.S. Application Data

(62) Division of application No. 11/272,509, filed on Nov. 10, 2005, now Pat. No. 7,696,202.

(60) Provisional application No. 60/626,761, filed on Nov. 10, 2004.

(51) Int. Cl.
    *A61K 31/5377* (2006.01)
(52) U.S. Cl. ............. 514/232.2; 514/235.2; 514/235.8
(58) Field of Classification Search ........... 514/232.2, 514/235.2, 235.8
    See application file for complete search history.

(56) References Cited

U.S. PATENT DOCUMENTS

| 4,478,835 | A | 10/1984 | Wade |
| 6,759,412 | B2 | 7/2004 | Strobel et al. |
| 7,696,202 | B2 * | 4/2010 | Sun et al. ........... 514/232.2 |
| 2004/0176385 | A1 | 9/2004 | Nuss et al. |

FOREIGN PATENT DOCUMENTS

| JP | 2004-518720 | 6/2004 |
| WO | WO-00/78757 | 12/2000 |
| WO | WO-03/035076 | 5/2003 |
| WO | WO-03/047516 | 6/2003 |
| WO | WO-2005/042524 | 5/2005 |

OTHER PUBLICATIONS

Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Database accession No. 1987:594785; CA—Chemical Abstracts Service, Desai et al., "Studies on quinoline and phenothiazine. Preparation and antimicrobial activity of 2-morpholino-4-(8-quinolinoxy)-6-phenylureido-s-triazines and 1, 3, 7, 9-tetrachloro-10-(acetylphenylureido)phenothiazines," J. Ind. Chem. Society, Jan. 1, 1987 (Abstract).
Supplementary European Search Report dated May 26, 2011 for related application EP05820870.3.
Desai, K.R. et al., "Studies on Quinoline and Phenothiazine. Preparation and Antimicrobial Activity of 2-morpholino-4(8-quinolinoxy)-6-phenylureido-s-triazines and 1,3,7,9-tetrachloro-10-(acetylphenylureido)phenothiazines", *Journal of the Indian Chemical Society*, 1987, vol. 64, No. 2, pp. 128-129.
Desai, K.R. et al., "Synthesis of Phenyl Thiourea Derivatives of Quioline and Phenothiazine", *Journal of the Institution of Chemists (India)*, 1986, vol. 58, No. 3, pp. 104-106.
Notice of Reasons for Rejection dated Oct. 11, 2011, in corresponding Japanese Patent Application No. 2007-541357 (with English translation).
Taiwanese Search Report dated Aug. 9, 2011 in corresponding Taiwan Patent Application No. 094139373 (with English translation).

* cited by examiner

*Primary Examiner* — Kamal Saeed
*Assistant Examiner* — Kristin Bianchi
(74) *Attorney, Agent, or Firm* — Edwards Wildman Palmer LLP; Jeffrey D. Hsi; Mark D. Russett

(57) ABSTRACT

The invention relates to heterocyclic compounds, compositions including the compounds and methods of using and methods of making thereof. The compounds (and compositions) are useful, inter alia, in modulating IL-12 production and processes mediated by IL-12.

6 Claims, 1 Drawing Sheet

IL-12 MODULATORY COMPOUNDS

CROSS-REFERENCE TO RELATED APPLICATIONS

This application is a division of U.S. patent application Ser. No. 11/272,509, filed on Nov. 10, 2005, now allowed, which claims the benefit of U.S. provisional patent application Ser. No. 60/626,761, filed on Nov. 10, 2004. The contents of each of these applications are hereby incorporated by reference in their entirety.

BACKGROUND

Interleukin-12 (IL-12) is a heterodimeric cytokine (p70) which plays key roles in immune responses by bridging innate resistance and antigen-specific adaptive immunity. Trinchieri (1993) *Immunol Today* 14: 335. For example, it promotes type 1 T helper cell ($T_H1$) responses and, hence, cell-mediated immunity. Chan et al. (1991) *J Exp Med* 173: 869; Seder et al. (1993) *Proc Natl Acad Sci USA* 90: 10188; Manetti et al. (1993) *J Exp Med* 177: 1199; and Hsieh et al. (1993) *Science* 260: 547. Interleukin-12 (IL-12) is a di-sulfide linked heterodimeric cytokine (p70) composed of two independently regulated subunits, p35 and p40. IL-12 is produced by phagocytic cells and antigen presenting cells, in particular, macrophages and dendritic cells, upon stimulation with bacteria, bacterial products such as lipopolysaccharide (LPS), and intracellular parasites. The well-documented biological functions of IL-12 are induction of interferon-γ expression from T and NK cells and differentiation toward the $T_H1$ T lymphocyte type. IFN-γ, expression of which is induced by IL-12, is a strong and selective enhancer of IL-12 production from monocytes and macrophages. The cytokine IL-23 is a heterodimer composed of a p19 subunit and the same p40 subunit of IL-12. IL-23, similarly to IL-12, is involved in type 1 immune defenses and induces IFN-γ secretion from T cells. IL-27 is formed by the association of EBI3, a polypeptide related to the p40 subunit of IL-12, and p28, a protein related to the p35 subunit of IL-12. IL-27 promotes the growth of T cells and is thought to play a role in the differentiation of $T_H1$ cells. Pflanz et al., *Immunity* (2002), 16:779-790.

It has been suggested that, particularly in chronic diseases in which there is ongoing production of IFN-γ, IL-12 production is augmented by IFN-γ. It is presumed that after an infective or inflammatory stimulus that provokes IL-12 production, the powerful feedback loop promotes IL-12- and IL-23-induced IFN-γ to further augment IL-12 production, leading to consequent excessive production of pro-inflammatory cytokines. Furthermore, it has been suggested that IL-27 induces the expression of T-bet, a major $T_H1$-specific transcription factor, and its downstream target IL-12R β2, independently of IFN-γ. In addition, IL-27 suppresses the expression of GATA-3. GATA-3 inhibits $T_H1$ development and causes loss of IL-12 signaling through suppression of IL-12R β2 and Stat4 expression. Lucas et al., *PNAS* (2003), 100: 15047-15052.

IL-12 plays a critical role in multiple-$T_H1$ dominant autoimmune diseases including, but not limited to, multiple sclerosis, sepsis, myasthenia gravis, autoimmune neuropathies, Guillain-Barré syndrome, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, psoriatic arthritis, dermatitis herpetiformis, pemphigus vulgaris, vitiligo, Crohn's disease, ulcerative colitis, interstitial pulmonary fibrosis, myelofibrosis, hepatic fibrosis, myocarditis, thyroditis, primary biliary cirrhosis, autoimmune hepatitis, Type 1 or immune-mediated diabetes mellitus, Grave's disease, Hashimoto's thyroiditis, autoimmune oophoritis and orchitis, autoimmune disease of the adrenal gland; rheumatoid arthritis, juvenile rheumatoid arthritis, systemic lupus erythematosus, scleroderma, common variable immunodeficiency (CVID), polymyositis, dermatomyositis, spondyloarthropathies, ankylosing spondylitis, Sjogren's syndrome and graft-versus-host disease. See, for example, Gately et al. (1998) *Annu Rev Immunol.* 16: 495; and Abbas et al. (1996) *Nature* 383: 787.

Inhibiting IL-12 overproduction, or inhibiting the production of cytokines such as IL-23 and IL-27 which promote IL-12 production and/or $T_H1$ development is an approach to treating the just-mentioned diseases. Trembleau et al. (1995) *Immmunol. Today* 16: 383; and Adorini et al. (1997) *Chem. Immunol.* 68: 175. For example, overproduction of IL-12 and the resultant excessive $T_H1$ type responses can be suppressed by modulating IL-12, IL-23 and/or IL-27 production. Therefore, compounds that down-regulate IL-12, IL-23 and/or IL-27 production can be used for treating inflammatory diseases. Ma et al. (1998) *Eur Cytokine Netw* 9: 54.

SUMMARY

In one aspect, this invention features compounds of formula (I):

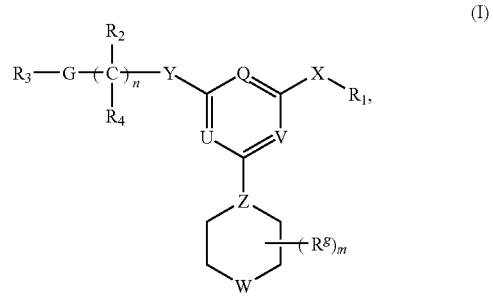

or a pharmaceutically acceptable salt, solvate, clathrate, hydrate, polymorph or prodrug thereof, In Formula (I), X and $R_1$, taken together, are —C(O) $NR^eR^d$; or X is represented by a formula selected from the group consisting of:

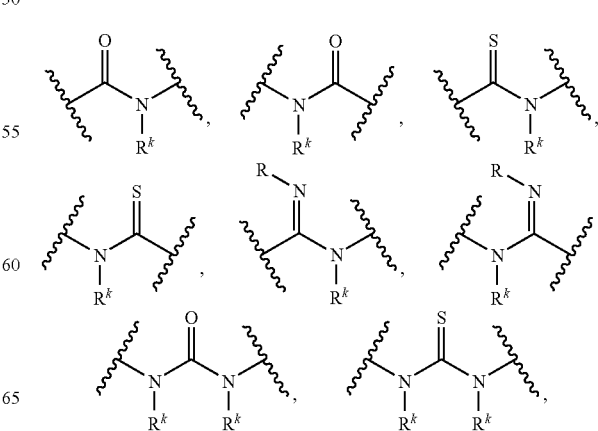

-continued

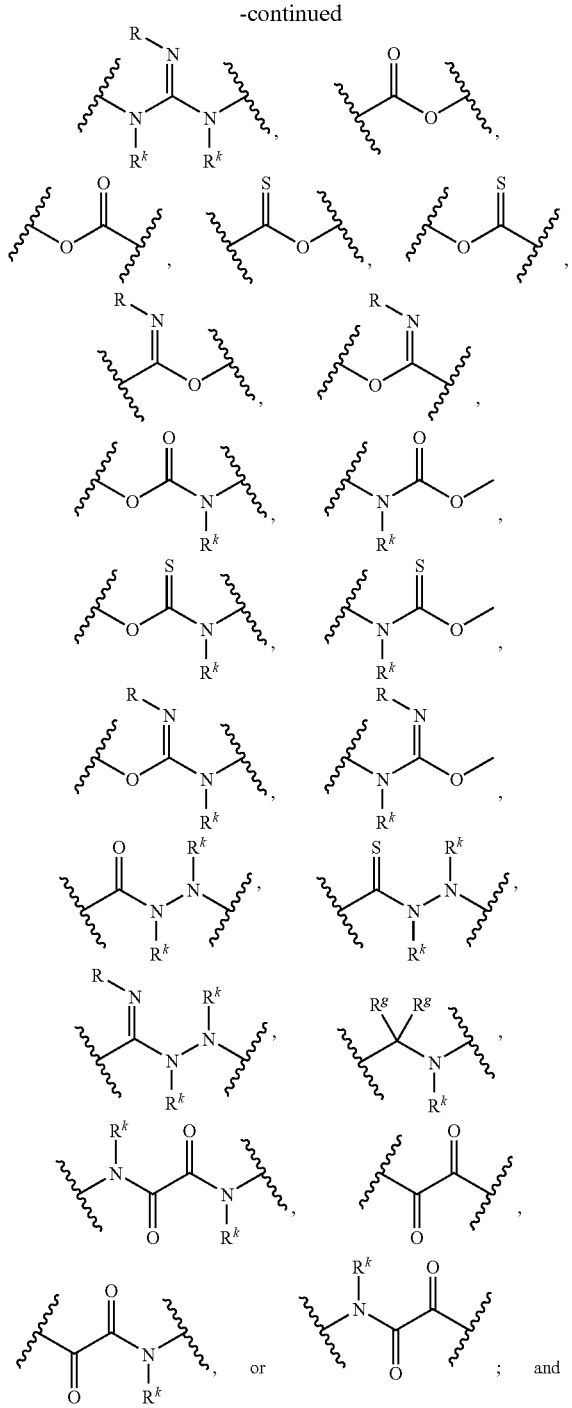

R, for each occurrence, is independently H, an optionally substituted alkyl, an optionally substituted cycloalkyl, an optionally substituted cyclyl, an optionally substituted heterocycloalkyl, an optionally substituted heterocyclyl, an optionally substituted aryl, an optionally substituted heteroaryl, an optionally substituted aralkyl, an optionally substituted heteroaralkyl, —C(O)R$^c$, —OR$^k$, —SR$^k$, —NR$^h$R$^j$, hydroxylalkyl, nitro, cyano, haloalkyl, aminoalkyl, or —S(O)$_2$R$^c$;

R$_1$ is R'-L'-R";

R' is an optionally substituted cycloalkyl, an optionally substituted cyclyl, an optionally substituted heterocycloalkyl, an optionally substituted aryl, an optionally substituted heteroaryl, an optionally substituted aralkyl, an optionally substituted heteroaralkyl, or absent;

L' is O, S(O)$_p$, N(R$^k$), N(R$^k$)C(O), C(O)N(R$^k$), C(O)O, or OC(O), or absent; and R" is H, an optionally substituted alkyl, an optionally substituted cycloalkyl, an optionally substituted cyclyl, an optionally substituted heterocycloalkyl, an optionally substituted heterocyclyl, an optionally substituted aryl, an optionally substituted heteroaryl, an optionally substituted aralkyl, an optionally substituted heteroaralkyl, N(R$^k$)(CH$_2$)$_n$R$^g$, —OR$^k$, —SR$^k$, —NR$^h$R$^j$, hydroxylalkyl, —C(O)R$^c$, —C(S)R$^c$, —C(NR)R$^c$, halo, haloalkyl, aminoalkyl, mercaptoalkyl, cyano, nitro, —S(O)R$^c$, —S(O)$_2$R$^c$, —P(O)R$^c$R$^c$, —P(S)R$^c$R$^c$, or an optionally substituted alkylcarbonylalkyl;

each of Q, U, and V are independently N or CR$^g$, wherein at least one of Q, U, or V is N; and each CR$^g$ may be the same or different;

R$_3$ is R$^g$, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —S(O)$_2$R$^c$, —S(O)R$^c$, —NR$^k$S(O)$_2$R$^c$, —OS(O)$_2$R$^c$, —OP(O)R$^c$R$^c$, or —P(O)R$^c$R$^c$;

R$_2$ and R$_4$ are, independently, H, an optionally substituted alkyl, an optionally substituted alkylcarbonyl, —OR$^k$, —SR$^k$, —NR$^h$R$^j$, hydroxylalkyl, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —SO$_2$R$^c$, —S(O)R$^c$, —NR$^k$SO$_2$R$^c$, —OS(O)$_2$R$^c$, —OP(O)R$^c$R$^c$, —P(O)R$^c$R$^c$, halo, haloalkyl, aminoalkyl, mercaptoalkyl, cyano, nitro, nitroso, azide, an optionally substituted alkylcarbonylalkyl, an optionally substituted cyclyl, an optionally substituted cycloalkyl, an optionally substituted heterocyclyl, an optionally substituted heterocycloalkyl, an optionally substituted aryl, an optionally substituted aralkyl, an optionally substituted heteroaryl, an optionally substituted heteroaralkyl, or isothionitro; or R$_2$ and R$_4$ taken together are =O, =S, or =NR;

R$^c$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —OR$^k$, —SR$^k$, —NR$^h$R$^j$, hydroxylalkyl, alkylcarbonylalkyl, mercaptoalkyl, aminoalkyl, sulfonylalkyl, sulfonylaryl, or thioalkoxy;

R$^d$ and R$^e$, together with the nitrogen to which they are attached, form an optionally substituted heterocycloalkyl, an optionally substituted heterocyclyl, or an optionally substituted heteroaryl;

R$^g$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —OR$^k$, —SR$^k$, —NR$^h$R$^j$, hydroxylalkyl, alkylcarbonylalkyl, mercaptoalkyl, aminoalkyl, sulfonylalkyl, sulfonylaryl, thioalkoxy, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —S(O)$_2$R$^c$, —S(O)R$^c$, —NR$^k$S(O)$_2$R$^c$, —OS(O)$_2$R$^c$, —OP(O)R$^c$R$^c$, —P(O)R$^c$R$^c$, halo, aminoalkyl, mercaptoalkyl, cyano, nitro, nitroso, or azide;

R$^h$ and R$^j$, for each occurrence, are independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl; or R$^h$ and R$^j$ taken together with the N to which they are attached is an optionally substituted heterocyclyl, an optionally substituted heterocycloalkyl, or an optionally substituted heteroaryl;

R$^k$, for each occurrence, is independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, or an optionally substituted heteroaryl;

G is: Hydrazide; Hydrazone; Hydrazine; Hydroxylamine; Oxime; Amide; Ester; Carbonate; Carbamate; Thiocarbamate; —NR$^k$—C(NR)—NR$^k$—; —NR$^k$—C(O)—NR$^k$—; —NR$^k$C(S)—NR$^k$—; —NR$^k$—S(O)$_2$—NR$^k$—; Phosphoryl; an optionally substituted-Cyclyl-; an optionally substituted-Heterocyclyl-; an optionally substituted-Aryl-; an optionally substituted-Heteroaryl-; an optionally substituted-Heteroarylalkyl-; an optionally substituted-Heteroaryl-NR$^k$—; an optionally substituted-Heteroaryl-S—; an optionally substituted-Heteroarylalkyl-O—; —Si(OR$^k$)$_2$—; —B(OR$^k$)—; —C(NR)—NR$^k$—; —N(R$^k$)—C(R$^g$R$^g$)—C(O)—; —C(O)—ON(R$^k$)—; —C(O)—N(R$^k$)O—; —C(S)—ON(R$^k$)—; —C(S)—N(R$^k$)O—; —C(N(R$^k$))—ON(R$^k$)—; —C(N(R$^k$))—NR$^k$O—; —OS(O)$_2$—N(R$^k$)N(R$^k$)—; —OC(O)—N(R$^k$)N(R$^k$)—; —OC(S)—N(R$^k$)N(R$^k$)—; —OC(N(R$^k$))—N(R$^k$)N(R$^k$)—; —N(R$^k$)N(R$^k$)S(O)$_2$O—; —N(R$^k$)N(R$^k$)C(S)O—; —N(R$^k$)N(R$^k$)C(N(R$^k$))O—; —OP(O)(R$^c$)O—; —N(R$^k$)P(O)(R$^c$)O—; —OP(O)(R$^c$)N(R$^k$)—; —N(R$^k$)P(O)(R$^c$)N(R$^k$)—; —P(O)(R$^c$)O—; —P(O)(R$^c$)N(R$^k$)—; —N(R$^k$)P(O)(R$^c$)—; —OP(O)(R$^c$)—; —O-alkyl-heterocyclyl-N(R$^k$)—; —N(R$^k$)CHR$^g$C(O)N(R$^k$)CHR$^g$C(O)—; —N(R$^k$)CHR$^g$C(O)—; —N(R$^k$)C(O)CHR$^g$—; —C(O)N(R$^k$)CHR$^g$C(O)—; or G is absent;

Y is a covalent bond, (CH(R$^g$))$_m$, C(O), C(NR), O, S, S(O), S(O)$_2$, N(OR$^k$) or N(R$^k$);

m is 0, 1, 2, 3, or 4; n is, independently for each occurrence, 0, 1, 2, 3, 4, 5, 6, or 7; p is 0, 1 or 2;

Z is N or CH; and

W is O, S, S(O), S(O)$_2$, NR''', or NC(O)R''', wherein R''' is H, an optionally substituted alkyl, an optionally substituted aryl, an optionally substituted heteroaryl, an optionally substituted cycloalkyl, an optionally substituted heterocycloalkyl, or —C(O)R$^c$.

In another aspect, this invention features a pharmaceutical composition that includes a pharmaceutically acceptable carrier and at least one of the heterocyclic compounds of this invention (e.g., a compound of formula (I) herein; any compound delineated herein).

In another aspect, the present invention features a method of inhibiting the production of IL-12 and/or inhibiting the production of a cytokine that stimulates or otherwise augments the production of IL-12 (e.g., IL-23 and IL-27) and/or inhibits the proliferation of T$_H$1 lymphocytes in a subject by administering to the subject an effective amount of a compound represented by formula (I) (or any of the formulae herein) or a pharmaceutically acceptable salt, solvate, clathrate, hydrate, polymorph, or prodrug thereof.

In another aspect, the invention features a method of inhibiting the production and/or development of T$_H$1 cells in a subject by administering to the subject an effective amount of a compound of formula (I) (or any of the formulae herein) or a pharmaceutically acceptable salt, solvate, clathrate, hydrate, polymorph, or prodrug thereof.

In another aspect, the present invention features a method for treating an IL-12 overproduction-related disorder (e.g., multiple sclerosis, sepsis, myasthenia gravis, autoimmune neuropathies, Guillain-Barré syndrome, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, psoriatic arthritis, dermatitis herpetiformis, pemphigus vulgaris, vitiligo, Crohn's disease, ulcerative colitis, interstitial pulmonary fibrosis, myelofibrosis, hepatic fibrosis, myocarditis, thyroditis, primary biliary cirrhosis, autoimmune hepatitis, Type 1 or immune-mediated diabetes mellitus, Grave's disease, Hashimoto's thyroiditis, autoimmune oophoritis and orchitis, autoimmune disease of the adrenal gland; rheumatoid arthritis, juvenile rheumatoid arthritis, systemic lupus erythematosus, scleroderma, common variable immunodeficiency (CVID), polymyositis, dermatomyositis, spondyloarthropathies, ankylosing spondylitis, Sjogren's syndrome and graft-versus-host disease). The method includes administering to a subject (e.g., a human or an animal) in need thereof an effective amount of one or more compounds of this invention (including a salt, solvate, clathrate, hydrate, polymorph, or prodrug thereof). The method can also include the step of identifying a subject in need of treatment of diseases or disorders described above. The identification can be in the judgment of a subject or a health professional and can be subjective (e.g., opinion) or objective (e.g., measurable by a test or a diagnostic method).

Also within the scope of this invention are compositions containing one or more of the compounds described above for use in treating an IL-12 overproduction-related disorder, and the use of such a composition for the manufacture of a medicament for the just-described use.

The compounds of the invention have many advantageous features. For example, the compounds of the invention have a high oral bioavailability and a simple metabolic profile.

Other features, objects, and advantages of the invention will be apparent from the description and from the claims.

DETAILED DESCRIPTION

Figure 1:
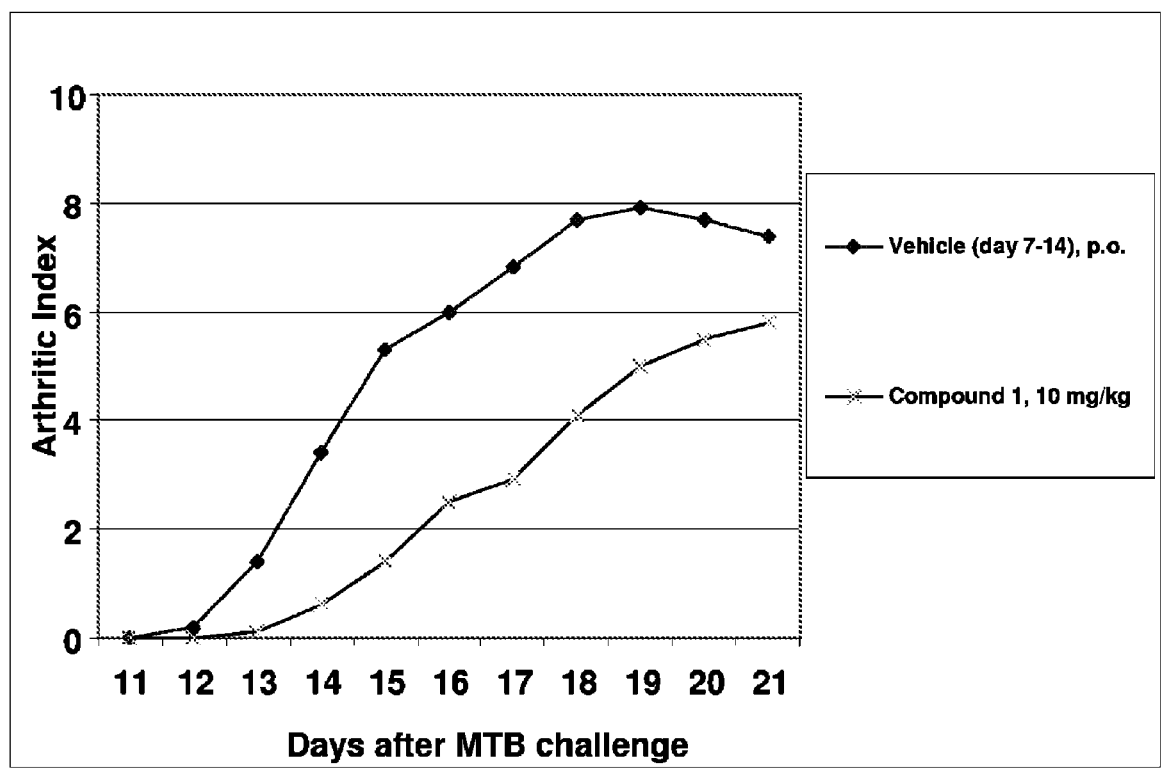
FIG. 1 shows the arthritic index as a function of time in a rat administered a compound of the invention.

In one aspect, the invention provides a compound of formula (I)

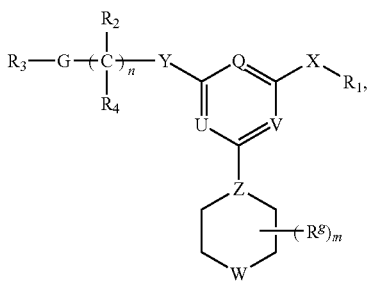

(I)

or a pharmaceutically acceptable salt, solvate, clathrate, hydrate, polymorph or prodrug thereof.

In Formula (I), X and $R_1$, taken together, are —C(O)NR$^e$R$^d$; or

X is represented by a formula selected from the group consisting of:

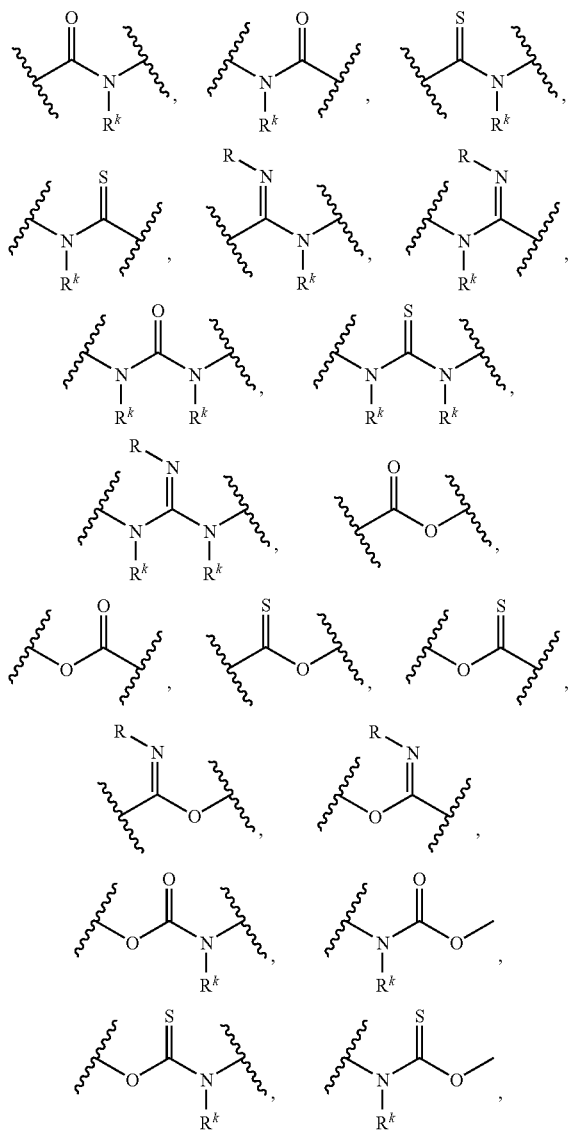

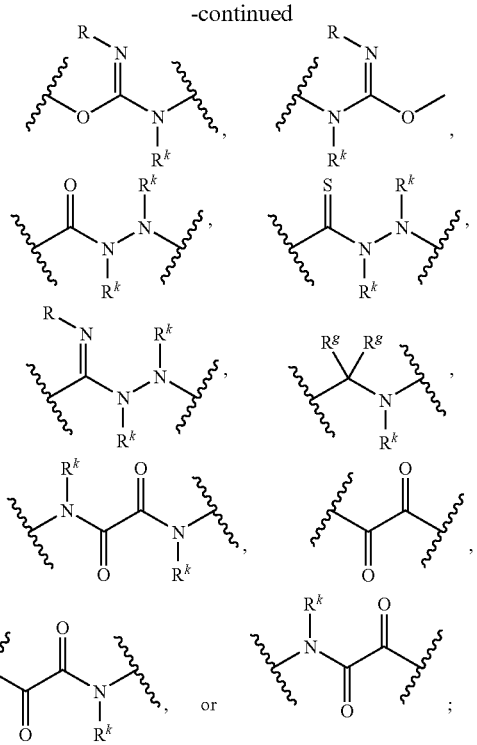

R, for each occurrence, is independently H, an optionally substituted alkyl, an optionally substituted cycloalkyl, an optionally substituted cyclyl, an optionally substituted heterocycloalkyl, an optionally substituted heterocyclyl, an optionally substituted aryl, an optionally substituted heteroaryl, an optionally substituted aralkyl, an optionally substituted heteroaralkyl, —C(O)R$^c$, —OR$^k$, —SR$^k$, —NR$^h$R$^j$, hydroxylalkyl, nitro, cyano, haloalkyl, aminoalkyl, or —S(O)$_2$R$^c$;

$R_1$ is R'-L'-R";

R' is an optionally substituted cycloalkyl, an optionally substituted cyclyl, an optionally substituted heterocycloalkyl, an optionally substituted aryl, an optionally substituted heteroaryl, an optionally substituted aralkyl, an optionally substituted heteroaralkyl, or absent;

L' is O, S(O)$_p$, N(R$^k$), N(R$^k$)C(O), C(O)N(R$^k$), C(O)O, or OC(O), or absent; and R" is H, an optionally substituted alkyl, an optionally substituted cycloalkyl, an optionally substituted cyclyl, an optionally substituted heterocycloalkyl, an optionally substituted heterocyclyl, an optionally substituted aryl, an optionally substituted heteroaryl, an optionally substituted aralkyl, an optionally substituted heteroaralkyl, N(R$^k$)(CH$_2$)$_n$R$^g$, —OR$^k$, —SR$^k$, —NR$^h$R$^j$, hydroxylalkyl, —C(O)R$^c$, —C(S)R$^c$, —C(NR)R$^c$, halo, haloalkyl, aminoalkyl, mercaptoalkyl, cyano, nitro, —S(O)R$^c$, —S(O)$_2$R$^c$, —P(O)R$^c$R$^c$, —P(S)R$^c$R$^c$, or an optionally substituted alkylcarbonylalkyl;

each of Q, U, and V are independently N or CR$^g$, wherein at least one of Q, U, or V is N; and each CR$^g$ may be the same or different;

$R_3$ is R$^g$, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —S(O)$_2$R$^c$, —S(O)R$^c$, —NR$^k$S(O)$_2$R$^c$, —OS(O)$_2$R$^c$, —OP(O)R$^c$R$^c$, or —P(O)R$^c$R$^c$;

$R_2$ and $R_4$ are, independently, H, an optionally substituted alkyl, an optionally substituted alkylcarbonyl, —$OR^k$, —$SR^k$, —$NR^hR^j$, hydroxylalkyl, —$C(O)R^c$, —$OC(O)R^c$, —$SC(O)R^c$, —$NR^kC(O)R^c$, —$C(S)R^c$, —$OC(S)R^c$, —$SC(S)R^c$, —$NR^kC(S)R^c$, —$C(NR)R^c$, —$OC(NR)R^c$, —$SC(NR)R^c$, —$NR^kC(NR)R^c$, —$SO_2R^c$, —$S(O)R^c$, —$NR^kSO_2R^c$, —$OS(O)_2R^c$, —$OP(O)R^cR^c$, —$P(O)R^cR^c$, halo, haloalkyl, aminoalkyl, mercaptoalkyl, cyano, nitro, nitroso, azide, an optionally substituted alkylcarbonylalkyl, an optionally substituted cyclyl, an optionally substituted cycloalkyl, an optionally substituted heterocyclyl, an optionally substituted heterocycloalkyl, an optionally substituted aryl, an optionally substituted aralkyl, an optionally substituted heteroaryl, an optionally substituted heteroaralkyl, or isothionitro; or $R_2$ and $R_4$ taken together are =O, =S, or =NR;

$R^c$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —$OR^k$, —$SR^k$, —$NR^hR^j$, hydroxylalkyl, alkylcarbonylalkyl, mercaptoalkyl, aminoalkyl, sulfonylalkyl, sulfonylaryl, or thioalkoxy;

$R^d$ and $R^e$, together with the nitrogen to which they are attached, form an optionally substituted heterocycloalkyl, an optionally substituted heterocyclyl, or an optionally substituted heteroaryl;

$R^g$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —$OR^k$, —$SR^k$, —$NR^hR^j$, hydroxylalkyl, alkylcarbonylalkyl, mercaptoalkyl, aminoalkyl, sulfonylalkyl, sulfonylaryl, thioalkoxy, —$C(O)R^c$, —$OC(O)R^c$, —$SC(O)R^c$, —$NR^kC(O)R^c$, —$C(S)R^c$, —$OC(S)R^c$, —$SC(S)R^c$, —$NR^kC(S)R^c$, —$C(NR)R^c$, —$OC(NR)R^c$, —$SC(NR)R^c$, —$NR^kC(NR)R^c$, —$S(O)_2R^c$, —$S(O)R^c$, —$NR^kS(O)_2R^c$, —$OS(O)_2R^c$, —$OP(O)R^cR^c$, —$P(O)R^cR^c$, halo, aminoalkyl, mercaptoalkyl, cyano, nitro, nitroso, or azide;

$R^h$ and $R^j$, for each occurrence, are independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl; or $R^h$ and $R^j$ taken together with the N to which they are attached is an optionally substituted heterocyclyl, an optionally substituted heterocycloalkyl, or an optionally substituted heteroaryl;

$R^k$, for each occurrence, is independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, or an optionally substituted heteroaryl;

G is: Hydrazide; Hydrazone; Hydrazine; Hydroxylamine; Oxime; Amide; Ester; Carbonate; Carbamate; Thiocarbamate; —$NR^k$—$C(NR)$—$NR^k$—; —$NR^k$—$C(O)$—$NR^k$—; —$NR^kC(S)$—$NR^k$—; —$NR^k$—$S(O)_2$—$NR^k$—; Phosphoryl; an optionally substituted-Cyclyl-; an optionally substituted-Heterocyclyl-; an optionally substituted-Aryl-; an optionally substituted-Heteroaryl-; an optionally substituted-Heteroarylalkyl-; an optionally substituted-Heteroaryl-$NR^k$—; an optionally substituted-Heteroaryl-S—; an optionally substituted-Heteroarylalkyl-O—; —Si$(OR^k)_2$—; —$B(OR^k)$—; —$C(NR)$—$NR^k$—; —$N(R^k)$—$C(R^gR^g)$—$C(O)$—; —$C(O)$—$ON(R^k)$—; —$C(O)$—$N(R^k)$O—; —$C(S)$—$ON(R^k)$—; —$C(S)$—$N(R^k)O$—; —$C(N(R^k))$—$ON(R^k)$—; —$C(N(R^k))$—$NR^kO$—; —$OS(O)_2$—N$(R^k)N(R^k)$—; —$OC(O)$—$N(R^k)N(R^k)$—; —$OC(S)$—N$(R^k)N(R^k)$—; —$OC(N(R^k))$—$N(R^k)N(R^k)$—; —$N(R^k)N(R^k)S(O)_2O$—; —$N(R^k)N(R^k)C(S)O$—; —$N(R^k)N(R^k)C(N(R^k))O$—; —$OP(O)(R^c)O$—; —$N(R^k)P(O)(R^c)O$—; —$OP(O)(R^c)N(R^k)$—; —$N(R^k)P(O)(R^c)N(R^k)$—; —$P(O)(R^c)O$—; —$P(O)(R^c)N(R^k)$—; —$N(R^k)P(O)(R^c)$—; —$OP(O)(R^c)$—; —O-alkyl-heterocyclyl-$N(R^k)$—; —$N(R^k)CHR^gC(O)N(R^k)CHR^gC(O)$—; —$N(R^k)CHR^gC(O)$—; —$N(R^k)C(O)CHR^g$—; —$C(O)N(R^k)CHR^gC(O)$—;

or G is absent;

Y is a covalent bond, $(CH(R^g))_m$, C(O), C(NR), O, S, S(O), $S(O)_2$, $N(OR^k)$ or $N(R^k)$;

m is 0, 1, 2, 3, or 4; n is, independently for each occurrence, 0, 1, 2, 3, 4, 5, 6, or 7; p is 0, 1 or 2;

Z is N or CH; and

W is O, S, S(O), $S(O)_2$, $NR^m$, or $NC(O)R^m$, wherein $R^m$ is H, an optionally substituted alkyl, an optionally substituted aryl, an optionally substituted heteroaryl, an optionally substituted cycloalkyl, an optionally substituted heterocycloalkyl, or —$C(O)R^c$.

In certain preferred embodiments of the compound of Formula (I), Q, U, and V are N. In other preferred embodiments, one of Q, U, or V is $CR^g$, and the other two are N; more preferably: V is $CR^g$, and Q and U are N; or Q is $CR^g$, and V and U are N. In still other preferred embodiments, one of Q, U, and V is N, and the other two are $CR^g$; more preferably: V is N, and Q and U are $CR^g$; or Q is N, and V and U are $CR^g$; or U is N, and Q and V are $CR^g$.

In certain preferred embodiments of the compound of formula (I), X is represented by one of the following formulas:

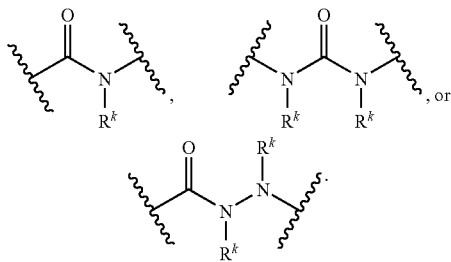

In certain more preferred embodiments, X is represented by the following formula:

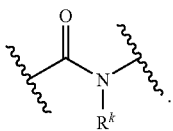

In certain more preferred embodiments, X is represented by the following formula:

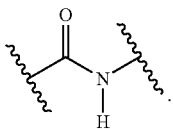

In certain preferred embodiments, X is represented by the following formula:

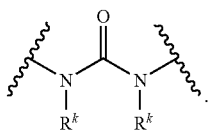

In certain more preferred embodiments, X is represented by the following formula:

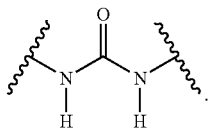

In certain preferred embodiments, X is represented by the following formula:

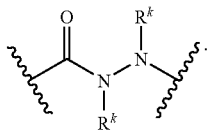

In certain more preferred embodiments, X is represented by the following formula:

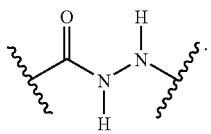

In certain preferred embodiments of the compound of formula (I), Y is O, while in other preferred embodiments, Y is a covalent bond.

In certain preferred embodiments, $R_3$ is $R^c$. In certain more preferred embodiments, $R_3$ is H, while in other more preferred embodiments, $R_3$ is an optionally substituted aryl or an optionally substituted heteroaryl, still more preferably an optionally substituted phenyl, an optionally substituted naphthyl, an optionally substituted anthracenyl, an optionally substituted fluorenyl, an optionally substituted indenyl, an optionally substituted azulenyl, an optionally substituted pyridyl, an optionally substituted 1-oxo-pyridyl, an optionally substituted furanyl, an optionally substituted benzo[1,3]dioxolyl, an optionally substituted benzo[1,4]dioxinyl, an optionally substituted thienyl, an optionally substituted pyrrolyl, an optionally substituted oxazolyl, an optionally substituted imidazolyl, an optionally substituted thiazolyl, an optionally substituted isoxazolyl, an optionally substituted quinolinyl, an optionally substituted pyrazolyl, an optionally substituted isothiazolyl, an optionally substituted pyridazinyl, an optionally substituted pyrimidinyl, an optionally substituted pyrazinyl, an optionally substituted triazinyl, an optionally substituted triazolyl, an optionally substituted thiadiazolyl, an optionally substituted isoquinolinyl, an optionally substituted indazolyl, an optionally substituted benzoxazolyl, an optionally substituted benzofuryl, an optionally substituted indolizinyl, an optionally substituted imidazopyridyl, an optionally substituted tetrazolyl, an optionally substituted benzimidazolyl, an optionally substituted benzothiazolyl, an optionally substituted benzothiadiazolyl, an optionally substituted benzoxadiazolyl, an optionally substituted indolyl, an optionally substituted tetrahydroindolyl, an optionally substituted azaindolyl, an optionally substituted indazolyl, an optionally substituted imidazopyridyl, an optionally substituted quinazolinyl, an optionally substituted purinyl, an optionally substituted pyrrolo[2,3]pyrimidinyl, an optionally substituted pyrazolo[3,4]pyrimidinyl, or an optionally substituted benzo(b)thienyl.

In other preferred embodiments of the compound of formula (I), if $R_3$ is $R^c$, then $R_3$ is an optionally substituted heterocyclyl or an optionally substituted heteroalkyl.

In certain preferred embodiments of the compound of formula (I), each of $R_2$ and $R_4$ is, independently, H, an optionally substituted alkyl, an optionally substituted alkylcarbonyl, an optionally substituted aryl, an optionally substituted heteroaryl, an optionally substituted cycloalkyl, an optionally substituted cyclyl, an optionally substituted heterocycloalkyl, or an optionally substituted heterocyclyl. In more preferred embodiments, each of $R_2$ and $R_4$ is H or a lower alkyl.

In certain preferred embodiments of the compound of formula (I), n is 0, 1, 2, 3, or 4.

In certain preferred embodiments of the compound of formula (I), G is an optionally substituted heteroaryl or an optionally substituted heterocyclyl. In other preferred embodiments, G is —C(O)NHNH—, —NHNHC(O)—, —C(O)NR$^h$NR$^j$—, —NR$^k$NR$^k$C(O)—, —CH=N—NH—, —NH—N=CH—, —CR$^g$=N—NR$^k$—, —NR$^k$—N=CR$^g$—, —NHNH—, —NR$^k$NR$^k$—, —NHO— —O—NH—, —O—NR$^k$—, —NR$^k$—O—, —CH=N—O—, —O—N=CH—, —CR$^c$=N—O—, —O—N=CR$^c$—, —O—C(O)—NH—, —O—C(O)—NR$^k$—, —O—C(S)—NH—, —NH—C(S)—O—, —O—C(S)—NR$^k$—, —NR—C(S)—O—, —NH—C(NH)—NH—, —NR$^k$—C(NH)—NH—, —NR$^k$—C(NR$^k$)—NH—, —NH—C(N(CN))—NH—, —NH—C(NSO$_2$R$^c$)—NH—, —NR$^c$—C(NSO$_2$R$^d$)—NH—, —NH—C(NNO$_2$)—NH—, —NH—C(NC(O)R$^c$)—NH—, —NH—C(O)—NH—, —NR$^c$—C(O)—NR$^c$—, —NH—C(S)—NH— and —NR$^c$—C(S)—NR$^c$—, —NH—S(O)$_2$—NH—, —NR$^k$—S(O)$_2$—NR$^k$—, —N(R$^k$)—S(O)$_2$—O—, —P(O)(R$^c$)—, —P(O)(R$^c$)—O—, —P(O)(R$^c$)—NR$^k$—, optionally substituted-Cyclyl-, optionally substituted-Heterocyclyl-, optionally substituted-Aryl-, optionally substituted-Heteroaryl-, optionally substituted-Heteroarylalkyl-, optionally substituted-Heteroaryl-NH—, optionally substituted-Heteroaryl-S—, optionally substituted-Heteroarylalkyl-O—, —C(N—CN)—NH—, —Si(OH)₂—, —B(OH)—, —C(NH)—NR$^c$—, —N(R$^k$)—CH₂—C(O)—, —C(O)—ON(R$^k$)—, —C(O)—N(R$^c$)—, —C(S)—ON(R$^c$)—, —C(S)—N(R$^c$)O—, —C(N(R$^d$))—ON(R$^c$)—, —C(N(R$^d$))—NR$^c$O—, —OS(O)₂—N(R$^c$)N(R$^c$)—, —OC(O)—N(R$^c$)N(R$^c$)—, —OC(S)—N(R$^c$)N(R$^c$)—, —OC(N(R$^d$))—N(R$^c$)N(R$^c$)—, —N(R$^c$)N(R$^c$)S(O)₂O—, —N(R$^c$)N(R$^c$)C(S)O—, —N(R$^c$)N(R$^c$)C(N(R$^d$))O—, —OP(O)₂O—, —N(R$^c$)P(O)₂O—, —OP(O)₂N(R$^c$)—, —N(R$^c$)P(O)₂N(R$^c$)—, —P(O)₂O—, —P(O)₂N(R$^c$)—, —N(R$^c$)P(O)₂—, —OP(O)₂—, —O-alkyl-heterocyclyl-N(R$^c$)—, —N(R$^c$)CHR$^d$C(O)N(R$^c$)CHR$^d$C(O)—, —N(R$^c$)CHR$^d$C(O)—, —N(R$^c$)C(O)CHR$^d$—, —C(O)N(R$^c$)CHR$^d$C(O)—, or absent. In certain more preferred embodiments, G is —C(O)NHNH—, —NHNHC(O)—, —CH=N—NH—, —NH—N=CH—, —NHNH—, —NHO—, —O—NH—, —NR$^k$—O—, —CH=N—O—, —O—N=CH—, —O—C(S)—NH—, or —NH—C(S)—O—. In other more preferred embodiments, G is —O—C(O)—NH—, —NH—C(NH)—NH—, —NR$^k$—C(NH)—NH—, —NR$^k$—C(NR$^k$)—NH—, —NH—C(N(CN))—NH—, —NH—C(NSO₂R$^c$)—NH—, —NR$^k$—C(NSO₂R$^d$)—NH—, —NH—C(NNO₂)—NH—, NH—C(NC(O)R)—NH—, —NH—C(O)—NH—, or —NH—C(S)—NH—. In other more preferred embodiments, G is —NH—S(O)₂—NH—, —N(R$^c$)—S(O)₂—O—, —P(O)(R$^c$)—, —P(O)(R$^c$)—O—, or —P(O)(R$^c$)—NR$^c$—. In still other more preferred embodiments, G is an optionally substituted cyclyl, an optionally substituted cycloalkyl, an optionally substituted heterocycloalkyl or an optionally substituted heterocyclyl; and in yet more preferable embodiments, G is an optionally substituted cyclopropyl, an optionally substituted cyclobutyl, an optionally substituted cyclopentyl, an optionally substituted cyclohexyl, an optionally substituted cycloheptyl, an optionally substituted aziridinyl, an optionally substituted oxiranyl, an optionally substituted azetidinyl, an optionally substituted oxetanyl, an optionally substituted morpholinyl, an optionally substituted piperazinyl or an optionally substituted piperidinyl. In other preferred embodiments, G is an optionally substituted aryl, an optionally substituted heteroaryl, an optionally substituted heteroarylalkyl, —C(N—CN)—NH—, —Si(OH)₂—, —C(NH)—NR$^k$—, or —NR$^k$—CH₂—C(O)—; more preferably, G is an optionally substituted imidazolyl, an optionally substituted imidazolidinone, an optionally substituted imidazolidineamine, an optionally substituted pyrrolidinyl, an optionally substituted pyrrolyl, an optionally substituted furanyl, an optionally substituted thienyl, an optionally substituted thiazolyl, an optionally substituted triazolyl, an optionally substituted oxadiazolyl, an optionally substituted thiadiazolyl, an optionally substituted pyrazolyl, an optionally substituted tetrazolyl, an optionally substituted oxazolyl, an optionally substituted isoxazolyl, an optionally substituted phenyl, an optionally substituted pyridyl, an optionally substituted pyrimidyl, an optionally substituted indolyl, or an optionally substituted benzothiazolyl.

In certain preferred embodiments of the compound of Formula (I), Z is N, and W is O.

In certain preferred embodiments of the compound of Formula (I), Y is O or CH₂, G is absent, and n is 0, 1, 2, 3 or 4.

In certain preferred embodiments of the compound of Formula (I), R' is absent and L' is absent; more preferably, R" is an optionally substituted alkyl, an optionally substituted aryl, an optionally substituted heteroaryl, an optionally substituted cycloalkyl, an optionally substituted cyclyl, an optionally substituted heterocycloalkyl, an optionally substituted heterocyclyl, nitro, cyano, halo, OR$^k$, SR$^k$, or NR$^h$R$^j$; yet more preferably, R" is an optionally substituted aryl or an optionally substituted heteroaryl; still more preferably, R" is an optionally substituted phenyl, an optionally substituted naphthyl, an optionally substituted anthracenyl, an optionally substituted fluorenyl, an optionally substituted indenyl, an optionally substituted azulenyl, an optionally substituted pyridyl, an optionally substituted 1-oxo-pyridyl, an optionally substituted furanyl, an optionally substituted benzo[1,3]dioxolyl, an optionally substituted benzo[1,4]dioxinyl, an optionally substituted thienyl, an optionally substituted pyrrolyl, an optionally substituted oxazolyl, an optionally substituted imidazolyl, an optionally substituted thiazolyl, an optionally substituted isoxazolyl, an optionally substituted quinolinyl, an optionally substituted pyrazolyl, an optionally substituted isothiazolyl, an optionally substituted pyridazinyl, an optionally substituted pyrimidinyl, an optionally substituted pyrazinyl, an optionally substituted triazinyl, an optionally substituted triazolyl, an optionally substituted thiadiazolyl, an optionally substituted isoquinolinyl, an optionally substituted indazolyl, an optionally substituted benzoxazolyl, an optionally substituted benzofuryl, an optionally substituted indolizinyl, an optionally substituted imidazopyridyl, an optionally substituted tetrazolyl, an optionally substituted benzimidazolyl, an optionally substituted benzothiazolyl, an optionally substituted benzothiadiazolyl, an optionally substituted benzoxadiazolyl, an optionally substituted indolyl, an optionally substituted tetrahydroindolyl, an optionally substituted azaindolyl, an optionally substituted indazolyl, an optionally substituted imidazopyridyl, an optionally substituted quinazolinyl, an optionally substituted purinyl, an optionally substituted pyrrolo[2,3]pyrimidinyl, an optionally substituted pyrazolo[3,4]pyrimidinyl, or an optionally substituted benzo(b)thienyl. Still more preferably, R" is a group represented by the following formula:

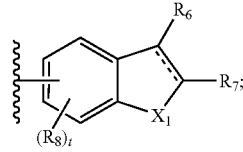

in which the dashed line indicates a double or a single bond;

X₁ is —O—, —S(O)$_p$—, —N(R$^k$)—, or —C(R$^g$)(R$^g$)—;

R₆ and R₇ are each, independently, R$^g$, —C(O)R$^c$, —C(S)R$^c$, —C(NR)R$^c$, —NR$^k$C(O)R$^c$, —OC(O)R$^c$, —SC(O)R$^c$, —NR$^k$C(S)R$^c$, —OC(S)R$^c$, —SC(S)R$^c$, —NR$^k$C(NR)R$^c$, —OC(NR)R$^c$, or —SC(NR)R$^c$; or R₆ and R₇, taken together with the carbons to which they are attached, form a 5- to 7-membered optionally substituted cycloalkyl, a 5- to 7-membered optionally substituted cyclocyclyl, a 5- to 7-membered optionally substituted aryl, a 5- to 7-membered optionally substituted heterocycloalkyl, a 5- to 7-membered optionally substituted heterocyclyl, a 5- to 7-membered optionally substituted heteroaryl;

R₈, for each occurrence, is, independently, R$^g$, —C(O)R$^c$, —C(S)R$^c$, —C(NR)R$^c$, —NR$^k$C(O)R$^c$, —OC(O)R$^c$, —SC(O)R$^c$, —NR$^k$C(S)R$^c$, —OC(S)R$^c$, —SC(S)R$^c$, —NR$^k$C(NR)R$^c$, —OC(NR)R$^c$, or —SC(NR)R$^c$; and t is 0, 1, 2, or 3. In more preferred embodiments, R" is (2,3-dimethyl-1H-indol-5-yl), (1H-indol-5-yl), or (6,7,8,9-tetrahydro-5H-carbazol-3-yl).

In other preferred embodiments, R" is a group represented by the following formula:

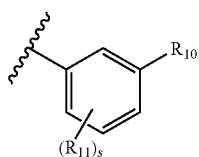

in which:

R$_{10}$ and R$_{11}$, for each occurrence, are, independently, R$^g$, —C(O)R$^c$, —C(S)R$^c$, —C(NR)R$^c$, —NR$^k$C(O)R$^c$, —OC(O)R$^c$, —SC(O)R$^c$, —NR$^k$C(S)R$^c$, —OC(S)R$^c$, —SC(S)R$^c$, —NR$^k$C(NR)R$^c$, —OC(NR)R$^c$, or —SC(NR)R$^c$; and s is 0, 1, 2, 3, or 4. More preferably, R" is a group represented by the following formula:

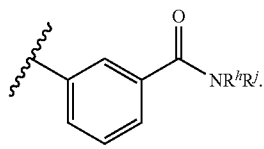

In other preferred embodiments, R" is a group represented by the following structural formula:

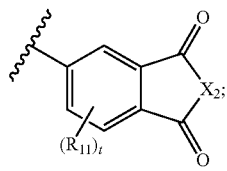

in which

X$_2$ is —O—, —S(O)$_p$—, or —NR$^k$—;

R$_{11}$, for each occurrence, is independently, R$^g$, —C(O)R$^c$, —C(S)R$^c$, —C(NR)R$^c$, —NR$^k$C(O)R$^c$, —OC(O)R$^c$, —SC(O)R$^c$, —NR$^k$C(S)R$^c$, —OC(S)R$^c$, —SC(S)R$^c$, —NR$^k$C(NR)R$^c$, —OC(NR)R$^c$, or —SC(NR)R$^c$; and t is 0, 1, 2, or 3.

In certain embodiments of the compound of formula (I), Y is absent, O, S, N(OR$^k$), N(R$^k$), or CH$_2$, and n is 0, 1, 2, 3, or 4.

In certain embodiments of the compound of formula (I), R$_3$ is an optionally substituted alkyl, an optionally substituted aryl, an optionally substituted heteroaryl, an optionally substituted cycloalkyl, an optionally substituted cyclyl, an optionally substituted heterocycloalkyl, an optionally substituted heterocyclyl, nitro, cyano, halo, OR$^k$, SR$^k$, or NR$^h$R$^j$; more preferably, R$_3$ is optionally substituted aryl or optionally substituted heteroaryl; still more preferably, R$_3$ is an optionally substituted phenyl, an optionally substituted naphthyl, an optionally substituted anthracenyl, an optionally substituted fluorenyl, an optionally substituted indenyl, an optionally substituted azulenyl, an optionally substituted pyridyl, an optionally substituted 1-oxo-pyridyl, an optionally substituted furanyl, an optionally substituted benzo[1,3]dioxolyl, an optionally substituted benzo[1,4]dioxinyl, an optionally substituted thienyl, an optionally substituted pyrrolyl, an optionally substituted oxazolyl, an optionally substituted imidazolyl, an optionally substituted thiazolyl, an optionally substituted isoxazolyl, an optionally substituted quinolinyl, an optionally substituted pyrazolyl, an optionally substituted isothiazolyl, an optionally substituted pyridazinyl, an optionally substituted pyrimidinyl, an optionally substituted pyrazinyl, an optionally substituted triazinyl, an optionally substituted triazolyl, an optionally substituted thiadiazolyl, an optionally substituted isoquinolinyl, an optionally substituted indazolyl, an optionally substituted benzoxazolyl, an optionally substituted benzofuryl, an optionally substituted indolizinyl, an optionally substituted imidazopyridyl, an optionally substituted tetrazolyl, an optionally substituted benzimidazolyl, an optionally substituted benzothiazolyl, an optionally substituted benzothiadiazolyl, an optionally substituted benzoxadiazolyl, an optionally substituted indolyl, an optionally substituted tetrahydroindolyl, an optionally substituted azaindolyl, an optionally substituted indazolyl, an optionally substituted imidazopyridyl, an optionally substituted quinazolinyl, an optionally substituted purinyl, an optionally substituted pyrrolo[2,3]pyrimidinyl, an optionally substituted pyrazolo[3,4]pyrimidinyl, or an optionally substituted benzo(b)thienyl.

In certain embodiments of the compound of formula (I), R$_3$ is an optionally substituted heterocycloalkyl; more preferably, R$_3$ is an optionally substituted piperidinyl, an optionally substituted piperazinyl, an optionally substituted 2-oxopiperazinyl, an optionally substituted 2-oxopiperidinyl, an optionally substituted 2-oxopyrrolidinyl, an optionally substituted 4-piperidonyl, an optionally substituted tetrahydropyranyl, an optionally substituted oxazolidinyl, an optionally substituted 2-oxo-oxazolidinyl, an optionally substituted tetrahydrothiopyranyl, an optionally substituted tetrahydrothiopyranyl sulfone, an optionally substituted morpholinyl, an optionally substituted thiomorpholinyl, an optionally substituted thiomorpholinyl sulfoxide, an optionally substituted thiomorpholinyl sulfone, an optionally substituted 1,3-dioxolanyl, an optionally substituted [1,4]dioxanyl, an optionally substituted 2-oxo-imidazolidinyl, tetrahydrofuranyl, or an optionally substituted tetrahydrothienyl.

In certain embodiments of the compound of formula (I), R$_3$ is OR$^k$, SR$^k$, C(O)OR$^k$, NR$^h$R$^j$, or C(O)NR$^h$R$^j$; more preferably, R$_3$ is —OR$^k$, —C(O)R$^c$, —OC(O)R$^c$, —NR$^k$C(O)R$^c$ or —NR$^h$R$^j$, and R$^k$, R$^h$ and R$^j$ are each, independently, H, an optionally substituted alkyl, an optionally substituted aryl, an optionally substituted heteroaryl, an optionally substituted cycloalkyl, or an optionally substituted heterocycloalkyl.

In another aspect, the invention provides a compound selected from the group consisting of 2-Morpholin-4-yl-6-(2-morpholin-4-yl-ethoxy)-pyrimidine-4-carboxylic acid (2,3-dimethyl-1H-indol-5-yl)-amide, 2-Morpholin-4-yl-6-(2-pyridin-2-yl-ethoxy)-pyrimidine-4-carboxylic acid (2,3-dimethyl-1H-indol-5-yl)-amide, [6-(2,3-Dimethyl-1H-indol-5-ylcarbamoyl)-2-morpholin-4-yl-pyrimidin-4-yloxy]-acetic acid ethyl ester, 2-Morpholin-4-yl-6-(2-pyridin-2-yl-ethoxy)-pyrimidine-4-carboxylic acid (1H-indol-5-yl)-amide, 2-Morpholin-4-yl-6-(2-pyridin-2-yl-ethoxy)-pyrimidine-4-carboxylic acid m-tolylamide, 6-(2-Hydroxy-2-methyl-propoxy)-2-morpholin-4-yl-pyrimidine-4-carboxylic acid (2,3-dimethyl-1H-indol-5-yl)-amide, 2-Morpholin-4-yl-6-(2-morpholin-4-yl-ethoxy)-pyrimidine-4-carboxylic acid (6,7,8,9-tetrahydro-5H-carbazol-3-yl)-amide, 2-Morpholin-4-yl-6-(2-morpholin-4-yl-ethoxy)-pyrimidine-4-carboxylic acid (5-furan-2-yl-1H-pyrazol-3-yl)-amide, 1-[2-Morpholin-4-yl-6-(2-morpholin-4-yl-ethoxy)-pyrimidin-4-yl]-3-m-tolyl-urea, 1-[6-(2-Methylamino-ethoxy)-2-morpholin-4-yl-pyrimidin-4-yl]-3-m-tolyl-urea, 1-[6-(2-Hydroxy-2-methyl-propoxy)-2-morpholin-4-yl-pyrimidin-4-yl]-3-m-tolyl-urea, 1-[6-Morpholin-4-yl-2-(2-morpholin-4-yl-ethoxy)-pyrimidin-4-yl]-3-p-tolyl-thiourea, 1-(2-Bromo-4-methyl-phenyl)-3-[6-morpholin-4-yl-2-(2-morpholin-4-yl-ethoxy)-pyrimidin-4-yl]-thiourea, 1-[2-

Morpholin-4-yl-6-(2-morpholin-4-yl-ethoxy)-pyrimidin-4-yl]-3-phenyl-urea, 1-[2-Morpholin-4-yl-6-(2-morpholin-4-yl-ethoxy)-pyrimidin-4-yl]-3-p-tolyl-urea, 1-(3-Methoxy-phenyl)-3-[2-morpholin-4-yl-6-(2-morpholin-4-yl-ethoxy)-pyrimidin-4-yl]-urea, 1-(4-Chloro-phenyl)-3-[2-morpholin-4-yl-6-(2-morpholin-4-yl-ethoxy)-pyrimidin-4-yl]-urea, 1-(2-Methoxy-phenyl)-3-[2-morpholin-4-yl-6-(2-morpholin-4-yl-ethoxy)-pyrimidin-4-yl]-urea, 1-Benzyl-3-[2-morpholin-4-yl-6-(2-morpholin-4-yl-ethoxy)-pyrimidin-4-yl]-urea, [6-(2,3-Dimethyl-1H-indol-5-ylcarbamoyl)-2-morpholin-4-yl-pyrimidin-4-yloxy]-acetic acid ethyl ester, 2-Morpholin-4-yl-6-[2-(2-oxo-oxazolidin-3-yl)-ethoxy]-pyrimidine-4-carboxylic acid (2,3-dimethyl-1H-indol-5-yl)-amide, 2,6-Di-morpholin-4-yl-pyrimidine-4-carboxylic acid (2,3-dimethyl-1H-indol-5-yl)-amide, 2-Morpholin-4-yl-6-(2-morpholin-4-yl-ethoxy)-pyrimidine-4-carboxylic acid (3,4-dimethyl-phenyl)-amide, 2-Morpholin-4-yl-6-(2-morpholin-4-yl-ethoxy)-pyrimidine-4-carboxylic acid (1,2,3-trimethyl-1H-indol-5-yl)-amide, 2-Morpholin-4-yl-6-(2-morpholin-4-yl-ethoxy)-pyrimidine-4-carboxylic acid (3-carbamoyl-phenyl)-amide, 2-Morpholin-4-yl-6-(2-morpholin-4-yl-ethoxy)-pyrimidine-4-carboxylic acid (3-dimethylamino-phenyl)-amide, 2-Morpholin-4-yl-6-[2-(4-oxy-morpholin-4-yl)-ethoxy]-pyrimidine-4-carboxylic acid (2,3-dimethyl-1H-indol-5-yl)-amide, 6-Methoxy-2-morpholin-4-yl-pyrimidine-4-carboxylic acid (2,3-dimethyl-1H-indol-5-yl)-amide, 6-Morpholin-4-yl-4-(2-morpholin-4-yl-ethoxy)-pyridine-2-carboxylic acid (2,3-dimethyl-1H-indol-5-yl)-amide, 4,6-Di-morpholin-4-yl-pyridine-2-carboxylic acid (2,3-dimethyl-1H-indol-5-yl)-amide, 2-Morpholin-4-yl-6-(2-morpholin-4-yl-ethoxy)-pyrimidine-4-carboxylic acid methyl-(1,2,3-trimethyl-1H-indol-5-yl)-amide, 2-Morpholin-4-yl-6-(2-pyridin-2-yl-ethoxy)-pyrimidine-4-carboxylic acid (6-methyl-benzothiazol-2-yl)-amide, 2-Morpholin-4-yl-6-(2-pyridin-2-yl-ethoxy)-pyrimidine-4-carboxylic acid (9-ethyl-9H-carbazol-2-yl)-amide, 2-Morpholin-4-yl-6-(2-pyridin-2-yl-ethoxy)-pyrimidine-4-carboxylic acid (6-methyl-pyridin-2-yl)-amide, 2-Morpholin-4-yl-6-(2-pyridin-2-yl-ethoxy)-pyrimidine-4-carboxylic acid (4-methyl-pyridin-2-yl)-amide, 2-Morpholin-4-yl-6-(2-pyridin-2-yl-ethoxy)-pyrimidine-4-carboxylic acid benzothiazol-6-ylamide, 2-Morpholin-4-yl-6-(2-pyridin-2-yl-ethoxy)-pyrimidine-4-carboxylic acid naphthalen-2-ylamide, 2-Morpholin-4-yl-6-(2-pyridin-2-yl-ethoxy)-pyrimidine-4-carboxylic acid quinolin-6-ylamide, 2-Morpholin-4-yl-6-(2-pyridin-2-yl-ethoxy)-pyrimidine-4-carboxylic acid quinolin-5-ylamide, 2-Morpholin-4-yl-6-(2-morpholin-4-yl-ethoxy)-pyrimidine-4-carboxylic acid indan-5-ylamide, 2-Morpholin-4-yl-6-(2-morpholin-4-yl-ethoxy)-pyrimidine-4-carboxylic acid (2,3-dimethyl-1H-indol-7-yl)-amide, 2-Morpholin-4-yl-6-(2-piperidin-1-yl-ethoxy)-pyrimidine-4-carboxylic acid (2,3-dimethyl-1H-indol-5-yl)-amide, 2-Morpholin-4-yl-6-[2-(2-oxo-oxazolidin-3-yl)-ethoxy]-pyrimidine-4-carboxylic acid (3-carbamoyl-phenyl)-amide, 2-Morpholin-4-yl-6-[2-(2-oxo-oxazolidin-3-yl)-ethoxy]-pyrimidine-4-carboxylic acid m-tolylamide, 2-Morpholin-4-yl-6-(2-morpholin-4-yl-ethoxy)-pyrimidine-4-carboxylic acid (5-thiophen-2-yl-1H-pyrazol-3-yl)-amide, 2-Morpholin-4-yl-6-(2-morpholin-4-yl-ethoxy)-pyrimidine-4-carboxylic acid (3-ethyl-phenyl)-amide, 2-Morpholin-4-yl-6-(2-morpholin-4-yl-ethoxy)-pyrimidine-4-carboxylic acid (3-bromo-phenyl)-amide, 2-Morpholin-4-yl-6-(2-morpholin-4-yl-ethoxy)-pyrimidine-4-carboxylic acid (5-methyl-isoxazol-3-yl)-amide, 2-Morpholin-4-yl-6-(2-morpholin-4-yl-ethoxy)-pyrimidine-4-carboxylic acid (2-acetylamino-phenyl)-amide, 2-Morpholin-4-yl-6-(2-morpholin-4-yl-ethoxy)-pyrimidine-4-carboxylic acid (3-sulfamoyl-phenyl)-amide, 2,6-Di-morpholin-4-yl-pyrimidine-4-carboxylic acid (3,4-dimethyl-phenyl)-amide, 2,6-Di-morpholin-4-yl-pyrimidine-4-carboxylic acid (3-carbamoyl-phenyl)-amide, 2-Morpholin-4-yl-6-(2-morpholin-4-yl-ethoxy)-pyrimidine-4-carboxylic acid (3-dimethylcarbamoyl-phenyl)-amide, Indol-1-yl-[2-morpholin-4-yl-6-(2-morpholin-4-yl-ethoxy)-pyrimidin-4-yl]-methanone, (3,4-Dihydro-1H-isoquinolin-2-yl)-[2-morpholin-4-yl-6-(2-morpholin-4-yl-ethoxy)-pyrimidin-4-yl]-methanone, 2-Morpholin-4-yl-6-(2-morpholin-4-yl-ethoxy)-pyrimidine-4-carboxylic acid m-tolylamide, 2-Morpholin-4-yl-6-(2-morpholin-4-yl-ethoxy)-pyrimidine-4-carboxylic acid (4-dimethylamino-phenyl)-amide, 2-Morpholin-4-yl-6-(2-morpholin-4-yl-ethoxy)-pyrimidine-4-carboxylic acid [3-(pyrrolidine-1-carbonyl)-phenyl]-amide, 2-Morpholin-4-yl-6-(2-morpholin-4-yl-ethoxy)-pyrimidine-4-carboxylic acid (1,3-dioxo-2,3-dihydro-1H-isoindol-5-yl)-amide, 2-Morpholin-4-yl-6-(2-morpholin-4-yl-ethoxy)-pyrimidine-4-carboxylic acid (2-methoxy-5-methyl-phenyl)-amide, 2-Morpholin-4-yl-6-(2-morpholin-4-yl-ethoxy)-pyrimidine-4-carboxylic acid (3-hydroxy-phenyl)-amide, 6-Morpholin-4-yl-2-(2-pyridin-2-yl-ethoxy)-pyrimidine-4-carboxylic acid m-tolylamide, 6-Morpholin-4-yl-2-(2-pyridin-2-yl-ethoxy)-pyrimidine-4-carboxylic acid (2,3-dimethyl-1H-indol-5-yl)-amide, 6-Morpholin-4-yl-2-(2-pyridin-2-yl-ethoxy)-pyrimidine-4-carboxylic acid (6-methyl-benzothiazol-2-yl)-amide, 2-[2-(3,4-Dimethoxy-phenyl)-ethoxy]-6-morpholin-4-yl-N-m-tolyl-isonicotinamide, N-(2,3-Dimethyl-1H-indol-5-yl)-2-morpholin-4-yl-6-(2-morpholin-4-yl-ethoxy)-isonicotinamide, 1-[2-Morpholin-4-yl-6-(2-pyridin-2-yl-ethoxy)-pyrimidin-4-yl]-3-m-tolyl-urea, 1-[6-Morpholin-4-yl-2-(2-pyridin-2-yl-ethoxy)-pyrimidin-4-yl]-3-m-tolyl-urea, 1-Methyl-3-[6-morpholin-4-yl-2-(2-pyridin-2-yl-ethoxy)-pyrimidin-4-yl]-1-m-tolyl-urea, 1-(4,6-Di-morpholin-4-yl-pyridin-2-yl)-3-m-tolyl-urea, 1-[4-Morpholin-4-yl-6-(2-pyridin-2-yl-ethoxy)-pyrimidin-2-yl]-3-m-tolyl-urea, 2-Morpholin-4-yl-6-(2-pyridin-2-yl-ethoxy)-pyrimidine-4-carboxylic acid 1H-indol-5-yl ester, 1H-Indole-5-carboxylic acid [2-morpholin-4-yl-6-(2-pyridin-2-yl-ethoxy)-pyrimidin-4-yl]-amide, 1H-Indole-5-carboxylic acid [6-morpholin-4-yl-2-(2-pyridin-2-yl-ethoxy)-pyrimidin-4-yl]-amide, 3-Methyl-N-[4-morpholin-4-yl-6-(2-pyridin-2-yl-ethoxy)-pyrimidin-2-yl]-benzamide, N-[4-Morpholin-4-yl-6-(2-pyridin-2-yl-ethoxy)-pyrimidin-2-yl]-isonicotinamide, 5-Methyl-isoxazole-3-carboxylic acid-[4-morpholin-4-yl-6-(2-pyridin-2-yl-ethoxy)-pyrimidin-2-yl]-amide, 6-Morpholin-4-yl-2-(2-pyridin-2-yl-ethoxy)-pyrimidine-4-carboxylic acid N'-m-tolyl-hydrazide, 2-Morpholin-4-yl-6-(2-pyridin-2-yl-ethoxy)-pyrimidine-4-carboxylic acid N'-m-tolyl-hydrazide, 6-Morpholin-4-yl-2-(2-morpholin-4-yl-ethoxy)-pyrimidine-4-carboxylic acid N'-m-tolyl-hydrazide, 6-Morpholin-4-yl-2-(2-morpholin-4-yl-ethoxy)-pyrimidine-4-carboxylic acid N'-(3,4-dimethyl-phenyl)-hydrazide, 2-Morpholin-4-yl-6-(2-morpholin-4-yl-ethoxy)-isonicotinic acid N'-m-tolyl-hydrazide, [2-Morpholin-4-yl-6-(2-pyridin-2-yl-ethoxy)-pyrimidin-4-yl]-carbamic acid m-tolyl ester, (2,3-Dimethyl-1H-indol-5-yl)-[2-morpholin-4-yl-6-(2-pyridin-2-yl-ethoxy)-pyrimidin-4-ylmethyl]-amine, N-[2-Morpholin-4-yl-6-(2-pyridin-2-yl-ethoxy)-pyrimidin-4-yl]-N'-m-tolyl-oxalamide, N-(3-Hydroxy-phenyl)-N'-[2-morpholin-4-yl-6-(2-pyridin-2-yl-ethoxy)-pyrimidin-4-yl]-oxalamide, N-(3-Hydroxy-phenyl)-N'-[6-morpholin-4-yl-2-(2-pyridin-2-yl-ethoxy)-pyrimidin-4-yl]-oxalamide, and [6-Morpholin-4-yl-2-(2-pyridin-2-yl-ethoxy)-pyrimidin-4-yl]-carbamic acid m-tolyl ester, 2-Morpholin-4-yl-6-(2-morpholin-4-yl-2-oxo-ethylamino)-pyrimidine-4-carboxylic acid (2,3-dimethyl-1H-indol-5-yl)-amide, 2-Morpholin-4-yl-6-(4-pyridin-2-yl-piperazin-1-yl)-pyrimidine-4-carboxylic acid (2,3-dimethyl-1H-indol-5-yl)-amide, 6-[Bis-(2-hydroxy-ethyl)-amino]-2-morpholin-4-yl-pyrimidine-4-carboxylic acid (2,3-dimethyl-1H-indol-5-yl)-amide, 6-Dibutylamino-2-morpholin-4-yl-pyrimidine-4-carboxylic acid (2,3-dimethyl-1H-indol-5-yl)-amide, 6-Diethylamino-2-morpholin-4-yl-pyrimidine-4-carboxylic acid (2,3-dimethyl-1H-indol-5-yl)-amide, 6-[4-(2-Hydroxy-ethyl)-piperazin-1-yl]-2-morpholin-4-yl-pyrimidine-4-carboxylic acid (2,3-dimethyl-1H-indol-5-yl)-amide, 6-(2-Dimethylamino-ethylamino)-2-morpholin-4-yl-pyrimidine-4-carboxylic acid (2,3-dimethyl-1H-indol-5-yl)-amide, [6-(2,3-Dimethyl-1H-indol-5-ylcarbamoyl)-2-morpholin-4-yl-pyrimidin-4-ylamino]-acetic acid, [6-(2,3-Dimethyl-1H-indol-5-ylcarbamoyl)-2-morpholin-4-yl-pyrimidin-4-ylamino]-acetic acid methyl ester, 6-{[(2-Methoxy-ethylcarbamoyl)-methyl]-amino}-2-morpholin-4-yl-pyrimidine-4-carboxylic acid (2,3-dimethyl-1H-indol-5-yl)-amide, 6-[2-(4-Carbamoyl-piperidin-1-yl)-2-oxo-ethylamino]-2-morpholin-4-yl-pyrimidine-4-carboxylic acid (2,3-dimethyl-1H-indol-5-yl)-amide, 6-[2-(4-Hydroxy-piperidin-1-yl)-2-oxo-ethylamino]-2-morpholin-4-yl-pyrimidine-4-carboxylic acid (2,3-dimethyl-1H-indol-5-yl)-amide, 6-({[2-Hydroxy-ethyl)-methyl-carbamoyl]-methyl}-amino)-2-morpholin-4-yl-pyrimidine-4-carboxylic acid (2,3-dimethyl-1H-indol-5-yl)-amide, 6-[2-(4-Acetyl-piperazin-1-yl)-2-oxo-ethylamino]-2-morpholin-4-yl-pyrimidine-4-carboxylic acid (2,3-dimethyl-1H-indol-5-yl)-amide, 6-[2-(3,4-Dihydro-1H-isoquinolin-2-yl)-2-oxo-ethylamino]-2-morpholin-4-yl-pyrimidine-4-carboxylic acid (2,3-dimethyl-1H-indol-5-yl)-amide, 6-(Carbamoylmethyl-amino)-2-morpholin-4-yl-pyrimidine-4-carboxylic acid (2,3-dimethyl-1H-indol-5-yl)-amide, 6-(Ethylcarbamoylmethyl-amino)-2-morpholin-4-yl-pyrimidine-4-carboxylic acid (2,3-dimethyl-1H-indol-5-yl)-amide, 6-[2-(4-Methyl-piperazin-1-yl)-2-oxo-ethylamino]-2-morpholin-4-yl-pyrimidine-4-carboxylic acid (2,3-dimethyl-1H-indol-5-yl)-amide, 6-{[(Butyl-methyl-carbamoyl)-methyl]-amino}-2-morpholin-4-yl-pyrimidine-4-carboxylic acid (2,3-dimethyl-1H-indol-5-yl)-amide, 2-Morpholin-4-yl-6-(2-oxo-2-pyrrolidin-1-yl-ethylamino)-pyrimidine-4-carboxylic acid (2,3-dimethyl-1H-indol-5-yl)-amide, 2-Morpholin-4-yl-6-(2-oxo-2-piperidin-1-yl-ethylamino)-pyrimidine-4-carboxylic acid (2,3-dimethyl-1H-indol-5-yl)-amide, 6-(Cyclopentylcarbamoylmethyl-amino)-2-morpholin-4-yl-pyrimidine-4-carboxylic acid (2,3-dimethyl-1H-indol-5-yl)-amide, 2-Morpholin-4-yl-6-[(m-tolylcarbamoyl-methyl)-amino]-pyrimidine-4-carboxylic acid (2,3-dimethyl-1H-indol-5-yl)-amide, 6-(Dimethylcarbamoylmethyl-amino)-2-morpholin-4-yl-pyrimidine-4-carboxylic acid (2,3-dimethyl-1H-indol-5-yl)-amide, 6-[Methyl-(2-oxo-2-piperidin-1-yl-ethyl)-amino]-2-morpholin-4-yl-pyrimidine-4-carboxylic acid (2,3-dimethyl-1H-indol-5-yl)-amide, 6-[Methyl-(2-morpholin-4-yl-2-oxo-ethyl)-amino]-2-morpholin-4-yl-pyrimidine-4-carboxylic acid (2,3-dimethyl-1H-indol-5-yl)-amide, 2-Morpholin-4-yl-6-(2-oxo-2-piperidin-1-yl-ethoxy)-pyrimidine-4-carboxylic acid (3-pyrazol-1-yl-phenyl)-amide, 6-[Methyl-(2-oxo-2-piperidin-1-yl-ethyl)-amino]-2-morpholin-4-yl-pyrimidine-4-carboxylic acid (3-dimethylamino-phenyl)-amide, 6-(Carbamoylmethyl-methyl-amino)-2-morpholin-4-yl-pyrimidine-4-carboxylic acid (2,3-dimethyl-1H-indol-5-yl)-amide, 1-(3-Bromo-phenyl)-3-[6-morpholin-4-yl-2-(2-morpholin-4-yl-ethoxy)-pyrimidin-4-yl]-urea, 1-(3,4-Dichloro-phenyl)-3-[6-morpholin-4-yl-2-(2-morpholin-4-yl-ethoxy)-pyrimidin-4-yl]-urea, 1-Indan-5-yl-3-[6-morpholin-4-yl-2-(2-morpholin-4-yl-ethoxy)-pyrimidin-4-yl]-urea, 1-[6-Morpholin-4-yl-2-(2-morpholin-4-yl-ethoxy)-pyrimidin-4-yl]-3-(3-trifluoromethyl-phenyl)-urea, 1-(3,4-Dimethyl-phenyl)-3-[6-morpholin-4-yl-2-(2-morpholin-4-yl-ethoxy)-pyrimidin-4-yl]-urea, 1-Benzo[1,3]dioxol-5-yl-3-[6-morpholin-4-yl-2-(2-morpholin-4-yl-ethoxy)-pyrimidin-4-yl]-urea, 1-[6-Morpholin-4-yl-2-(2-morpholin-4-yl-ethoxy)-pyrimidin-4-yl]-3-naphthalen-2-yl-urea, 1-(3-Fluoro-phenyl)-3-[2-morpholin-4-yl-6-(2-morpholin-4-yl-ethoxy)-pyrimidin-4-yl]-urea, 1-(3-Chloro-phenyl)-3-[2-morpholin-4-yl-6-(2-morpholin-4-yl-ethoxy)-pyrimidin-4-yl]-urea, 1-(3-Cyano-phenyl)-3-[2-morpholin-4-yl-6-(2-morpholin-4-yl-ethoxy)-pyrimidin-4-yl]-urea, 1-[2-Morpholin-4-yl-6-(2-morpholin-4-yl-ethoxy)-pyrimidin-4-yl]-3-(3-nitro-phenyl)-urea, 1-(2-Bromo-phenyl)-3-[2-morpholin-4-yl-6-(2-morpholin-4-yl-ethoxy)-pyrimidin-4-yl]-urea, 1-(3-Iodo-phenyl)-3-[2-morpholin-4-yl-6-(2-morpholin-4-yl-ethoxy)-pyrimidin-4-yl]-urea, 1-(3-Ethyl-phenyl)-3-[2-morpholin-4-yl-6-(2-morpholin-4-yl-ethoxy)-pyrimidin-4-yl]-urea, 1-(2-Chloro-phenyl)-3-[2-morpholin-4-yl-6-(2-morpholin-4-yl-ethoxy)-pyrimidin-4-yl]-urea, 1-(3-Methyl-2-oxo-2,3-dihydro-benzothiazol-6-yl)-3-[2-morpholin-4-yl-6-(2-morpholin-4-yl-ethoxy)-pyrimidin-4-yl]-urea, 1-(3-Methyl-2-oxo-2,3-dihydro-benzooxazol-6-yl)-3-[2-morpholin-4-yl-6-(2-morpholin-4-yl-ethoxy)-pyrimidin-4-yl]-urea, 1-(6-Chloro-benzooxazol-2-yl)-3-[2-morpholin-4-yl-6-(2-morpholin-4-yl-ethoxy)-pyrimidin-4-yl]-urea, 1-(2-Methyl-quinolin-6-yl)-3-[2-morpholin-4-yl-6-(2-morpholin-4-yl-ethoxy)-pyrimidin-4-yl]-urea, 1-(1H-Indol-5-yl)-3-[2-morpholin-4-yl-6-(2-morpholin-4-yl-ethoxy)-pyrimidin-4-yl]-urea, 1-(5-Hydroxy-naphthalen-1-yl)-3-[2-morpholin-4-yl-6-(2-morpholin-4-yl-ethoxy)-pyrimidin-4-yl]-urea, 1-(6-Chloro-benzothiazol-2-yl)-3-[2-morpholin-4-yl-6-(2-morpholin-4-yl-ethoxy)-pyrimidin-4-yl]-urea, 1-[2-Morpholin-4-yl-6-(2-morpholin-4-yl-ethoxy)-pyrimidin-4-yl]-3-quinolin-5-yl-urea, 1-(5-Cyclopropyl-[1,3,4]thiadiazol-2-yl)-3-[2-morpholin-4-yl-6-(2-morpholin-4-yl-ethoxy)-pyrimidin-4-yl]-urea, 1-[2-Morpholin-4-yl-6-(2-morpholin-4-yl-ethoxy)-pyrimidin-4-yl]-3-(4-p-tolyl-thiazol-2-yl)-urea, 1-(4-Hydroxy-phenyl)-3-[2-morpholin-4-yl-6-(2-morpholin-4-yl-ethoxy)-pyrimidin-4-yl]-urea, 1-(5-Furan-2-yl-2H-pyrazol-3-yl)-3-[2-morpholin-4-yl-6-(2-morpholin-4-yl-ethoxy)-pyrimidin-4-yl]-urea, 4,6-Di-morpholin-4-yl-pyridine-2-carboxylic acid (2,3-dimethyl-1H-indol-5-yl)-amide (compound with methanesulfonic acid), 6-Morpholin-4-yl-4-(2-morpholin-4-yl-ethoxy)-pyridine-2-carboxylic acid (1,2,3-trimethyl-1H-indol-5-yl)-amide, 4,6-Di-morpholin-4-yl-pyridine-2-carboxylic acid (1,2,3-trimethyl-1H-indol-5-yl)-amide; 6-Morpholin-4-yl-4-(2-morpholin-4-yl-ethoxy)-pyridine-2-carboxylic acid (2,3-dimethyl-1H-indol-5-yl)-amide (compound with methanesulfonic acid), 2-Morpholin-4-yl-6-(2-morpholin-4-yl-ethoxy)-pyrimidine-4-carboxylic acid (2-chloro-pyridin-4-yl)-amide, 2-Morpholin-4-yl-6-(2-morpholin-4-yl-ethoxy)-pyrimidine-4-carboxylic acid (5-carbamoyl-pyridin-2-yl)-amide, 2-Morpholin-4-yl-6-(2-morpholin-4-yl-ethoxy)-pyrimidine-4-carboxylic acid (2-pyrrolidin-1-yl-pyridin-4-yl)-amide, 2-Morpholin-4-yl-6-(2-morpholin-4-yl-ethoxy)-pyrimidine-4-carboxylic acid (3-acetyl-phenyl)-amide, (E)-N-(3-(1-(2,2-dimethylhydrazono)ethyl)phenyl)-2-morpholino-6-(2-morpholinoethoxy)pyrimidine-4-carboxamide, (E)-N-(3-(1-(methoxyimino)ethyl)phenyl)-2-morpholino-6-(2-morpholinoethoxy)pyrimidine-4-carboxamide, 6-Morpholin-4-yl-4-(2-morpholin-4-yl-ethoxy)-pyridine-2-carboxylic acid (3-dimethylamino-phenyl)-amide, 6-[(2-Methoxy-ethyl)-methyl-amino]-4-morpholin-4-yl-pyridine-2-carboxylic acid (2,3-dimethyl-1H-indol-5-yl)-amide, 6-[(2-Methoxy-ethyl)-methyl-amino]-4-morpholin-4-yl-pyridine-2-carboxylic acid (3-dimethylamino-phenyl)-amide, 4-[(2-Methoxy-ethyl)- methyl-amino]-6-morpholin-4-yl-pyridine-2-carboxylic acid (2,3-dimethyl-1H-indol-5-yl)-amide, 4-[(2-Methoxy-ethyl)-methyl-amino]-6-morpholin-4-yl-pyridine-2-carboxylic acid (3-dimethylamino-phenyl)-amide, 4-Methoxyamino-6-morpholin-4-yl-pyridine-2-carboxylic acid (3-dimethylamino-phenyl)-amide, 4-Methoxyamino-6-morpholin-4-yl-pyridine-2-carboxylic acid (2,3-dimethyl-1H-indol-5-yl)-amide, 6-[(2-Methoxy-ethyl)-methyl-amino]-2-morpholin-4-yl-pyrimidine-4-carboxylic acid (2-dimethylamino-ethyl)-amide, 2-Morpholin-4-yl-6-(2-morpholin-4-yl-ethoxy)-pyrimidine-4-carboxylic acid (5-cyclopropyl-[1,3,4]thiadiazol-2-yl)-amide, 6-[(2-Methoxy-ethyl)-methyl-amino]-2-morpholin-4-yl-pyrimidine-4-carboxylic acid (3-diethylaminomethyl-4-hydroxy-phenyl)-amide, 6-[(2-Methoxy-ethyl)-methyl-amino]-2-morpholin-4-yl-pyrimidine-4-carboxylic acid (4-acetylamino-phenyl)-amide, 6-[(2-Methoxy-ethyl)-methyl-amino]-2-morpholin-4-yl-pyrimidine-4-carboxylic acid [3-(acetyl-methyl-amino)-phenyl]-amide, (E)-N-(3-(1-(2,2-dimethylhydrazono)ethyl)phenyl)-6-((2-methoxyethyl)(methyl)amino)-2-morpholinopyrimidine-4-carboxamide, 6-Morpholin-4-yl-pyridine-2-carboxylic acid (2,3-dimethyl-1H-indol-5-yl)-amide, 4-(4-Acetyl-piperazin-1-yl)-6-morpholin-4-yl-pyridine-2-carboxylic acid (2,3-dimethyl-1H-indol-5-yl)-amide, 2-Morpholin-4-yl-6-(2-morpholin-4-yl-ethoxy)-pyrimidine-4-carboxylic acid [3-(2-methyl-pyrimidin-4-yl)-phenyl]-amide, 4-Hydroxy-6'-morpholin-4-yl-3,4,5,6-tetrahydro-2H-[1,4']bipyridinyl-2'-carboxylic acid (2,3-dimethyl-1H-indol-5-yl)-amide, 6-(1,4-Dioxa-8-aza-spiro[4.5]dec-8-yl)-2-morpholin-4-yl-pyrimidine-4-carboxylic acid (2,3-dimethyl-1H-indol-5-yl)-amide, 6-(4-Hydroxy-piperidin-1-yl)-2-morpholin-4-yl-pyrimidine-4-carboxylic acid (2,3-dimethyl-1H-indol-5-yl)-amide, 4-Hydroxy-6'-morpholin-4-yl-3,4,5,6-tetrahydro-2H-[1,4']bipyridinyl-2'-carboxylic acid (3-ethyl-1H-indol-5-yl)-amide, 6-(1,4-Dioxa-8-aza-spiro[4.5]dec-8-yl)-2-morpholin-4-yl-pyrimidine-4-carboxylic acid (3-ethyl-1H-indol-5-yl)-amide, 2'-(2,3-Dimethyl-1H-indol-5-ylcarbamoyl)-6'-morpholin-4-yl-3,4,5,6-tetrahydro-2H-[1,4']bipyridinyl-4-carboxylic acid ethyl ester, 6-(4-Hydroxy-piperidin-1-yl)-2-morpholin-4-yl-pyrimidine-4-carboxylic acid (3-ethyl-2-methyl-1H-indol-5-yl)-amide, 6-(4-Methyl-piperidin-1-yl)-2-morpholin-4-yl-pyrimidine-4-carboxylic acid (3-ethyl-1H-indol-5-yl)-amide, 2-Morpholin-4-yl-6-piperidin-1-yl-pyrimidine-4-carboxylic acid (3-ethyl-1H-indol-5-yl)-amide, 6-(1,4-Dioxa-8-aza-spiro[4.5]dec-8-yl)-2-morpholin-4-yl-pyrimidine-4-carboxylic acid (3-ethyl-2-methyl-1H-indol-5-yl)-amide, 4-(4-Acetyl-piperazin-1-yl)-6-morpholin-4-yl-pyridine-2-carboxylic acid (3-ethyl-1H-indol-5-yl)-amide, 6'-Morpholin-4-yl-3,4,5,6-tetrahydro-2H-[1,4']bipyridinyl-2'-carboxylic acid (2,3-dimethyl-1H-indol-5-yl)-amide, 6-(4-Carbamoyl-piperidin-1-yl)-2-morpholin-4-yl-pyrimidine-4-carboxylic acid (3-ethyl-2-methyl-1H-indol-5-yl)-amide, 6-(4-Hydroxy-piperidin-1-yl)-2-morpholin-4-yl-pyrimidine-4-carboxylic acid (6,7,8,9-tetrahydro-5H-carbazol-3-yl)-amide, 4-Hydroxy-6'-morpholin-4-yl-3,4,5,6-tetrahydro-2H-[1,4']bipyridinyl-2'-carboxylic acid (6,7,8,9-tetrahydro-5H-carbazol-3-yl)-amide (compound with methanesulfonic acid), 4-Hydroxy-6'-morpholin-4-yl-3,4,5,6-tetrahydro-2H-[1,4']bipyridinyl-2'-carboxylic acid (6,7,8,9-tetrahydro-5H-carbazol-3-yl)-amide, 6-(4-Hydroxy-piperidin-1-yl)-2-morpholin-4-yl-pyrimidine-4-carboxylic acid (3-methyl-1H-indol-5-yl)-amide, 6-(4-Hydroxy-piperidin-1-yl)-2-morpholin-4-yl-pyrimidine-4-carboxylic acid (6,7,8,9-tetrahydro-5H-carbazol-3-yl)-amide (compound with methanesulfonic acid), N-(2,3-dimethyl-1H-indol-5-yl)-6-((2-hydroxyethyl)(methyl)amino)-2-morpholinopyrimidine-4-carboxamide, 2-morpholino-6-(2-morpholinoethylamino)-N-(2-(trifluoromethyl)-1H-benzo[d]imidazol-5-yl)pyrimidine-4-carboxamide, 2-morpholino-6-(2-morpholinoethylamino)-N-(4-(trifluoromethyl)phenyl)pyrimidine-4-carboxamide, 2-morpholino-6-(2-morpholinoethylamino)-N-(2-oxo-4-(trifluoromethyl)-2H-chromen-7-yl)pyrimidine-4-carboxamide, N-(2,3-dimethyl-1H-indol-5-yl)-6-(methoxy(methyl)amino)-2-morpholinopyrimidine-4-carboxamide, N-(2,3-dimethyl-1H-indol-5-yl)-6-(2-hydroxyethylamino)-2-morpholinopyrimidine-4-carboxamide, N-(2,3-dimethyl-1H-indol-5-yl)-6-(methoxy(2-morpholinoethyl)amino)-2-morpholinopyrimidine-4-carboxamide, N-(3-(dimethylamino)phenyl)-6-(methoxyamino)-2-morpholinopyrimidine-4-carboxamide, 2-morpholino-6-(2-morpholinoethoxy)-N-(2-oxoindolin-5-yl)pyrimidine-4-carboxamide, N-(3-(3,3-diethylureido)phenyl)-2-morpholino-6-(2-morpholinoethoxy)pyrimidine-4-carboxamide, 2-morpholino-6-(2-morpholinoethoxy)-N-(3-oxo-3,4-dihydro-2H-benzo[b][1,4]oxazin-6-yl)pyrimidine-4-carboxamide, N-(2,3-dihydrobenzo[b][1,4]dioxin-6-yl)-6-((2-methoxyethyl)(methyl)amino)-2-morpholinopyrimidine-4-carboxamide, N-(4-tert-butylthiazol-2-yl)-6-(2-methoxyethyl)(methyl)amino)-2-morpholinopyrimidine-4-carboxamide, 6-((2-methoxyethyl)(methyl)amino)-N-(2-methylquinolin-6-yl)-2-morpholinopyrimidine-4-carboxamide, N-(5,6-dimethylbenzo[d]thiazol-2-yl)-6-((2-methoxyethyl)(methyl)amino)-2-morpholinopyrimidine-4-carboxamide, N-(2,5-diethoxy-4-morpholinophenyl)-6-((2-methoxyethyl)(methyl)amino)-2-morpholinopyrimidine-4-carboxamide, N-(3-isopropylphenyl)-6-((2-methoxyethyl)(methyl)amino)-2-morpholinopyrimidine-4-carboxamide, N-(1-acetylindolin-5-yl)-6-((2-methoxyethyl)(methyl)amino)-2-morpholinopyrimidine-4-carboxamide, 6-((2-methoxyethyl)(methyl)amino)-N-(3-(3-methyl-1,2,4-oxadiazol-5-yl)phenyl)-2-morpholinopyrimidine-4-carboxamide, 6-((2-methoxyethyl)(methyl)amino)-N-(3-(4-methyl-4H-1,2,4-triazol-3-yl)phenyl)-2-morpholinopyrimidine-4-carboxamide, 6-((2-methoxyethyl)(methyl)amino)-2-morpholino-N-(3-(trifluoromethyl)phenyl)pyrimidine-4-carboxamide, N-(benzo[d][1,3]dioxol-5-yl)-6-((2-methoxyethyl)(methyl)amino)-2-morpholinopyrimidine-4-carboxamide, 6-((2-methoxyethyl)(methyl)amino)-N-(1-methylindolin-6-yl)-2-morpholinopyrimidine-4-carboxamide, N-(5-(dimethylamino)-2-fluorophenyl)-6-((2-methoxyethyl)(methyl)amino)-2-morpholinopyrimidine-4-carboxamide, N-(3-isopropylphenyl)-2-morpholino-6-(2-morpholinoethoxy)pyrimidine-4-carboxamide, N-(1-methylindolin-6-yl)-2-morpholino-6-(2-morpholinoethoxy)pyrimidine-4-carboxamide, N-(3-(dimethylamino)-4-fluorophenyl)-6-((2-methoxyethyl)(methyl)amino)-2-morpholinopyrimidine-4-carboxamide, N-(1-methyl-1H-indazol-6-yl)-2-morpholino-6-(2-morpholinoethoxy)pyrimidine-4-carboxamide, 6-((2-methoxyethyl)(methyl)amino)-N-(1-methyl-1H-indazol-6-yl)-2-morpholinopyrimidine-4-carboxamide, N-(3-methyl-2-oxo-2,3-dihydrobenzo[d]oxazol-5-yl)-2-morpholino-6-(2-morpholinoethoxy)pyrimidine-4-carboxamide, 2-morpholino-6-(2-morpholinoethoxy)-N-(1,3,3-trimethyl-2-oxoindolin-5-yl)pyrimidine-4-carboxamide, N-(1-ethyl-1H-indol-6-yl)-2-morpholino-6-(2-morpholinoethoxy)pyrimidine-4-carboxamide, N-(1-ethylindolin-6-yl)-2-morpholino-6-(2-morpholinoethoxy)pyrimidine-4-carboxamide, 2-Morpholin-4-yl-6-[2-(2-oxo-oxazolidin-3-yl)-ethoxy]-pyrimidine-4-carboxylic acid (3-ethyl-2-methyl-1H-indol-5-yl)-amide, 2-Morpholin-4-yl-6-[2-(2-oxooxazolidin-3-yl)-ethoxy]-pyrimidine-4-carboxylic acid (6,7,8,9-tetrahydro-5H-carbazol-3-yl)-amide, 2-Morpholin-4-yl-6-(2-(2,2,3,3,5,5,6,6-octadeuteromorpholin-4-yl-ethoxy)-pyrimidine-4-carboxylic acid (6,7,8,9-tetrahydro-5H-carbazol-3-yl)-amide, 6-[(2-Methoxy-ethyl)-methyl-amino]-2-morpholin-4-yl-pyrimidine-4-carboxylic acid (5-tert-butyl-2-hydroxy-phenyl)-amide, 6-[(2-Methoxy-ethyl)-methyl-amino]-2-morpholin-4-yl-pyrimidine-4-carboxylic acid [3-(3-hydroxy-3-methyl-but-1-ynyl)-phenyl]-amide, 6-[(2-Methoxy-ethyl)-methyl-amino]-2-morpholin-4-yl-pyrimidine-4-carboxylic acid [5-(4-chloro-phenyl)-2-methyl-2H-pyrazol-3-yl]-amide, 6-[(2-Methoxy-ethyl)-methyl-amino]-2-morpholin-4-yl-pyrimidine-4-carboxylic acid (5-tert-butyl-isoxazol-3-yl)-amide, 6-[(2-Methoxy-ethyl)-methyl-amino]-2-morpholin-4-yl-pyrimidine-4-carboxylic acid (4-isopropyl-3-methyl-phenyl)-amide, 6-[(2-Methoxy-ethyl)-methyl-amino]-2-morpholin-4-yl-pyrimidine-4-carboxylic acid (4-bromo-3-methyl-phenyl)-amide, 6-[(2-Methoxy-ethyl)-methyl-amino]-2-morpholin-4-yl-pyrimidine-4-carboxylic acid (3-methanesulfonyl-phenyl)-amide, 6-[(2-Methoxy-ethyl)-methyl-amino]-2-morpholin-4-yl-pyrimidine-4-carboxylic acid (3-benzoyl-phenyl)-amide, 6-[(2-Methoxy-ethyl)-methyl-amino]-2-morpholin-4-yl-pyrimidine-4-carboxylic acid (2-p-tolyl-ethyl)-amide, 6-[(2-Methoxy-ethyl)-methyl-amino]-2-morpholin-4-yl-pyrimidine-4-carboxylic acid (3-carbamoyl-4-morpholin-4-yl-phenyl)-amide, 6-[(2-Methoxy-ethyl)-methyl-amino]-2-morpholin-4-yl-pyrimidine-4-carboxylic acid [3-(4-bromo-1-methyl-1H-pyrazol-3-yl)-phenyl]-amide, 6-[(2-Methoxy-ethyl)-methyl-amino]-2-morpholin-4-yl-pyrimidine-4-carboxylic acid (5-tert-butyl[1,3,4]thiadiazol-2-yl)-amide, 6-[(2-Methoxy-ethyl)-methyl-amino]-2-morpholin-4-yl-pyrimidine-4-carboxylic acid (5-methyl-isoxazol-3-yl)-amide, 6-[(2-Methoxy-ethyl)-methyl-amino]-2-morpholin-4-yl-pyrimidine-4-carboxylic acid (4,6-dimethyl-pyridin-2-yl)-amide, 6-[(2-Methoxy-ethyl)-methyl-amino]-2-morpholin-4-yl-pyrimidine-4-carboxylic acid (3-methyl-isothiazol-5-yl)-amide, 6-[(2-Methoxy-ethyl)-methyl-amino]-2-morpholin-4-yl-pyrimidine-4-carboxylic acid (4,6-dimethyl-pyrimidin-2-yl)-amide, 6-[(2-Methoxy-ethyl)-methyl-amino]-2-morpholin-4-yl-pyrimidine-4-carboxylic acid (2,3-dimethyl-quinoxalin-6-yl)-amide, 6-[(2-Methoxy-ethyl)-methyl-amino]-2-morpholin-4-yl-pyrimidine-4-carboxylic acid (3-quinoxalin-2-yl-phenyl)-amide, 6-[(2-Methoxy-ethyl)-methyl-amino]-2-morpholin-4-yl-pyrimidine-4-carboxylic acid (5,7-bis-trifluoromethyl-[1,8]naphthyridin-2-yl)-amide, 6-[(2-Methoxy-ethyl)-methyl-amino]-2-morpholin-4-yl-pyrimidine-4-carboxylic acid (3-trifluoromethoxy-phenyl)-amide, 6-[(2-Methoxy-ethyl)-methyl-amino]-2-morpholin-4-yl-pyrimidine-4-carboxylic acid [3-(2-methyl-thiazol-4-yl)-phenyl]-amide, N-(2,3-dimethyl-1H-indol-5-yl)-2-morpholino-6-(2-(piperazin-1-yl)ethoxy)pyrimidine-4-carboxamide, N-(2,3-dimethyl-1H-indol-5-yl)-6-(methylamino)-2-morpholino-pyrimidine-4-carboxamide, N-(2,3-dimethyl-1H-indol-5-yl)-6-(dimethylamino)-2-morpholino-pyrimidine-4-carboxamide, N-(2,3-dimethyl-1H-indol-5-yl)-6-(2-(methylsulfonyl)ethoxy)-2-morpholinopyrimidine-4-carboxamide, 6-(2-cyanoethoxy)-N-(2,3-dimethyl-1H-indol-5-yl)-2-morpholinopyrimidine-4-carboxamide, N-(2,3-dimethyl-1H-indol-5-yl)-6-(4-methylpiperazin-1-yl)-2-morpholinopyrimidine-4-carboxamide, N-(2,3-dimethyl-1H-indol-5-yl)-6-(2-methoxyethylamino)-2-morpholinopyrimidine-4-carboxamide, N-(2,3-dimethyl-1H-indol-5-yl)-6-methyl-2-morpholinopyrimidine-4-carboxamide, N-(2,3-dimethyl-1H-indol-5-yl)-6-hydroxy-2-morpholinopyrimidine-4-carboxamide, N-(2,3-dimethyl-1H-indol-5-yl)-6-(2,3-dimethyl-1H-indol-5-ylamino)-2-morpholinopyrimidine-4-carboxamide, 6-(2-(diethylamino)-2-oxoethoxy)-N-(2,3-dimethyl-1H-indol-5-yl)-2-morpholinopyrimidine-4-carboxamide, 6-(4-acetylpiperazin-1-yl)-N-(2,3-dimethyl-1H-indol-5-yl)-2-morpholinopyrimidine-4-carboxamide, 6-(bis(2-methoxyethyl)amino)-N-(2,3-dimethyl-1H-indol-5-yl)-2-morpholinopyrimidine-4-carboxamide, N-(2,3-dimethyl-1H-indol-5-yl)-2-morpholino-6-(morpholinomethyl)pyrimidine-4-carboxamide, (S)-6-(3-acetamidopyrrolidin-1-yl)-N-(3-methyl-1H-indol-5-yl)-2-morpholinopyrimidine-4-carboxamide, 6-(4-acetylpiperazin-1-yl)-N-(3-methyl-1H-indol-5-yl)-2-morpholinopyrimidine-4-carboxamide, 6-(4-acetylpiperazin-1-yl)-2-morpholino-N-(2,3,4,9-tetrahydro-1H-carbazol-6-yl)pyrimidine-4-carboxamide, 1-(2,3-dimethyl-1H-indol-5-yl)-3-(6-methyl-2-morpholinopyrimidin-4-yl)urea, 1-(6-(4-acetylpiperazin-1-yl)-2-morpholinopyrimidin-4-yl)-3-(2,3-dimethyl-1H-indol-5-yl)urea, 1-(2,3-dimethyl-1H-indol-5-yl)-3-(6-((2-methoxyethyl)(methyl)amino)-2-morpholinopyrimidin-4-yl)urea, 1-(6-(4-acetylpiperazin-1-yl)-2-morpholinopyrimidin-4-yl)-3-(3-ethyl-2-methyl-1H-indol-5-yl)urea, 1-(3-ethyl-2-methyl-1H-indol-5-yl)-3-(6-methyl-2-morpholinopyrimidin-4-yl)urea, 1-(2,3-dimethyl-1H-indol-5-yl)-3-(2-morpholino-6-(4-(pyridin-2-yl)piperazin-1-yl)pyrimidin-4-yl)urea, 1-(3-ethyl-2-methyl-1H-indol-5-yl)-3-(2-morpholino-6-(4-(pyridin-2-yl)piperazin-1-yl)pyrimidin-4-yl)urea, 1-(3-ethyl-2-methyl-1H-indol-5-yl)-3-(2-morpholino-6-(2-morpholinoethylamino)pyrimidin-4-yl)urea, 2-Morpholin-4-yl-6-(2-morpholin-4-yl-ethoxy)-pyrimidine-4-carboxylic acid (5-methyl-2-nitro-phenyl)-amide, 2-Morpholin-4-yl-6-(2-morpholin-4-yl-ethoxy)-pyrimidine-4-carboxylic acid (2-amino-5-methyl-phenyl)-amide, 6-(2-Amino-ethoxy)-2-morpholin-4-yl-pyrimidine-4-carboxylic acid (2,3-dimethyl-1H-indol-5-yl)-amide, 2-Morpholin-4-yl-6-(2-morpholin-4-yl-ethoxy)-pyrimidine-4-carboxylic acid (2-methyl-1,3-dioxo-2,3-dihydro-1H-isoindol-5-yl)-amide, 2-Morpholin-4-yl-6-(2-morpholin-4-yl-ethoxy)-pyrimidine-4-carboxylic acid (1H-indol-6-yl)-amide, 2-Morpholin-4-yl-6-(2-morpholin-4-yl-ethoxy)-pyrimidine-4-carboxylic acid (3-nitro-phenyl)-amide, 2-Morpholin-4-yl-6-(2-morpholin-4-yl-ethoxy)-pyrimidine-4-carboxylic acid (3-amino-phenyl)-amide, 2-Morpholin-4-yl-6-(2-morpholin-4-yl-ethoxy)-pyrimidine-4-carboxylic acid (3-pyrrolidin-1-yl-phenyl)-amide, 2-Morpholin-4-yl-6-(2-morpholin-4-yl-ethoxy)-pyrimidine-4-carboxylic acid (3-methoxy-phenyl)-amide, 2-Morpholin-4-yl-6-(2-morpholin-4-yl-ethoxy)-pyrimidine-4-carboxylic acid (3-methylamino-phenyl)-amide, 2-(2,6-Dimethyl-morpholin-4-yl)-6-morpholin-4-yl-pyrimidine-4-carboxylic acid (2,3-dimethyl-1H-indol-5-yl)-amide, 2-Morpholin-4-yl-6-(2-morpholin-4-yl-ethoxy)-pyrimidine-4-carboxylic acid (3,5-dimethyl-phenyl)-amide, 2,6-Di-morpholin-4-yl-pyrimidine-4-carboxylic acid (1,2,3-trimethyl-1H-indol-5-yl)-amide, 2-Morpholin-4-yl-6-(2-morpholin-4-yl-ethoxy)-pyrimidine-4-carboxylic acid (4-phenylamino-phenyl)-amide, 2-Morpholin-4-yl-6-(2-morpholin-4-yl-ethoxy)-pyrimidine-4-carboxylic acid (3-pyrrol-1-yl-phenyl)-amide, 6-(2-Methylamino-ethoxy)-2-morpholin-4-yl-pyrimidine-4-carboxylic acid (1,2,3-trimethyl-1H-indol-5-yl)-amide, 2-Morpholin-4-yl-6-(2-morpholin-4-yl-ethoxy)-pyrimidine-4-carboxylic acid (3-chloro-phenyl)-amide, 2-Morpholin-4-yl-6-(2-morpholin-4-yl-ethoxy)-pyrimidine-4-carboxylic acid (4-dimethylamino-3-methyl-phenyl)-amide, 2-Morpholin-4-yl-6-(2-morpholin-4-yl-ethoxy)-pyrimidine-4-carboxylic acid (3-methyl-4-methylamino-phenyl)-amide, 2-Morpholin-4-yl-6-(2-morpholin-4-yl-ethoxy)-pyrimidine- 4-carboxylic acid (3-dimethylamino-4-methyl-phenyl)-amide, 2-Morpholin-4-yl-6-(2-morpholin-4-yl-ethoxy)-pyrimidine-4-carboxylic acid (4-methyl-3-methylamino-phenyl)-amide, 2-Morpholin-4-yl-6-(2-morpholin-4-yl-ethoxy)-pyrimidine-4-carboxylic acid pyridin-3-ylamide, 2-Morpholin-4-yl-6-(2-morpholin-4-yl-ethoxy)-pyrimidine-4-carboxylic acid (5-morpholin-4-yl-4H-[1,2,4]triazol-3-yl)-amide, {2-[6-(2,3-Dimethyl-1H-indol-5-ylcarbamoyl)-2-morpholin-4-yl-pyrimidin-4-yloxy]-ethyl}-carbamic acid methyl ester, 2-Morpholin-4-yl-6-(2-morpholin-4-yl-ethoxy)-pyrimidine-4-carboxylic acid (3-morpholin-4-yl-phenyl)-amide, 2-Morpholin-4-yl-6-(2-morpholin-4-yl-ethoxy)-pyrimidine-4-carboxylic acid (1,2,3,4-tetrahydro-quinolin-7-yl)-amide, 2-Morpholin-4-yl-6-(2-morpholin-4-yl-ethoxy)-pyrimidine-4-carboxylic acid (6-methyl-pyridin-3-yl)-amide, 6-[(2-Hydroxy-ethyl)-methyl-amino]-2-morpholin-4-yl-pyrimidine-4-carboxylic acid m-tolylamide, 2-Morpholin-4-yl-6-(2-morpholin-4-yl-ethoxy)-pyrimidine-4-carboxylic acid (2-methyl-1,2,3,4-tetrahydro-quinolin-7-yl)-amide, 2-Morpholin-4-yl-6-(2-morpholin-4-yl-ethoxy)-pyrimidine-4-carboxylic acid (3-diethylamino-phenyl)-amide, 6-(2-Methoxy-ethoxy)-2-morpholin-4-yl-pyrimidine-4-carboxylic acid (2,3-dimethyl-1H-indol-5-yl)-amide, 6-[(2-Methoxy-ethyl)-methyl-amino]-2-morpholin-4-yl-pyrimidine-4-carboxylic acid (3-dimethylamino-phenyl)-amide, 6-[(2-Hydroxy-ethyl)-methyl-amino]-2-morpholin-4-yl-pyrimidine-4-carboxylic acid (3-dimethylamino-phenyl)-amide, 6-[(2-Hydroxy-ethyl)-methyl-amino]-2-morpholin-4-yl-pyrimidine-4-carboxylic acid (3-pyrrol-1-yl-phenyl)-amide, 2-Morpholin-4-yl-6-(2-morpholin-4-yl-ethoxy)-pyrimidine-4-carboxylic acid (3-imidazol-1-yl-phenyl)-amide, 2,6-Di-morpholin-4-yl-pyrimidine-4-carboxylic acid (3-dimethylamino-phenyl)-amide, 6-(2-Hydroxy-ethoxy)-2-morpholin-4-yl-pyrimidine-4-carboxylic acid (2,3-dimethyl-1H-indol-5-yl)-amide, 2-Morpholin-4-yl-6-(2-morpholin-4-yl-ethoxy)-pyrimidine-4-carboxylic acid [3-(isopropyl-methyl-amino)-phenyl]-amide, 6-(2-Hydroxy-ethoxy)-2-morpholin-4-yl-pyrimidine-4-carboxylic acid (3-dimethylamino-phenyl)-amide, 6-[(2-Hydroxy-ethyl)-methyl-amino]-2-morpholin-4-yl-pyrimidine-4-carboxylic acid (3-pyrrolidin-1-yl-phenyl)-amide, 6-[(2-Methoxy-ethyl)-methyl-amino]-2-morpholin-4-yl-pyrimidine-4-carboxylic acid (3-pyrazol-1-yl-phenyl)-amide, 2-Morpholin-4-yl-6-(2-morpholin-4-yl-ethoxy)-pyrimidine-4-carboxylic acid [3-(ethyl-methyl-amino)-phenyl]-amide, 2-Morpholin-4-yl-6-(2-morpholin-4-yl-ethoxy)-pyrimidine-4-carboxylic acid (3-pyrazol-1-yl-phenyl)-amide, 6-(2-Hydroxy-2-methyl-propoxy)-2-morpholin-4-yl-pyrimidine-4-carboxylic acid (2,3-dimethyl-1H-indol-5-yl)-amide, 6-[(2-Hydroxy-ethyl)-methyl-amino]-2-morpholin-4-yl-pyrimidine-4-carboxylic acid (3-pyrazol-1-yl-phenyl)-amide, [6-(2,3-Dimethyl-1H-indol-5-ylcarbamoyl)-2-morpholin-4-yl-pyrimidin-4-yloxy]-acetic acid tert-butyl ester, 2-Morpholin-4-yl-6-(2-morpholin-4-yl-ethoxy)-pyrimidine-4-carboxylic acid (1-methyl-1,2,3,4-tetrahydro-quinolin-7-yl)-amide, 2-Morpholin-4-yl-6-(2-morpholin-4-yl-ethoxy)-pyrimidine-4-carboxylic acid (1-methyl-1,2,3,4-tetrahydro-quinolin-6-yl)-amide, 6-Methyl-2-morpholin-4-yl-pyrimidine-4-carboxylic acid (1-hydroxy-2,3-dimethyl-1H-indol-5-yl)-amide, 2-Morpholin-4-yl-6-(2-morpholin-4-yl-ethoxy)-pyrimidine-4-carboxylic acid (1-hydroxy-2,3-dimethyl-1H-indol-5-yl)-amide, 2-Morpholin-4-yl-6-(2-morpholin-4-yl-ethoxy)-pyrimidine-4-carboxylic acid (1,2-dimethyl-1,2,3,4-tetrahydro-quinolin-7-yl)-amide, 2-Morpholin-4-yl-6-[2-(1-oxy-pyridin-2-yl)-ethoxy]-pyrimidine-4-carboxylic acid (6,7,8,9-tetrahydro-5H-carbazol-3-yl)-amide, 1-(2,3-Dimethyl-1H-indol-5-yl)-3-[2-morpholin-4-yl-6-(2-morpholin-4-yl-ethoxy)-pyrimidin-4-yl]-urea, 1-(3-Amino-phenyl)-3-[2-morpholin-4-yl-6-(2-morpholin-4-yl-ethoxy)-pyrimidin-4-yl]-urea, 1-[2-Morpholin-4-yl-6-(2-morpholin-4-yl-ethoxy)-pyrimidin-4-yl]-3-(6,7,8,9-tetrahydro-5H-carbazol-3-yl)-urea, 1-{6-[(2-Hydroxy-ethyl)-methyl-amino]-2-morpholin-4-yl-pyrimidin-4-yl}-3-(6,7,8,9-tetrahydro-5H-carbazol-3-yl)-urea, 1-[2-Morpholin-4-yl-6-(2-morpholin-4-yl-ethoxy)-pyrimidin-4-yl]-3-(3-pyrazol-1-yl-phenyl)-urea, 1-(3-Imidazol-1-yl-phenyl)-3-[2-morpholin-4-yl-6-(2-morpholin-4-yl-ethoxy)-pyrimidin-4-yl]-urea, 1-(4-Isopropyl-3-methyl-phenyl)-3-[2-morpholin-4-yl-6-(2-morpholin-4-yl-ethoxy)-pyrimidin-4-yl]-urea, 1-(3-Isopropyl-phenyl)-3-[2-morpholin-4-yl-6-(2-morpholin-4-yl-ethoxy)-pyrimidin-4-yl]-urea, or a pharmaceutically acceptable salt, solvate, clathrate, hydrate, or polymorph thereof.

In another aspect, the invention provides a pharmaceutical composition, including a compound of the invention (e.g., a compound of formula (I), including a pharmaceutically acceptable salt, solvate, clathrate, hydrate, polymorph or prodrug thereof), and a pharmaceutically acceptable carrier.

In another aspect, the invention provides a method of inhibiting IL-12 production in a subject. The method includes the step of administering to the subject an effective amount of a compound of the invention (e.g., a compound of formula (I), including a pharmaceutically acceptable salt, solvate, clathrate, hydrate, polymorph or prodrug thereof).

In another aspect, the invention provides a method for treating an interleukin-12 over-production-related disorder. The method includes the step of administering to a subject in need thereof an effective amount of a compound of the invention (e.g., a compound of formula (I), including a pharmaceutically acceptable salt, solvate, clathrate, hydrate, polymorph or prodrug thereof). In preferred embodiments, the disorder is selected from the group consisting of multiple sclerosis, sepsis, myasthenia gravis, autoimmune neuropathies, Guillain-Barré syndrome, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, psoriatic arthritis, dermatitis herpetiformis, pemphigus vulgaris, vitiligo, Crohn's disease, ulcerative colitis, interstitial pulmonary fibrosis, myelofibrosis, hepatic fibrosis, myocarditis, thyroditis, primary biliary cirrhosis, autoimmune hepatitis, immune-mediated diabetes mellitus, Grave's disease, Hashimoto's thyroiditis, autoimmune oophoritis and orchitis, autoimmune disease of the adrenal gland; rheumatoid arthritis, juvenile rheumatoid arthritis, systemic lupus erythematosus, scleroderma, common variable immunodeficiency (CVID), polymyositis, dermatomyositis, spondyloarthropathies, ankylosing spondylitis, Sjogren's syndrome and graft-versus-host disease. In certain embodiments, the disorder is rheumatoid arthritis, sepsis, Crohn's disease, multiple sclerosis, psoriasis, or immune-mediated diabetes mellitus.

In still another aspect, the invention provides a method for treating an interleukin-12 production-related disorder, comprising administering to a subject in need thereof an effective amount of a compound represented by formula (I) (including a pharmaceutically acceptable salt, solvate, clathrate, hydrate, polymorph or prodrug thereof), in which R' is absent and L' is absent.

In still another aspect, the invention provides a method for treating or preventing disorders associated with excessive bone loss, the method comprising administering to a subject in need thereof an effective amount of a compound of the invention (e.g., a compound of formula (I), including a pharmaceutically acceptable salt, solvate, clathrate, hydrate, polymorph or prodrug thereof). In certain embodiments, the disorder is periodontal disease, non-malignant bone disorders, osteoporosis, Paget's disease of bone, osteogenesis imperfecta, fibrous dysplasia, and primary hyperparathyroidism, estrogen deficiency, inflammatory bone loss, bone malignancy, arthritis, osteopetrosis, hypercalcemia of malignancy (HCM), osteolytic bone lesions of multiple myeloma and osteolytic bone metastases of breast cancer, and metastatic cancers.

In still another aspect, the invention provides a method for inhibiting osteoclast formation in vitro or in vivo, the method comprising contacting a pre-osteoclast cell with an effective amount of a compound of the invention (e.g., a compound of formula (I), including apharmaceutically acceptable salt, solvate, clathrate, hydrate, polymorph or prodrug thereof).

In yet another aspect, the invention provides a method of treating or preventing a disorder associated with excessive bone resorption by osteoclasts in a subject in need thereof, the method comprising administering to the subject an effective amount of a compound of the invention (e.g., a compound of formula (I), including a pharmaceutically acceptable salt, solvate, clathrate, hydrate, polymorph or prodrug thereof).

In still another aspect, the invention provides a method of inhibiting proliferation of $T_H 1$ cells in a subject comprising administering to the subject an effective amount of a compound of the invention (e.g., a compound of formula (I), including a pharmaceutically acceptable salt, solvate, clathrate, hydrate, polymorph or prodrug thereof).

In still another aspect, the invention provides a method of inhibiting the production of IL-12 in a subject comprising administering to the subject an effective amount of a compound of the invention (e.g., a compound of formula (I), including a pharmaceutically acceptable salt, solvate, clathrate, hydrate, polymorph or prodrug thereof).

In still another aspect, the invention provides a method of inhibiting IL-23 production in a subject, comprising administering to the subject an effective amount of a compound of formula (I), including a pharmaceutically acceptable salt, solvate, clathrate, hydrate, polymorph or prodrug thereof. In preferred embodiments, the method further includes inhibiting the production of IL-12.

In yet another aspect, the invention provides a method of inhibiting IL-27 production in a subject, comprising administering to the subject an effective amount of a compound of formula (I), including a pharmaceutically acceptable salt, solvate, clathrate, hydrate, polymorph or prodrug thereof. In certain embodiments, the method further includes inhibiting $T_H 1$ lymphocyte proliferation, and preferably further includes inhibiting the production of IL-12.

In still another aspect, the invention provides a method of treating an inflammatory disorder in a subject in need of such treatment, the method comprising administering to the subject an effective amount of a compound of the invention (e.g., a compound of formula (I), including a pharmaceutically acceptable salt, solvate, clathrate, hydrate, polymorph or prodrug thereof).

In still another aspect, the invention provides a method of treating an immune disease in a subject in need of such treatment, the method comprising administering to the subject an effective amount of a compound of the invention (e.g., a compound of formula (I), including a pharmaceutically acceptable salt, solvate, clathrate, hydrate, polymorph or prodrug thereof).

In still another aspect, the invention provides a method of treating a neurological disorder in a subject in need of such treatment, the method comprising administering to the subject an effective amount of a compound of the invention (e.g., a compound of formula (I), including a pharmaceutically acceptable salt, solvate, clathrate, hydrate, polymorph or prodrug thereof).

Other embodiments include the compounds, intermediates, or a pharmaceutically acceptable salt, solvate, clatharate, hydrate, polymorph or prodrug thereof delineated herein, or compositions including them; as well as their methods of use for treatment or prevention of disease, inhibition of IL-12, or modulation of IL-12 mediated disease; and methods of making the compounds and intermediates herein.

Another embodiment is a method of making a compound of any of the formulae herein using any one, or combination of, reactions delineated herein. The method can include the use of one or more intermediates or chemical reagents delineated herein.

Another aspect is an isotopically labelled compound of any of the formulae delineated herein. Such compounds have one or more isotopic atoms (which may or may not be radioactive) (e.g., $^3H$, $^2H$, $^{14}C$, $^{13}C$, $^{32}P$, $^{35}S$, $^{125}I$, $^{131}I$) introduced into the compound. Such compounds are useful for drug metabolism studies and diagnostics, as well as for therapeutic treatment.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical. The term "ester" refers to a —C(O)O—$R^k$; or, where a divalent group is indicated, an "ester" group is —C(O)O— or —OC(O)—. An "amido" is an —C(O)NH$_2$, and an "N-alkyl-substituted amido" is of the formula C(O)NHR$^k$; where a divalent "amide" group is indicated, the group is —C(O)N$^k$— or —N$^k$C(O)—.

The term "mercapto" refers to a —SH group.

As used herein, the term "halogen" or "halo" means —F, —Cl, —Br or —I.

As used herein, the term "haloalkyl" means and alkyl group in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

The term "cycloalkyl" refers to a hydrocarbon 3-8 membered monocyclic or 7-14 membered bicyclic ring system having at least one non-aromatic, completely saturated ring. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclooctyl, cyclononyl, and cyclodecyl.

The term "cyclyl" refers to a hydrocarbon 3-8 membered monocyclic or 7-14 membered bicyclic ring system having at least one non-aromatic ring, wherein the non-aromatic ring has some degree of unsaturation. Cyclyl groups may be optionally substituted with one or more substituents. In one embodiment, 0, 1, 2, 3, or 4 atoms of each ring of a cyclyl group may be substituted by a substituent. Examples of cyclyl groups include cyclohexenyl, bicyclo[2.2.1]hept-2-enyl, dihydronaphthalenyl, benzocyclopentyl, cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

As used herein, the term "aralkyl" means an aryl group that is attached to another group by a $(C_1-C_6)$alkylene group. Aralkyl groups may be optionally substituted, either on the aryl portion of the aralkyl group or on the alkylene portion of the aralkyl group, with one or more substituent. Representative aralkyl groups include benzyl, 2-phenyl-ethyl, naphth-3-yl-methyl and the like.

As used herein, the term "alkylene" refers to an alkyl group that has two points of attachment. The term "$(C_1-C_6)$alkylene" refers to an alkylene group that has from one to six carbon atoms. Non-limiting examples of alkylene groups include methylene (—$CH_2$—), ethylene (—$CH_2CH_2$—), n-propylene (—$CH_2CH_2CH_2$—), isopropylene (—$CH_2CH(CH_3)$—), and the like.

The term "arylalkoxy" refers to an alkoxy substituted with aryl.

The term "heteroaryl" refers to a 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated), wherein at least one ring in the ring system is aromatic. Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, benzo[1,3]dioxolyl, benzo[1,4]dioxinyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, and benzo(b)thienyl, 3H-thiazolo[2,3-c][1,2,4]thiadiazolyl, imidazo[1,2-d]-1,2,4-thiadiazolyl, imidazo[2,1-b]-1,3,4-thiadiazolyl, 1H,2H-furo[3,4-d]-1,2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 1H,3H-pyrrolo[1,2-c]oxazolyl, pyrrolo[2,1b]oxazolyl, and the like.

As used herein, the term "heteroaralkyl" or "heteroarylalkyl" means a heteroaryl group that is attached to another group by a $(C_1-C_6)$alkylene. Heteroaralkyl groups may be optionally substituted, either on the heteroaryl portion of the heteroaralkyl group or on the alkylene portion of the heteroaralkyl group, with one or more substituent. Representative heteroaralkyl groups include 2-(pyridin-4-yl)-propyl, 2-(thien-3-yl)-ethyl, imidazol-4-yl-methyl and the like.

The term "heterocycloalkyl" refers to a nonaromatic, completely saturated 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P and Si, preferably O, N, or S. Bicyclic and tricyclic ring systems may be fused ring systems or spiro ring systems. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, 2-oxopiperazinyl, 2-oxopiperidinyl, 2-oxopyrrolidinyl, 4-piperidonyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, 1,4-dioxa-8-aza-spiro[4.5]dec-8-yl, tetrahydrofuranyl, tetrahydrothienyl, and thiirene.

The term "heterocyclyl" refers to a nonaromatic 5-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system has some degree of unsaturation. Heterocyclyl groups may be optionally substituted with one or more substituents. In one embodiment, 0, 1, 2, 3, or 4 atoms of each ring of a heterocyclyl group may be substituted by a substituent. Examples of these groups include thiirenyl, thiadiazirinyl, dioxazolyl, 1,3-oxathiolyl, 1,3-dioxolyl, 1,3-dithiolyl, oxathiazinyl, dioxazinyl, dithiazinyl, oxadiazinyl, thiadiazinyl, oxazinyl, thiazinyl, 1,4-oxathiin, 1,4-dioxin, 1,4-dithiin, 1H-pyranyl, oxathiepinyl, 5H-1,4-dioxepinyl, 5H-1,4-dithiepinyl, 6H-isoxazolo[2,3-d]1,2,4-oxadiazolyl, 7aH-oxazolo[3,2-d]1,2,4-oxadiazolyl, and the like.

The term "alkylamino" refers to an amino substituent which is further substituted with one or two alkyl groups. The term "aminoalkyl" refers to an alkyl substituent which is further substituted with one or more amino groups. The term "mercaptoalkyl" refers to an alkyl substituent which is further substituted with one or more mercapto groups. The term "hydroxyalkyl" or "hydroxylalkyl" refers to an alkyl substituent which is further substituted with one or more hydroxyl groups. The term "sulfonylalkyl" refers to an alkyl substituent which is further substituted with one or more sulfonyl groups. The term "sulfonylaryl" refers to an aryl substituent which is further substituted with one or more sulfonyl groups. The term alkylcarbonyl refers to an —C(O)-alkyl. The term "mercaptoalkoxy" refers to an alkoxy substituent which is further substituted with one or more mercapto groups. The term "alkylcarbonylalkyl" refers to an alkyl substituent which is further substituted with —C(O)-alkyl. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

As used herein the term "substituent" or "substituted" means that a hydrogen radical on a compound or group (such as, for example, alkyl, alkenyl, alkynyl, alkylene, aryl, aralkyl, heteroaryl, heteroaralkyl, cycloalkyl, cyclyl, heterocycloalkyl, or heterocyclyl group) is replaced with any desired group that do not substantially adversely affect the stability of the compound. In one embodiment, desired substituents are those which do not adversely affect the activity of a compound. A substituent that substantially affects the activity of a compound is one that causes the $IC_{50}$ of the compound to be greater than 100 μM. In preferred embodiments, a compound of the invention has an $IC_{50}$ in an assay or test indicative of activity useful for treatment of IL-12- or IL-23- or IL-27-related diseases or conditions. Such assays are known to one of ordinary skill in the art, and include, e.g., the assays described herein, e.g., the assays of Examples 16-18. In preferred embodiments, the assay is an assay of Example 16 and the compound has an $IC_{50}$ less than 1.0 mM, more preferably less than 100 μM, more preferably less than 10 μM, more preferably less than 1 μM, more preferably less than 100 nM, and more preferably less than 10 nM. The term "substituted" refers to one or more substituents (which may be the same or different), each replacing a hydrogen atom. Examples of substituents include, but are not limited to, halogen (F, Cl, Br, or I), hydroxyl, amino, alkylamino, arylamino, dialkylamino, diarylamino, alkylarylamino, cyano, nitro, mercapto, thio, imino, formyl, carbamido, carbamyl, carboxyl, thioureido, thiocyanato, sulfoamido, sulfonylalkyl, sulfonylaryl, alkyl, alkenyl, alkoxy, alkoxyalkyl, mercaptoalkoxy, aryl, heteroaryl, cyclyl, heterocyclyl, wherein alkyl, alkenyl, alkyloxy, aryl, heteroaryl, cyclyl, and heterocyclyl are optionally substituted with alkyl, aryl, heteroaryl, halogen, hydroxyl, amino, mercapto, cyano, nitro, oxo (=O), thioxo (=S), imino (=$NR^c$) or C(=N—$NR^k$)$R^k$, or C(=N—$OR^k$)$R^k$.

In other embodiments, substituents on any group (such as, for example, alkyl, alkenyl, alkynyl, aryl, aralkyl, heteroaryl, heteroaralkyl, cycloalkyl, cyclyl, heterocycloalkyl, and heterocyclyl) can be at any atom of that group, wherein any group that can be substituted (such as, for example, alkyl, alkenyl, alkynyl, aryl, aralkyl, heteroaryl, heteroaralkyl, cycloalkyl, cyclyl, heterocycloalkyl, and heterocyclyl) can be optionally substituted with one or more substituents (which may be the same or different), each replacing a hydrogen atom. Examples of suitable substituents include, but not limited to alkyl, alkenyl, alkynyl, cyclyl, cycloalkyl, heterocyclyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, or alkoxycarbonylamino; alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Additional suitable substituents for an alkyl, alkenyl, alkynyl, aryl, aralkyl, heteroaryl, heteroaralkyl, cycloalkyl, cyclyl, heterocycloalkyl, or heterocyclyl group include, without limitation halogen, CN, $NO_2$, $OR^{15}$, $SR^{15}$, $S(O)_2OR^{15}$, $NR15R^{16}$, $C_1$-$C_2$ perfluoroalkyl, $C_1$-$C_2$ perfluoroalkoxy, 1,2-methylenedioxy, (=O), (=S), (=$NR^{15}$), C(O)$OR^{15}$, C(O)$NR^{15}R^{16}$, OC(O)$NR^{15}R^{16}$, $NR^{15}$C(O)$NR^{15}R^{16}$, C($NR^{16}$)$NR^{15}R^{16}$, $NR^{15}$C($NR^{16}$)$NR^{15}R^{16}$, $S(O)_2NR^{15}R^{16}$, $R^{17}$, C(O)H, C(O)$R^{17}$, $NR^{15}$C(O)$R^{17}$, Si($R^{15}$)$_3$, OSi($R^{15}$)$_3$, Si(OH)$_2$$R^{15}$, B(OH)$_2$, P(O)(O$R^{15}$)$_2$, S(O)$R^{17}$, or $S(O)_2R^{17}$. Each $R^{15}$ is independently hydrogen, $C_1$-$C_6$ alkyl optionally substituted with cycloalkyl, aryl, heterocyclyl, or heteroaryl. Each $R^{16}$ is independently hydrogen, $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $R^{17}$ is independently $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $C_3$-$C_6$ cycloalkyl, aryl, heterocyclyl, heteroaryl and $C_1$-$C_4$ alkyl in each $R^{15}$, $R^{16}$ and $R^{17}$ can optionally be substituted with halogen, CN, $C_1$-$C_4$ alkyl, OH, $C_1$-$C_4$ alkoxy, COOH, C(O)O$C_1$-$C_4$ alkyl, $NH_2$, $C_1$-$C_4$ alkylamino, or $C_1$-$C_4$ dialkylamino.

As used herein, the term "lower" refers to a group having up to six atoms. For example, a "lower alkyl" refers to an alkyl radical having from 1 to 6 carbon atoms, and a "lower alkenyl" or "lower alkynyl" refers to an alkenyl or alkynyl radical having from 2 to 6 carbon atoms, respectively.

Note that unless otherwise depicted, in the groups described above that have one point of attachment, the left atom shown in any substituted group is the point of attachment.

In the compounds represented by formula (I), when n is 2 or greater, a compound of the invention may have two or more different C($R^2R^4$) moieties. When there are more than one group having a designation (e.g., $R^c$-containing substituted groups) in a compound of the invention, the moieties (e.g., $R^c$) can be the same or different. The same rules apply to other R-groups (e.g., R, $R^c$, $R^d$, $R^e$, $R^g$, $R^h$, $R^j$, $R^k$, etc).

The recitation of a listing of chemical groups in any definition of a variable herein includes definitions of that variable as any single group or combination of listed groups.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., formulation into therapeutic products, intermediates for use in production of therapeutic compounds, isolatable or storable intermediate compounds, treating IL-12 overproduction-related disorders such as rheumatoid arthritis, sepsis, Crohn's disease, multiple sclerosis, psoriasis, or insulin-dependent diabetes mellitus). The compounds produced by the methods herein can be incorporated into compositions, including solutions, capsules, cremes, or ointments for administration to a subject (e.g., human, animal). Such compositions (e.g., pharmaceuticals) are useful for providing to the subject desirable health or other physiological benefits that are associated with such compounds.

Nucleophilic agents are known in the art and are described in the chemical texts and treatises referred to herein. The chemicals used in the aforementioned methods may include, for example, solvents, reagents, catalysts, protecting group and deprotecting group reagents and the like. The methods described above may also additionally include steps, either before or after the steps described specifically herein, to add or remove suitable protecting groups in order to ultimately allow synthesis of the compound of the formulae described herein. The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, crystallization, chromatography). Other embodiments relate to the intermediate compounds delineated herein, and their use in the methods (e.g., treatment, synthesis) delineated herein.

The compounds of this invention include the compounds themselves, as well as their salts, solvate, clathrate, hydrate, polymorph, or prodrugs, if applicable. As used herein, the term "pharmaceutically acceptable salt," is a salt formed from, for example, an acid and a basic group of a compound of any one of the formulae disclosed herein. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N, N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of any one of the formulae disclosed herein having a basic functional group, such as an amino functional group, and a pharmaceutically acceptable inorganic or organic acid. Suitable acids include hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

As used herein, the term "polymorph" means solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "hydrate" means a compound of the present invention or a salt thereof, which further includes a stoichiometric or non-stoichiometric amount of water bound by non-covalent intermolecular forces.

As used herein, the term "clathrate" means a compound of the present invention or a salt thereof in the form of a crystal lattice that contains spaces (e.g., channels) that have a guest molecule (e.g., a solvent or water) trapped within.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by 1 BURGER'S MEDICINAL CHEMISTRY AND DRUG DISCOVERY (1995) 172-178, 949-982 (Manfred E. Wolff ed., 5$^{th}$ ed).

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

In addition, some of the heterocyclic compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Further, the aforementioned heterocyclic compounds also include their N-oxides. The term "N-oxides" refers to one or more nitrogen atoms, when present in a compound of the invention, are in N-oxide form, i.e., N→O. For example, in compounds of formula (I), when one of Q, U, or V is N, also included are compounds in which Q, U, or V, respectively, is N→O.

As used herein, the term "pharmaceutically acceptable solvate," is a solvate formed from the association of one or more solvent molecules to one of the compounds of formula (I). The term solvate includes hydrates (e.g., mono-hydrate, dihydrate, trihydrate, tetrahydrate, and the like).

As used herein, the term "pre-osteoclast cell" is a cell capable of forming an osteoclast cell upon differentiation and/or fusion and includes without limitation, circulating monocytes and tissue macrophages (N. Kurihara et al., Endocrinology 126: 2733-41 (1990)). Without wishing to be bound by theory, pre-osteoclasts are converted to activated osteoclasts in a process thought to involve two factors produced by pre-osteoblasts, M-CSF and ODF. These factors activate certain genes that are needed for the conversion of a pre-osteoclast into an osteoclast.

Set forth below are exemplary compounds of this invention:

Compound 1

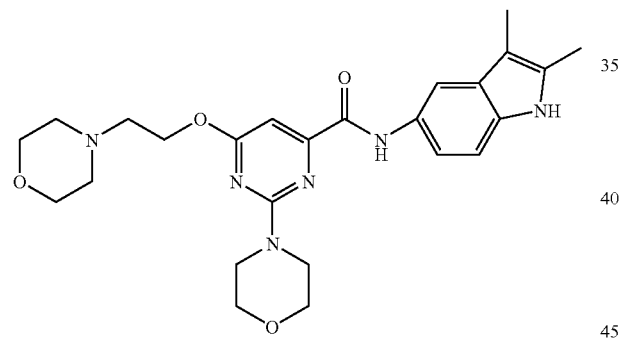

2-Morpholin-4-yl-6-(2-morpholin-4-yl-ethoxy)-pyrimidine-4-carboxylic acid (2,3-dimethyl-1H-indol-5-yl)-amide Compound 2

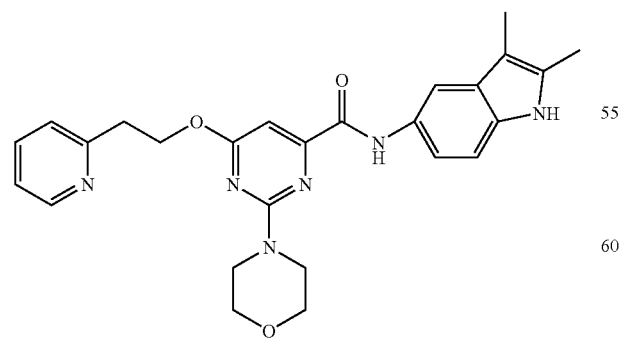

2-Morpholin-4-yl-6-(2-pyridin-2-yl-ethoxy)-pyrimidine-4-carboxylic acid (2,3-dimethyl-1H-indol-5-yl)-amide Compound 3

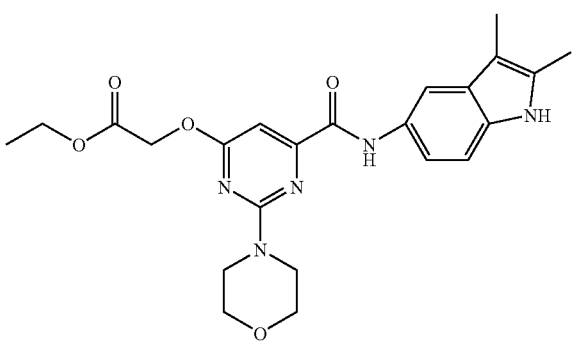

[6-(2,3-Dimethyl-1H-indol-5-ylcarbamoyl)-2-morpholin-4-yl-pyrimidin-4-yloxy]-acetic acid ethyl ester Compound 4

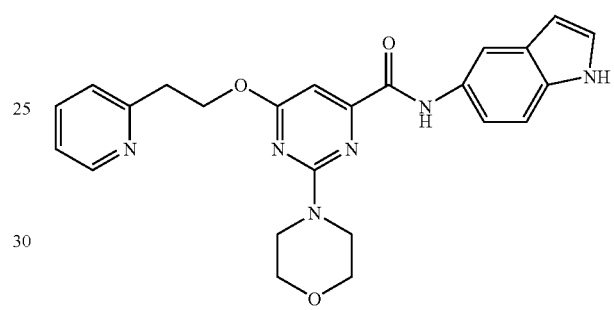

2-Morpholin-4-yl-6-(2-pyridin-2-yl-ethoxy)-pyrimidine-4-carboxylic acid (1H-indol-5-yl)-amide Compound 5

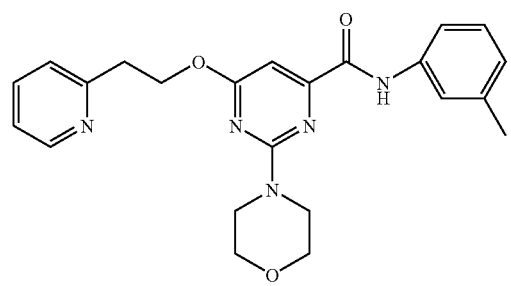

2-Morpholin-4-yl-6-(2-pyridin-2-yl-ethoxy)-pyrimidine-4-carboxylic acid m-tolylamide Compound 6

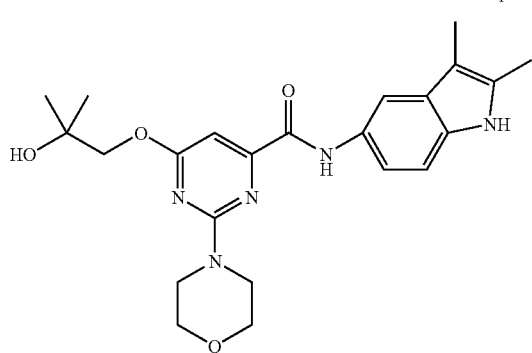

6-(2-Hydroxy-2-methyl-propoxy)-2-morpholin-4-yl-pyrimidine-4-carboxylic acid (2,3-dimethyl-1H-indol-5-yl)-amide

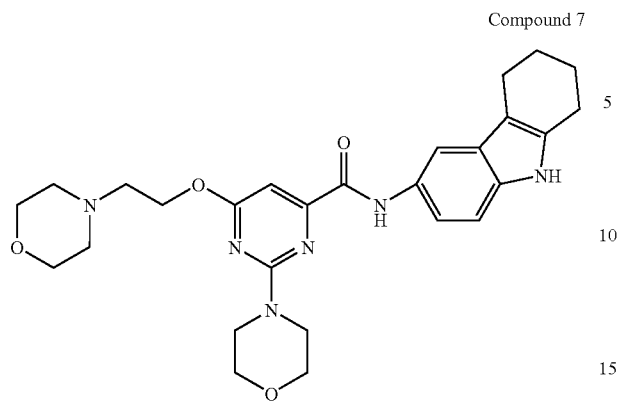

Compound 7

2-Morpholin-4-yl-6-(2-morpholin-4-yl-ethoxy)-pyrimidine-4-carboxylic acid (6,7,8,9-tetrahydro-5H-carbazol-3-yl)-amide

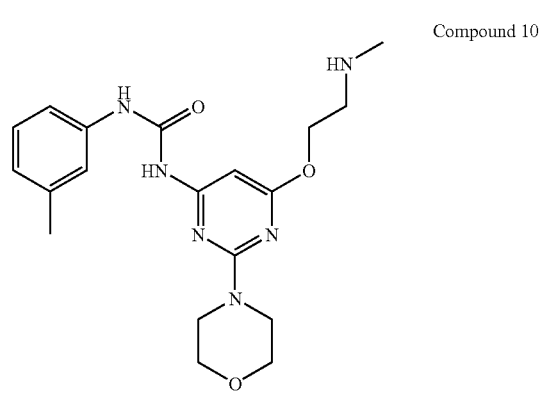

Compound 10

1-[6-(2-Methylamino-ethoxy)-2-morpholin-4-yl-pyrimidin-4-yl]-3-m-tolyl-urea

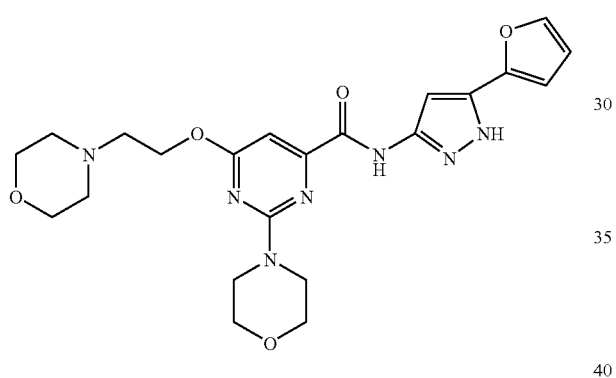

Compound 8

2-Morpholin-4-yl-6-(2-morpholin-4-yl-ethoxy)-pyrimidine-4-carboxylic acid (5-furan-2-yl-1H-pyrazol-3-yl)-amide

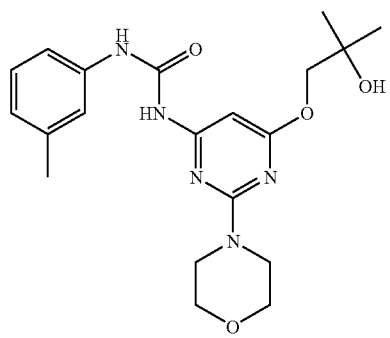

Compound 11

1-[6-(2-Hydroxy-2-methyl-propoxy)-2-morpholin-4-yl-pyrimidin-4-yl]-3-m-tolyl-urea

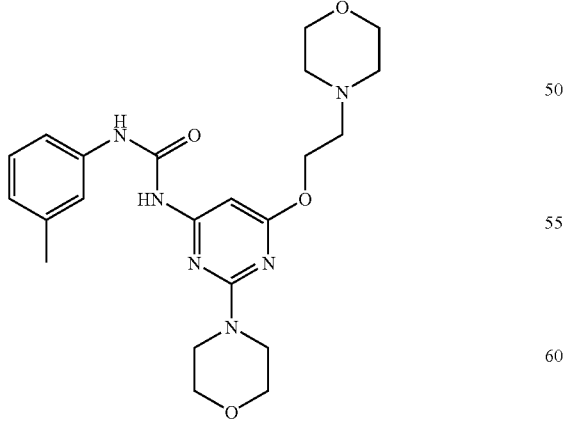

Compound 9

1-[2-Morpholin-4-yl-6-(2-morpholin-4-yl-ethoxy)-pyrimidin-4-yl]-3-m-tolyl-urea

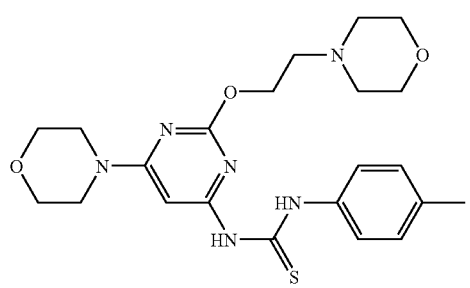

Compound 12

1-[6-Morpholin-4-yl-2-(2-morpholin-4-yl-ethoxy)-pyrimidin-4-yl]-3-p-tolyl-thiourea Compound 13

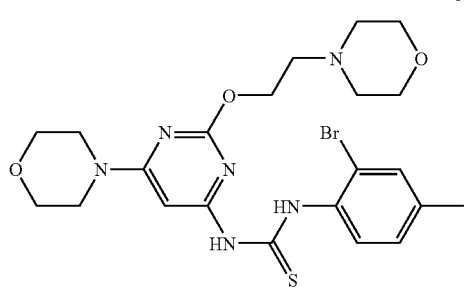

1-(2-Bromo-4-methyl-phenyl)-3-[6-morpholin-4-yl-
2-(2-morpholin-4-yl-ethoxy)-pyrimidin-4-yl]-thio-
urea Compound 14

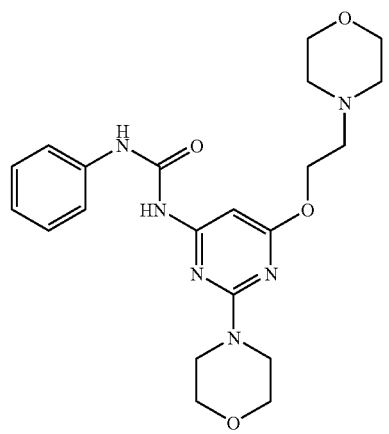

1-[2-Morpholin-4-yl-6-(2-morpholin-4-yl-ethoxy)-
pyrimidin-4-yl]-3-phenyl-urea

Compound 15

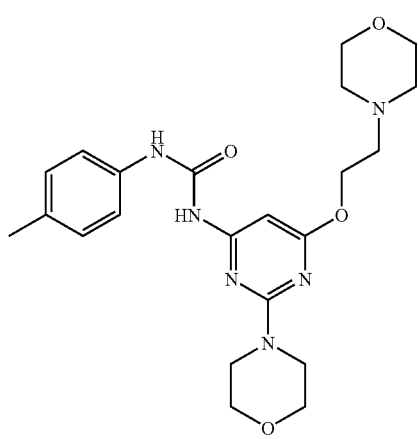

1-[2-Morpholin-4-yl-6-(2-morpholin-4-yl-ethoxy)-
pyrimidin-4-yl]-3-p-tolyl-urea

Compound 16

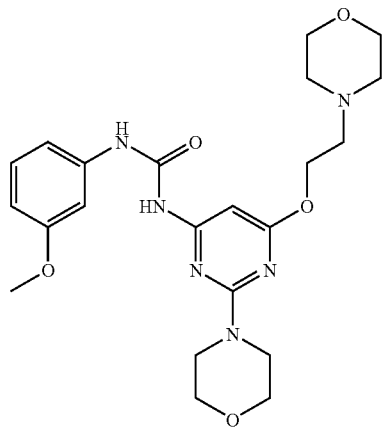

1-(3-Methoxy-phenyl)-3-[2-morpholin-4-yl-6-(2-
morpholin-4-yl-ethoxy)-pyrimidin-4-yl]-urea Compound 17

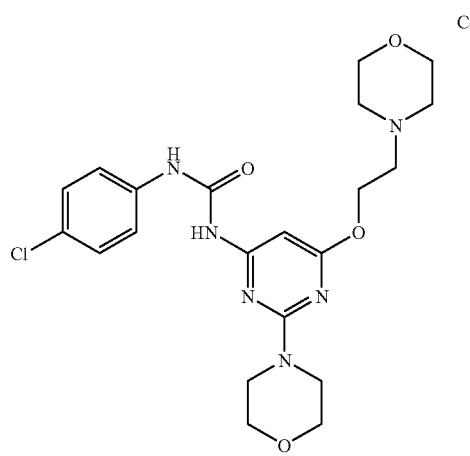

1-(4-Chloro-phenyl)-3-[2-morpholin-4-yl-6-(2-mor-
pholin-4-yl-ethoxy)-pyrimidin-4-yl]-urea Compound 18

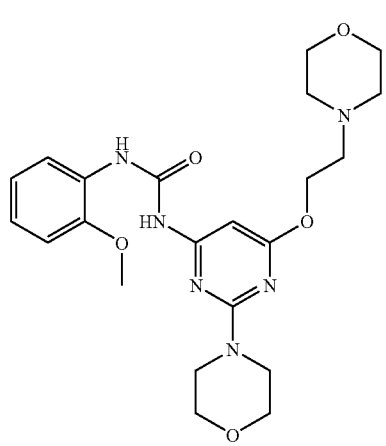

1-(2-Methoxy-phenyl)-3-[2-morpholin-4-yl-6-(2-
morpholin-4-yl-ethoxy)-pyrimidin-4-yl]-urea Compound 19

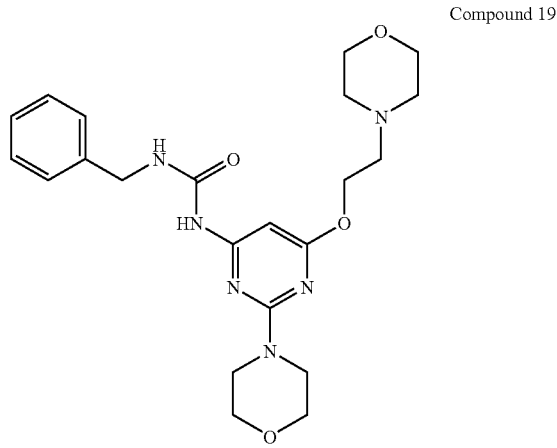

1-Benzyl-3-[2-morpholin-4-yl-6-(2-morpholin-4-yl-ethoxy)-pyrimidin-4-yl]-urea

Compound 22

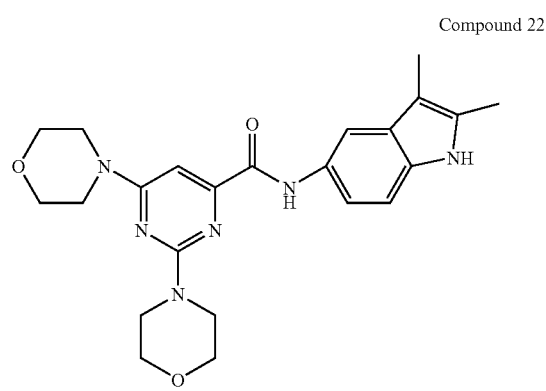

2,6-Di-morpholin-4-yl-pyrimidine-4-carboxylic acid (2,3-dimethyl-1H-indol-5-yl)-amide Compound 20

[6-(2,3-Dimethyl-1H-indol-5-ylcarbamoyl)-2-morpholin-4-yl-pyrimidin-4-yloxy]-acetic acid ethyl ester Compound 23

2-Morpholin-4-yl-6-(2-morpholin-4-yl-ethoxy)-pyrimidine-4-carboxylic acid (3,4-dimethyl-phenyl)-amide Compound 21

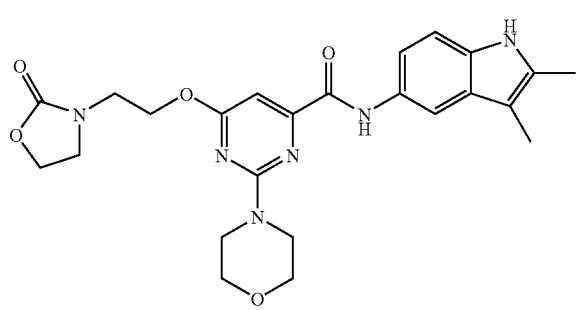

2-Morpholin-4-yl-6-[2-(2-oxo-oxazolidin-3-yl)-ethoxy]-pyrimidine-4-carboxylic acid (2,3-dimethyl-1H-indol-5-yl)-amide Compound 24

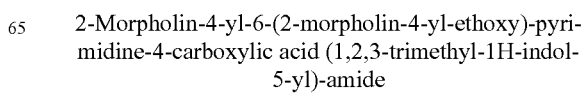

2-Morpholin-4-yl-6-(2-morpholin-4-yl-ethoxy)-pyrimidine-4-carboxylic acid (1,2,3-trimethyl-1H-indol-5-yl)-amide Compound 25

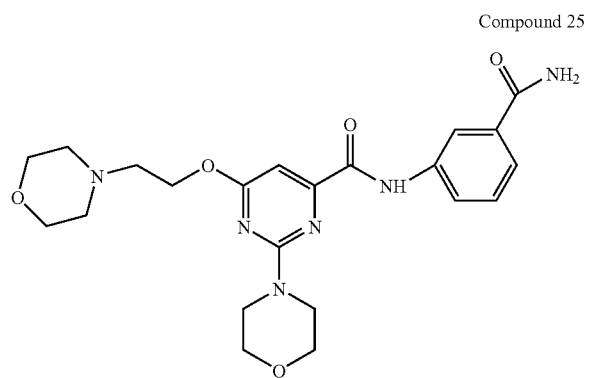

2-Morpholin-4-yl-6-(2-morpholin-4-yl-ethoxy)-pyrimidine-4-carboxylic acid (3-carbamoyl-phenyl)-amide Compound 28

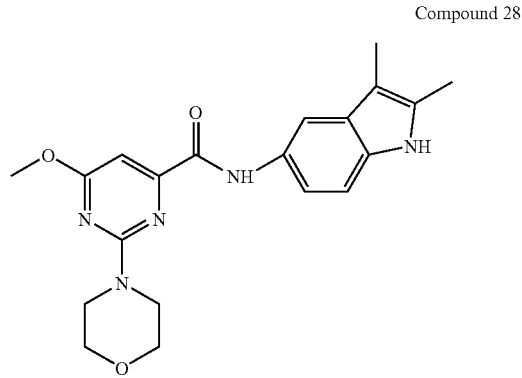

6-Methoxy-2-morpholin-4-yl-pyrimidine-4-carboxylic acid (2,3-dimethyl-1H-indol-5-yl)-amide Compound 26

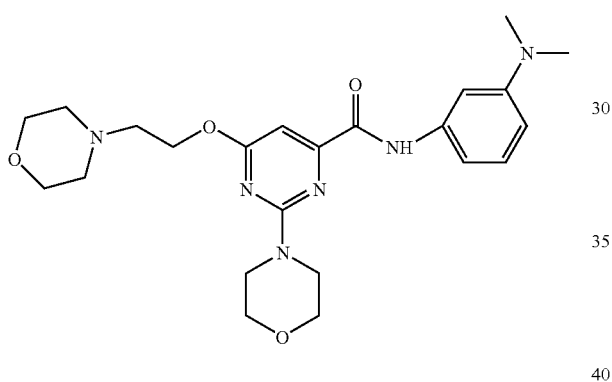

2-Morpholin-4-yl-6-(2-morpholin-4-yl-ethoxy)-pyrimidine-4-carboxylic acid (3-dimethylamino-phenyl)-amide Compound 29

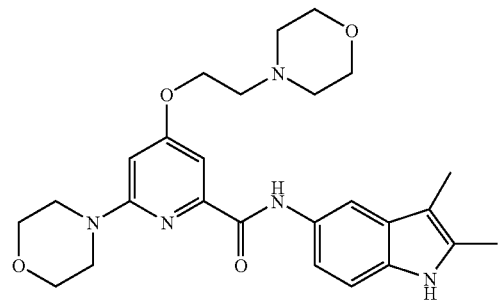

6-Morpholin-4-yl-4-(2-morpholin-4-yl-ethoxy)-pyridine-2-carboxylic acid (2,3-dimethyl-1H-indol-5-yl)-amide Compound 27

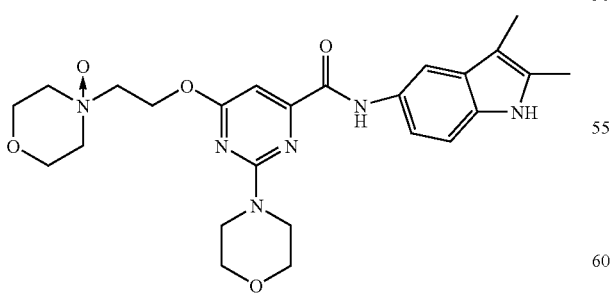

2-Morpholin-4-yl-6-[2-(4-oxy-morpholin-4-yl)-ethoxy]-pyrimidine-4-carboxylic acid (2,3-dimethyl-1H-indol-5-yl)-amide Compound 30

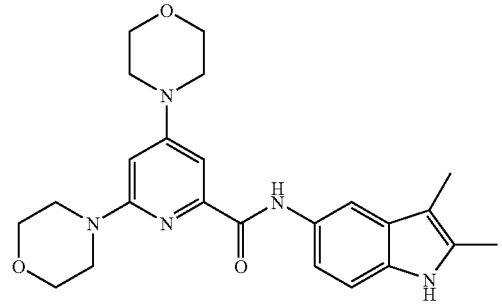

4,6-Di-morpholin-4-yl-pyridine-2-carboxylic acid (2,3-dimethyl-1H-indol-5-yl)-amide Compound 31

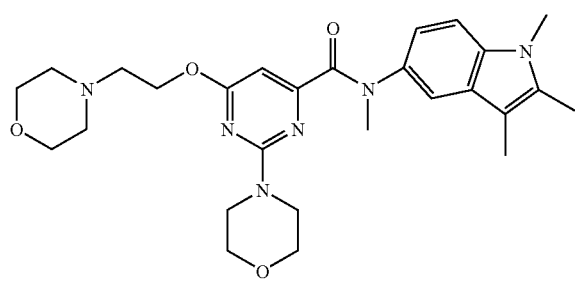

2-Morpholin-4-yl-6-(2-morpholin-4-yl-ethoxy)-pyrimidine-4-carboxylic acid methyl-(1,2,3-trimethyl-1H-indol-5-yl)-amide Compound 34

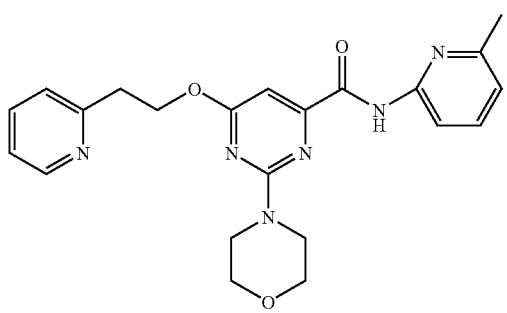

2-Morpholin-4-yl-6-(2-pyridin-2-yl-ethoxy)-pyrimidine-4-carboxylic acid (6-methyl-pyridin-2-yl)-amide Compound 32

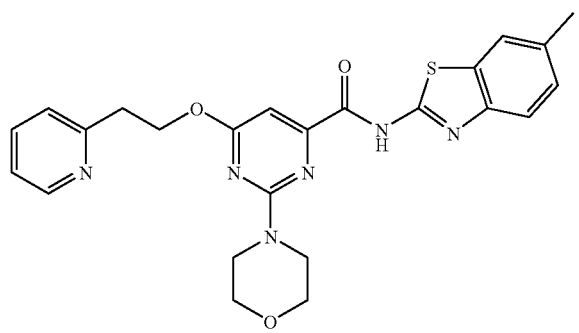

2-Morpholin-4-yl-6-(2-pyridin-2-yl-ethoxy)-pyrimidine-4-carboxylic acid (6-methyl-benzothiazol-2-yl)-amide Compound 35

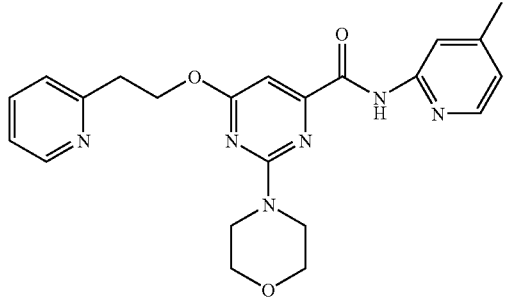

2-Morpholin-4-yl-6-(2-pyridin-2-yl-ethoxy)-pyrimidine-4-carboxylic acid (4-methyl-pyridin-2-yl)-amide Compound 33

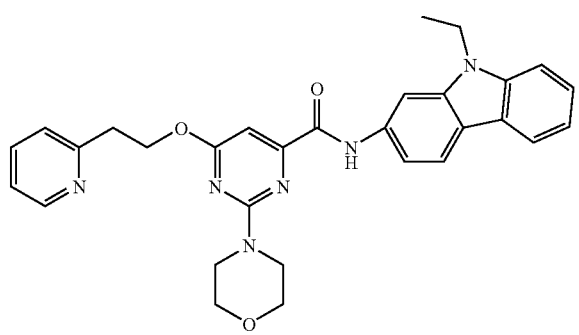

2-Morpholin-4-yl-6-(2-pyridin-2-yl-ethoxy)-pyrimidine-4-carboxylic acid (9-ethyl-9H-carbazol-2-yl)-amide Compound 36

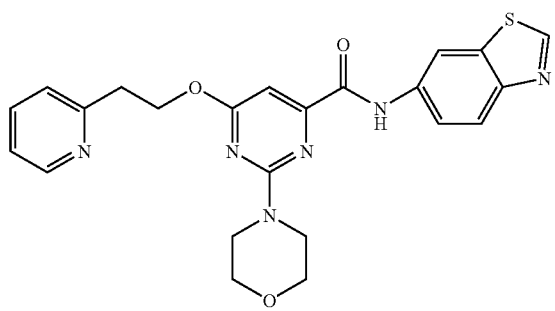

2-Morpholin-4-yl-6-(2-pyridin-2-yl-ethoxy)-pyrimidine-4-carboxylic acid benzothiazol-6-ylamide Compound 37

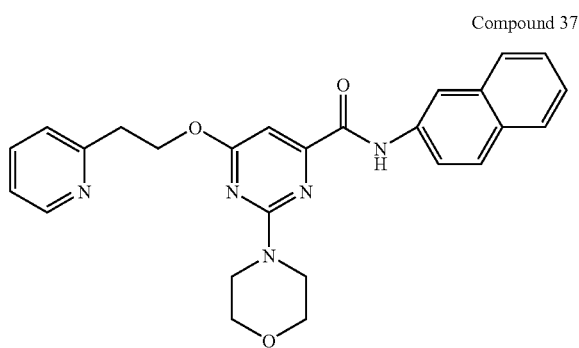

2-Morpholin-4-yl-6-(2-pyridin-2-yl-ethoxy)-pyrimidine-4-carboxylic acid naphthalen-2-ylamide Compound 38

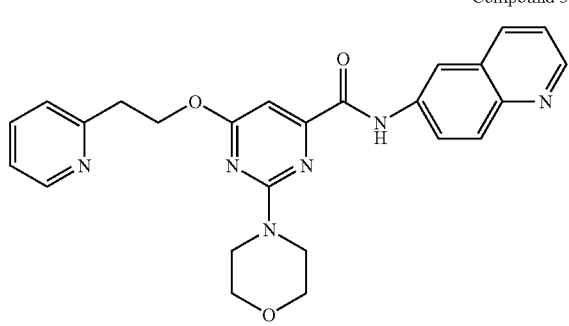

2-Morpholin-4-yl-6-(2-pyridin-2-yl-ethoxy)-pyrimidine-4-carboxylic acid quinolin-6-ylamide Compound 39

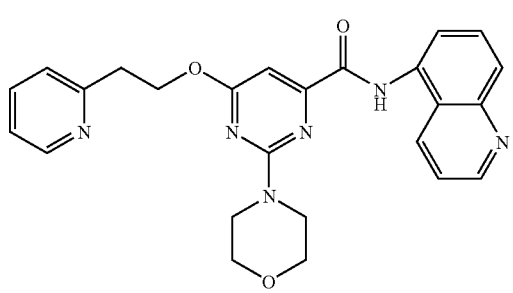

2-Morpholin-4-yl-6-(2-pyridin-2-yl-ethoxy)-pyrimidine-4-carboxylic acid quinolin-5-ylamide Compound 40

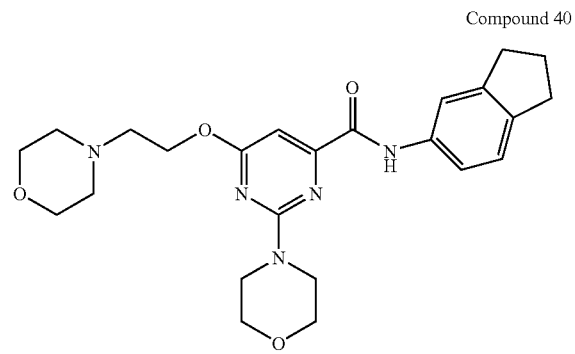

2-Morpholin-4-yl-6-(2-morpholin-4-yl-ethoxy)-pyrimidine-4-carboxylic acid indan-5-ylamide Compound 41

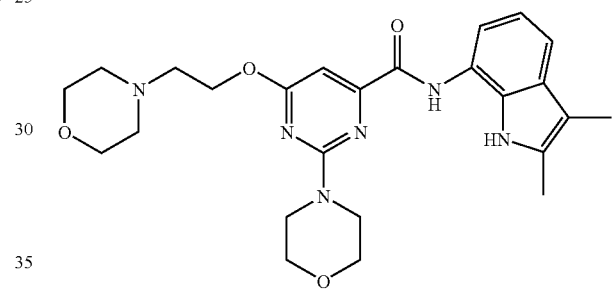

2-Morpholin-4-yl-6-(2-morpholin-4-yl-ethoxy)-pyrimidine-4-carboxylic acid (2,3-dimethyl-1H-indol-7-yl)-amide Compound 42

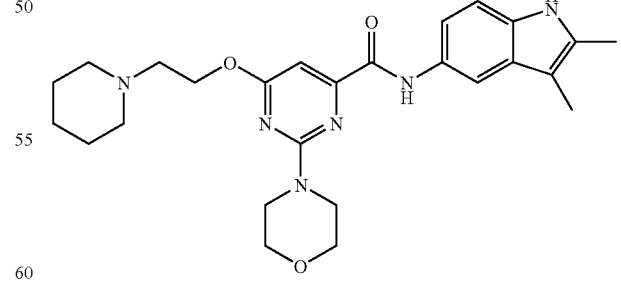

2-Morpholin-4-yl-6-(2-piperidin-1-yl-ethoxy)-pyrimidine-4-carboxylic acid (2,3-dimethyl-1H-indol-5-yl)-amide Compound 43

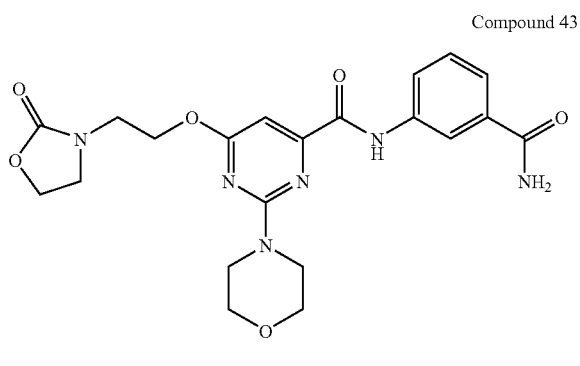

2-Morpholin-4-yl-6-[2-(2-oxo-oxazolidin-3-yl)-ethoxy]-pyrimidine-4-carboxylic acid (3-carbamoyl-phenyl)-amide Compound 46

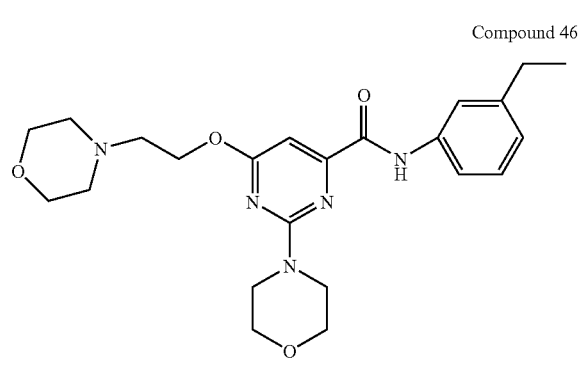

2-Morpholin-4-yl-6-(2-morpholin-4-yl-ethoxy)-pyrimidine-4-carboxylic acid (3-ethyl-phenyl)-amide Compound 44

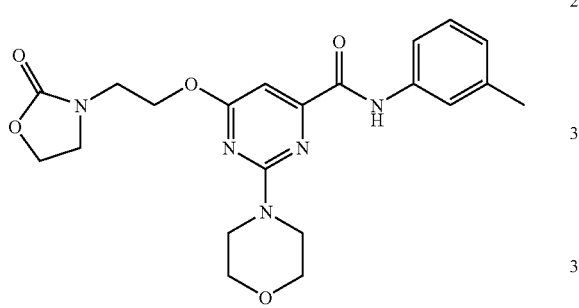

2-Morpholin-4-yl-6-[2-(2-oxo-oxazolidin-3-yl)-ethoxy]-pyrimidine-4-carboxylic acid m-tolylamide Compound 47

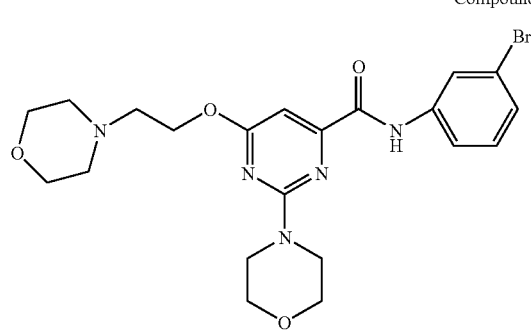

2-Morpholin-4-yl-6-(2-morpholin-4-yl-ethoxy)-pyrimidine-4-carboxylic acid (3-bromo-phenyl)-amide Compound 45

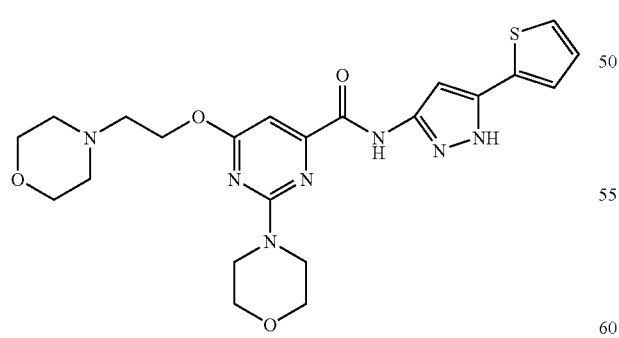

2-Morpholin-4-yl-6-(2-morpholin-4-yl-ethoxy)-pyrimidine-4-carboxylic acid (5-thiophen-2-yl-1H-pyrazol-3-yl)-amide Compound 48

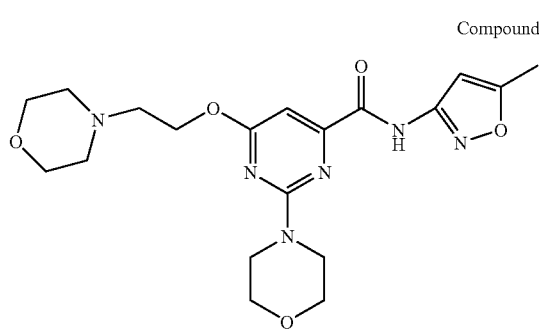

2-Morpholin-4-yl-6-(2-morpholin-4-yl-ethoxy)-pyrimidine-4-carboxylic acid (5-methyl-isoxazol-3-yl)-amide Compound 49

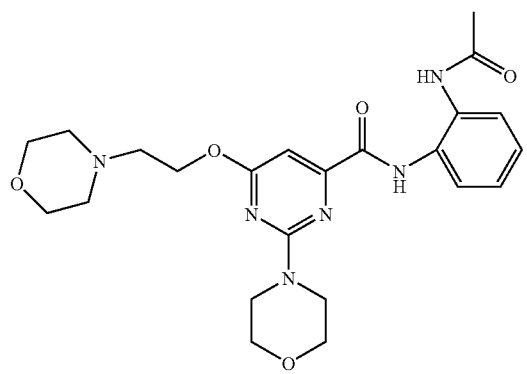

2-Morpholin-4-yl-6-(2-morpholin-4-yl-ethoxy)-pyrimidine-4-carboxylic acid (2-acetylamino-phenyl)-amide Compound 52

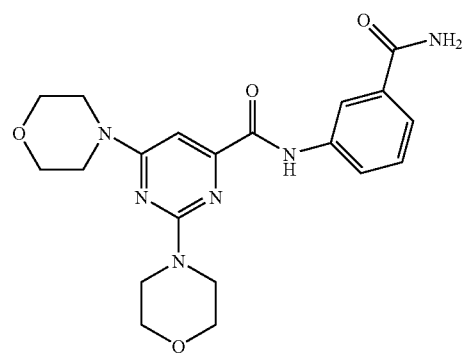

2,6-Di-morpholin-4-yl-pyrimidine-4-carboxylic acid (3-carbamoyl-phenyl)-amide

Compound 50

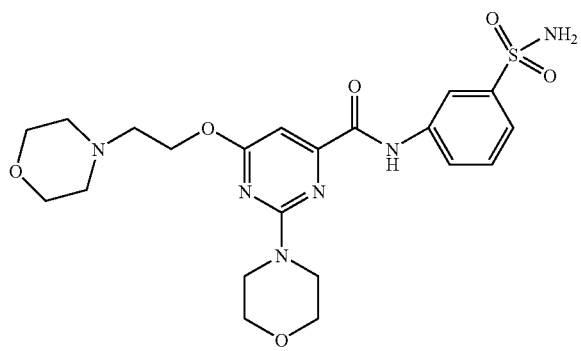

2-Morpholin-4-yl-6-(2-morpholin-4-yl-ethoxy)-pyrimidine-4-carboxylic acid (3-sulfamoyl-phenyl)-amide Compound 53

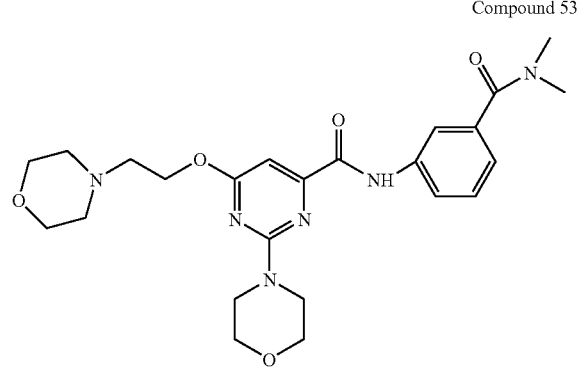

2-Morpholin-4-yl-6-(2-morpholin-4-yl-ethoxy)-pyrimidine-4-carboxylic acid (3-dimethylcarbamoyl-phenyl)-amide Compound 51

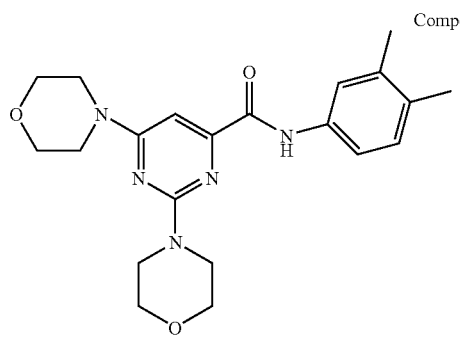

2,6-Di-morpholin-4-yl-pyrimidine-4-carboxylic acid (3,4-dimethyl-phenyl)-amide

Compound 54

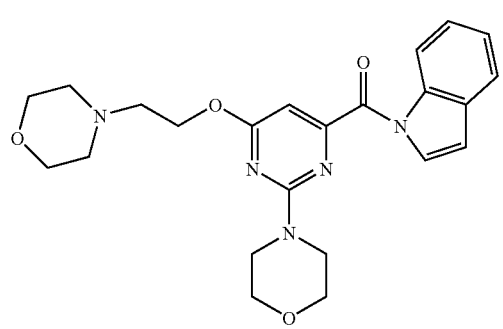

Indol-1-yl-[2-morpholin-4-yl-6-(2-morpholin-4-yl-ethoxy)-pyrimidin-4-yl]-methanone Compound 55

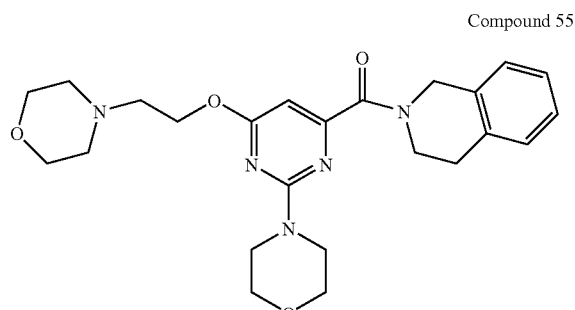

(3,4-Dihydro-1H-isoquinolin-2-yl)-[2-morpholin-4-yl-6-(2-morpholin-4-yl-ethoxy)-pyrimidin-4-yl]-methanone Compound 56

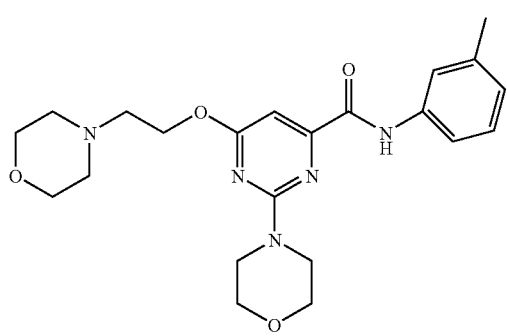

2-Morpholin-4-yl-6-(2-morpholin-4-yl-ethoxy)-pyrimidine-4-carboxylic acid m-tolylamide Compound 57

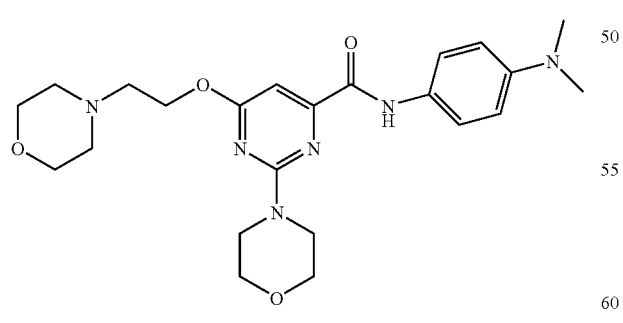

2-Morpholin-4-yl-6-(2-morpholin-4-yl-ethoxy)-pyrimidine-4-carboxylic acid (4-dimethylamino-phenyl)-amide Compound 58

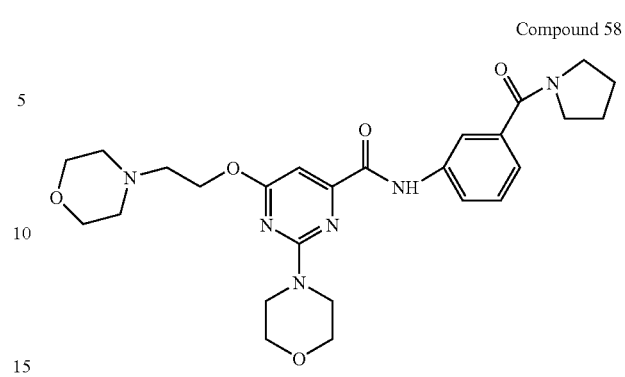

2-Morpholin-4-yl-6-(2-morpholin-4-yl-ethoxy)-pyrimidine-4-carboxylic acid [3-(pyrrolidine-1-carbonyl)-phenyl]-amide Compound 59

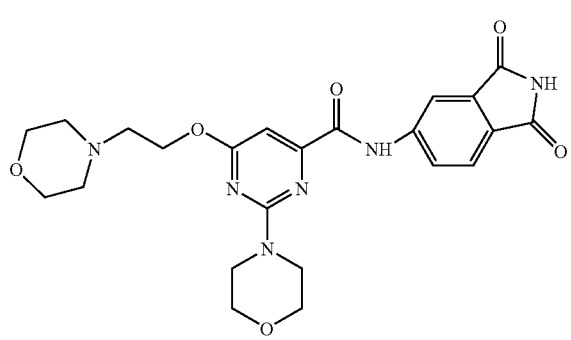

2-Morpholin-4-yl-6-(2-morpholin-4-yl-ethoxy)-pyrimidine-4-carboxylic acid (1,3-dioxo-2,3-dihydro-1H-isoindol-5-yl)-amide Compound 60

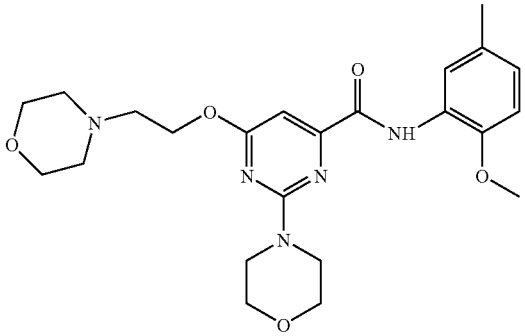

2-Morpholin-4-yl-6-(2-morpholin-4-yl-ethoxy)-pyrimidine-4-carboxylic acid (2-methoxy-5-methyl-phenyl)-amide Compound 61

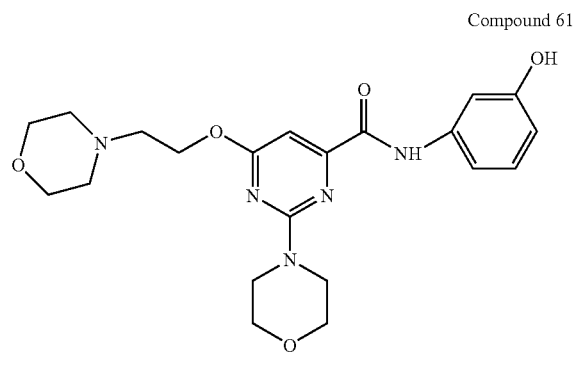

2-Morpholin-4-yl-6-(2-morpholin-4-yl-ethoxy)-pyrimidine-4-carboxylic acid (3-hydroxy-phenyl)-amide Compound 64

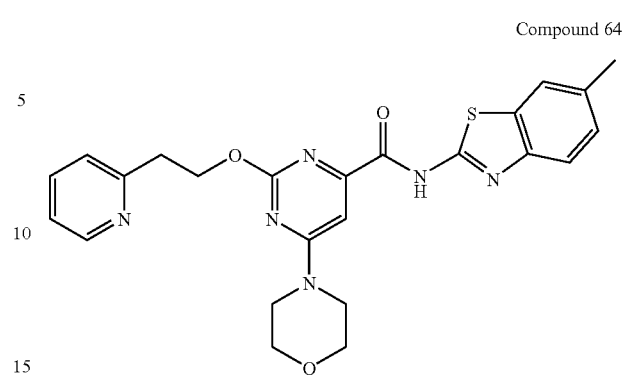

6-Morpholin-4-yl-2-(2-pyridin-2-yl-ethoxy)-pyrimidine-4-carboxylic acid (6-methyl-benzothiazol-2-yl)-amide Compound 62

6-Morpholin-4-yl-2-(2-pyridin-2-yl-ethoxy)-pyrimidine-4-carboxylic acid m-tolylamide Compound 65

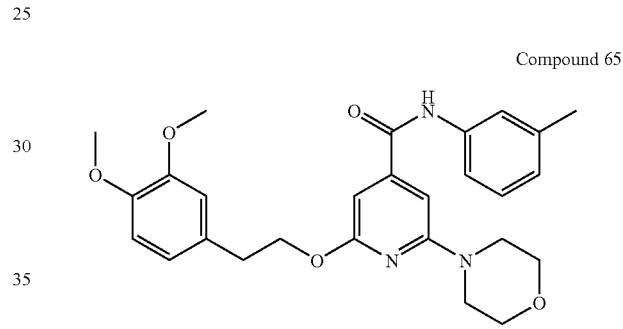

2-[2-(3,4-Dimethoxy-phenyl)-ethoxy]-6-morpholin-4-yl-N-m-tolyl-isonicotinamide

Compound 63

6-Morpholin-4-yl-2-(2-pyridin-2-yl-ethoxy)-pyrimidine-4-carboxylic acid (2,3-dimethyl-1H-indol-5-yl)-amide Compound 66

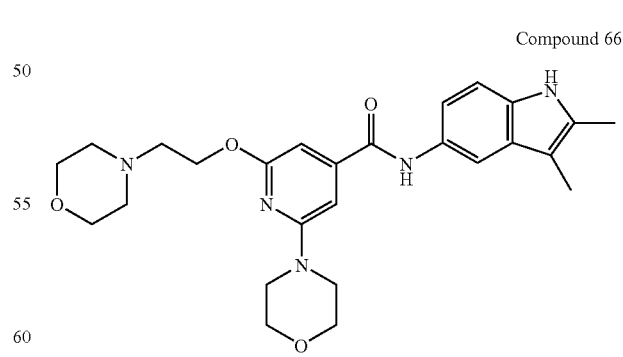

N-(2,3-Dimethyl-1H-indol-5-yl)-2-morpholin-4-yl-6-(2-morpholin-4-yl-ethoxy)-isonicotinamide Compound 67

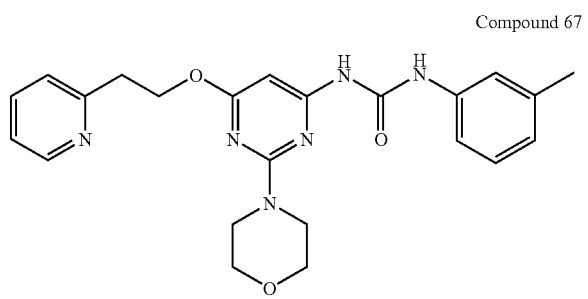

1-[2-Morpholin-4-yl-6-(2-pyridin-2-yl-ethoxy)-pyrimidin-4-yl]-3-m-tolyl-urea

Compound 68

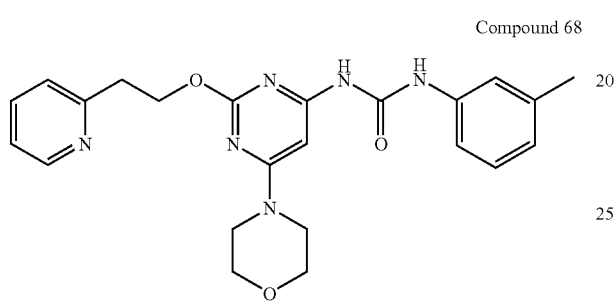

1-[6-Morpholin-4-yl-2-(2-pyridin-2-yl-ethoxy)-pyrimidin-4-yl]-3-m-tolyl-urea

Compound 69

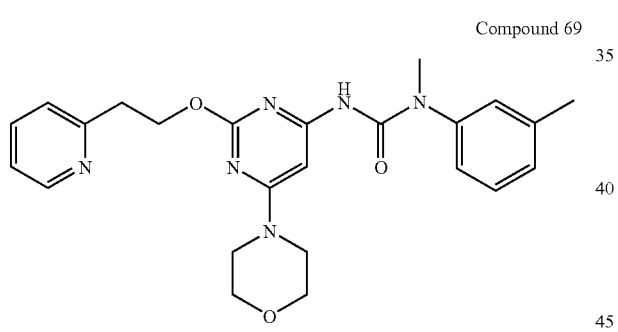

1-Methyl-3-[6-morpholin-4-yl-2-(2-pyridin-2-yl-ethoxy)-pyrimidin-4-yl]-1-m-tolyl-urea Compound 70

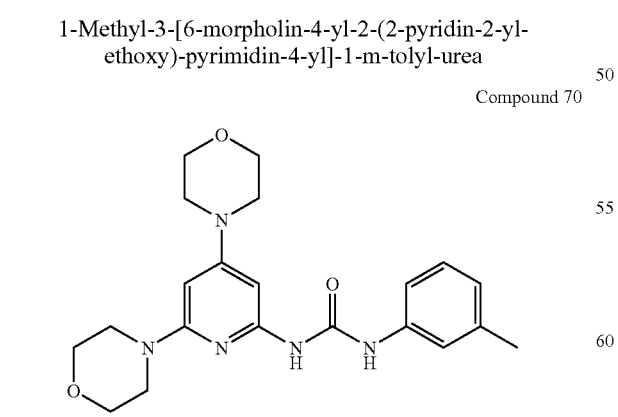

1-(4,6-Di-morpholin-4-yl-pyridin-2-yl)-3-m-tolyl-urea

Compound 71

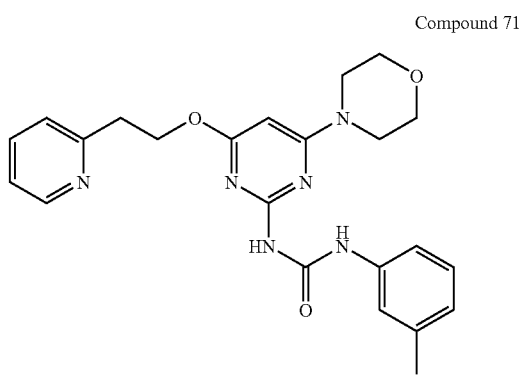

1-[4-Morpholin-4-yl-6-(2-pyridin-2-yl-ethoxy)-pyrimidin-2-yl]-3-m-tolyl-urea

Compound 72

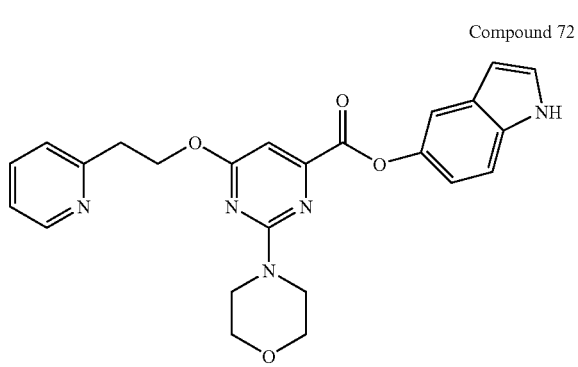

2-Morpholin-4-yl-6-(2-pyridin-2-yl-ethoxy)-pyrimidine-4-carboxylic acid 1H-indol-5-yl ester Compound 73

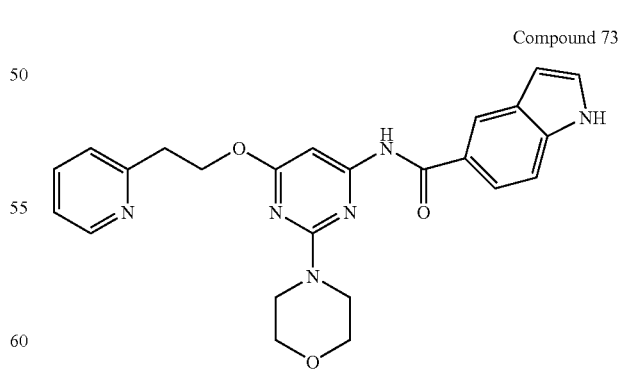

1H-Indole-5-carboxylic acid [2-morpholin-4-yl-6-(2-pyridin-2-yl-ethoxy)-pyrimidin-4-yl]-amide Compound 74

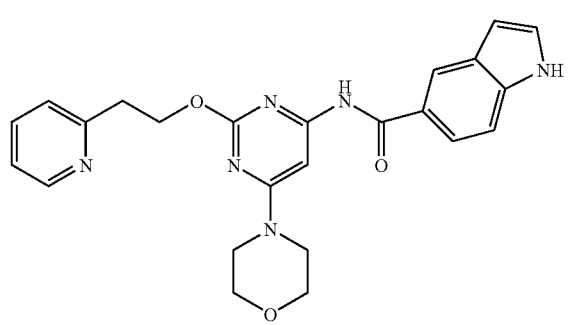

1H-Indole-5-carboxylic acid [6-morpholin-4-yl-2-(2-pyridin-2-yl-ethoxy)-pyrimidin-4-yl]-amide Compound 75

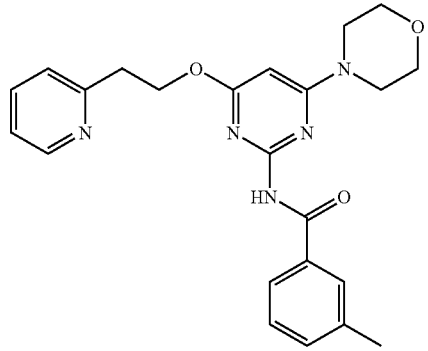

3-Methyl-N-[4-morpholin-4-yl-6-(2-pyridin-2-yl-ethoxy)-pyrimidin-2-yl]-benzamide Compound 76

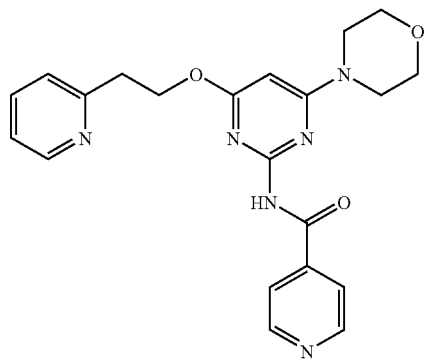

N-[4-Morpholin-4-yl-6-(2-pyridin-2-yl-ethoxy)-pyrimidin-2-yl]-isonicotinamide

Compound 77

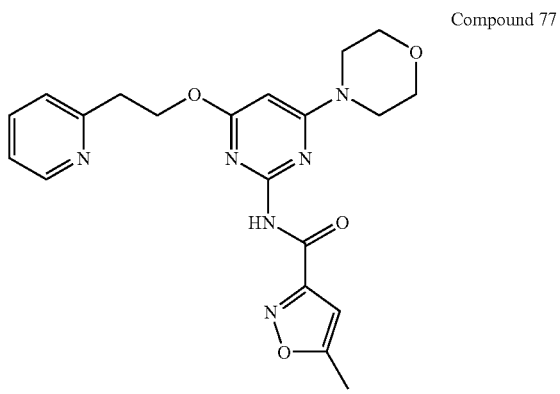

5-Methyl-isoxazole-3-carboxylic acid-[4-morpholin-4-yl-6-(2-pyridin-2-yl-ethoxy)-pyrimidin-2-yl]-amide Compound 78

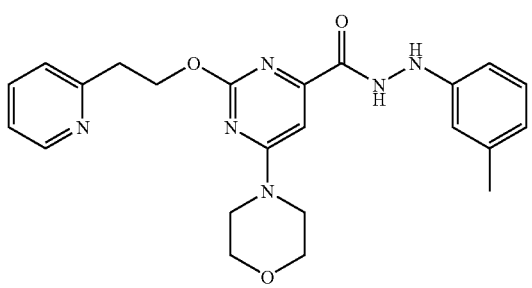

6-Morpholin-4-yl-2-(2-pyridin-2-yl-ethoxy)-pyrimidine-4-carboxylic acid N'-m-tolyl-hydrazide Compound 79

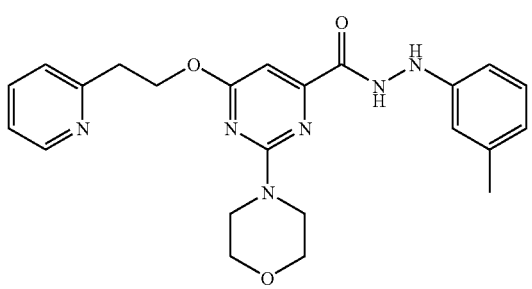

2-Morpholin-4-yl-6-(2-pyridin-2-yl-ethoxy)-pyrimidine-4-carboxylic acid N'-m-tolyl-hydrazide Compound 80

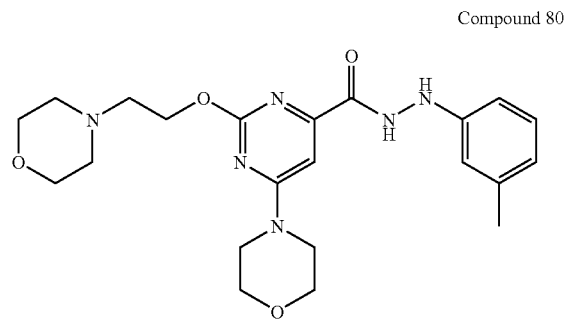

6-Morpholin-4-yl-2-(2-morpholin-4-yl-ethoxy)-pyrimidine-4-carboxylic acid N'-m-tolyl-hydrazide Compound 81

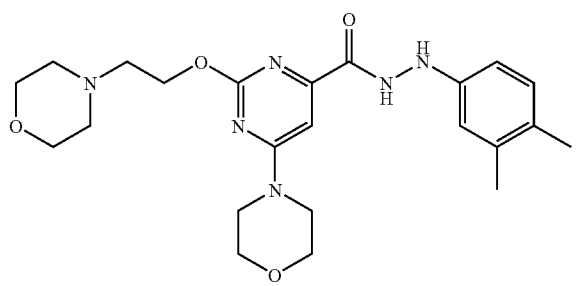

6-Morpholin-4-yl-2-(2-morpholin-4-yl-ethoxy)-pyrimidine-4-carboxylic acid N'-(3,4-dimethyl-phenyl)-hydrazide Compound 82

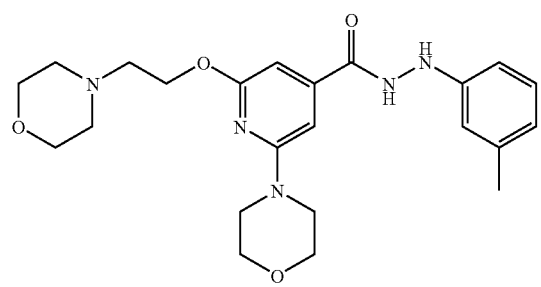

2-Morpholin-4-yl-6-(2-morpholin-4-yl-ethoxy)-isonicotinic acid N'-m-tolyl-hydrazide Compound 83

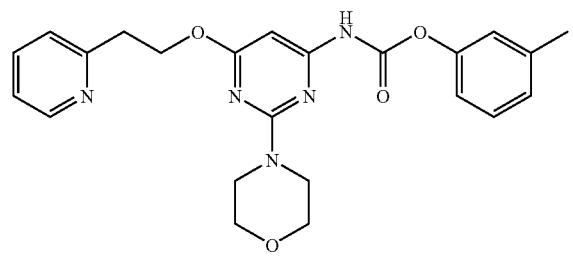

[2-Morpholin-4-yl-6-(2-pyridin-2-yl-ethoxy)-pyrimidin-4-yl]-carbamic acid m-tolyl ester Compounds 84

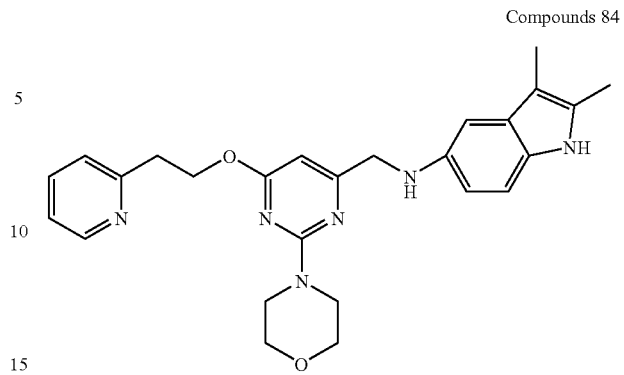

(2,3-Dimethyl-1H-indol-5-yl)-[2-morpholin-4-yl-6-(2-pyridin-2-yl-ethoxy)-pyrimidin-4-ylmethyl]-amine Compound 85

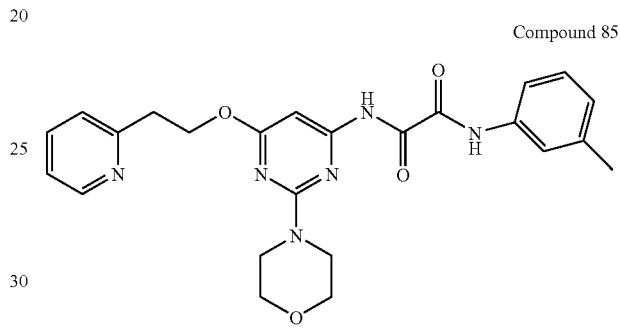

N-[2-Morpholin-4-yl-6-(2-pyridin-2-yl-ethoxy)-pyrimidin-4-yl]-N'-m-tolyl-oxalamide Compound 86

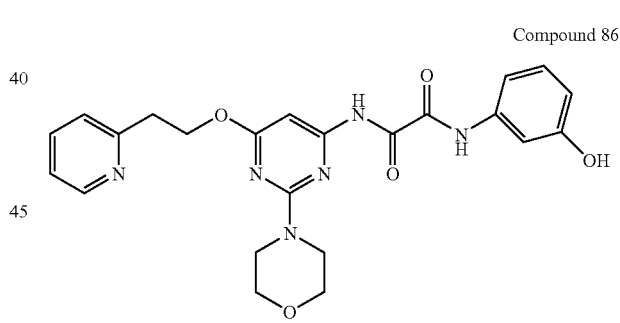

N-(3-Hydroxy-phenyl)-N'-[2-morpholin-4-yl-6-(2-pyridin-2-yl-ethoxy)-pyrimidin-4-yl]-oxalamide Compound 87

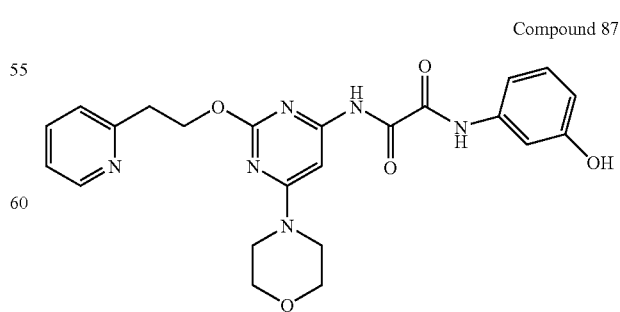

N-(3-Hydroxy-phenyl)-N'-[6-morpholin-4-yl-2-(2-pyridin-2-yl-ethoxy)-pyrimidin-4-yl]-oxalamide Compound 88

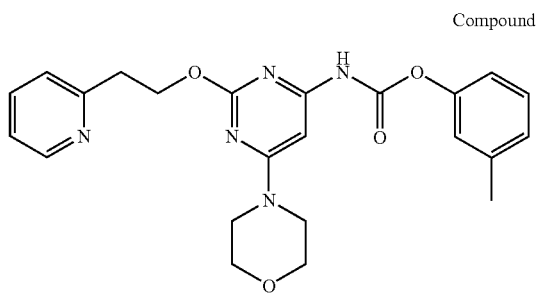

[6-Morpholin-4-yl-2-(2-pyridin-2-yl-ethoxy)-pyrimidin-4-yl]-carbamic acid m-tolyl ester Compound 89

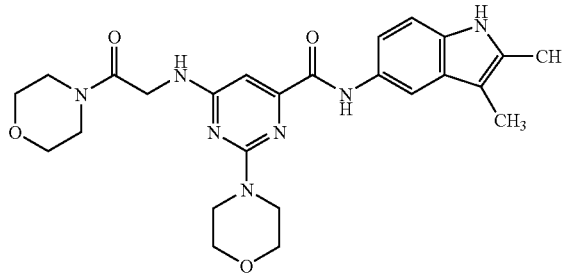

2-Morpholin-4-yl-6-(2-morpholin-4-yl-2-oxo-ethylamino)-pyrimidine-4-carboxylic acid (2,3-dimethyl-1H-indol-5-yl)-amide Compound 90

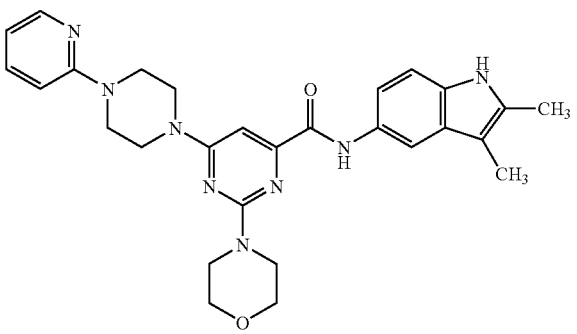

2-Morpholin-4-yl-6-(4-pyridin-2-yl-piperazin-1-yl)-pyrimidine-4-carboxylic acid (2,3-dimethyl-1H-indol-5-yl)-amide Compound 91

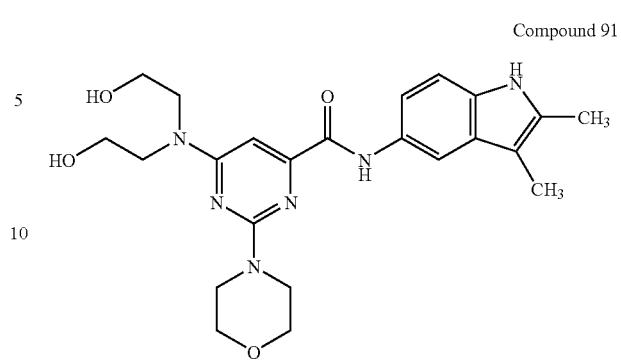

6-[Bis-(2-hydroxy-ethyl)-amino]-2-morpholin-4-yl-pyrimidine-4-carboxylic acid (2,3-dimethyl-1H-indol-5-yl)-amide Compound 92

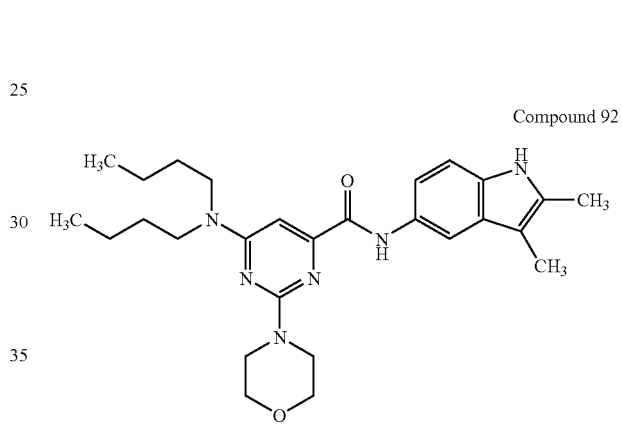

6-Dibutylamino-2-morpholin-4-yl-pyrimidine-4-carboxylic acid (2,3-dimethyl-1H-indol-5-yl)-amide Compound 93

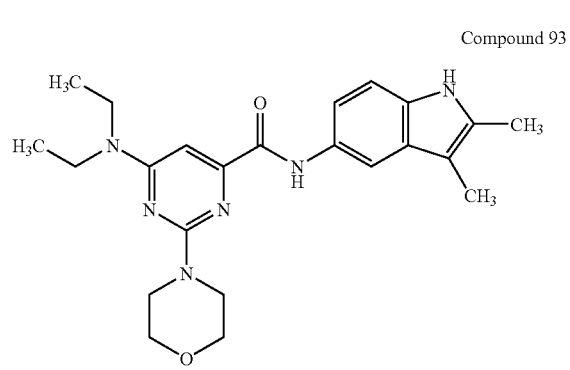

6-Diethylamino-2-morpholin-4-yl-pyrimidine-4-carboxylic acid (2,3-dimethyl-1H-indol-5-yl)-amide

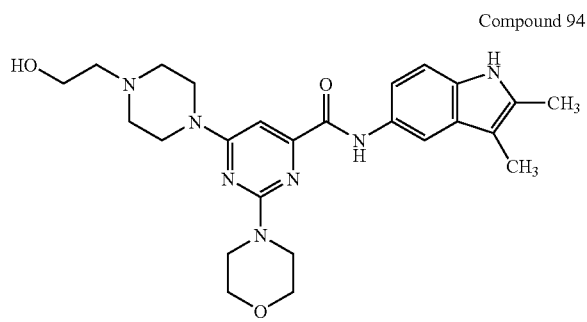

Compound 94

6-[4-(2-Hydroxy-ethyl)-piperazin-1-yl]-2-morpholin-4-yl-pyrimidine-4-carboxylic acid (2,3-dimethyl-1H-indol-5-yl)-amide

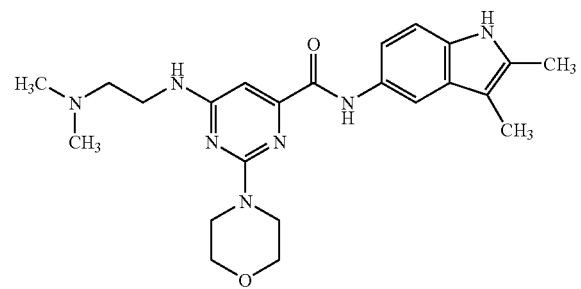

Compound 95

6-(2-Dimethylamino-ethylamino)-2-morpholin-4-yl-pyrimidine-4-carboxylic acid (2,3-dimethyl-1H-indol-5-yl)-amide

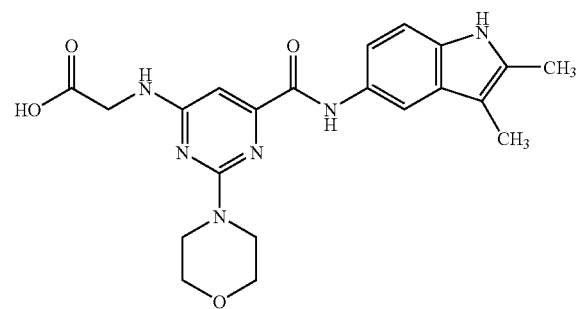

Compound 96

[6-(2,3-Dimethyl-1H-indol-5-ylcarbamoyl)-2-morpholin-4-yl-pyrimidin-4-ylamino]-acetic acid

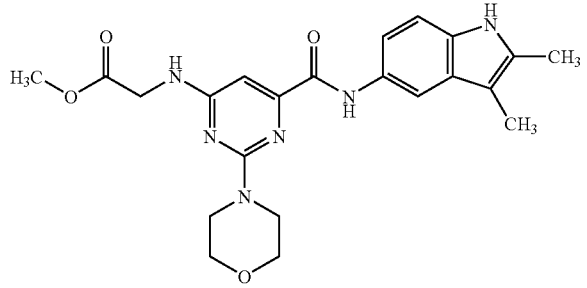

Compound 97

[6-(2,3-Dimethyl-1H-indol-5-ylcarbamoyl)-2-morpholin-4-yl-pyrimidin-4-ylamino]-acetic acid methyl ester

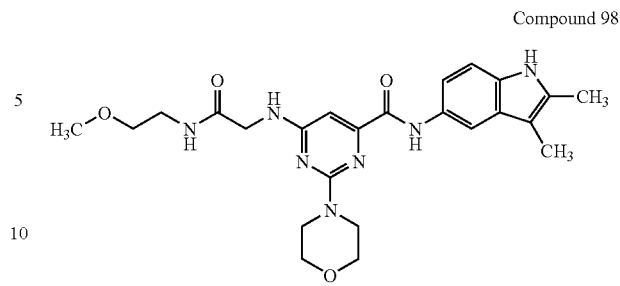

Compound 98

6-{[(2-Methoxy-ethylcarbamoyl)-methyl]-amino}-2-morpholin-4-yl-pyrimidine-4-carboxylic acid (2,3-dimethyl-1H-indol-5-yl)-amide

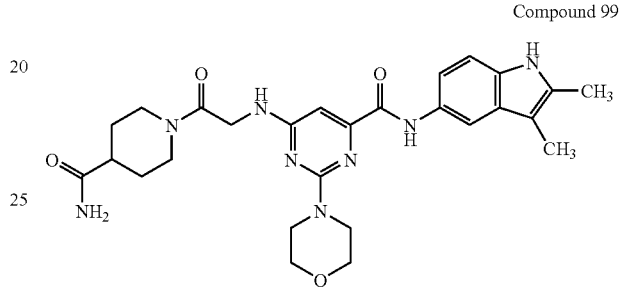

Compound 99

6-[2-(4-Carbamoyl-piperidin-1-yl)-2-oxo-ethylamino]-2-morpholin-4-yl-pyrimidine-4-carboxylic acid (2,3-dimethyl-1H-indol-5-yl)-amide

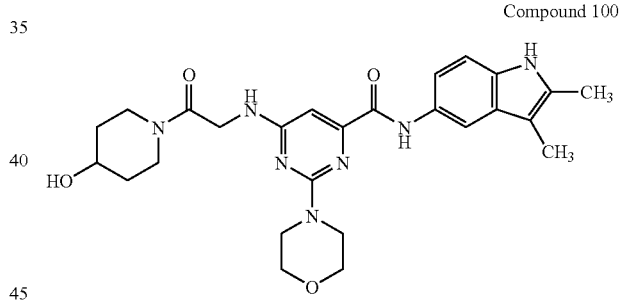

Compound 100

6-[2-(4-Hydroxy-piperidin-1-yl)-2-oxo-ethylamino]-2-morpholin-4-yl-pyrimidine-4-carboxylic acid (2,3-dimethyl-1H-indol-5-yl)-amide

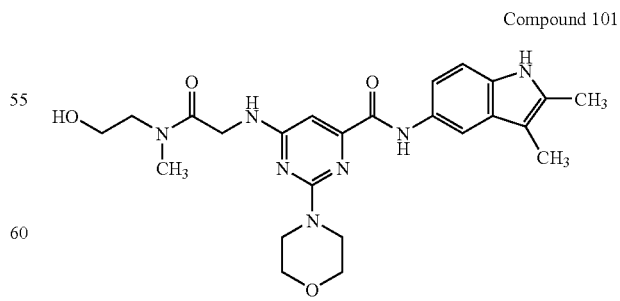

Compound 101

6-({[(2-Hydroxy-ethyl)-methyl-carbamoyl]-methyl}-amino)-2-morpholin-4-yl-pyrimidine-4-carboxylic acid (2,3-dimethyl-1H-indol-5-yl)-amide

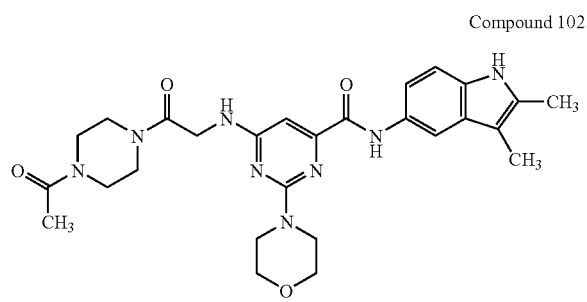

Compound 102

6-[2-(4-Acetyl-piperazin-1-yl)-2-oxo-ethylamino]-2-morpholin-4-yl-pyrimidine-4-carboxylic acid (2,3-dimethyl-1H-indol-5-yl)-amide

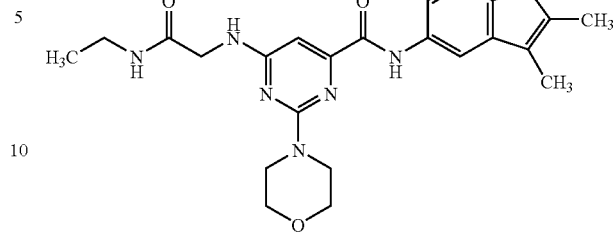

Compound 105

6-(Ethylcarbamoylmethyl-amino)-2-morpholin-4-yl-pyrimidine-4-carboxylic acid (2,3-dimethyl-1H-indol-5-yl)-amide

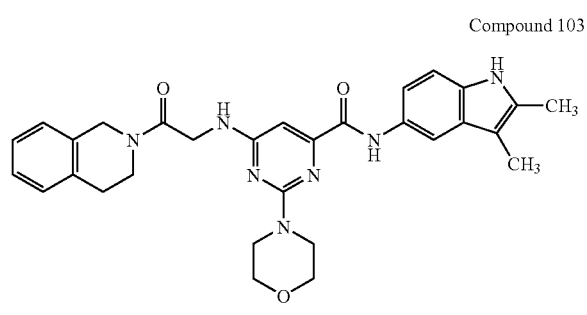

Compound 103

6-[2-(3,4-Dihydro-1H-isoquinolin-2-yl)-2-oxo-ethylamino]-2-morpholin-4-yl-pyrimidine-4-carboxylic acid (2,3-dimethyl-1H-indol-5-yl)-amide

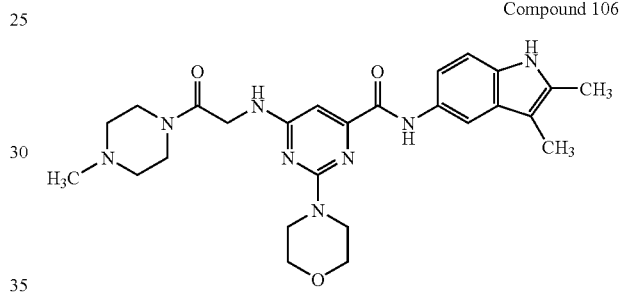

Compound 106

6-[2-(4-Methyl-piperazin-1-yl)-2-oxo-ethylamino]-2-morpholin-4-yl-pyrimidine-4-carboxylic acid (2,3-dimethyl-1H-indol-5-yl)-amide

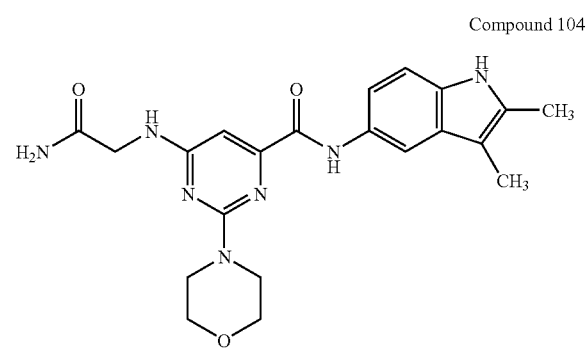

Compound 104

6-(Carbamoylmethyl-amino)-2-morpholin-4-yl-pyrimidine-4-carboxylic acid (2,3-dimethyl-1H-indol-5-yl)-amide

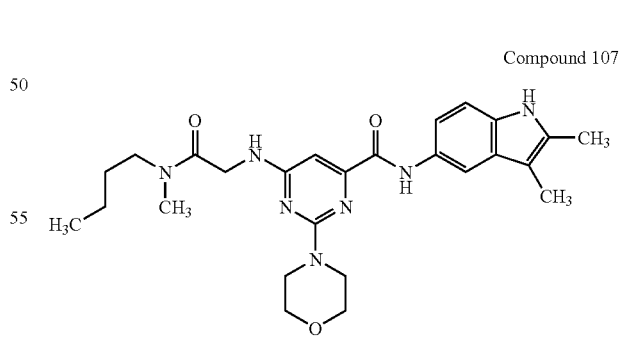

Compound 107

6-{[(Butyl-methyl-carbamoyl)-methyl]-amino}-2-morpholin-4-yl-pyrimidine-4-carboxylic acid (2,3-dimethyl-1H-indol-5-yl)-amide Compound 108

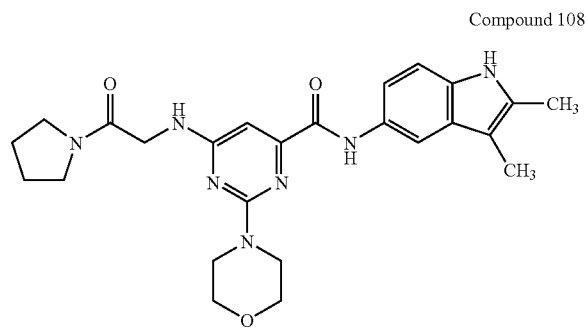

2-Morpholin-4-yl-6-(2-oxo-2-pyrrolidin-1-yl-ethylamino)-pyrimidine-4-carboxylic acid (2,3-dimethyl-1H-indol-5-yl)-amide Compound 111

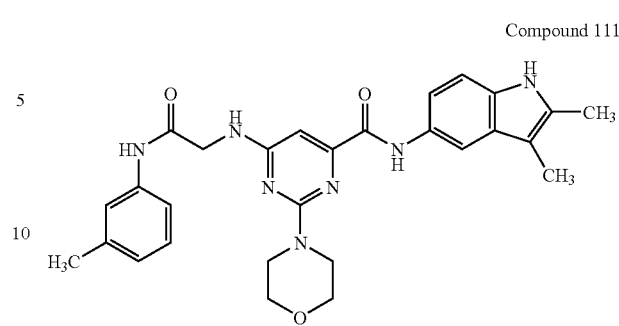

2-Morpholin-4-yl-6-[(m-tolylcarbamoyl-methyl)-amino]-pyrimidine-4-carboxylic acid (2,3-dimethyl-1H-indol-5-yl)-amide Compound 109

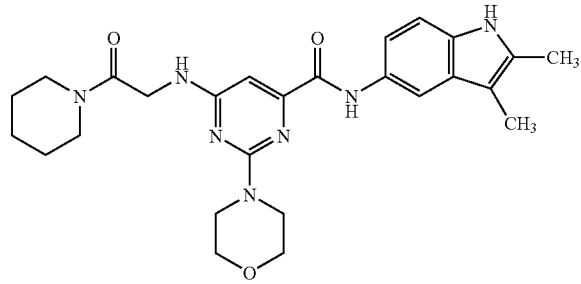

2-Morpholin-4-yl-6-(2-oxo-2-piperidin-1-yl-ethylamino)-pyrimidine-4-carboxylic acid (2,3-dimethyl-1H-indol-5-yl)-amide Compound 112

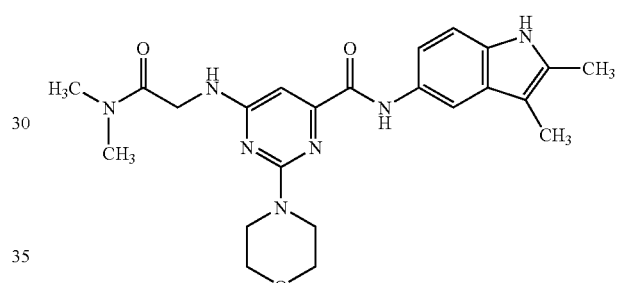

6-(Dimethylcarbamoylmethyl-amino)-2-morpholin-4-yl-pyrimidine-4-carboxylic acid (2,3-dimethyl-1H-indol-5-yl)-amide Compound 110

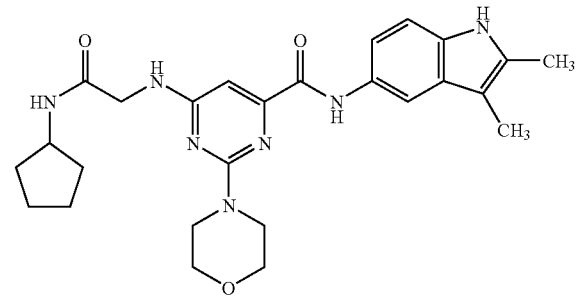

6-(Cyclopentylcarbamoylmethyl-amino)-2-morpholin-4-yl-pyrimidine-4-carboxylic acid (2,3-dimethyl-1H-indol-5-yl)-amide Compound 113

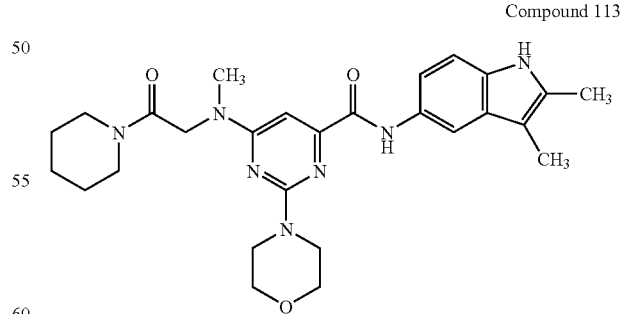

6-[Methyl-(2-oxo-2-piperidin-1-yl-ethyl)-amino]-2-morpholin-4-yl-pyrimidine-4-carboxylic acid (2,3-dimethyl-1H-indol-5-yl)-amide Compound 114

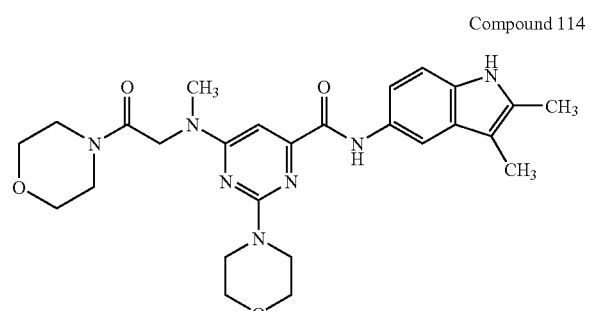

6-[Methyl-(2-morpholin-4-yl-2-oxo-ethyl)-amino]-2-morpholin-4-yl-pyrimidine-4-carboxylic acid (2,3-dimethyl-1H-indol-5-yl)-amide Compound 115

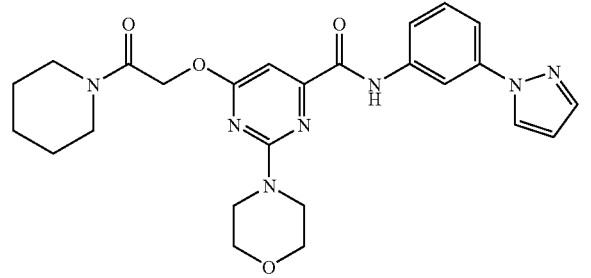

2-Morpholin-4-yl-6-(2-oxo-2-piperidin-1-yl-ethoxy)-pyrimidine-4-carboxylic acid (3-pyrazol-1-yl-phenyl)-amide Compound 116

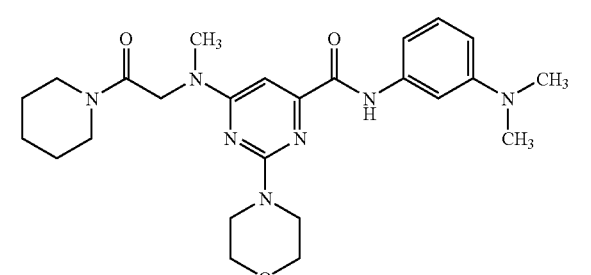

6-[Methyl-(2-oxo-2-piperidin-1-yl-ethyl)-amino]-2-morpholin-4-yl-pyrimidine-4-carboxylic acid (3-dimethylamino-phenyl)-amide Compound 117

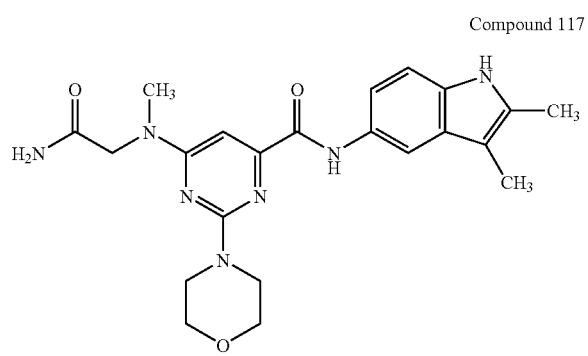

6-(Carbamoylmethyl-methyl-amino)-2-morpholin-4-yl-pyrimidine-4-carboxylic acid (2,3-dimethyl-1H-indol-5-yl)-amide Compound 118

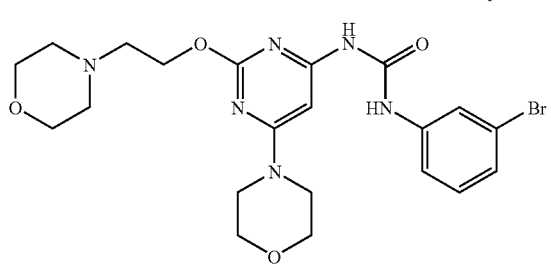

1-(3-Bromo-phenyl)-3-[6-morpholin-4-yl-2-(2-morpholin-4-yl-ethoxy)-pyrimidin-4-yl]-urea Compound 119

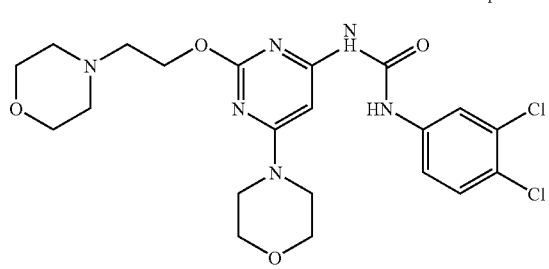

1-(3,4-Dichloro-phenyl)-3-[6-morpholin-4-yl-2-(2-morpholin-4-yl-ethoxy)-pyrimidin-4-yl]-urea Compound 120

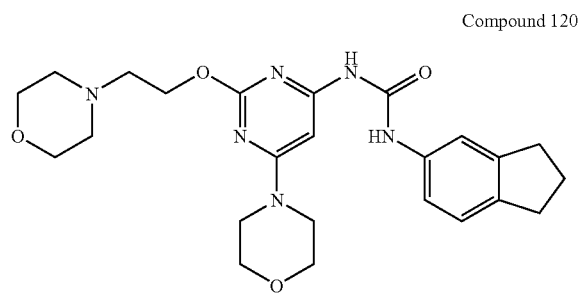

1-Indan-5-yl-3-[6-morpholin-4-yl-2-(2-morpholin-4-yl-ethoxy)-pyrimidin-4-yl]-urea Compound 121

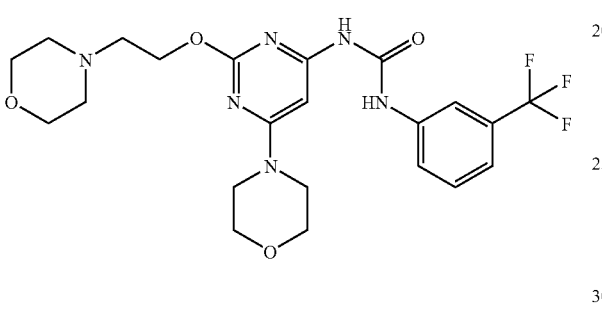

1-[6-Morpholin-4-yl-2-(2-morpholin-4-yl-ethoxy)-pyrimidin-4-yl]-3-(3-trifluoromethyl-phenyl)-urea Compound 122

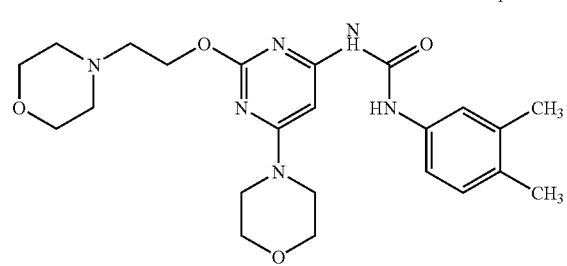

1-(3,4-Dimethyl-phenyl)-3-[6-morpholin-4-yl-2-(2-morpholin-4-yl-ethoxy)-pyrimidin-4-yl]-urea Compound 123

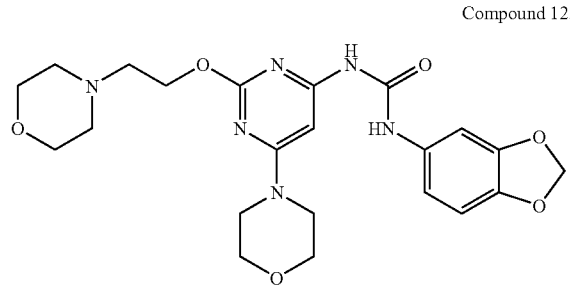

1-Benzo[1,3]dioxol-5-yl-3-[6-morpholin-4-yl-2-(2-morpholin-4-yl-ethoxy)-pyrimidin-4-yl]-urea Compound 124

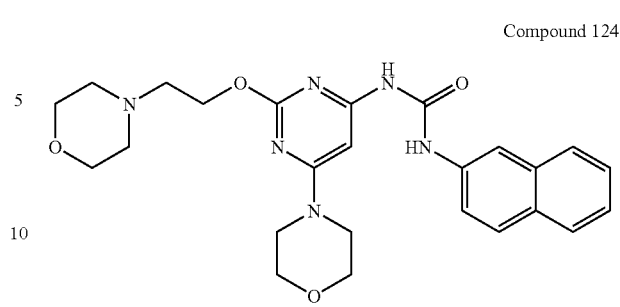

1-[6-Morpholin-4-yl-2-(2-morpholin-4-yl-ethoxy)-pyrimidin-4-yl]-3-naphthalen-2-yl-urea Compound 125

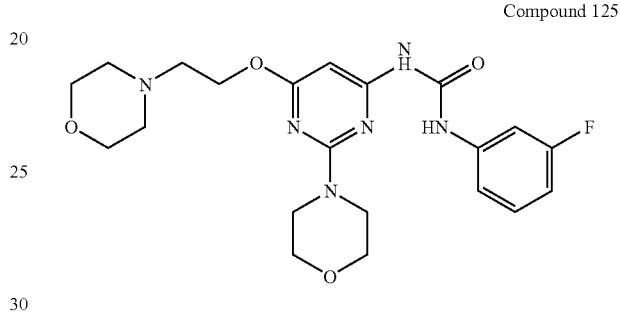

1-(3-Fluoro-phenyl)-3-[2-morpholin-4-yl-6-(2-morpholin-4-yl-ethoxy)-pyrimidin-4-yl]-urea Compound 126

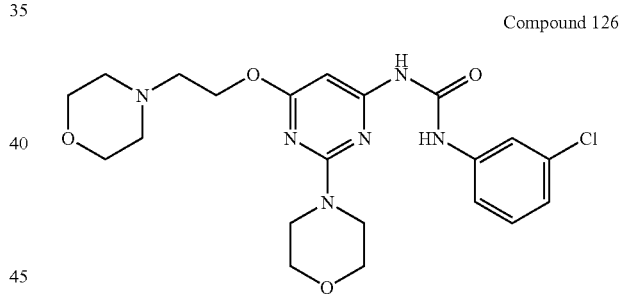

1-(3-Chloro-phenyl)-3-[2-morpholin-4-yl-6-(2-morpholin-4-yl-ethoxy)-pyrimidin-4-yl]-urea Compound 127

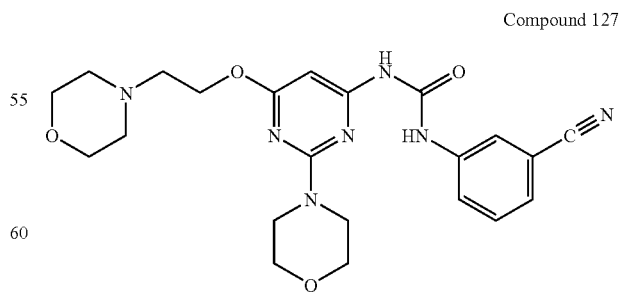

1-(3-Cyano-phenyl)-3-[2-morpholin-4-yl-6-(2-morpholin-4-yl-ethoxy)-pyrimidin-4-yl]-urea Compound 128

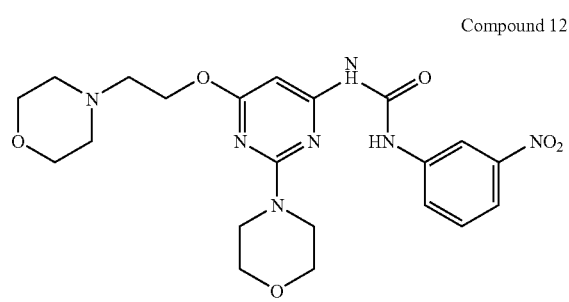

1-[2-Morpholin-4-yl-6-(2-morpholin-4-yl-ethoxy)-
pyrimidin-4-yl]-3-(3-nitro-phenyl)-urea Compound 129

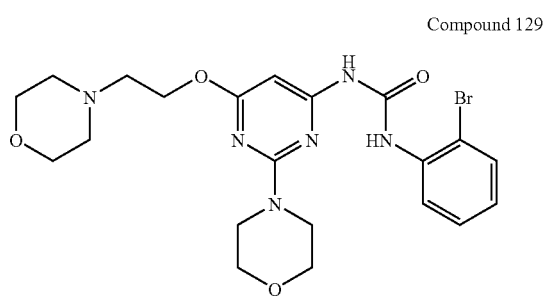

1-(2-Bromo-phenyl)-3-[2-morpholin-4-yl-6-(2-mor-
pholin-4-yl-ethoxy)-pyrimidin-4-yl]-urea Compound 130

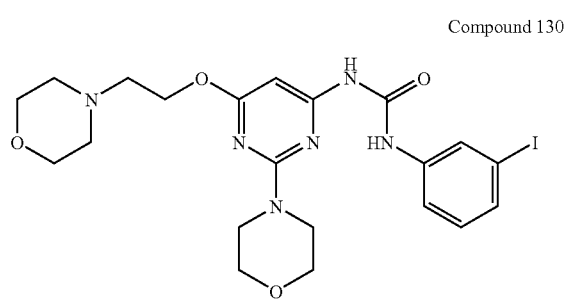

1-(3-Iodo-phenyl)-3-[2-morpholin-4-yl-6-(2-mor-
pholin-4-yl-ethoxy)-pyrimidin-4-yl]-urea Compound 131

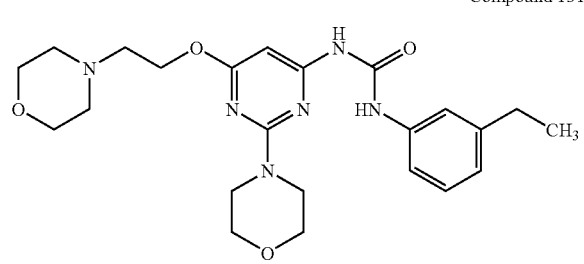

1-(3-Ethyl-phenyl)-3-[2-morpholin-4-yl-6-(2-mor-
pholin-4-yl-ethoxy)-pyrimidin-4-yl]-urea Compound 132

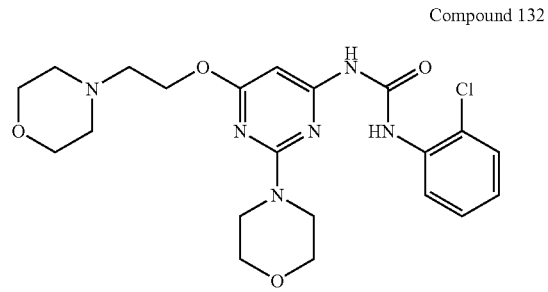

1-(2-Chloro-phenyl)-3-[2-morpholin-4-yl-6-(2-mor-
pholin-4-yl-ethoxy)-pyrimidin-4-yl]-urea Compound 133

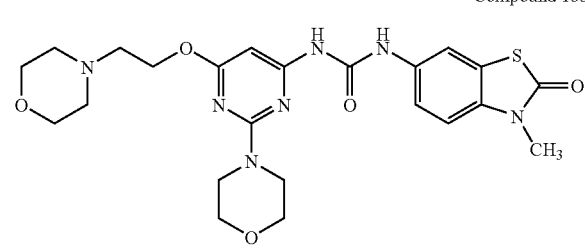

1-(3-Methyl-2-oxo-2,3-dihydro-benzothiazol-6-yl)-
3-[2-morpholin-4-yl-6-(2-morpholin-4-yl-ethoxy)-
pyrimidin-4-yl]-urea Compound 134

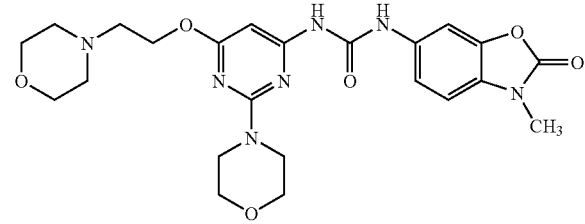

1-(3-Methyl-2-oxo-2,3-dihydro-benzooxazol-6-yl)-
3-[2-morpholin-4-yl-6-(2-morpholin-4-yl-ethoxy)-
pyrimidin-4-yl]-urea Compound 135

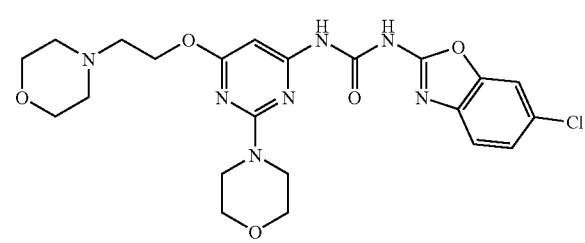

1-(6-Chloro-benzooxazol-2-yl)-3-[2-morpholin-4-yl-
6-(2-morpholin-4-yl-ethoxy)-pyrimidin-4-yl]-urea Compound 136

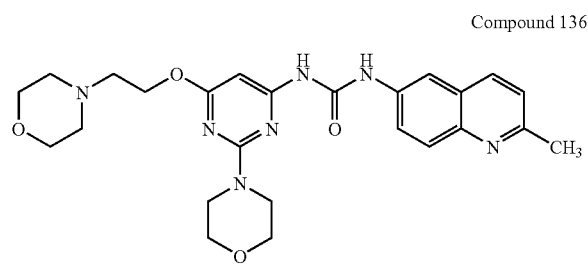

1-(2-Methyl-quinolin-6-yl)-3-[2-morpholin-4-yl-6-(2-morpholin-4-yl-ethoxy)-pyrimidin-4-yl]-urea Compound 137

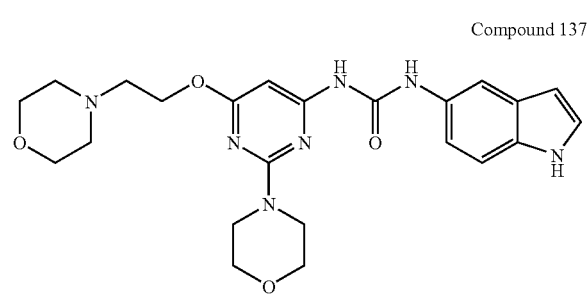

1-(1H-Indol-5-yl)-3-[2-morpholin-4-yl-6-(2-morpholin-4-yl-ethoxy)-pyrimidin-4-yl]-urea Compound 138

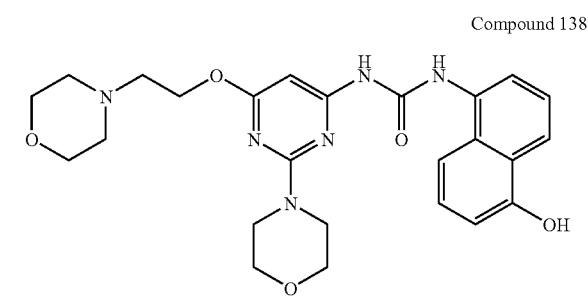

1-(5-Hydroxy-naphthalen-1-yl)-3-[2-morpholin-4-yl-6-(2-morpholin-4-yl-ethoxy)-pyrimidin-4-yl]-urea Compound 139

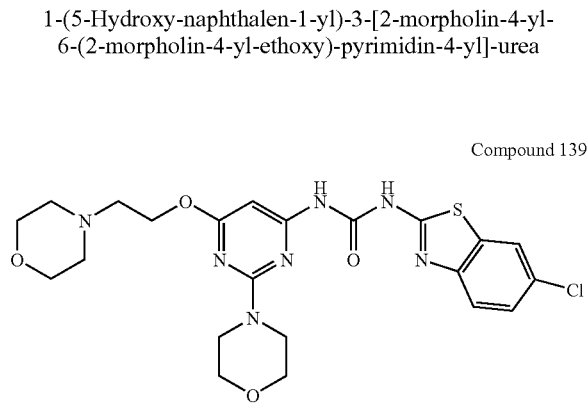

1-(6-Chloro-benzothiazol-2-yl)-3-[2-morpholin-4-yl-6-(2-morpholin-4-yl-ethoxy)-pyrimidin-4-yl]-urea Compound 140

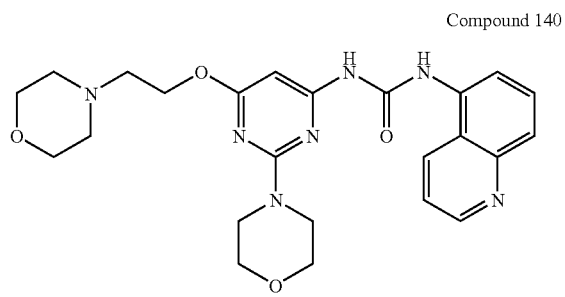

1-[2-Morpholin-4-yl-6-(2-morpholin-4-yl-ethoxy)-pyrimidin-4-yl]-3-quinolin-5-yl-urea Compound 141

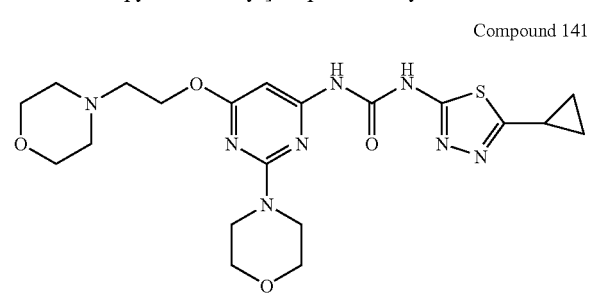

1-(5-Cyclopropyl-[1,3,4]thiadiazol-2-yl)-3-[2-morpholin-4-yl-6-(2-morpholin-4-yl-ethoxy)-pyrimidin-4-yl]-urea Compound 142

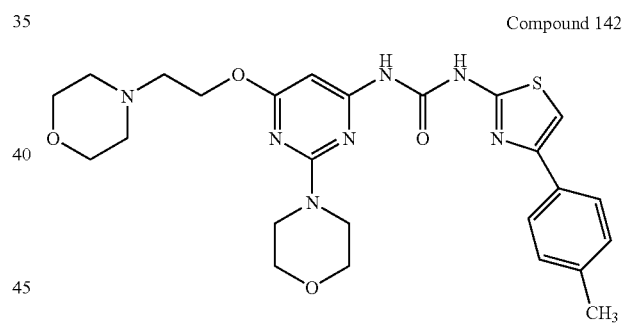

1-[2-Morpholin-4-yl-6-(2-morpholin-4-yl-ethoxy)-pyrimidin-4-yl]-3-(4-p-tolyl-thiazol-2-yl)-urea Compound 143

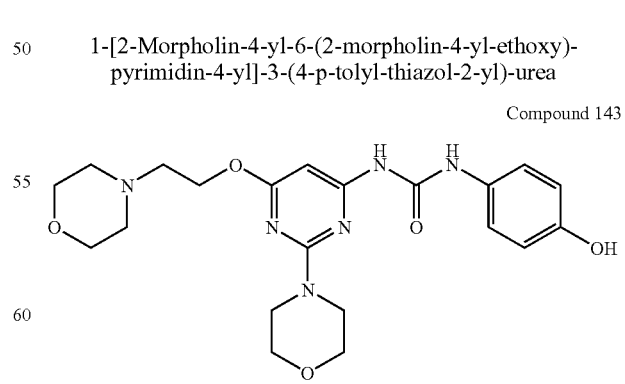

1-(4-Hydroxy-phenyl)-3-[2-morpholin-4-yl-6-(2-morpholin-4-yl-ethoxy)-pyrimidin-4-yl]-urea Compound 144

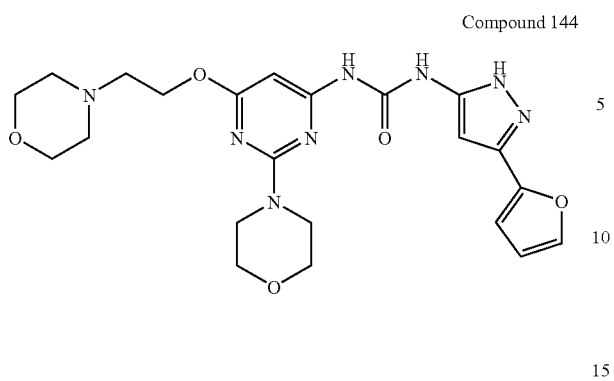

1-(5-Furan-2-yl-2H-pyrazol-3-yl)-3-[2-morpholin-4-yl-6-(2-morpholin-4-yl-ethoxy)-pyrimidin-4-yl]-urea Compound 145

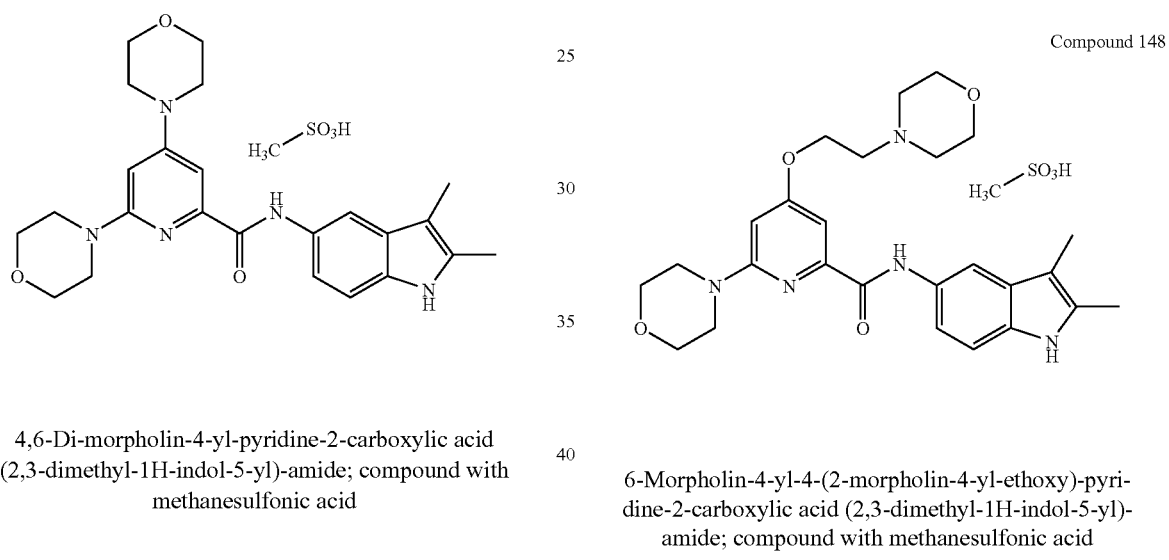

4,6-Di-morpholin-4-yl-pyridine-2-carboxylic acid (2,3-dimethyl-1H-indol-5-yl)-amide; compound with methanesulfonic acid Compound 146

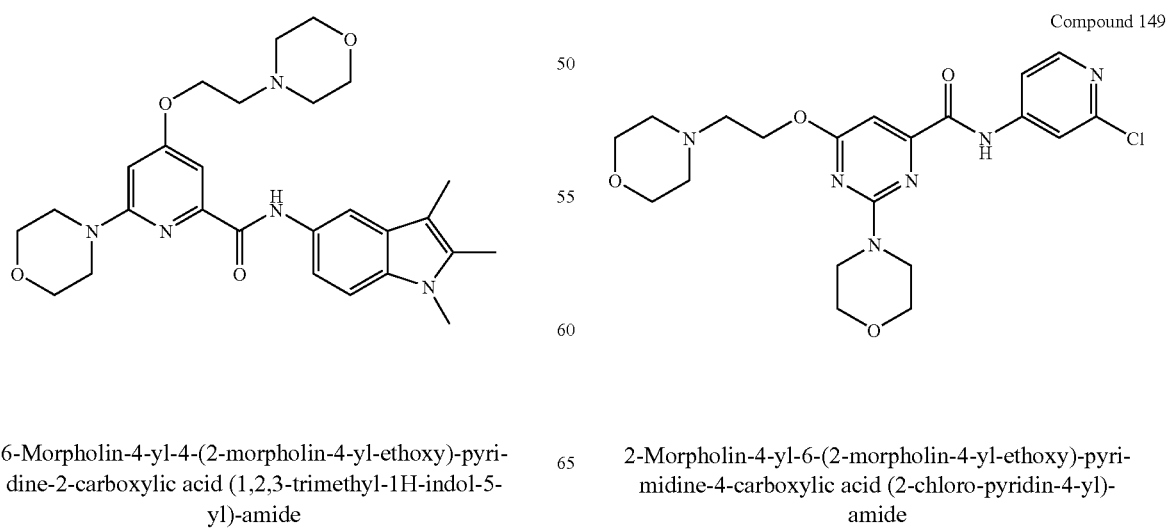

6-Morpholin-4-yl-4-(2-morpholin-4-yl-ethoxy)-pyridine-2-carboxylic acid (1,2,3-trimethyl-1H-indol-5-yl)-amide Compound 147

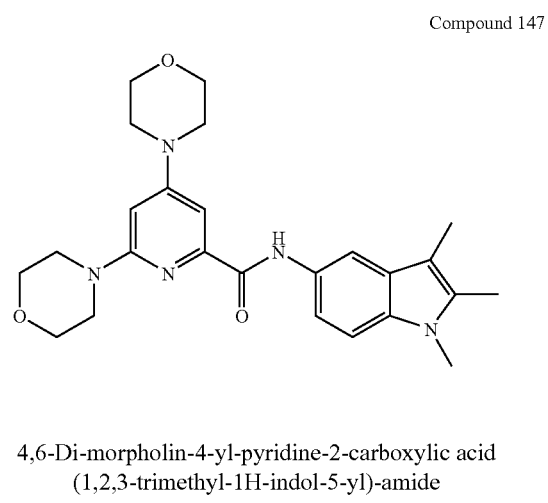

4,6-Di-morpholin-4-yl-pyridine-2-carboxylic acid (1,2,3-trimethyl-1H-indol-5-yl)-amide Compound 148

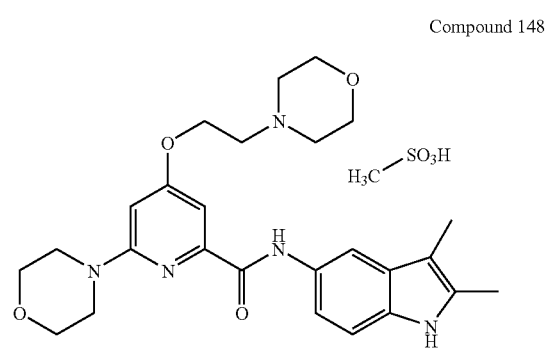

6-Morpholin-4-yl-4-(2-morpholin-4-yl-ethoxy)-pyridine-2-carboxylic acid (2,3-dimethyl-1H-indol-5-yl)-amide; compound with methanesulfonic acid Compound 149

2-Morpholin-4-yl-6-(2-morpholin-4-yl-ethoxy)-pyrimidine-4-carboxylic acid (2-chloro-pyridin-4-yl)-amide Compound 150

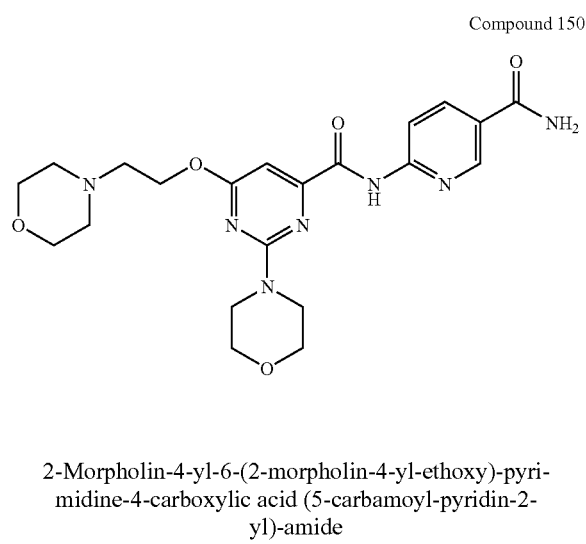

2-Morpholin-4-yl-6-(2-morpholin-4-yl-ethoxy)-pyrimidine-4-carboxylic acid (5-carbamoyl-pyridin-2-yl)-amide Compound 151

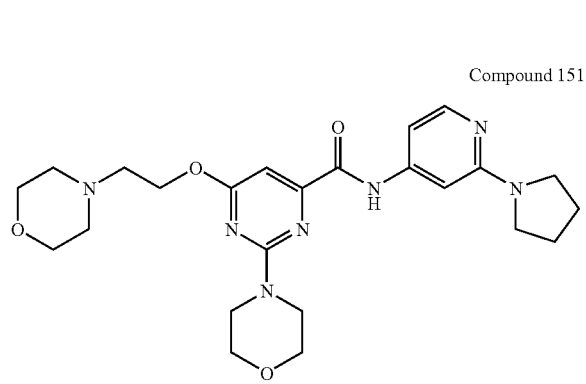

2-Morpholin-4-yl-6-(2-morpholin-4-yl-ethoxy)-pyrimidine-4-carboxylic acid (2-pyrrolidin-1-yl-pyridin-4-yl)-amide Compound 152

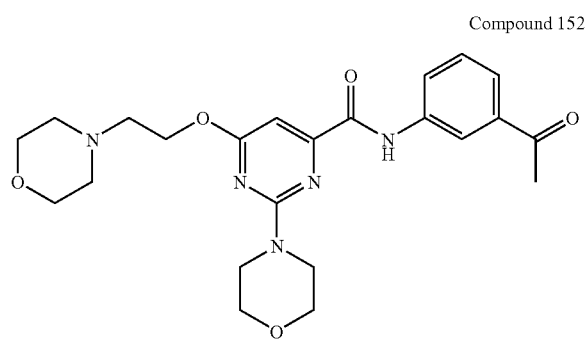

2-Morpholin-4-yl-6-(2-morpholin-4-yl-ethoxy)-pyrimidine-4-carboxylic acid (3-acetyl-phenyl)-amide Compound 153

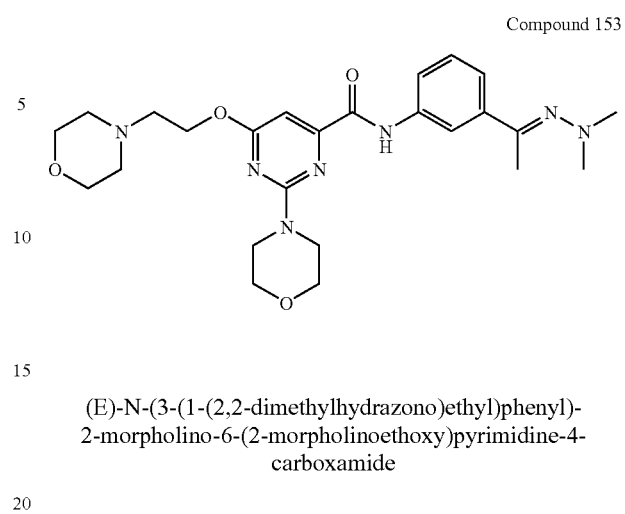

(E)-N-(3-(1-(2,2-dimethylhydrazono)ethyl)phenyl)-2-morpholino-6-(2-morpholinoethoxy)pyrimidine-4-carboxamide Compound 154

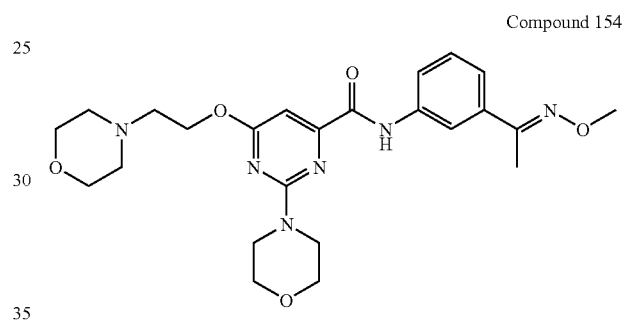

(E)-N-(3-(1-(methoxyimino)ethyl)phenyl)-2-morpholino-6-(2-morpholinoethoxy)pyrimidine-4-carboxamide Compound 155

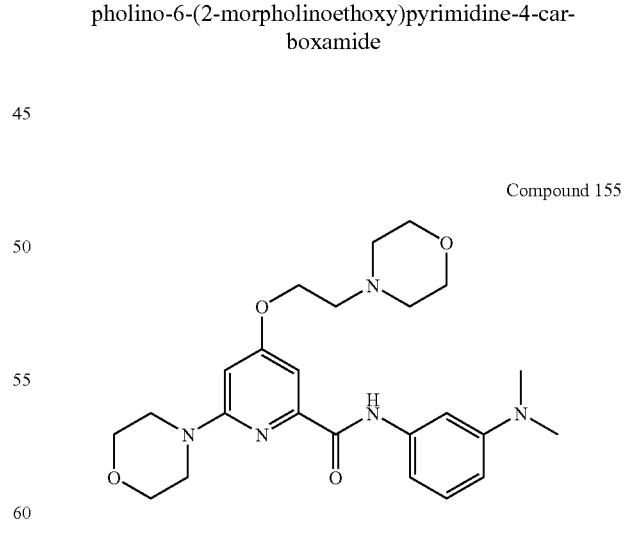

6-Morpholin-4-yl-4-(2-morpholin-4-yl-ethoxy)-pyridine-2-carboxylic acid (3-dimethylamino-phenyl)-amide Compound 156

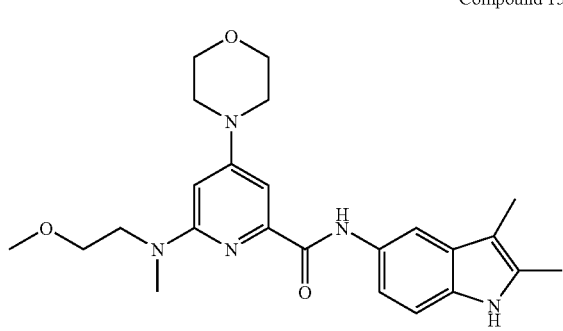

6-[(2-Methoxy-ethyl)-methyl-amino]-4-morpholin-
4-yl-pyridine-2-carboxylic acid (2,3-dimethyl-1H-
indol-5-yl)-amide Compound 157

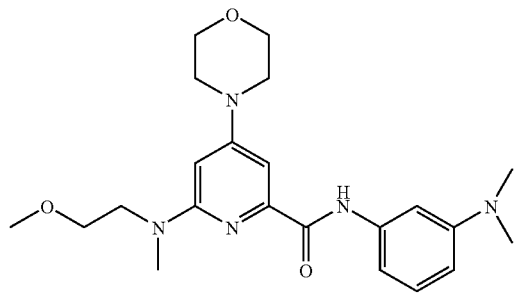

6-[(2-Methoxy-ethyl)-methyl-amino]-4-morpholin-
4-yl-pyridine-2-carboxylic acid (3-dimethylamino-
phenyl)-amide Compound 158

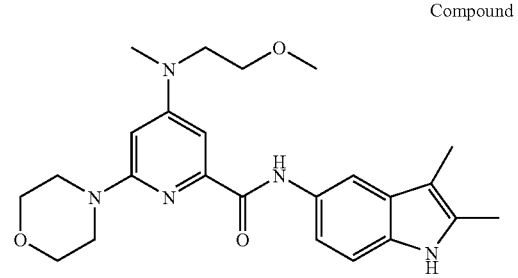

4-[(2-Methoxy-ethyl)-methyl-amino]-6-morpholin-
4-yl-pyridine-2-carboxylic acid (2,3-dimethyl-1H-
indol-5-yl)-amide Compound 159

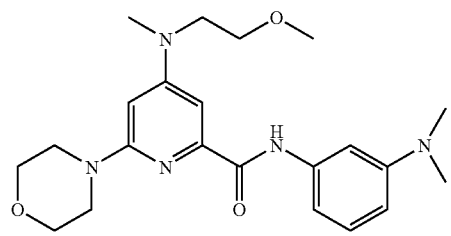

4-[(2-Methoxy-ethyl)-methyl-amino]-6-morpholin-
4-yl-pyridine-2-carboxylic acid (3-dimethylamino-
phenyl)-amide Compound 160

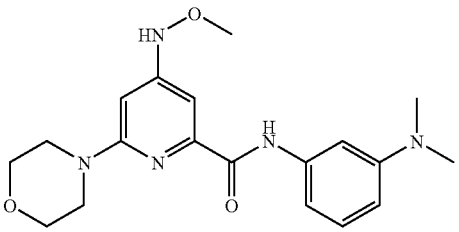

4-Methoxyamino-6-morpholin-4-yl-pyridine-2-car-
boxylic acid (3-dimethylamino-phenyl)-amide Compound 161

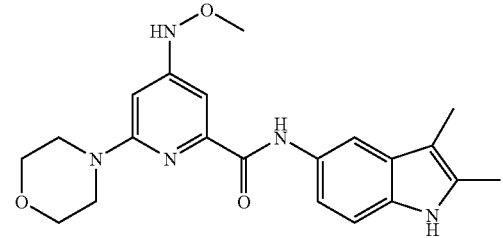

4-Methoxyamino-6-morpholin-4-yl-pyridine-2-car-
boxylic acid (2,3-dimethyl-1H-indol-5-yl)-amide Compound 162

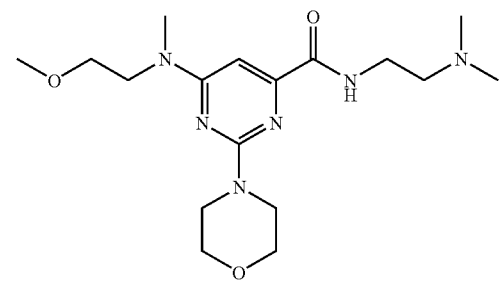

6-[(2-Methoxy-ethyl)-methyl-amino]-2-morpholin-
4-yl-pyrimidine-4-carboxylic acid (2-dimethy-
lamino-ethyl)-amide Compound 163

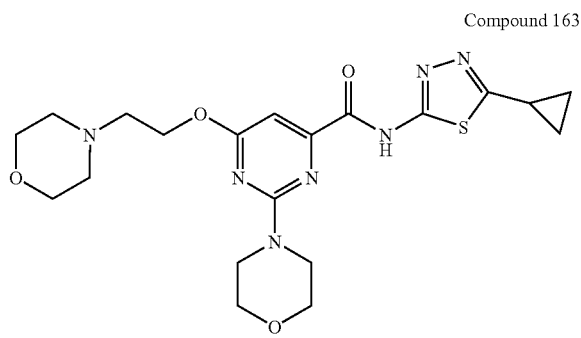

2-Morpholin-4-yl-6-(2-morpholin-4-yl-ethoxy)-pyrimidine-4-carboxylic acid (5-cyclopropyl-[1,3,4]thiadiazol-2-yl)-amide Compound 164

6-[(2-Methoxy-ethyl)-methyl-amino]-2-morpholin-4-yl-pyrimidine-4-carboxylic acid (3-diethylaminomethyl-4-hydroxy-phenyl)-amide, Compound 165

6-[(2-Methoxy-ethyl)-methyl-amino]-2-morpholin-4-yl-pyrimidine-4-carboxylic acid (4-acetylaminophenyl)-amide Compound 166

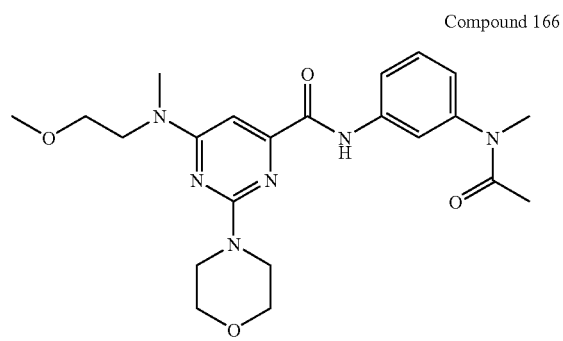

6-[(2-Methoxy-ethyl)-methyl-amino]-2-morpholin-4-yl-pyrimidine-4-carboxylic acid [3-(acetyl-methyl-amino)-phenyl]-amide Compound 167

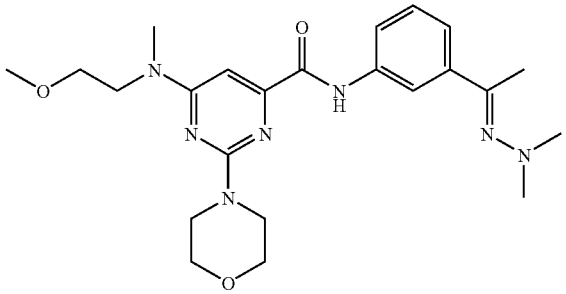

(E)-N-(3-(1-(2,2-dimethylhydrazono)ethyl)phenyl)-6-((2-methoxyethyl)(methyl)amino)-2-morpholinopyrimidine-4-carboxamide Compound 168

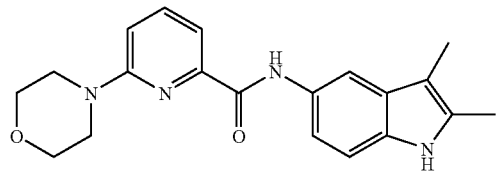

6-Morpholin-4-yl-pyridine-2-carboxylic acid (2,3-dimethyl-1H-indol-5-yl)-amide

Compound 169

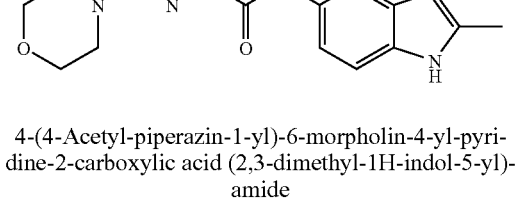

4-(4-Acetyl-piperazin-1-yl)-6-morpholin-4-yl-pyridine-2-carboxylic acid (2,3-dimethyl-1H-indol-5-yl)-amide Compound 170

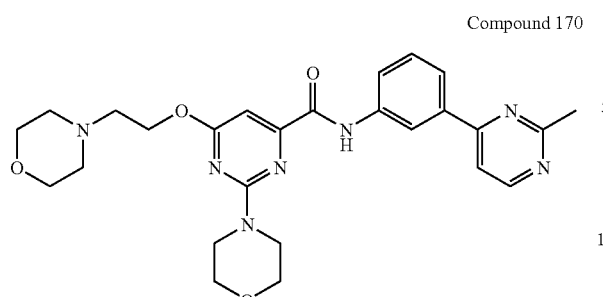

2-Morpholin-4-yl-6-(2-morpholin-4-yl-ethoxy)-pyrimidine-4-carboxylic acid [3-(2-methyl-pyrimidin-4-yl)-phenyl]-amide Compound 171

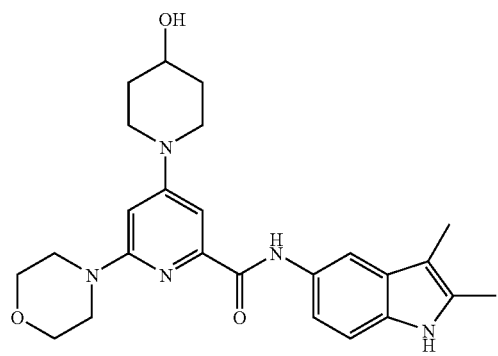

4-Hydroxy-6'-morpholin-4-yl-3,4,5,6-tetrahydro-2H-[1,4']bipyridinyl-2'-carboxylic acid (2,3-dimethyl-1H-indol-5-yl)-amide Compound 172

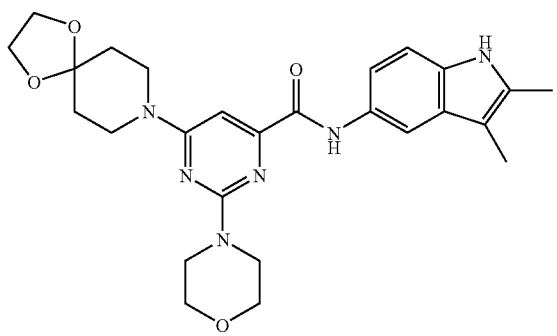

6-(1,4-Dioxa-8-aza-spiro[4.5]dec-8-yl)-2-morpholin-4-yl-pyrimidine-4-carboxylic acid (2,3-dimethyl-1H-indol-5-yl)-amide Compound 173

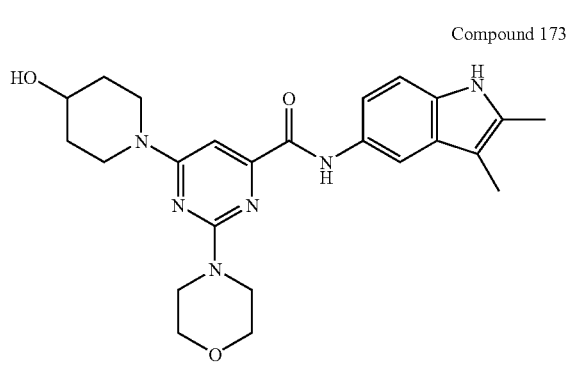

6-(4-Hydroxy-piperidin-1-yl)-2-morpholin-4-yl-pyrimidine-4-carboxylic acid (2,3-dimethyl-1H-indol-5-yl)-amide Compound 174

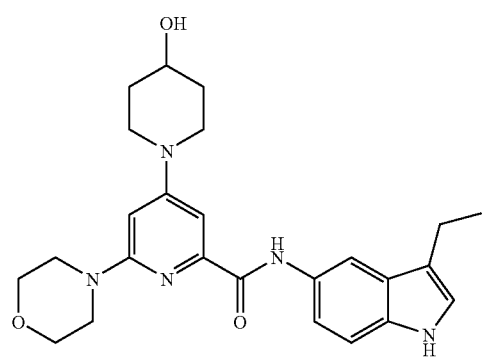

4-Hydroxy-6'-morpholin-4-yl-3,4,5,6-tetrahydro-2H-[1,4']bipyridinyl-2'-carboxylic acid (3-ethyl-1H-indol-5-yl)-amide Compound 175

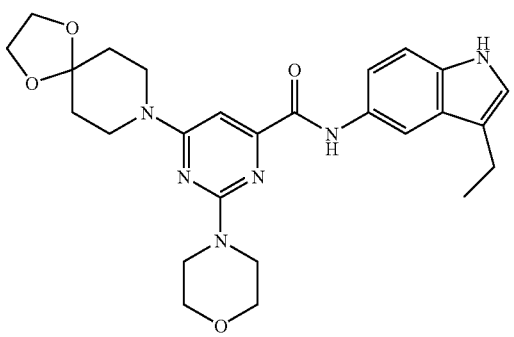

6-(1,4-Dioxa-8-aza-spiro[4.5]dec-8-yl)-2-morpholin-4-yl-pyrimidine-4-carboxylic acid (3-ethyl-1H-indol-5-yl)-amide Compound 176

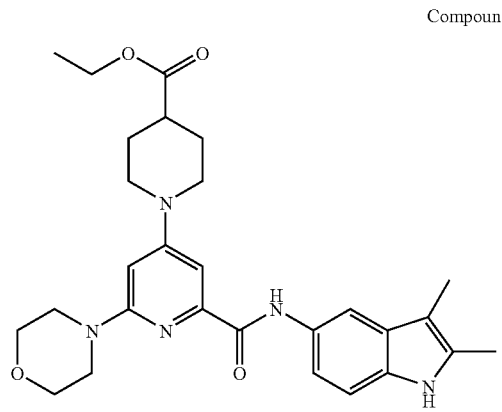

2'-(2,3-Dimethyl-1H-indol-5-ylcarbamoyl)-6'-morpholin-4-yl-3,4,5,6-tetrahydro-2H-[1,4]bipyridinyl-4-carboxylic acid ethyl ester Compound 177

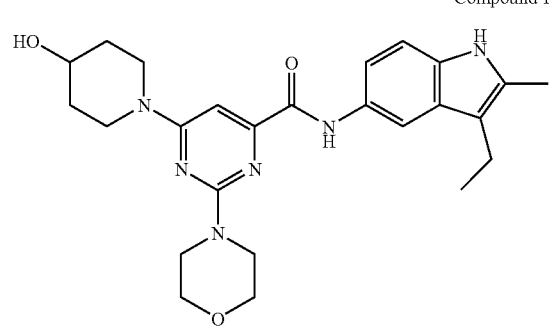

6-(4-Hydroxy-piperidin-1-yl)-2-morpholin-4-yl-pyrimidine-4-carboxylic acid (3-ethyl-2-methyl-1H-indol-5-yl)-amide Compound 178

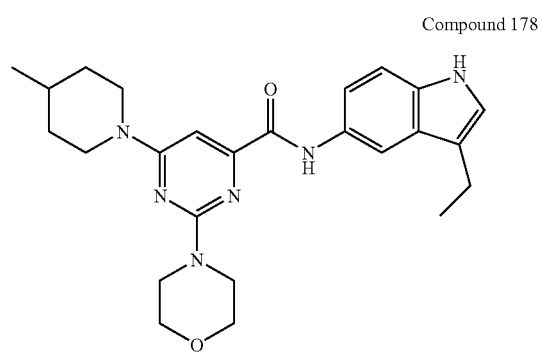

6-(4-Methyl-piperidin-1-yl)-2-morpholin-4-yl-pyrimidine-4-carboxylic acid (3-ethyl-1H-indol-5-yl)-amide Compound 179

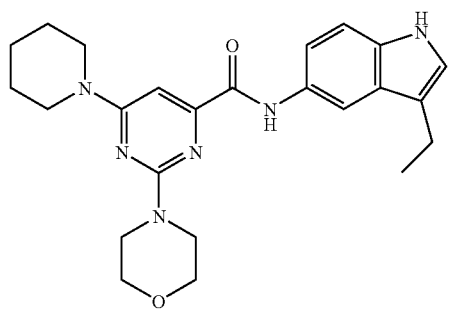

2-Morpholin-4-yl-6-piperidin-1-yl-pyrimidine-4-carboxylic acid (3-ethyl-1H-indol-5-yl)-amide Compound 180

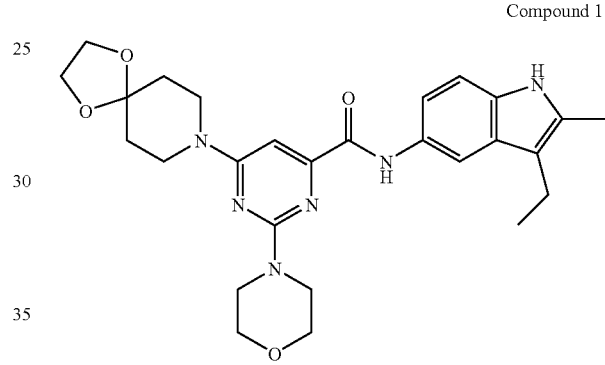

6-(1,4-Dioxa-8-aza-spiro[4.5]dec-8-yl)-2-morpholin-4-yl-pyrimidine-4-carboxylic acid (3-ethyl-2-methyl-1H-indol-5-yl)-amide Compound 181

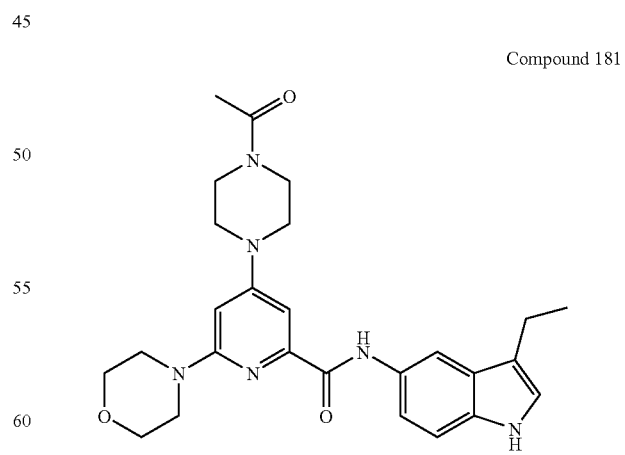

4-(4-Acetyl-piperazin-1-yl)-6-morpholin-4-yl-pyridine-2-carboxylic acid (3-ethyl-1H-indol-5-yl)-amide Compound 182

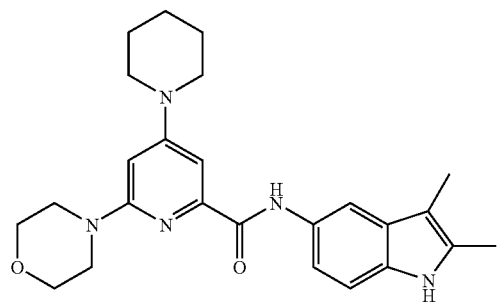

6-Morpholin-4-yl-3,4,5,6-tetrahydro-2H-[1,4']bipy-
ridinyl-2'-carboxylic acid (2,3-dimethyl-1H-indol-5-
yl)-amide Compound 183

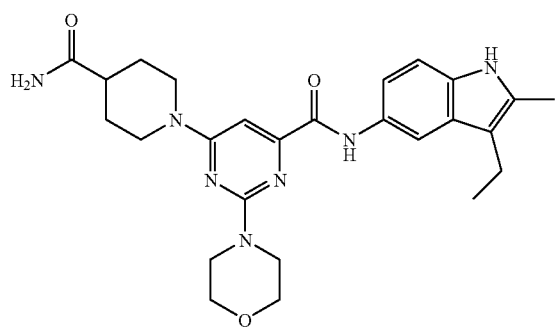

6-(4-Carbamoyl-piperidin-1-yl)-2-morpholin-4-yl-
pyrimidine-4-carboxylic acid (3-ethyl-2-methyl-1H-
indol-5-yl)-amide Compound 184

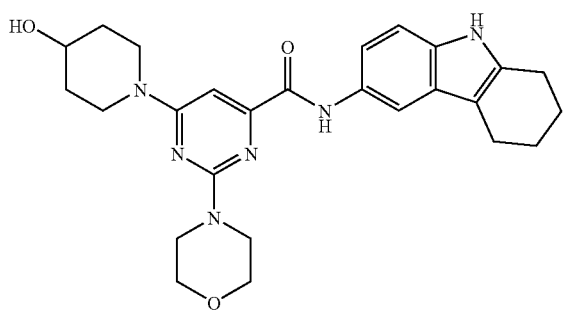

6-(4-Hydroxy-piperidin-1-yl)-2-morpholin-4-yl-
pyrimidine-4-carboxylic acid (6,7,8,9-tetrahydro-
5H-carbazol-3-yl)-amide Compound 185

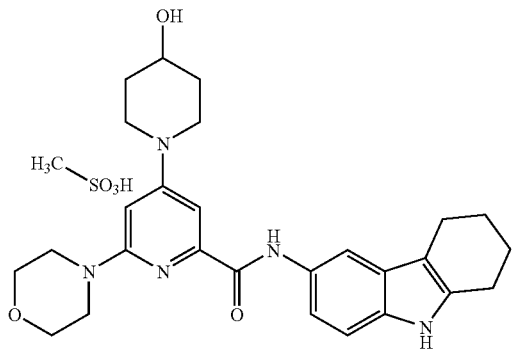

4-Hydroxy-6'-morpholin-4-yl-3,4,5,6-tetrahydro-2H-
[1,4']bipyridinyl-2'-carboxylic acid (6,7,8,9-tetrahy-
dro-5H-carbazol-3-yl)-amide; compound with meth-
anesulfonic acid Compound 186

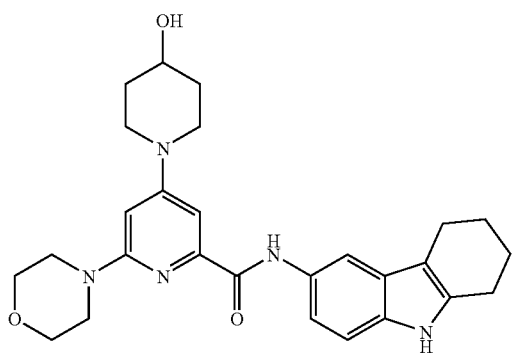

4-Hydroxy-6'-morpholin-4-yl-3,4,5,6-tetrahydro-2H-
[1,4']bipyridinyl-2'-carboxylic acid (6,7,8,9-tetrahy-
dro-5H-carbazol-3-yl)-amide Compound 187

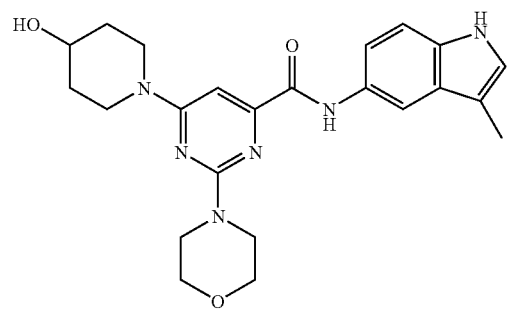

6-(4-Hydroxy-piperidin-1-yl)-2-morpholin-4-yl-
pyrimidine-4-carboxylic acid (3-methyl-1H-indol-5-
yl)-amide Compound 188

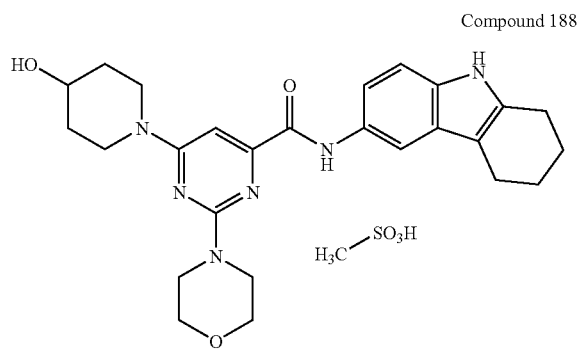

6-(4-Hydroxy-piperidin-1-yl)-2-morpholin-4-yl-pyrimidine-4-carboxylic acid (6,7,8,9-tetrahydro-5H-carbazol-3-yl)-amide; compound with methane-sulfonic acid Compound 189

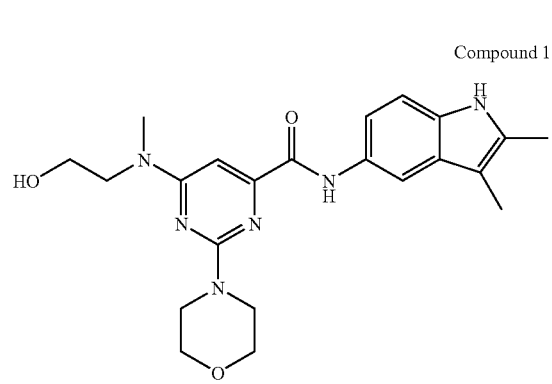

N-(2,3-dimethyl-1H-indol-5-yl)-6-((2-hydroxyethyl)(methyl)amino)-2-morpholinopyrimidine-4-carboxamide Compound 190

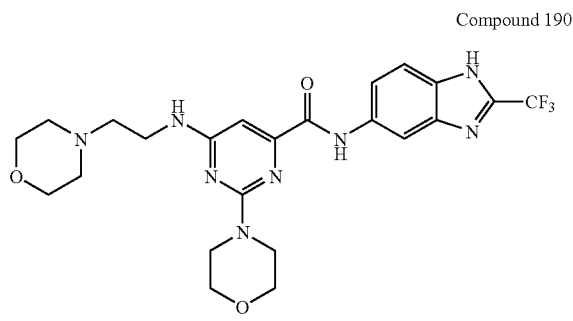

2-morpholino-6-(2-morpholinoethylamino)-N-(2-(trifluoromethyl)-1H-benzo[d]imidazol-5-yl)pyrimidine-4-carboxamide Compound 191

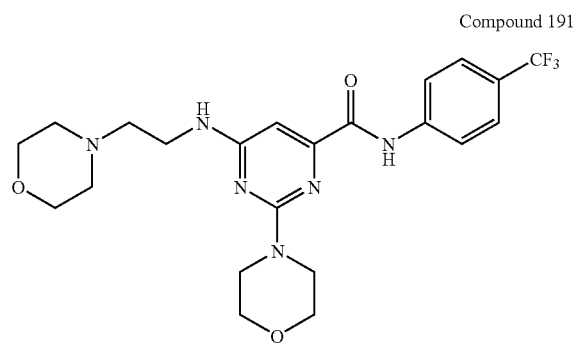

2-morpholino-6-(2-morpholinoethylamino)-N-(4-(trifluoromethyl)phenyl)pyrimidine-4-carboxamide Compound 192

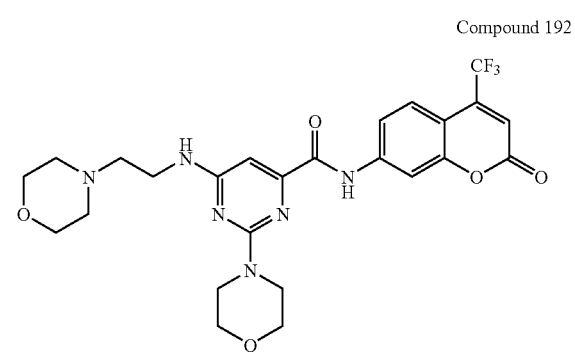

2-morpholino-6-(2-morpholinoethylamino)-N-(2-oxo-4-(trifluoromethyl)-2H-chromen-7-yl)pyrimidine-4-carboxamide Compound 193

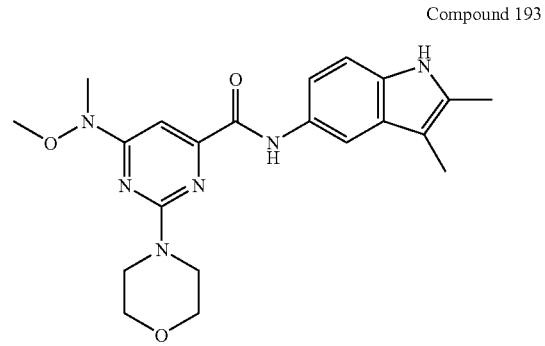

N-(2,3-dimethyl-1H-indol-5-yl)-6-(methoxy(methyl)amino)-2-morpholinopyrimidine-4-carboxamide Compound 194

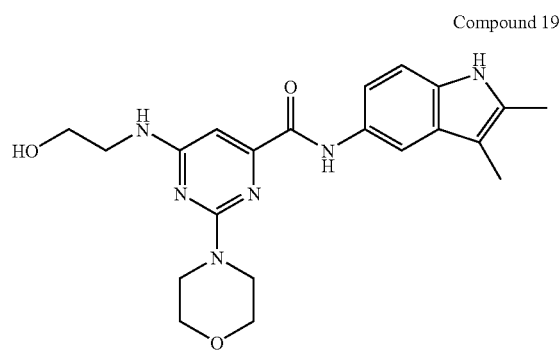

N-(2,3-dimethyl-1H-indol-5-yl)-6-(2-hydroxyethylamino)-2-morpholinopyrimidine-4-carboxamide Compound 197

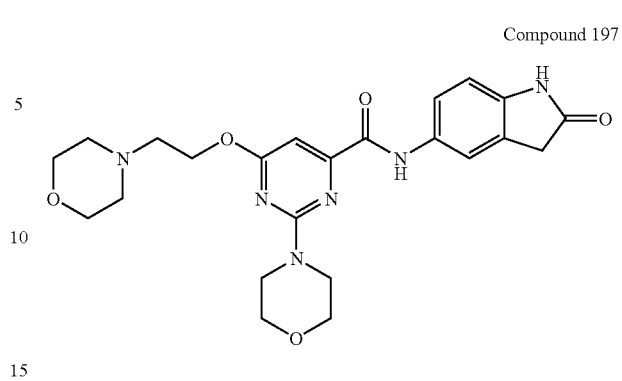

2-morpholino-6-(2-morpholinoethoxy)-N-(2-oxoindolin-5-yl)pyrimidine-4-carboxamide Compound 195

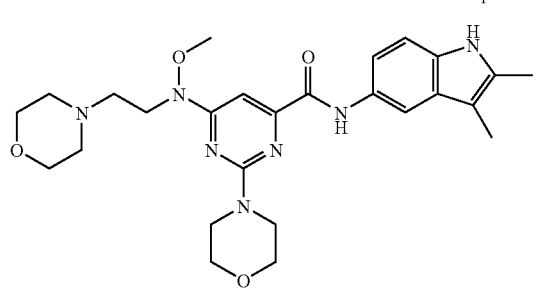

N-(2,3-dimethyl-1H-indol-5-yl)-6-(methoxy(2-morpholinoethyl)amino)-2-morpholinopyrimidine-4-carboxamide Compound 198

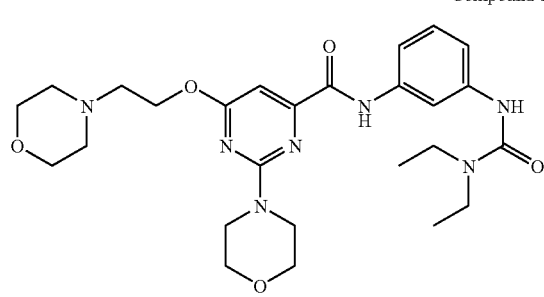

N-(3-(3,3-diethylureido)phenyl)-2-morpholino-6-(2-morpholinoethoxy)pyrimidine-4-carboxamide Compound 196

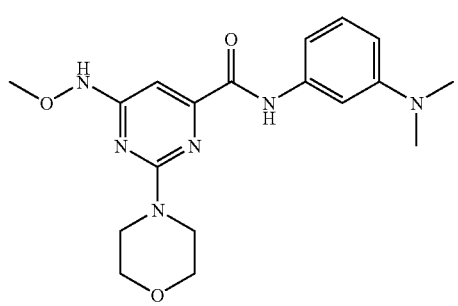

N-(3-(dimethylamino)phenyl)-6-(methoxyamino)-2-morpholinopyrimidine-4-carboxamide Compound 199

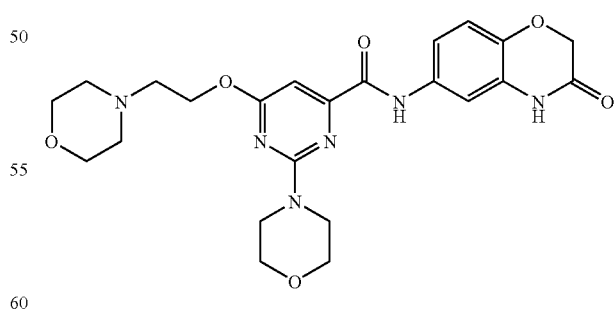

2-morpholino-6-(2-morpholinoethoxy)-N-(3-oxo-3,4-dihydro-2H-benzo[b][1,4]oxazin-6-yl)pyrimidine-4-carboxamide

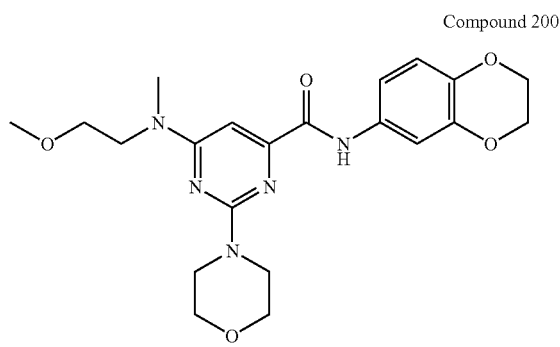

Compound 200

N-(2,3-dihydrobenzo[b][1,4]dioxin-6-yl)-6-(2-methoxyethyl)(methyl)amino)-2-morpholinopyrimidine-4-carboxamide

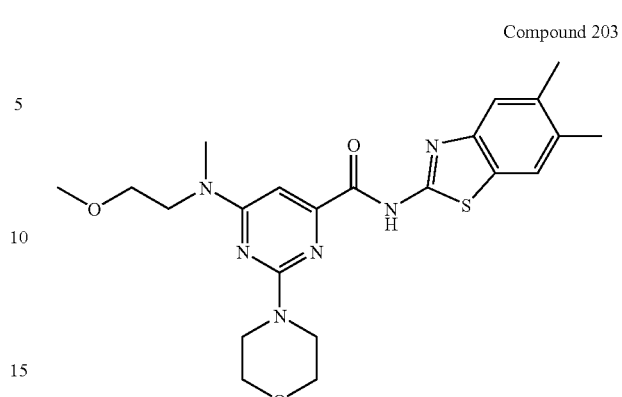

Compound 203

N-(5,6-dimethylbenzo[d]thiazol-2-yl)-6-((2-methoxyethyl)(methyl)amino)-2-morpholinopyrimidine-4-carboxamide

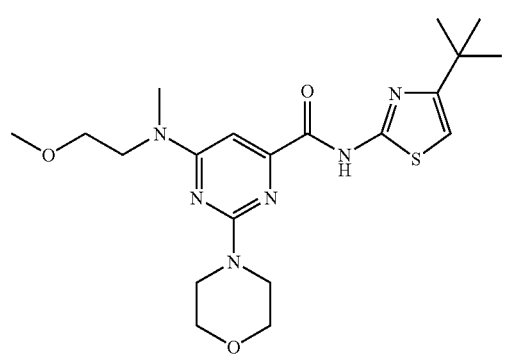

Compound 201

N-(4-tert-butylthiazol-2-yl)-6-((2-methoxyethyl)(methyl)amino)-2-morpholinopyrimidine-4-carboxamide

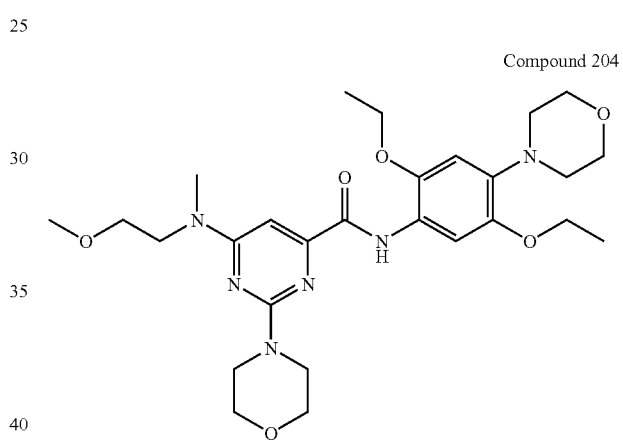

Compound 204

N-(2,5-diethoxy-4-morpholinophenyl)-6-((2-methoxyethyl)(methyl)amino)-2-morpholinopyrimidine-4-carboxamide

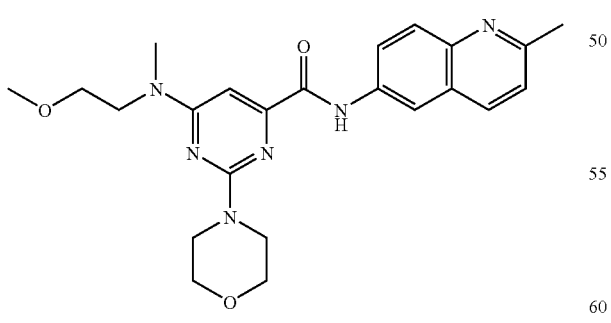

Compound 202

6-((2-methoxyethyl)(methyl)amino)-N-(2-methylquinolin-6-yl)-2-morpholinopyrimidine-4-carboxamide

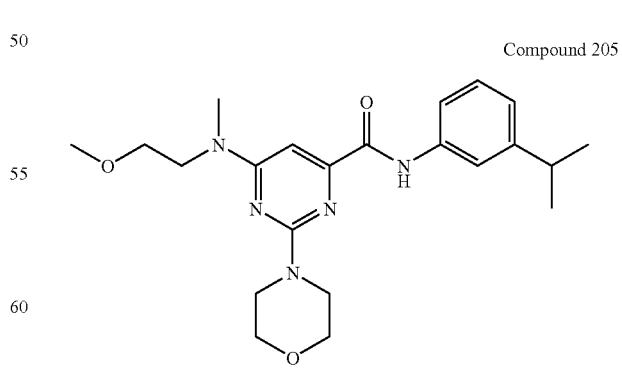

Compound 205

N-(3-isopropylphenyl)-6-((2-methoxyethyl)(methyl)amino)-2-morpholinopyrimidine-4-carboxamide Compound 206

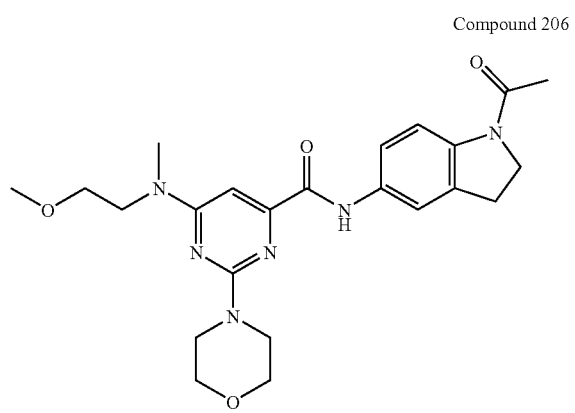

N-(1-acetylindolin-5-yl)-6-((2-methoxyethyl)(methyl)amino)-2-morpholinopyrimidine-4-carboxamide Compound 207

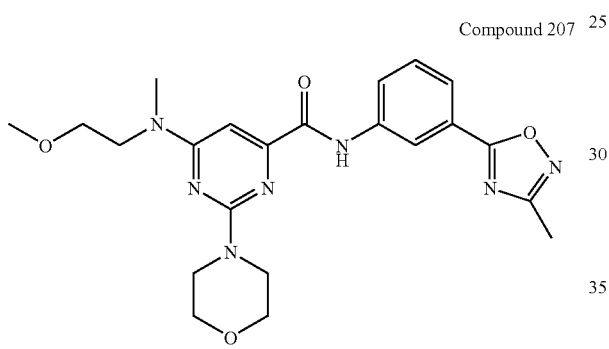

6-((2-methoxyethyl)(methyl)amino)-N-(3-(3-methyl-1,2,4-oxadiazol-5-yl)phenyl)-2-morpholinopyrimidine-4-carboxamide Compound 208

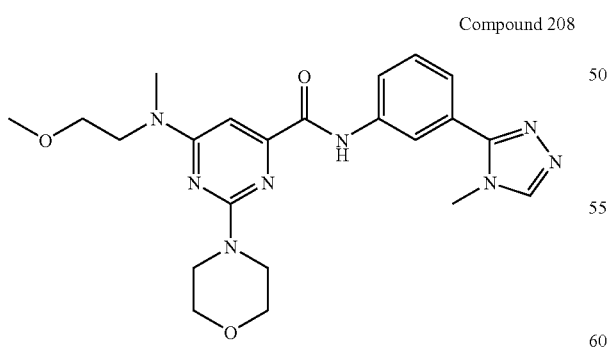

6-((2-methoxyethyl)(methyl)amino)-N-(3-(4-methyl-4H-1,2,4-triazol-3-yl)phenyl)-2-morpholinopyrimidine-4-carboxamide Compound 209

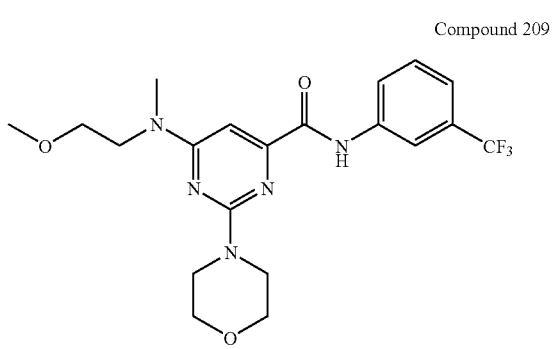

6-((2-methoxyethyl)(methyl)amino)-2-morpholino-N-(3-(trifluoromethyl)phenyl)pyrimidine-4-carboxamide Compound 210

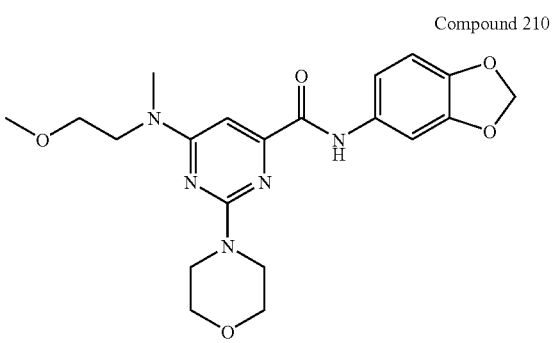

N-(benzo[d][1,3]dioxol-5-yl)-6-((2-methoxyethyl)(methyl)amino)-2-morpholinopyrimidine-4-carboxamide Compound 211

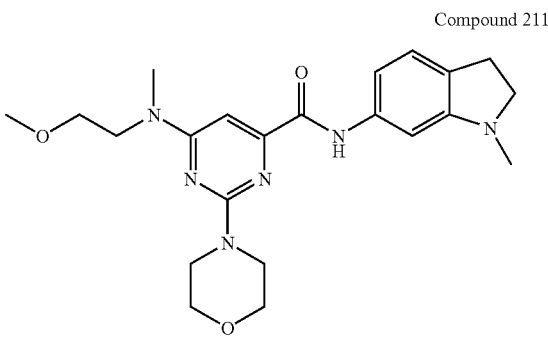

6-((2-methoxyethyl)(methyl)amino)-N-(1-methylindolin-6-yl)-2-morpholinopyrimidine-4-carboxamide

101

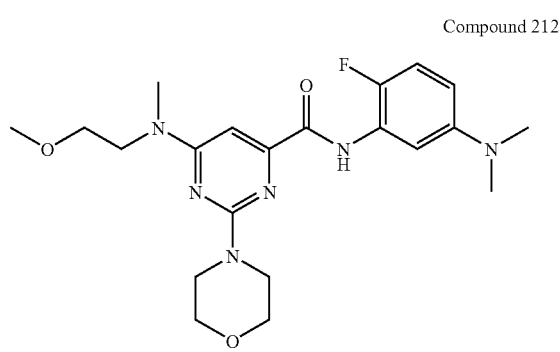

Compound 212

N-(5-(dimethylamino)-2-fluorophenyl)-6-((2-methoxyethyl)(methyl)amino)-2-morpholinopyrimidine-4-carboxamide

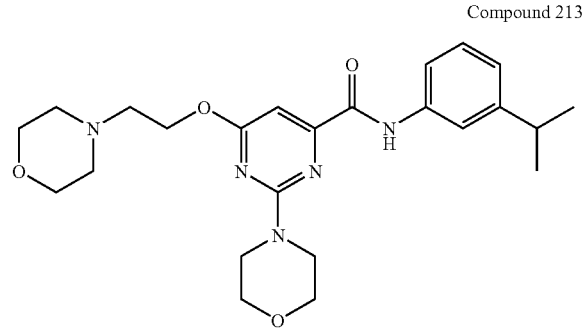

Compound 213

N-(3-isopropylphenyl)-2-morpholino-6-(2-morpholinoethoxy)pyrimidine-4-carboxamide

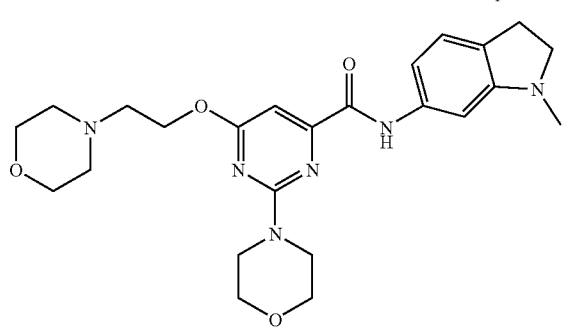

Compound 214

N-(1-methylindolin-6-yl)-2-morpholino-6-(2-morpholinoethoxy)pyrimidine-4-carboxamide

102

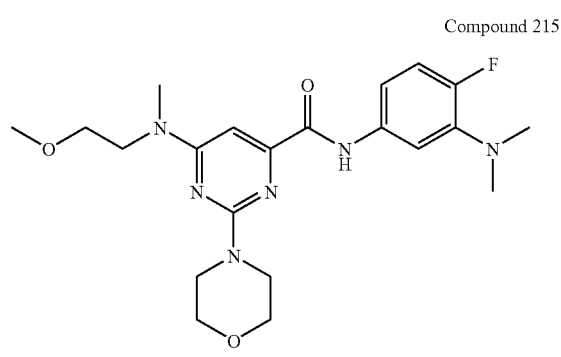

Compound 215

N-(3-(dimethylamino)-4-fluorophenyl)-6-((2-methoxyethyl)(methyl)amino)-2-morpholinopyrimidine-4-carboxamide

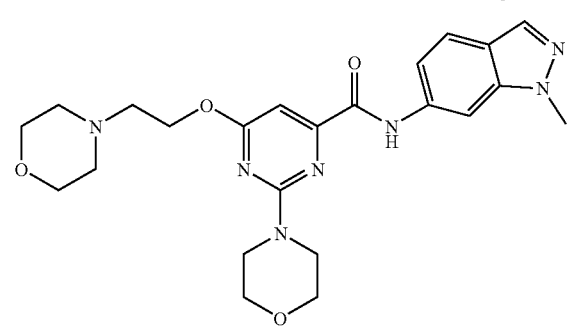

Compound 216

N-(1-methyl-1H-indazol-6-yl)-2-morpholino-6-(2-morpholinoethoxy)pyrimidine-4-carboxamide

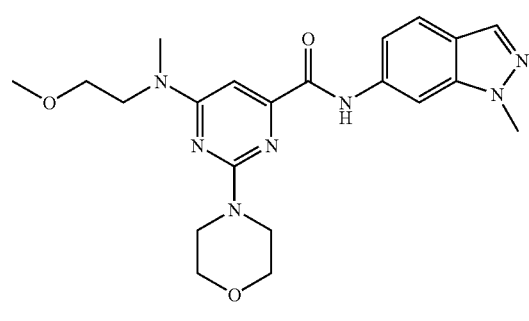

Compound 217

6-((2-methoxyethyl)(methyl)amino)-N-(1-methyl-1H-indazol-6-yl)-2-morpholinopyrimidine-4-carboxamide Compound 218

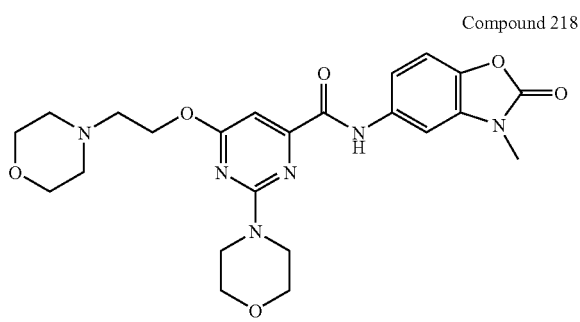

N-(3-methyl-2-oxo-2,3-dihydrobenzo[d]oxazol-5-yl)-2-morpholino-6-(2-morpholinoethoxy)pyrimidine-4-carboxamide Compound 219

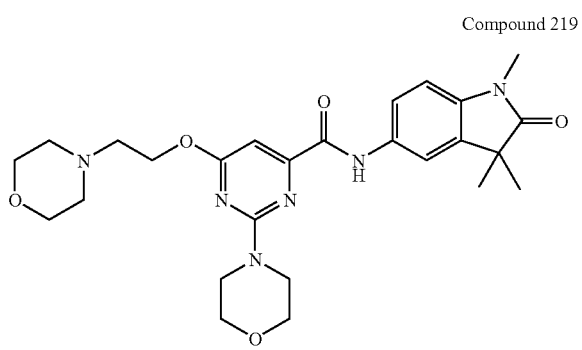

2-morpholino-6-(2-morpholinoethoxy)-N-(1,3,3-trimethyl-2-oxoindolin-5-yl)pyrimidine-4-carboxamide Compound 220

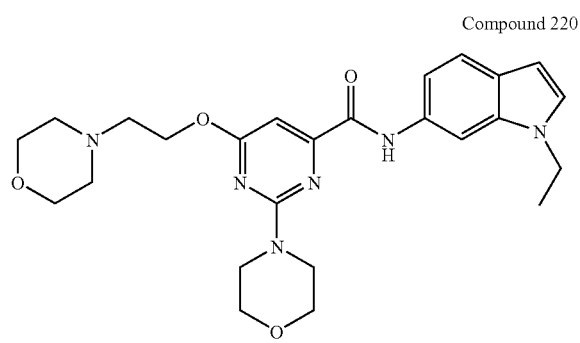

N-(1-ethyl-1H-indol-6-yl)-2-morpholino-6-(2-morpholinoethoxy)pyrimidine-4-carboxamide Compound 221

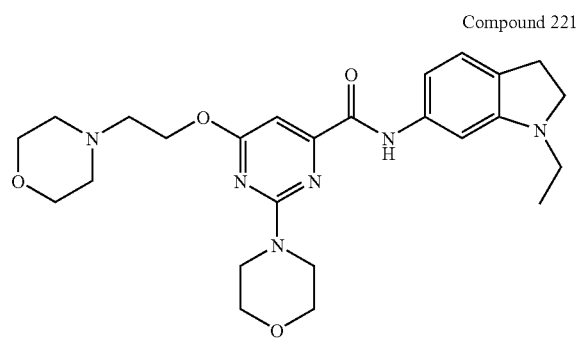

N-(1-ethylindolin-6-yl)-2-morpholino-6-(2-morpholinoethoxy)pyrimidine-4-carboxamide Compound 222

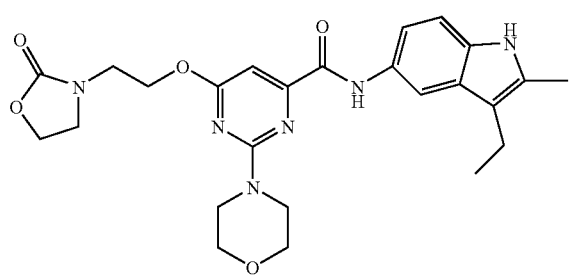

2-Morpholin-4-yl-6-[2-(2-oxo-oxazolidin-3-yl)-ethoxy]-pyrimidine-4-carboxylic acid (3-ethyl-2-methyl-1H-indol-5-yl)-amide Compound 223

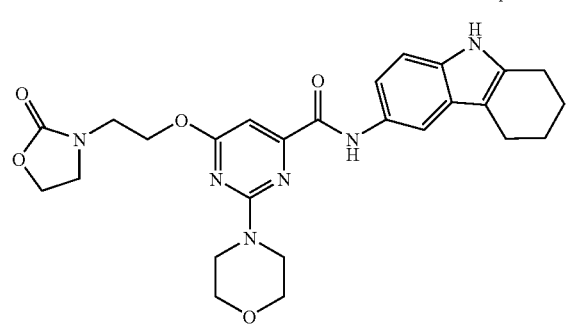

2-Morpholin-4-yl-6-[2-(2-oxo-oxazolidin-3-yl)-ethoxy]-pyrimidine-4-carboxylic acid (6,7,8,9-tetrahydro-5H-carbazol-3-yl)-amide Compound 224

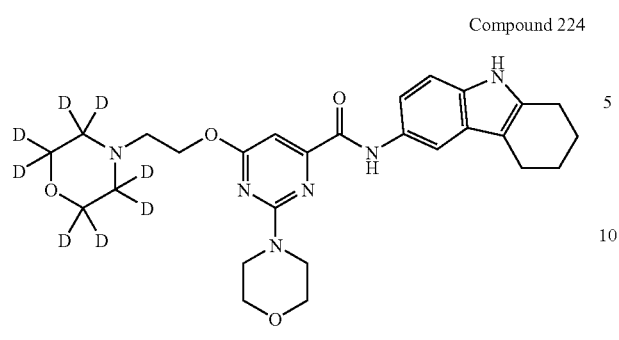

2-Morpholin-4-yl-6-(2-(2,2,3,3,5,5,6,6-octadeutero-morpholin-4-yl-ethoxy)-pyrimidine-4-carboxylic acid (6,7,8,9-tetrahydro-5H-carbazol-3-yl)-amide Compound 225

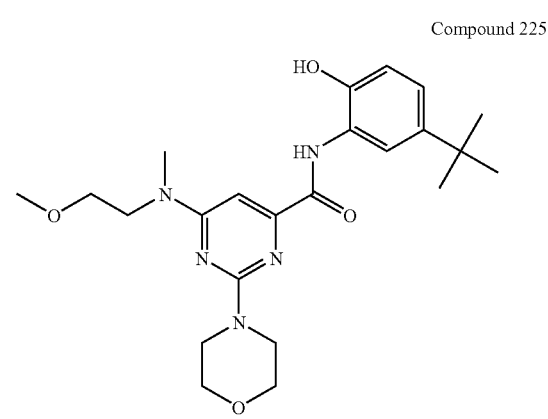

6-[(2-Methoxy-ethyl)-methyl-amino]-2-morpholin-4-yl-pyrimidine-4-carboxylic acid (5-tert-butyl-2-hydroxy-phenyl)-amide Compound 226

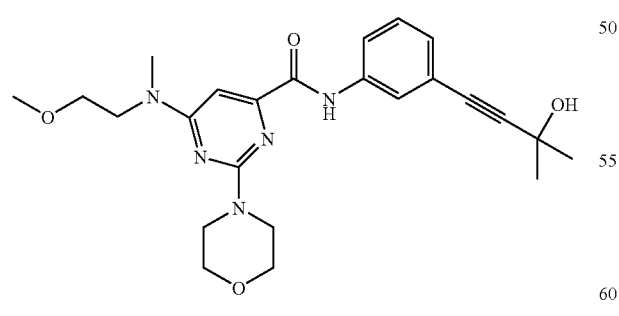

6-[(2-Methoxy-ethyl)-methyl-amino]-2-morpholin-4-yl-pyrimidine-4-carboxylic acid [3-(3-hydroxy-3-methyl-but-1-ynyl)-phenyl]-amide Compound 227

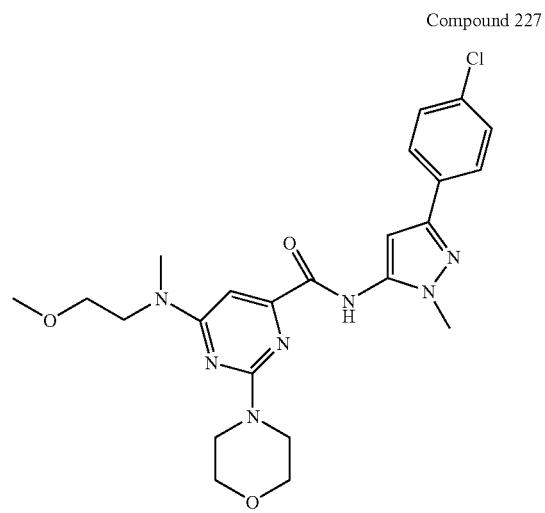

6-[(2-Methoxy-ethyl)-methyl-amino]-2-morpholin-4-yl-pyrimidine-4-carboxylic acid [5-(4-chloro-phenyl)-2-methyl-2H-pyrazol-3-yl]-amide Compound 228

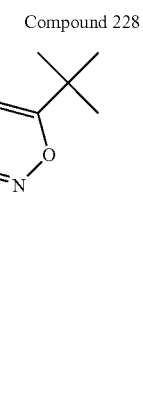

6-[(2-Methoxy-ethyl)-methyl-amino]-2-morpholin-4-yl-pyrimidine-4-carboxylic acid (5-tert-butyl-isoxazol-3-yl)-amide Compound 229

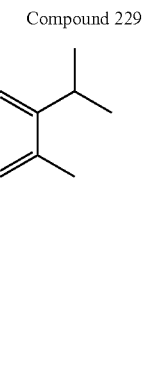

6-[(2-Methoxy-ethyl)-methyl-amino]-2-morpholin-4-yl-pyrimidine-4-carboxylic acid (4-isopropyl-3-methyl-phenyl)-amide Compound 230

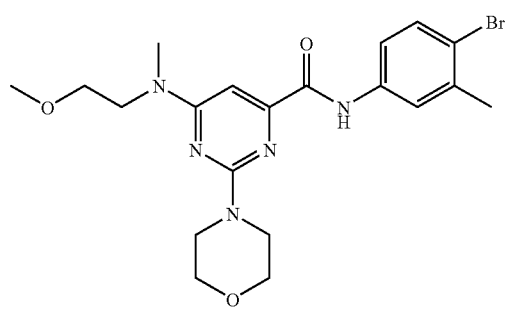

6-[(2-Methoxy-ethyl)-methyl-amino]-2-morpholin-4-yl-pyrimidine-4-carboxylic acid (4-bromo-3-methyl-phenyl)-amide Compound 233

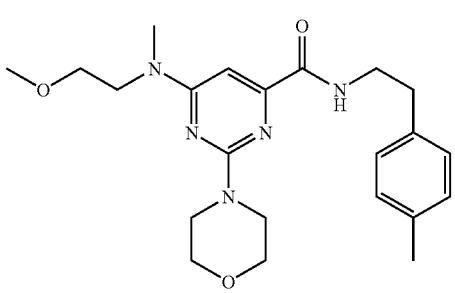

6-[(2-Methoxy-ethyl)-methyl-amino]-2-morpholin-4-yl-pyrimidine-4-carboxylic acid (2-p-tolyl-ethyl)-amide Compound 231

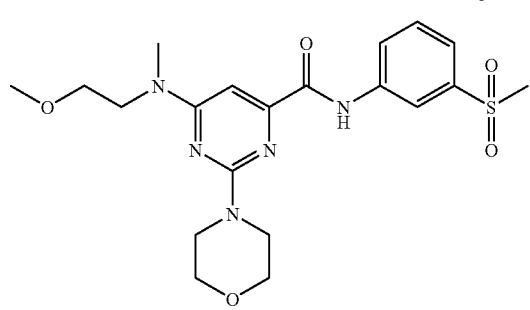

6-[(2-Methoxy-ethyl)-methyl-amino]-2-morpholin-4-yl-pyrimidine-4-carboxylic acid (3-methanesulfonyl-phenyl)-amide Compound 234

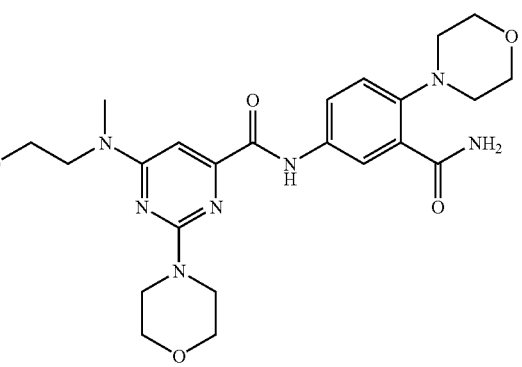

6-[(2-Methoxy-ethyl)-methyl-amino]-2-morpholin-4-yl-pyrimidine-4-carboxylic acid (3-carbamoyl-4-morpholin-4-yl-phenyl)-amide Compound 232

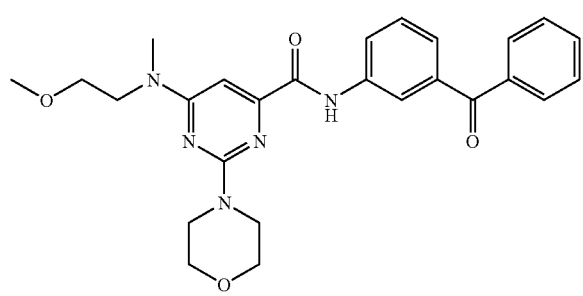

6-[(2-Methoxy-ethyl)-methyl-amino]-2-morpholin-4-yl-pyrimidine-4-carboxylic acid (3-benzoyl-phenyl)-amide Compound 235

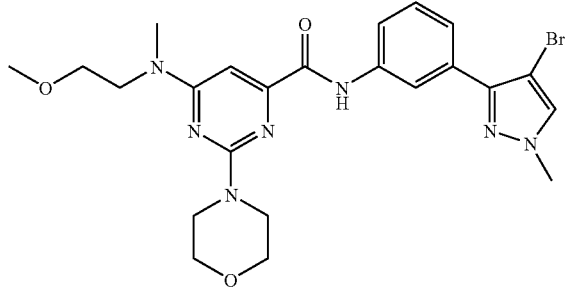

6-[(2-Methoxy-ethyl)-methyl-amino]-2-morpholin-4-yl-pyrimidine-4-carboxylic acid [3-(4-bromo-1-methyl-1H-pyrazol-3-yl)-phenyl]-amide Compound 236

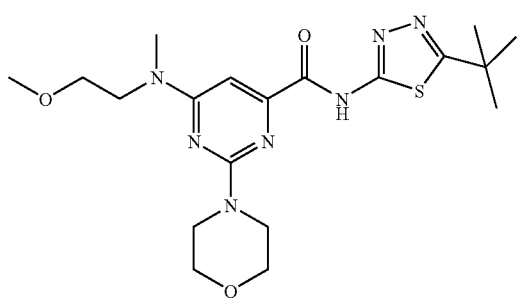

6-[(2-Methoxy-ethyl)-methyl-amino]-2-morpholin-4-yl-pyrimidine-4-carboxylic acid (5-tert-butyl-[1,3,4]thiadiazol-2-yl)-amide Compound 237

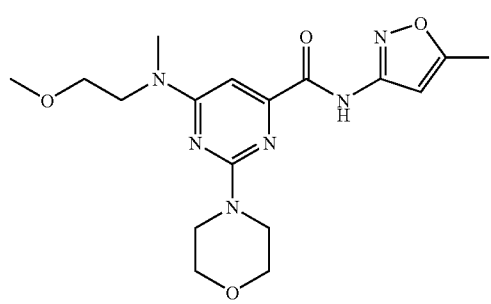

6-[(2-Methoxy-ethyl)-methyl-amino]-2-morpholin-4-yl-pyrimidine-4-carboxylic acid (5-methyl-isoxazol-3-yl)-amide Compound 238

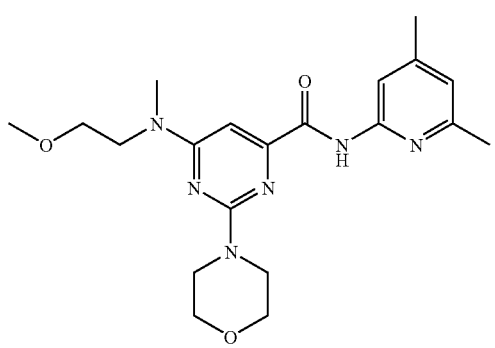

6-[(2-Methoxy-ethyl)-methyl-amino]-2-morpholin-4-yl-pyrimidine-4-carboxylic acid (4,6-dimethyl-pyridin-2-yl)-amide Compound 239

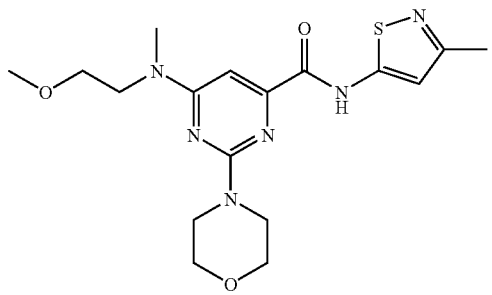

6-[(2-Methoxy-ethyl)-methyl-amino]-2-morpholin-4-yl-pyrimidine-4-carboxylic acid (3-methyl-isothiazol-5-yl)-amide Compound 240

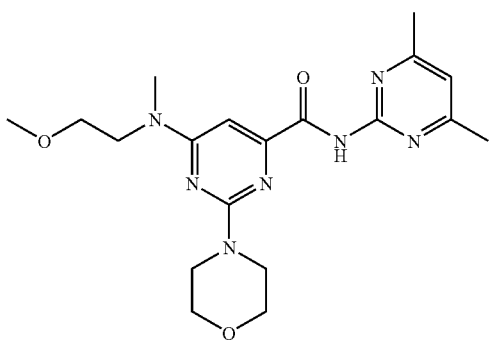

6-[(2-Methoxy-ethyl)-methyl-amino]-2-morpholin-4-yl-pyrimidine-4-carboxylic acid (4,6-dimethyl-pyrimidin-2-yl)-amide Compound 241

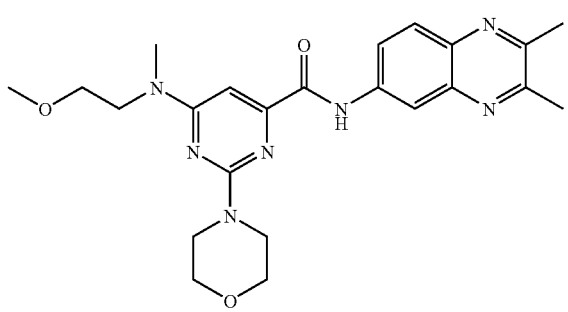

6-[(2-Methoxy-ethyl)-methyl-amino]-2-morpholin-4-yl-pyrimidine-4-carboxylic acid (2,3-dimethyl-quinoxalin-6-yl)-amide Compound 242

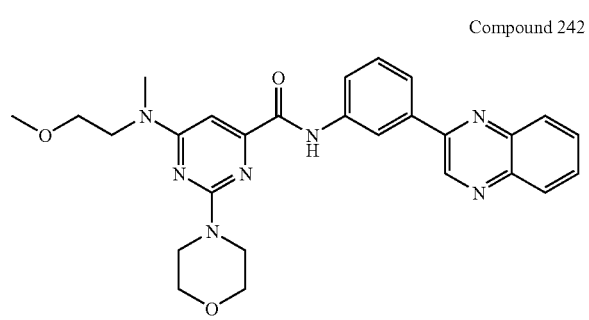

6-[(2-Methoxy-ethyl)-methyl-amino]-2-morpholin-4-yl-pyrimidine-4-carboxylic acid (3-quinoxalin-2-yl-phenyl)-amide Compound 245

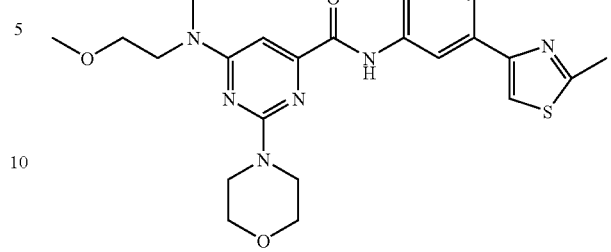

6-[(2-Methoxy-ethyl)-methyl-amino]-2-morpholin-4-yl-pyrimidine-4-carboxylic acid [3-(2-methyl-thiazol-4-yl)-phenyl]-amide Compound 243

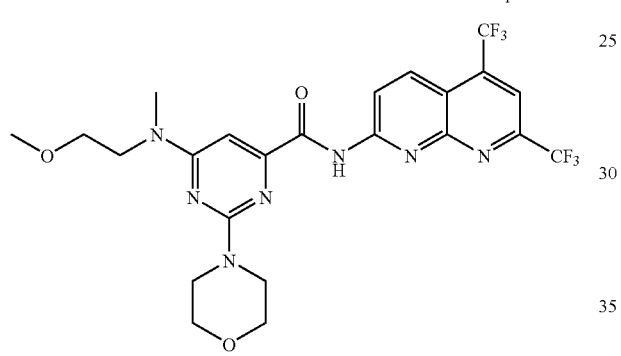

6-[(2-Methoxy-ethyl)-methyl-amino]-2-morpholin-4-yl-pyrimidine-4-carboxylic acid (5,7-bis-trifluoromethyl-[1,8]naphthyridin-2-yl)-amide Compound 246

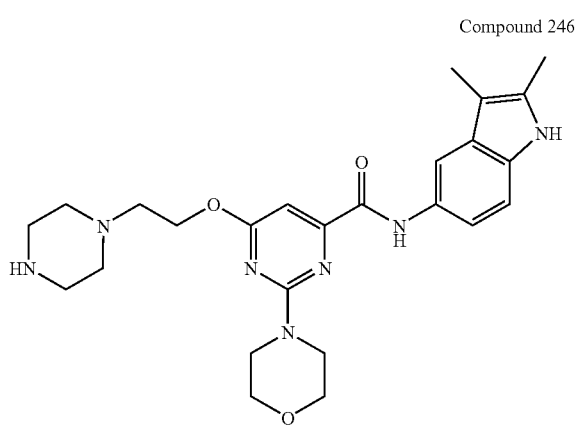

N-(2,3-dimethyl-1H-indol-5-yl)-2-morpholino-6-(2-(piperazin-1-yl)ethoxy)pyrimidine-4-carboxamide Compound 244

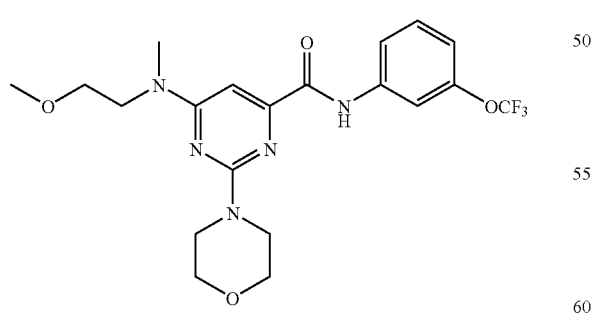

6-[(2-Methoxy-ethyl)-methyl-amino]-2-morpholin-4-yl-pyrimidine-4-carboxylic acid (3-trifluoromethoxy-phenyl)-amide Compound 247

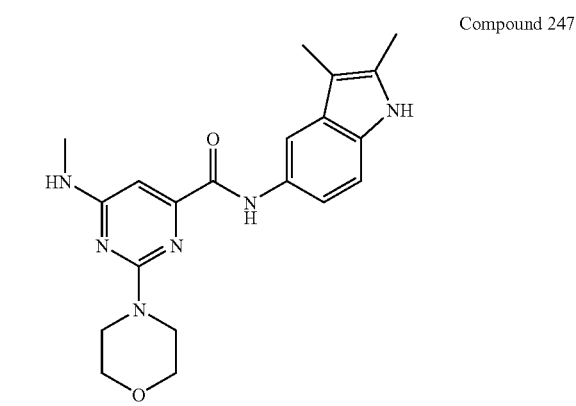

N-(2,3-dimethyl-1H-indol-5-yl)-6-(methylamino)-2-morpholinopyrimidine-4-carboxamide Compound 248

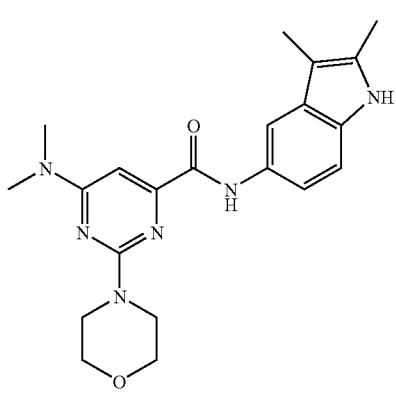

N-(2,3-dimethyl-1H-indol-5-yl)-6-(dimethylamino)-2-morpholinopyrimidine-4-carboxamide Compound 249

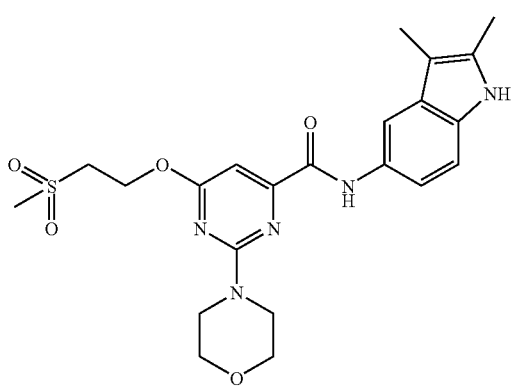

N-(2,3-dimethyl-1H-indol-5-yl)-6-(2-(methylsulfonyl)ethoxy)-2-morpholinopyrimidine-4-carboxamide Compound 250

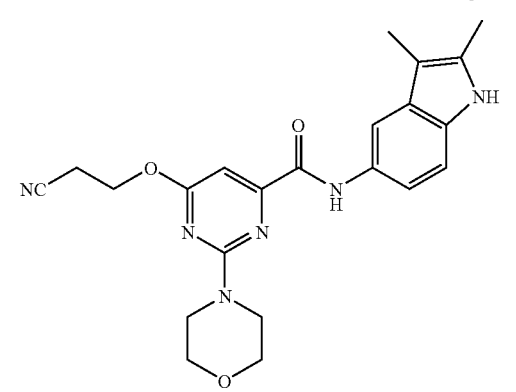

6-(2-cyanoethoxy)-N-(2,3-dimethyl-1H-indol-5-yl)-2-morpholinopyrimidine-4-carboxamide Compound 251

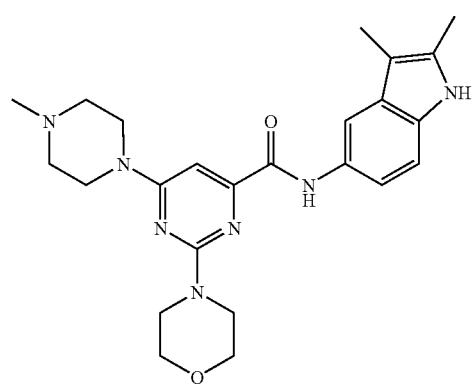

N-(2,3-dimethyl-1H-indol-5-yl)-6-(4-methylpiperazin-1-yl)-2-morpholinopyrimidine-4-carboxamide Compound 252

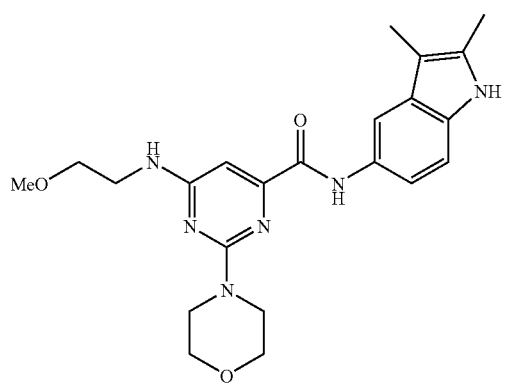

N-(2,3-dimethyl-1H-indol-5-yl)-6-(2-methoxyethylamino)-2-morpholinopyrimidine-4-carboxamide Compound 253

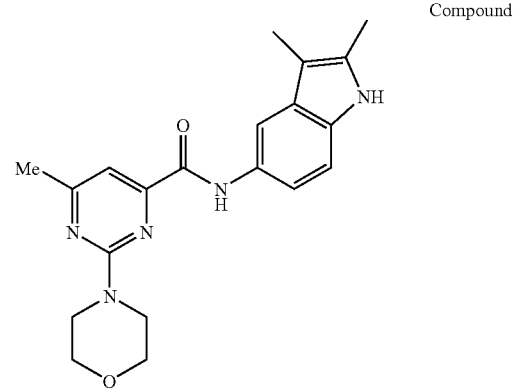

N-(2,3-dimethyl-1H-indol-5-yl)-6-methyl-2-morpholinopyrimidine-4-carboxamide

Compound 254

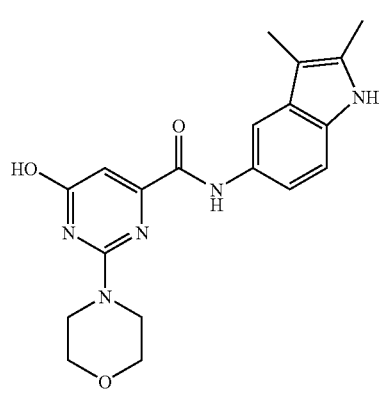

N-(2,3-dimethyl-1H-indol-5-yl)-6-hydroxy-2-morpholinopyrimidine-4-carboxamide

Compound 255

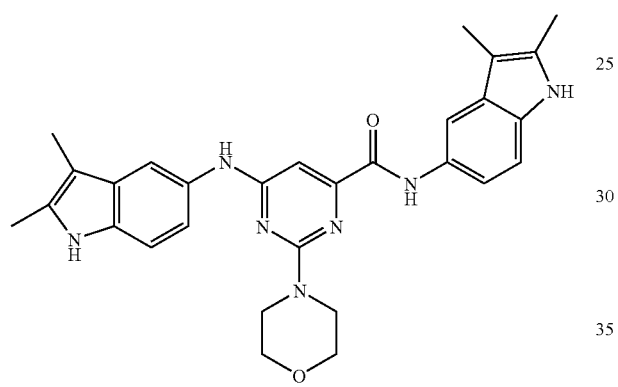

N-(2,3-dimethyl-1H-indol-5-yl)-6-(2,3-dimethyl-1H-indol-5-ylamino)-2-morpholinopyrimidine-4-carboxamide Compound 256

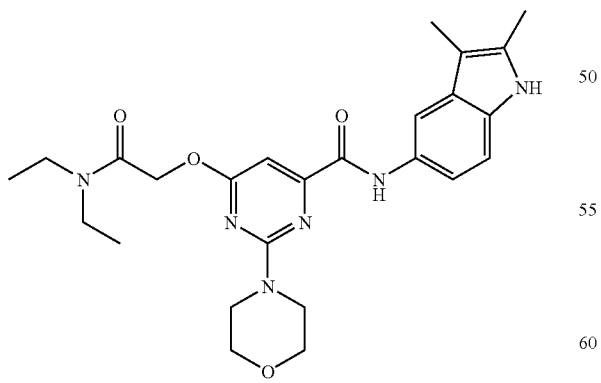

6-(2-(diethylamino)-2-oxoethoxy)-N-(2,3-dimethyl-1H-indol-5-yl)-2-morpholinopyrimidine-4-carboxamide Compound 257

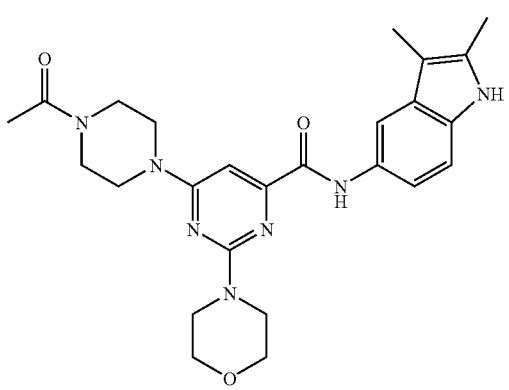

6-(4-acetylpiperazin-1-yl)-N-(2,3-dimethyl-1H-indol-5-yl)-2-morpholinopyrimidine-4-carboxamide Compound 258

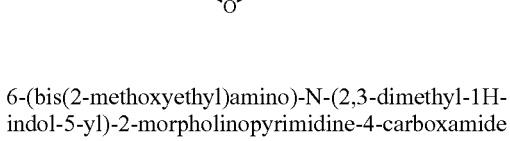

6-(bis(2-methoxyethyl)amino)-N-(2,3-dimethyl-1H-indol-5-yl)-2-morpholinopyrimidine-4-carboxamide Compound 259

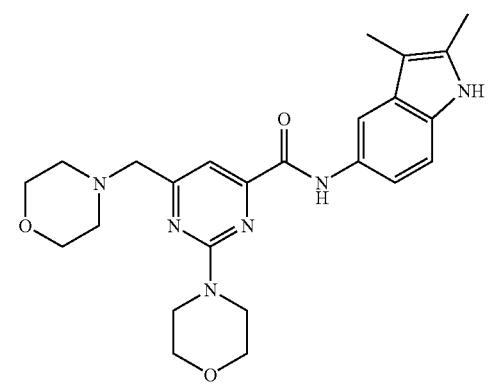

N-(2,3-dimethyl-1H-indol-5-yl)-2-morpholino-6-(morpholinomethyl)pyrimidine-4-carboxamide Compound 260

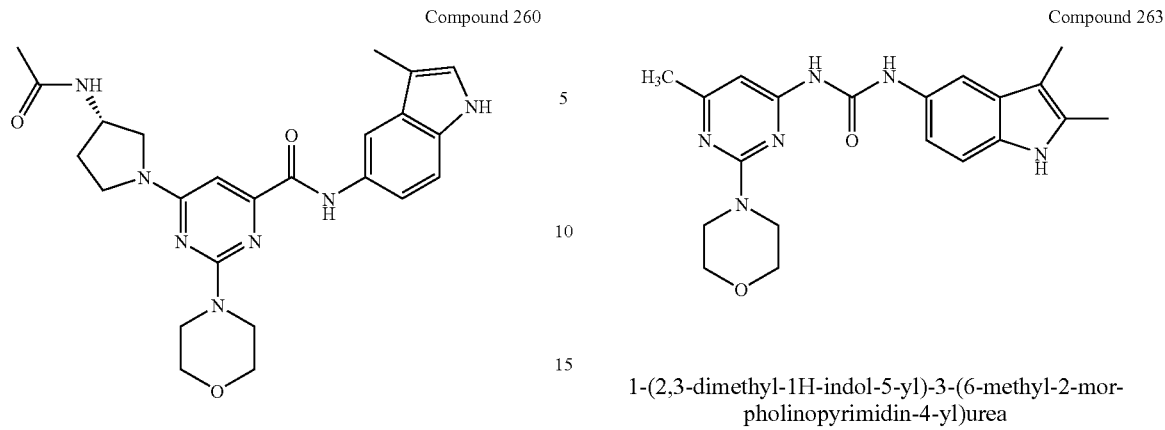

(S)-6-(3-acetamidopyrrolidin-1-yl)-N-(3-methyl-1H-indol-5-yl)-2-morpholinopyrimidine-4-carboxamide Compound 261

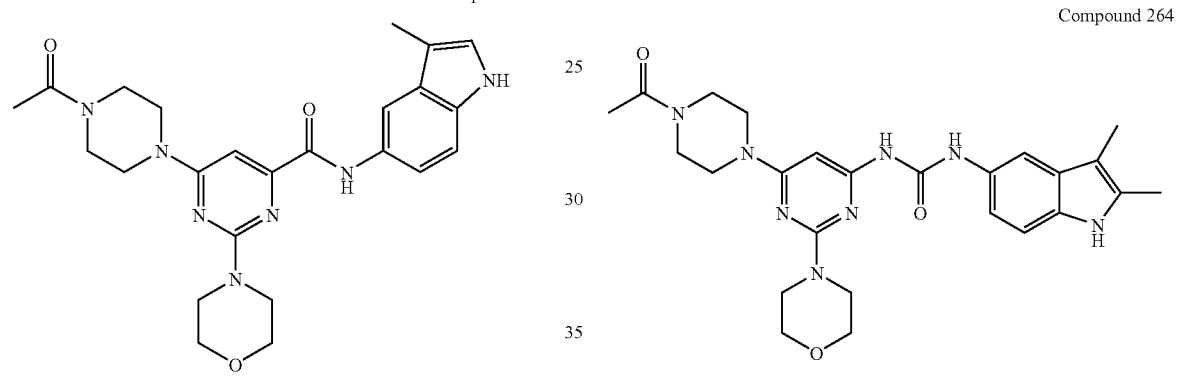

6-(4-acetylpiperazin-1-yl)-N-(3-methyl-1H-indol-5-yl)-2-morpholinopyrimidine-4-carboxamide Compound 262

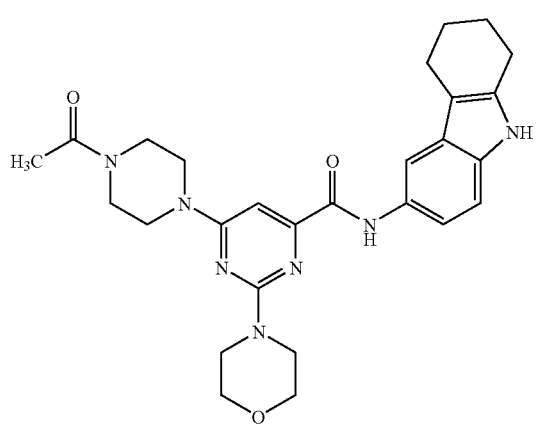

6-(4-acetylpiperazin-1-yl)-2-morpholino-N-(2,3,4,9-tetrahydro-1H-carbazol-6-yl)pyrimidine-4-carboxamide Compound 263

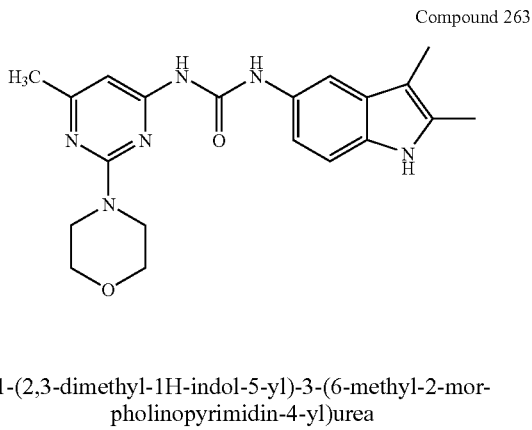

1-(2,3-dimethyl-1H-indol-5-yl)-3-(6-methyl-2-morpholinopyrimidin-4-yl)urea

Compound 264

1-(6-(4-acetylpiperazin-1-yl)-2-morpholinopyrimidin-4-yl)-3-(2,3-dimethyl-1H-indol-5-yl)urea Compound 265

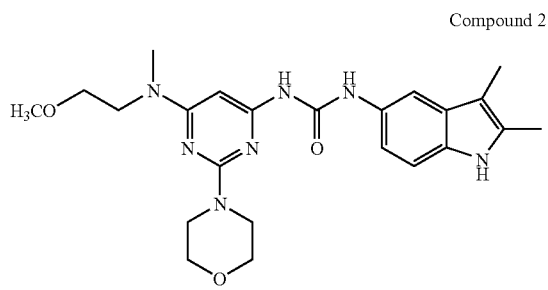

1-(2,3-dimethyl-1H-indol-5-yl)-3-(6-((2-methoxyethyl)(methyl)amino)-2-morpholinopyrimidin-4-yl)urea Compound 266

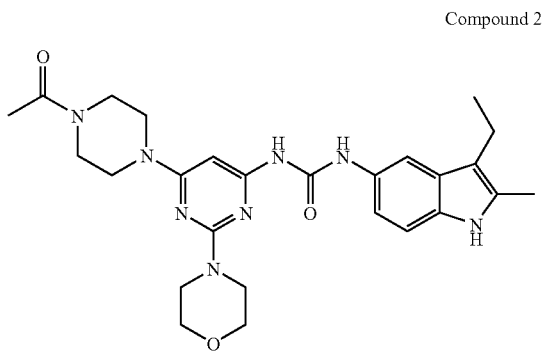

1-(6-(4-acetylpiperazin-1-yl)-2-morpholinopyrimidin-4-yl)-3-(3-ethyl-2-methyl-1H-indol-5-yl)urea Compound 267

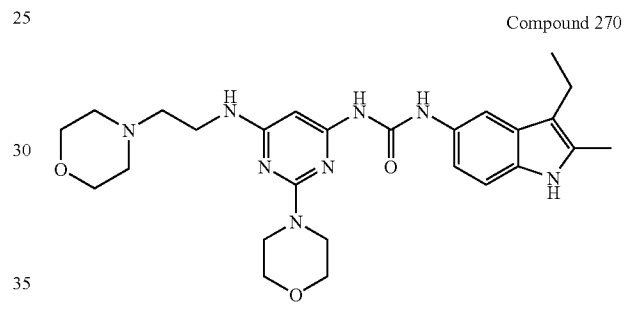

1-(3-ethyl-2-methyl-1H-indol-5-yl)-3-(6-methyl-2-morpholinopyrimidin-4-yl)urea

Compound 268

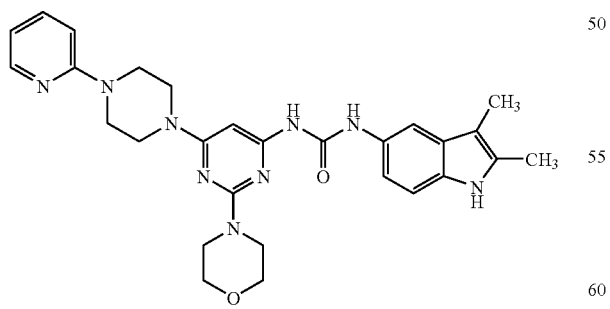

1-(2,3-dimethyl-1H-indol-5-yl)-3-(2-morpholino-6-(4-(pyridin-2-yl)piperazin-1-yl)pyrimidin-4-yl)urea Compound 269

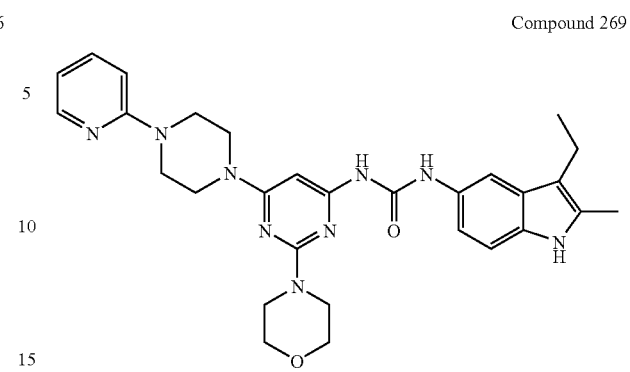

1-(3-ethyl-2-methyl-1H-indol-5-yl)-3-(2-morpholino-6-(4-(pyridin-2-yl)piperazin-1-yl)pyrimidin-4-yl)urea Compound 270

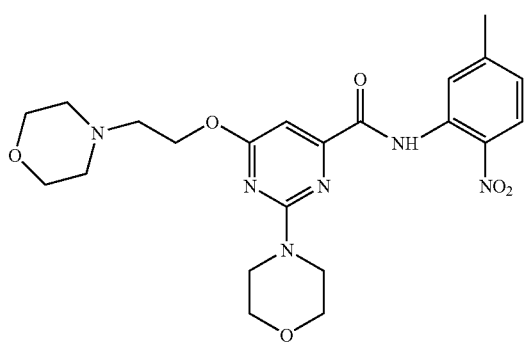

1-(3-ethyl-2-methyl-1H-indol-5-yl)-3-(2-morpholino-6-(2-morpholinoethylamino)pyrimidin-4-yl)urea Compound 271

2-Morpholin-4-yl-6-(2-morpholin-4-yl-ethoxy)-pyrimidine-4-carboxylic acid (5-methyl-2-nitro-phenyl)-amide Compound 272

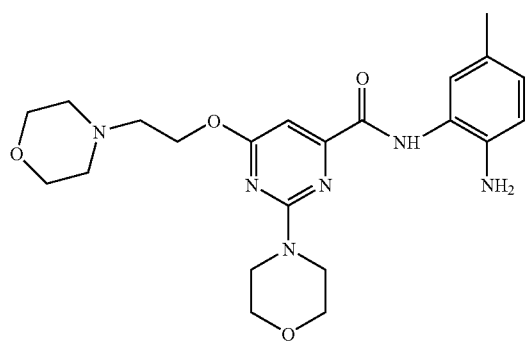

2-Morpholin-4-yl-6-(2-morpholin-4-yl-ethoxy)-pyrimidine-4-carboxylic acid (2-amino-5-methyl-phenyl)-amide Compound 275

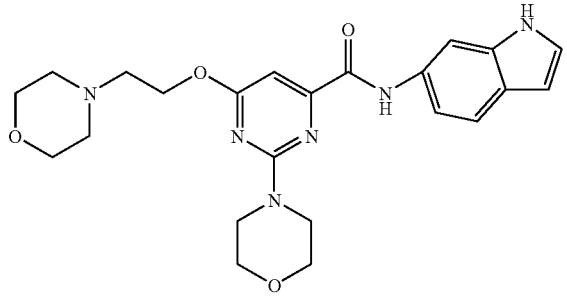

2-Morpholin-4-yl-6-(2-morpholin-4-yl-ethoxy)-pyrimidine-4-carboxylic acid (1H-indol-6-yl)-amide Compound 273

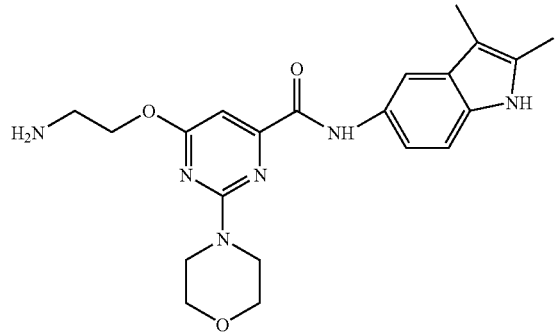

6-(2-Amino-ethoxy)-2-morpholin-4-yl-pyrimidine-4-carboxylic acid (2,3-dimethyl-1H-indol-5-yl)-amide Compound 276

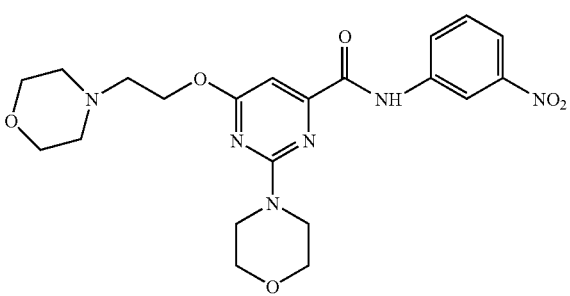

2-Morpholin-4-yl-6-(2-morpholin-4-yl-ethoxy)-pyrimidine-4-carboxylic acid (3-nitro-phenyl)-amide Compound 274

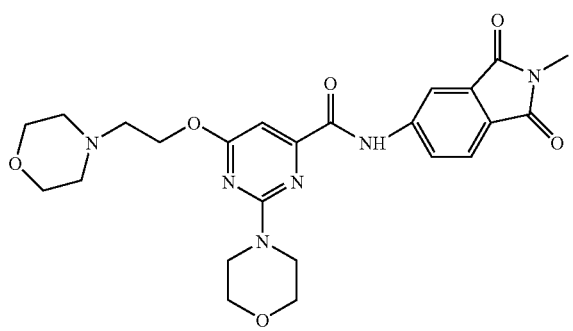

2-Morpholin-4-yl-6-(2-morpholin-4-yl-ethoxy)-pyrimidine-4-carboxylic acid (2-methyl-1,3-dioxo-2,3-dihydro-1H-isoindol-5-yl)-amide Compound 277

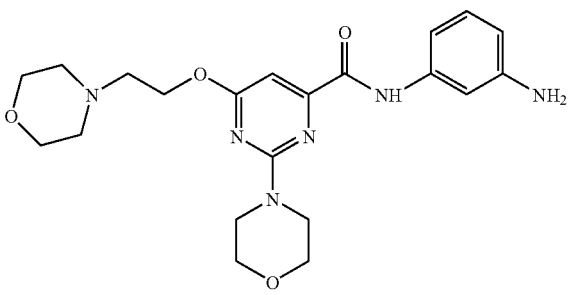

2-Morpholin-4-yl-6-(2-morpholin-4-yl-ethoxy)-pyrimidine-4-carboxylic acid (3-amino-phenyl)-amide Compound 278

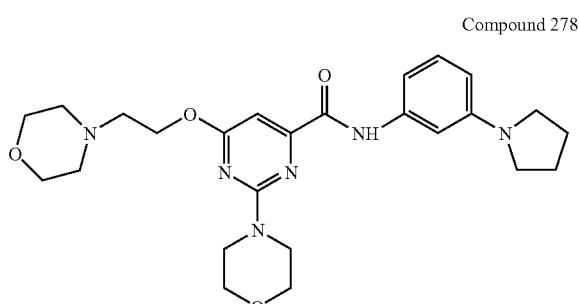

2-Morpholin-4-yl-6-(2-morpholin-4-yl-ethoxy)-pyrimidine-4-carboxylic acid (3-pyrrolidin-1-yl-phenyl)-amide Compound 279

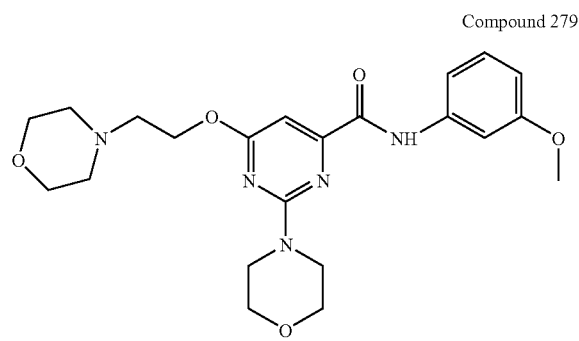

2-Morpholin-4-yl-6-(2-morpholin-4-yl-ethoxy)-pyrimidine-4-carboxylic acid (3-methoxy-phenyl)-amide Compound 280

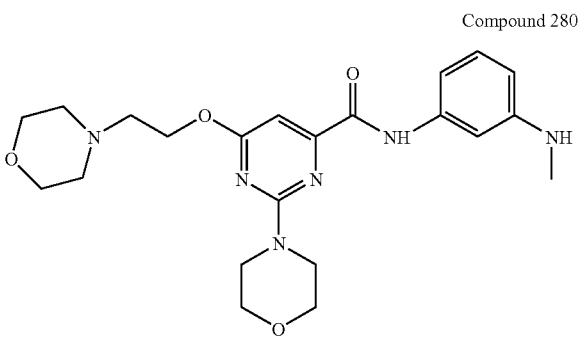

2-Morpholin-4-yl-6-(2-morpholin-4-yl-ethoxy)-pyrimidine-4-carboxylic acid (3-methylamino-phenyl)-amide Compound 281

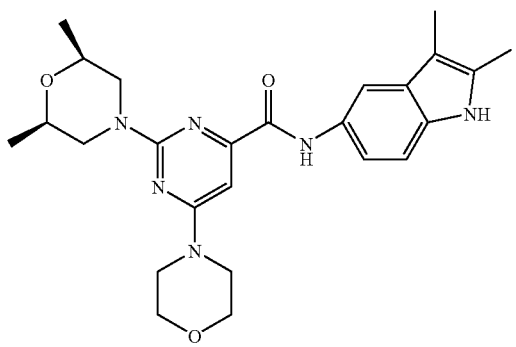

2-(2,6-Dimethyl-morpholin-4-yl)-6-morpholin-4-yl-pyrimidine-4-carboxylic acid (2,3-dimethyl-1H-indol-5-yl)-amide Compound 282

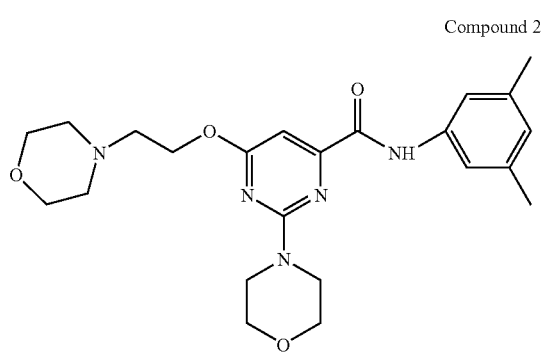

2-Morpholin-4-yl-6-(2-morpholin-4-yl-ethoxy)-pyrimidine-4-carboxylic acid (3,5-dimethyl-phenyl)-amide Compound 283

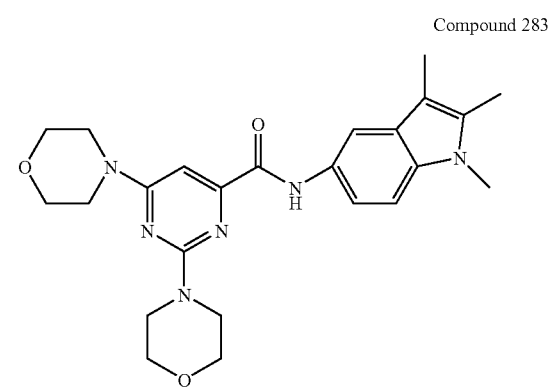

2,6-Di-morpholin-4-yl-pyrimidine-4-carboxylic acid (1,2,3-trimethyl-1H-indol-5-yl)-amide Compound 284

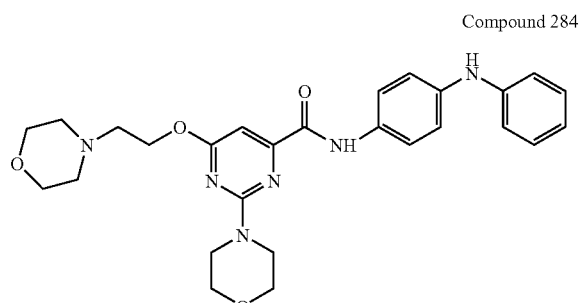

2-Morpholin-4-yl-6-(2-morpholin-4-yl-ethoxy)-pyrimidine-4-carboxylic acid (4-phenylamino-phenyl)-amide Compound 287

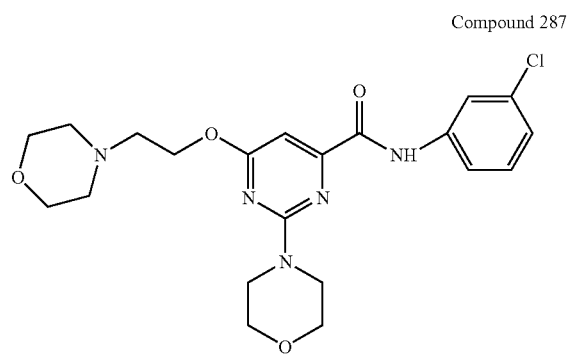

2-Morpholin-4-yl-6-(2-morpholin-4-yl-ethoxy)-pyrimidine-4-carboxylic acid (3-chloro-phenyl)-amide Compound 285

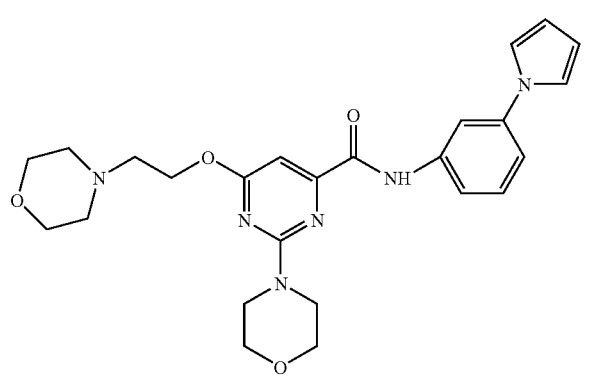

2-Morpholin-4-yl-6-(2-morpholin-4-yl-ethoxy)-pyrimidine-4-carboxylic acid (3-pyrrol-1-yl-phenyl)-amide Compound 288

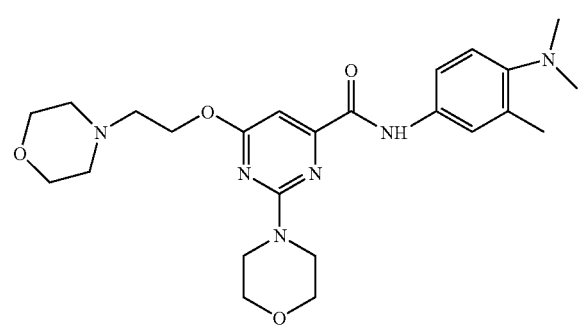

2-Morpholin-4-yl-6-(2-morpholin-4-yl-ethoxy)-pyrimidine-4-carboxylic acid (4-dimethylamino-3-methyl-phenyl)-amide Compound 286

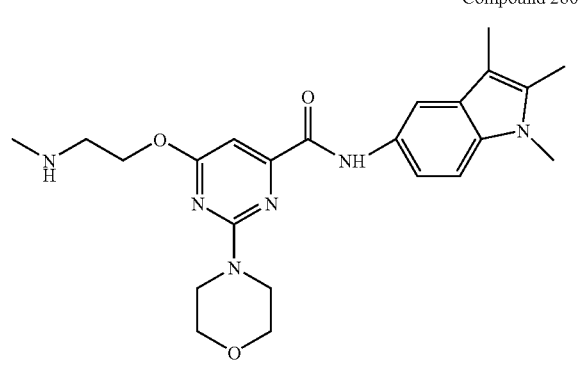

6-(2-Methylamino-ethoxy)-2-morpholin-4-yl-pyrimidine-4-carboxylic acid (1,2,3-trimethyl-1H-indol-5-yl)-amide Compound 289

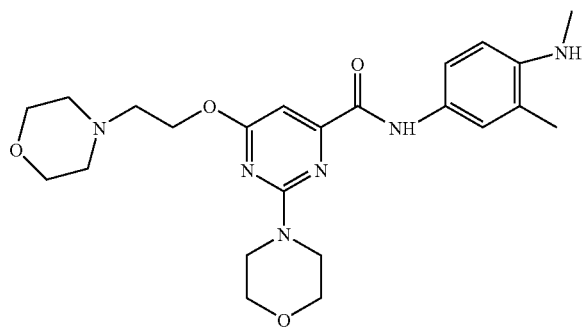

2-Morpholin-4-yl-6-(2-morpholin-4-yl-ethoxy)-pyrimidine-4-carboxylic acid (3-methyl-4-methylamino-phenyl)-amide Compound 290

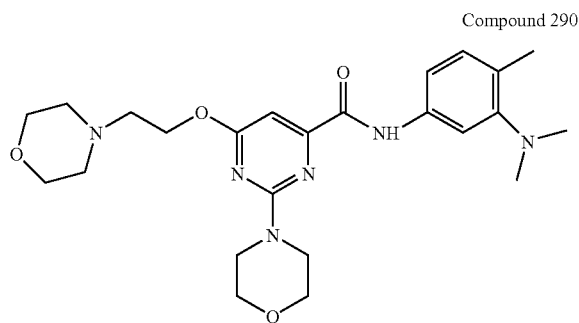

2-Morpholin-4-yl-6-(2-morpholin-4-yl-ethoxy)-pyrimidine-4-carboxylic acid (3-dimethylamino-4-methyl-phenyl)-amide Compound 291

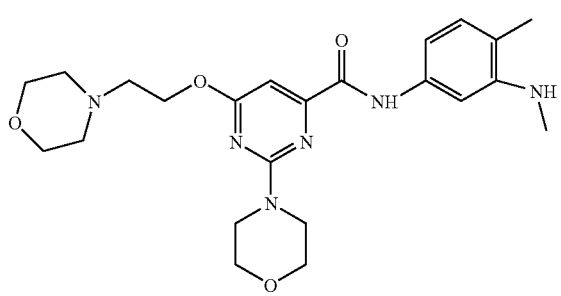

2-Morpholin-4-yl-6-(2-morpholin-4-yl-ethoxy)-pyrimidine-4-carboxylic acid (4-methyl-3-methylamino-phenyl)-amide Compound 292

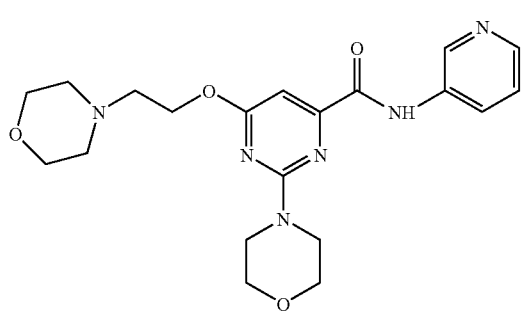

2-Morpholin-4-yl-6-(2-morpholin-4-yl-ethoxy)-pyrimidine-4-carboxylic acid pyridin-3-ylamide Compound 293

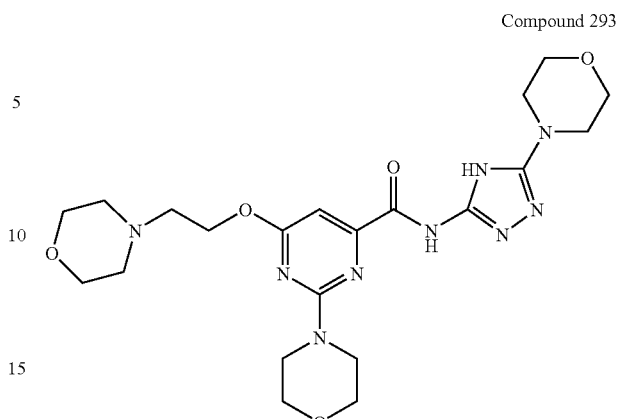

2-Morpholin-4-yl-6-(2-morpholin-4-yl-ethoxy)-pyrimidine-4-carboxylic acid (5-morpholin-4-yl-4H-[1,2,4]triazol-3-yl)-amide Compound 294

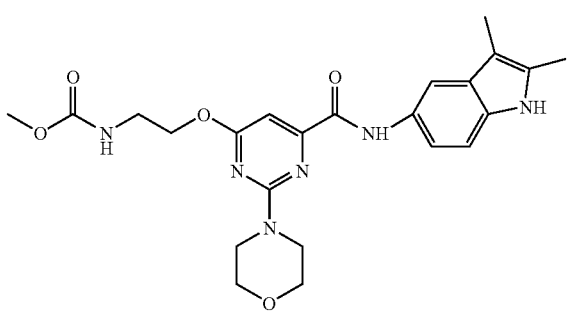

{2-[6-(2,3-Dimethyl-1H-indol-5-ylcarbamoyl)-2-morpholin-4-yl-pyrimidin-4-yloxy]-ethyl}-carbamic acid methyl ester Compound 295

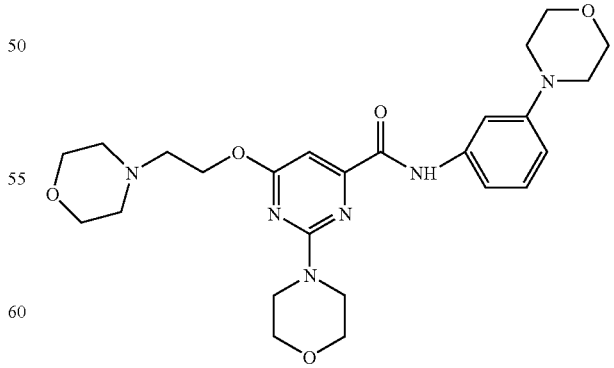

2-Morpholin-4-yl-6-(2-morpholin-4-yl-ethoxy)-pyrimidine-4-carboxylic acid (3-morpholin-4-yl-phenyl)-amide

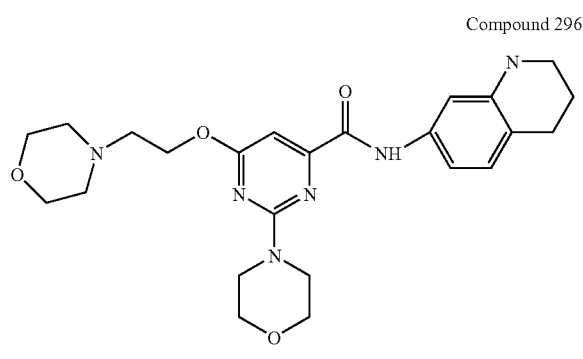

Compound 296

2-Morpholin-4-yl-6-(2-morpholin-4-yl-ethoxy)-pyrimidine-4-carboxylic acid (1,2,3,4-tetrahydro-quinolin-7-yl)-amide

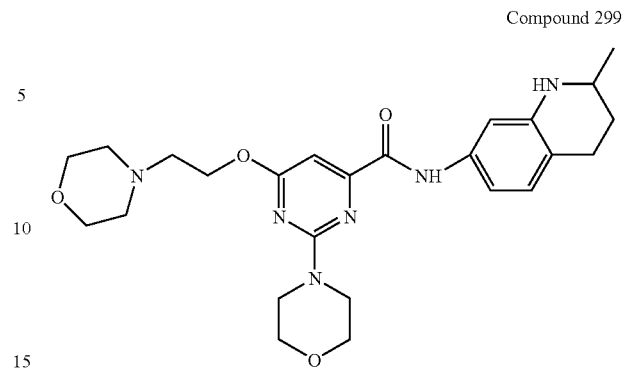

Compound 299

2-Morpholin-4-yl-6-(2-morpholin-4-yl-ethoxy)-pyrimidine-4-carboxylic acid (2-methyl-1,2,3,4-tetrahydro-quinolin-7-yl)-amide Compound 297

2-Morpholin-4-yl-6-(2-morpholin-4-yl-ethoxy)-pyrimidine-4-carboxylic acid (6-methyl-pyridin-3-yl)-amide

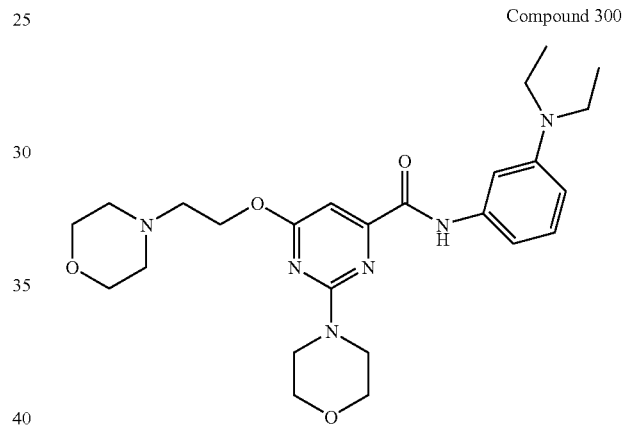

Compound 300

2-Morpholin-4-yl-6-(2-morpholin-4-yl-ethoxy)-pyrimidine-4-carboxylic acid (3-diethylamino-phenyl)-amide Compound 298

6-[(2-Hydroxy-ethyl)-methyl-amino]-2-morpholin-4-yl-pyrimidine-4-carboxylic acid m-tolylamide

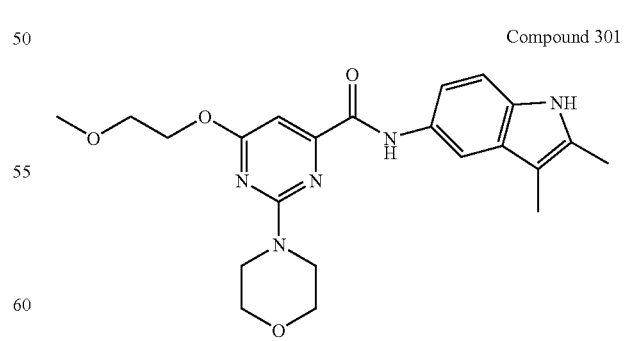

Compound 301

6-(2-Methoxy-ethoxy)-2-morpholin-4-yl-pyrimidine-4-carboxylic acid (2,3-dimethyl-1H-indol-5-yl)-amide Compound 302

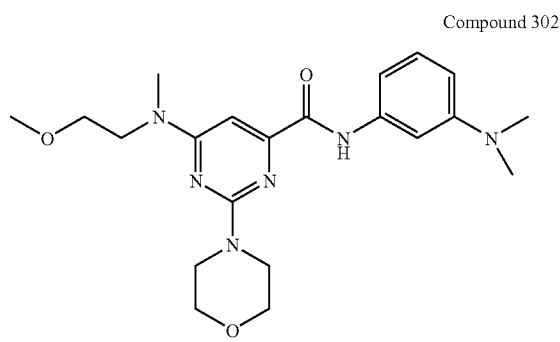

6-[(2-Methoxy-ethyl)-methyl-amino]-2-morpholin-4-yl-pyrimidine-4-carboxylic acid (3-dimethylamino-phenyl)-amide Compound 303

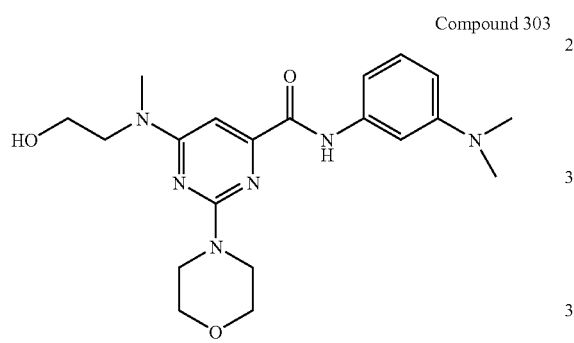

6-[(2-Hydroxy-ethyl)-methyl-amino]-2-morpholin-4-yl-pyrimidine-4-carboxylic acid (3-dimethylamino-phenyl)-amide Compound 304

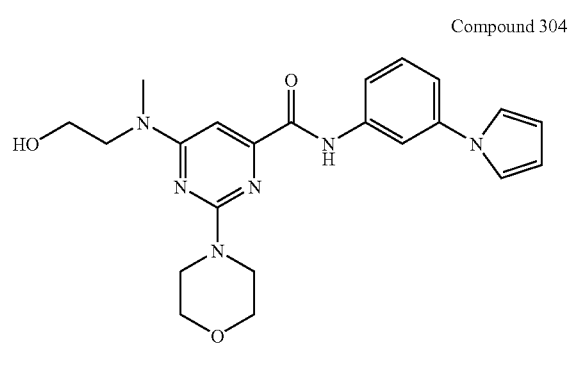

6-[(2-Hydroxy-ethyl)-methyl-amino]-2-morpholin-4-yl-pyrimidine-4-carboxylic acid (3-pyrrol-1-yl-phenyl)-amide Compound 305

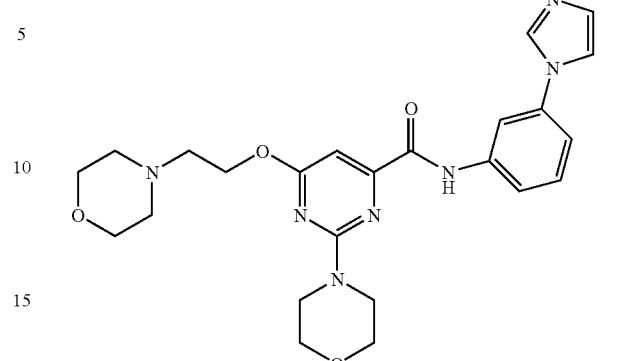

2-Morpholin-4-yl-6-(2-morpholin-4-yl-ethoxy)-pyrimidine-4-carboxylic acid (3-imidazol-1-yl-phenyl)-amide Compound 306

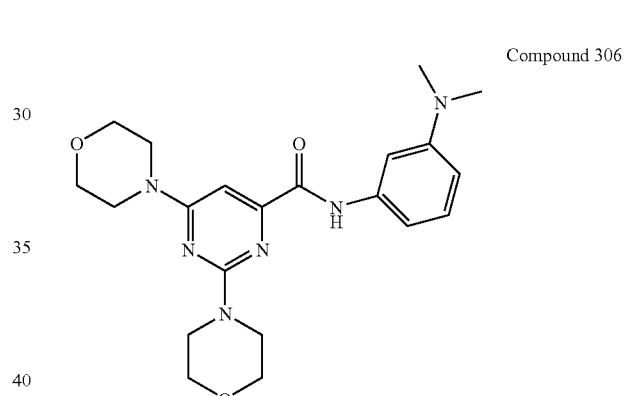

2,6-Di-morpholin-4-yl-pyrimidine-4-carboxylic acid (3-dimethylamino-phenyl)-amide Compound 307

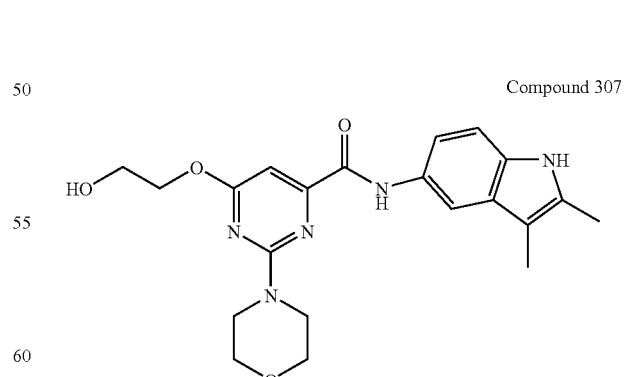

6-(2-Hydroxy-ethoxy)-2-morpholin-4-yl-pyrimidine-4-carboxylic acid (2,3-dimethyl-1H-indol-5-yl)-amide Compound 308

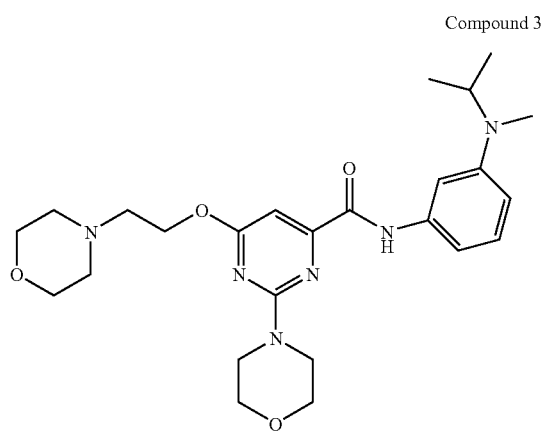

2-Morpholin-4-yl-6-(2-morpholin-4-yl-ethoxy)-pyrimidine-4-carboxylic acid [3-(isopropyl-methyl-amino)-phenyl]-amide Compound 309

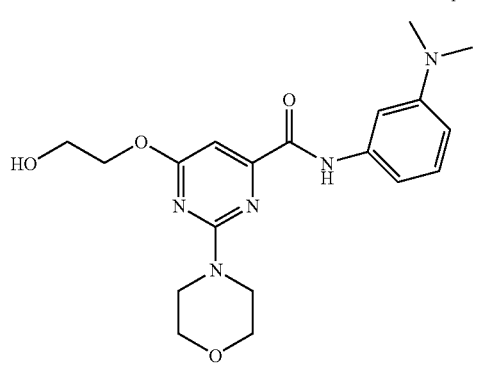

6-(2-Hydroxy-ethoxy)-2-morpholin-4-yl-pyrimidine-4-carboxylic acid (3-dimethylamino-phenyl)-amide Compound 310

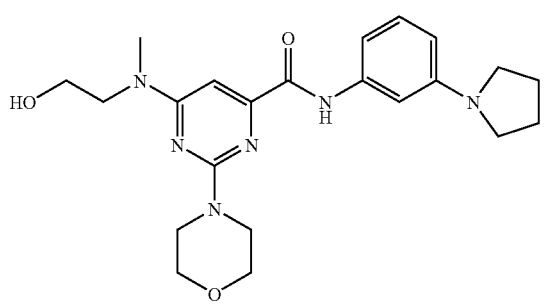

6-[(2-Hydroxy-ethyl)-methyl-amino]-2-morpholin-4-yl-pyrimidine-4-carboxylic acid (3-pyrrolidin-1-yl-phenyl)-amide Compound 311

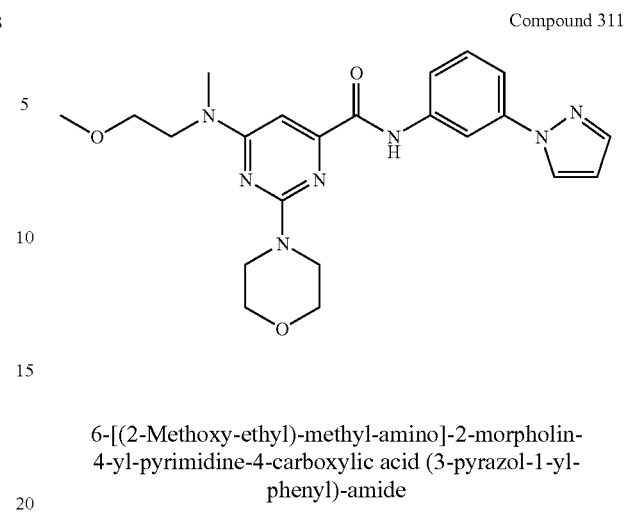

6-[(2-Methoxy-ethyl)-methyl-amino]-2-morpholin-4-yl-pyrimidine-4-carboxylic acid (3-pyrazol-1-yl-phenyl)-amide Compound 312

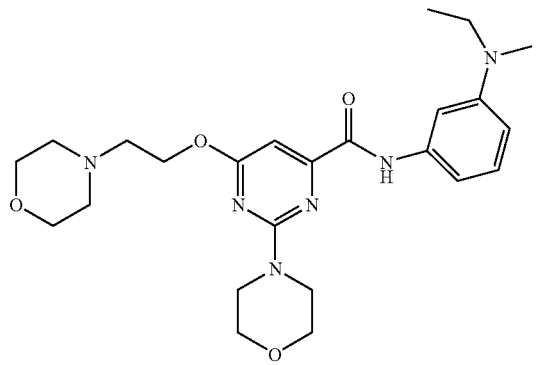

2-Morpholin-4-yl-6-(2-morpholin-4-yl-ethoxy)-pyrimidine-4-carboxylic acid [3-(ethyl-methyl-amino)-phenyl]-amide Compound 313

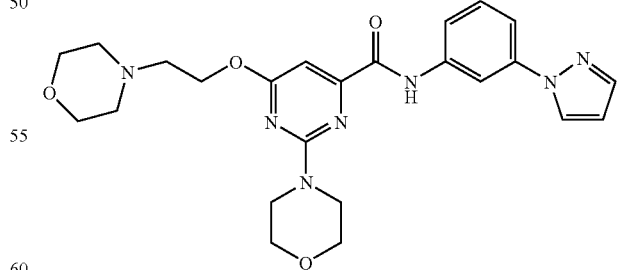

2-Morpholin-4-yl-6-(2-morpholin-4-yl-ethoxy)-pyrimidine-4-carboxylic acid (3-pyrazol-1-yl-phenyl)-amide Compound 314

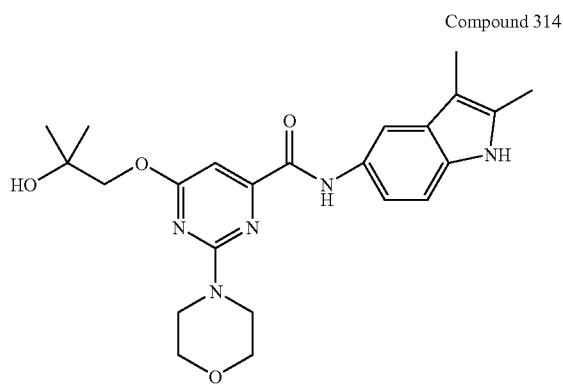

6-(2-Hydroxy-2-methyl-propoxy)-2-morpholin-4-yl-pyrimidine-4-carboxylic acid (2,3-dimethyl-1H-indol-5-yl)-amide Compound 315

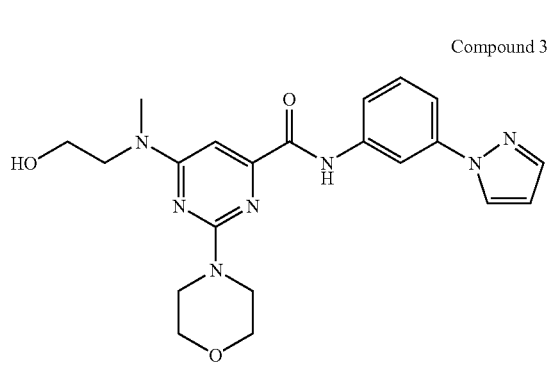

6-[(2-Hydroxy-ethyl)-methyl-amino]-2-morpholin-4-yl-pyrimidine-4-carboxylic acid (3-pyrazol-1-yl-phenyl)-amide Compound 316

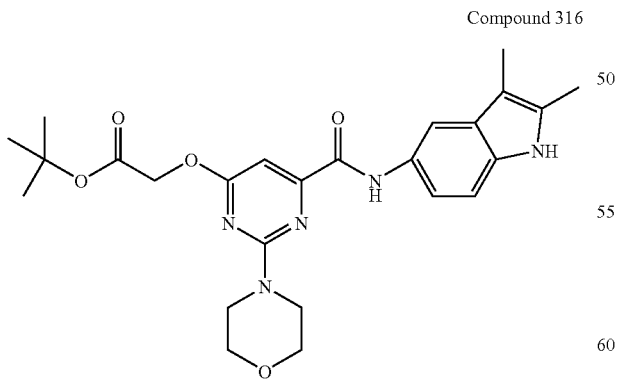

[6-(2,3-Dimethyl-1H-indol-5-ylcarbamoyl)-2-morpholin-4-yl-pyrimidin-4-yloxy]-acetic acid tert-butyl ester Compound 317

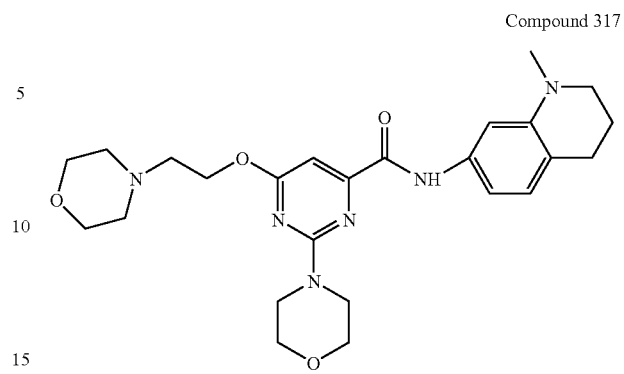

2-Morpholin-4-yl-6-(2-morpholin-4-yl-ethoxy)-pyrimidine-4-carboxylic acid (1-methyl-1,2,3,4-tetrahydro-quinolin-7-yl)-amide Compound 318

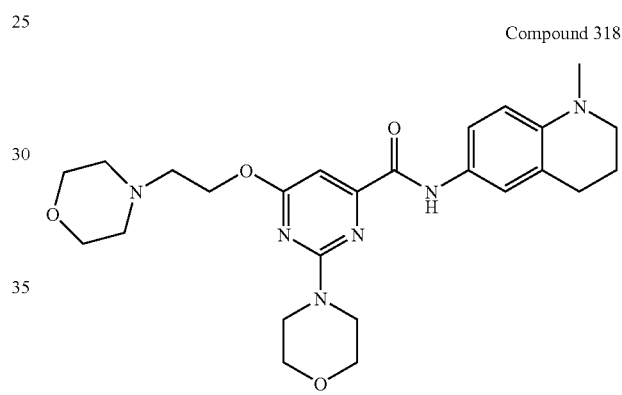

2-Morpholin-4-yl-6-(2-morpholin-4-yl-ethoxy)-pyrimidine-4-carboxylic acid (1-methyl-1,2,3,4-tetrahydro-quinolin-6-yl)-amide Compound 319

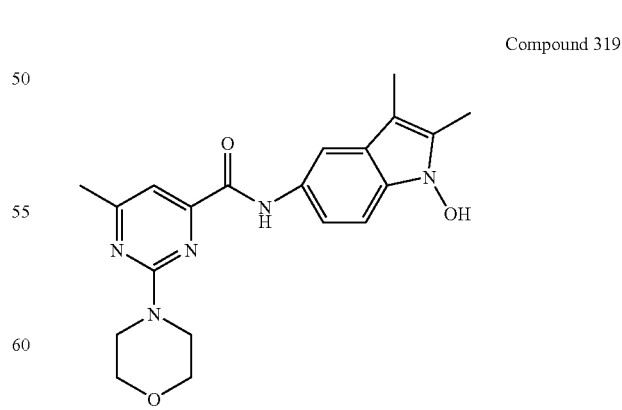

6-Methyl-2-morpholin-4-yl-pyrimidine-4-carboxylic acid (1-hydroxy-2,3-dimethyl-1H-indol-5-yl)-amide Compound 320

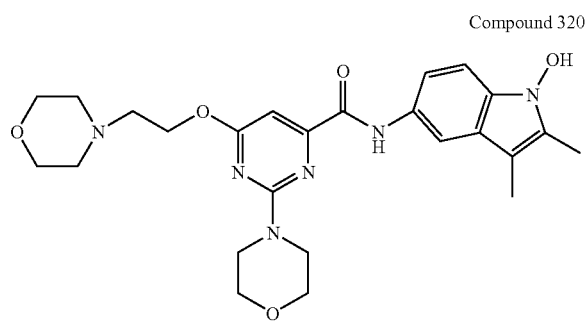

2-Morpholin-4-yl-6-(2-morpholin-4-yl-ethoxy)-pyrimidine-4-carboxylic acid (1-hydroxy-2,3-dimethyl-1H-indol-5-yl)-amide Compound 321

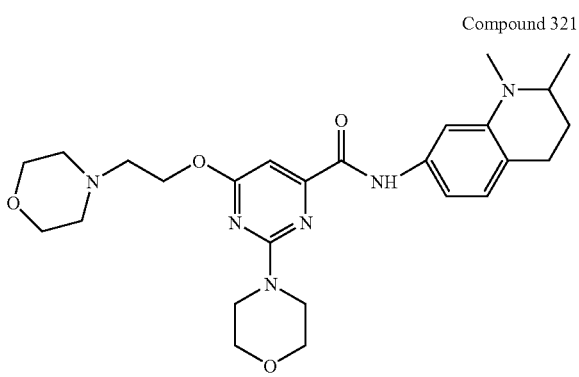

2-Morpholin-4-yl-6-(2-morpholin-4-yl-ethoxy)-pyrimidine-4-carboxylic acid (1,2-dimethyl-1,2,3,4-tetrahydro-quinolin-7-yl)-amide Compound 322

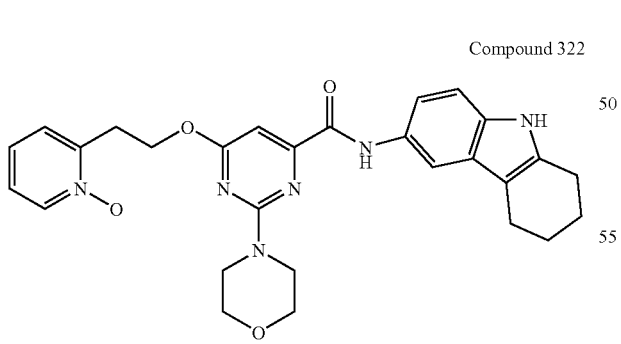

2-Morpholin-4-yl-6-[2-(1-oxy-pyridin-2-yl)-ethoxy]-pyrimidine-4-carboxylic acid (6,7,8,9-tetrahydro-5H-carbazol-3-yl)-amide Compound 323

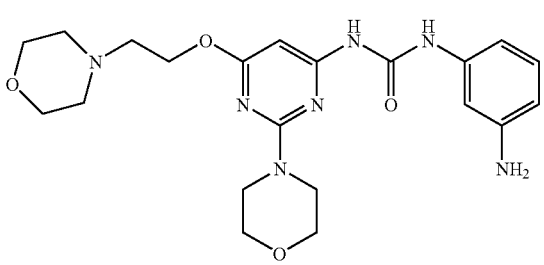

1-(2,3-Dimethyl-1H-indol-5-yl)-3-[2-morpholin-4-yl-6-(2-morpholin-4-yl-ethoxy)-pyrimidin-4-yl]-urea Compound 324

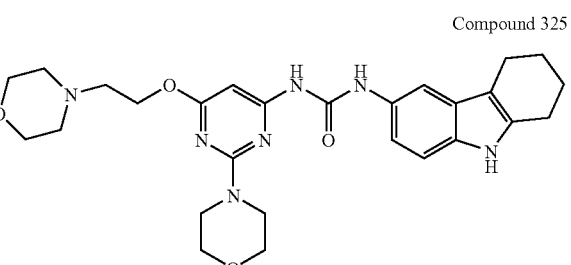

1-(3-Amino-phenyl)-3-[2-morpholin-4-yl-6-(2-morpholin-4-yl-ethoxy)-pyrimidin-4-yl]-urea Compound 325

1-[2-Morpholin-4-yl-6-(2-morpholin-4-yl-ethoxy)-pyrimidin-4-yl]-3-(6,7,8,9-tetrahydro-5H-carbazol-3-yl)-urea Compound 326

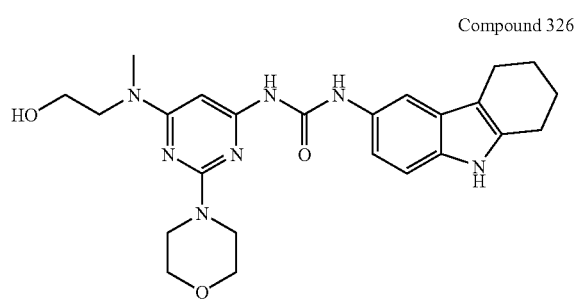

1-{6-[(2-Hydroxy-ethyl)-methyl-amino]-2-morpholin-4-yl-pyrimidin-4-yl}-3-(6,7,8,9-tetrahydro-5H-carbazol-3-yl)-urea Compound 327

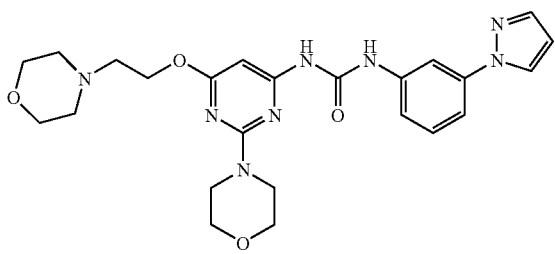

1-[2-Morpholin-4-yl-6-(2-morpholin-4-yl-ethoxy)-pyrimidin-4-yl]-3-(3-pyrazol-1-yl-phenyl)-urea Compound 328

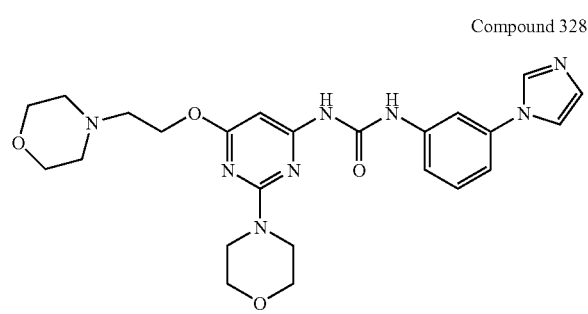

1-(3-Imidazol-1-yl-phenyl)-3-[2-morpholin-4-yl-6-(2-morpholin-4-yl-ethoxy)-pyrimidin-4-yl]-urea Compound 329

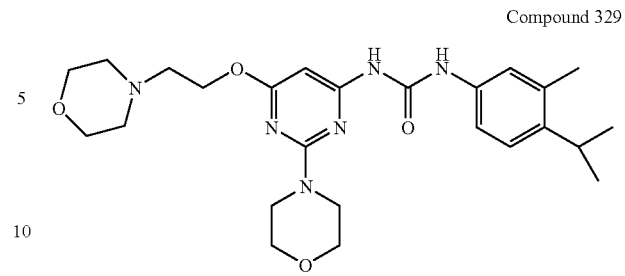

1-(4-Isopropyl-3-methyl-phenyl)-3-[2-morpholin-4-yl-6-(2-morpholin-4-yl-ethoxy)-pyrimidin-4-yl]-urea Compound 330

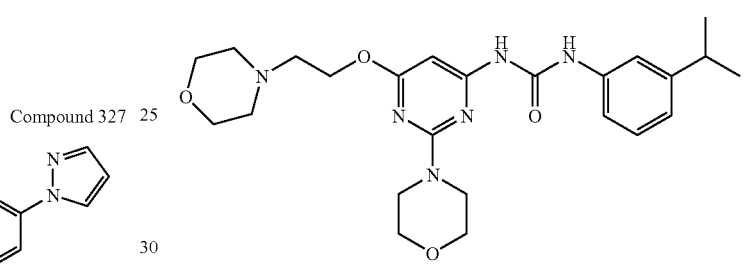

1-(3-Isopropyl-phenyl)-3-[2-morpholin-4-yl-6-(2-morpholin-4-yl-ethoxy)-pyrimidin-4-yl]-urea The heterocyclic compounds of this invention include the compounds themselves, as well as their salts and their prodrugs, if applicable. Such salts, for example, can be formed between a positively charged substituent (e.g., amino) on a compound and an anion. Suitable anions include, but are not limited to, chloride, bromide, iodide, sulfate, nitrate, phosphate, citrate, methanesulfonate, trifluoroacetate, and acetate. Likewise, a negatively charged substituent (e.g., carboxylate) on a compound can form a salt with a cation. Suitable cations include, but are not limited to, sodium ion, potassium ion, magnesium ion, calcium ion, and an ammonium cation such as teteramethylammonium ion. Examples of prodrugs include esters and other pharmaceutically acceptable derivatives, which, upon administration to a subject, are capable of providing the heterocyclic compounds described above in vivo(see Goodman and Gilman's, The Pharmacological basis of Therapeutics, $8^{th}$ ed., McGraw-Hill, Int. Ed. 1992, "Biotransformation of Drugs").

In addition, some of the heterocyclic compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Also within the scope of this invention is a pharmaceutical composition that contains an effective amount of one or more of the heterocyclic compounds of this invention or a pharmaceutically acceptable salt, solvate, clathrate, or prodrug thereof, and a pharmaceutically acceptable carrier. The compounds described herein are useful to treat and prevent any IL-12 production-related disorders, e.g., inflammatory disorders, immune diseases, neurological disorders and bone loss diseases.

The compounds of the invention are particularly useful in inhibiting the production of IL-12 and/or inhibiting the production of cytokines such as IL-23 and IL-27 which stimulate and/or otherwise augment the production of IL-12 and/or the proliferation of $T_H1$ lymphocytes. Thus, in one aspect, the present invention provides a method of inhibiting the production of IL-12 and/or inhibiting the production of a cytokine that stimulates or facilitates the production of IL-12 (e.g., IL-23 and IL-27) in a subject by administering to the subject an effective amount of a compound of any of the formulae herein, or a pharmaceutically acceptable salt, solvate, clathrate, hydrate, polymorph, or prodrug thereof.

In another aspect, the invention provides method for treating an interleukin-12 production-related disorder, comprising administering to a subject in need thereof an effective amount of a compound of any of the formulae herein, or a pharmaceutically acceptable salt, solvate, clathrate, hydrate, polymorph, or prodrug thereof. In certain embodiments, the disorder is selected from the group consisting of multiple sclerosis, sepsis, myasthenia gravis, autoimmune neuropathies, Guillain-Barré syndrome, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, psoriatic arthritis, dermatitis herpetiformis, pemphigus vulgaris, vitiligo, Crohn's disease, ulcerative colitis, interstitial pulmonary fibrosis, myelofibrosis, hepatic fibrosis, myocarditis, thyroditis, primary biliary cirrhosis, autoimmune hepatitis, immune-mediated diabetes mellitus, Grave's disease, Hashimoto's thyroiditis, autoimmune oophoritis and orchitis, autoimmune disease of the adrenal gland; rheumatoid arthritis, juvenile rheumatoid arthritis, systemic lupus erythematosus, scleroderma, common variable immunodeficiency (CVID), polymyositis, dermatomyositis, spondyloarthropathies, ankylosing spondylitis, Sjogren's syndrome and graft-versus-host disease, more preferably rheumatoid arthritis, sepsis, Crohn's disease, multiple sclerosis, psoriasis, or immune-mediated diabetes mellitus.

The term "inflammatory disorders" includes any inflammatory disease, disorder or condition caused, exasperated or mediated by IL-12 production. Such inflammatory disorders may include, without limitation, asthma, adult respiratory distress syndrome, systemic lupus erythematosus, inflammatory bowel disease (including Crohn's disease and ulcerative colitis), multiple sclerosis, insulin-dependent diabetes mellitus, autoimmune arthritis (including rheumatoid arthritis, juvenile rheumatoid arthritis, psoriatic arthritis), inflammatory pulmonary syndrome, pemphigus vulgaris, idiopathic thrombocytopenic purpura, autoimmune meningitis, myasthenia gravis, autoimmune thyroiditis, dermatitis (including atopic dermatitis and eczematous dermatitis), psoriasis, Sjogren's Syndrome (including keratoconjunctivitis sicca secondary to Sjogren's Syndrome), alopecia areata, allergic responses due to arthropod bite reactions, aphthous ulcer, iritis, conjunctivitis, keratoconjunctivitis, cutaneous lupus erythematosus, scleroderma, vaginitis, proctitis, drug eruptions (such as Stevens-Johnson syndrome), leprosy reversal reactions, erythema nodosum leprosum, autoimmune uveitis, allergic encephalomyelitis, aplastic anemia, pure red cell anemia, idiopathic thrombocytopenia, polychondritis, Wegener's granulomatosis, chronic active hepatitis, Graves ophthalmopathy, primary biliary cirrhosis, uveitis posterior and interstitial lung fibrosis.

"Inflammatory disorders" expressly include acute inflammatory disorders. Examples of acute inflammatory disorders include graft versus host disease, transplant rejection, septic shock, endotoxemia, Lyme arthritis, infectious meningitis (e.g., viral, bacterial, Lyme disease-associated), an acute episode of asthma and acute episodes of an autoimmune disease.

"Inflammatory disorders" expressly include chronic inflammatory disorders. Nonlimiting examples of chronic inflammatory disorder include asthma, rubella arthritis, and chronic autoimmune diseases, such as systemic lupus erythematosus, psoriasis, inflammatory bowel disease, including Crohn's disease and ulcerative colitis, multiple sclerosis and rheumatoid arthritis.

The term "immune diseases" includes any immune disease, disorder or condition caused, exasperated or mediated by IL-12 production. Such immune diseases may include, without limitation, rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosus, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited to asthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The term "neurological disorder" includes any neurological disease, disorder or condition caused, exasperated or mediated by IL-12 production. Such neurological disorders may include, without limitation, neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi.system disorder); demyelinating core disorders, such as multiple sclerosis, acute transverse myelitis; and disorders of the motor unit such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like. Such a method can optionally comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, 16, Edition, Merck & Company, Rahway, N.J. (1992)

In the case of overlap in these definitions, the disease, condition or disorder may be considered to be a member of any of the above listed classes of IL-12 production-related disorders.

In still another aspect, the present invention features a method for treating an IL-12 production-related disorder (e.g., rheumatoid arthritis, sepsis, Crohn's disease, multiple sclerosis, psoriasis, or insulin-dependent diabetes mellitus). The method includes administering to a subject (e.g., a human or an animal) in need thereof an effective amount of one or more compounds of formula (I) or a pharmaceutically acceptable salt, solvate, clathrate, or prodrug thereof, or a pharmaceutical composition having an effective amount of one or more compounds of formula (I) or a pharmaceutically acceptable salt, solvate, clathrate, or prodrug thereof. The method can also include the step of identifying that the subject is in need of treatment of diseases or disorders described above. The identification can be in the judgment of a subject or a health professional and can be subjective (e.g., opinion) or objective (e.g., measurable by a test or a diagnostic method).

In one aspect, this invention features a method for treating or preventing disorders associated with excessive bone loss, e.g., periodontal disease, non-malignant bone disorders (e.g., osteoporosis, Paget's disease of bone, osteogenesis imperfecta, fibrous dysplasia, and primary hyperparathyroidism), estrogen deficiency, inflammatory bone loss, bone malignancy, arthritis, osteopetrosis, and certain cancer-related disorders (e.g., hypercalcemia of malignancy (HCM), osteolytic bone lesions of multiple myeloma and osteolytic bone metastases of breast cancer and other metastatic cancers). The method includes administering to a subject (e.g., a human or an animal) in need thereof an effective amount of one or more compounds of formula (I) or a pharmaceutically acceptable salt, solvate, clathrate, or prodrug thereof, or a pharmaceutical composition having an effective amount of one or more compounds of formula (I) or a pharmaceutically acceptable salt, solvate, clathrate, or prodrug thereof. The method can also include the step of identifying that the subject is in need of treatment of diseases or disorders described above. The identification can be in the judgment of a subject or a health professional and can be subjective (e.g., opinion) or objective (e.g., measurable by a test or a diagnostic method).

In another aspect, this invention features methods for inhibiting osteoclast formation in vitro or in vivo. The method includes contacting a pre-osteoclast cell (e.g., a cell capable of forming an osteoclast cell upon differentiation and/or fusion) with an effective amount of a compound of formula (I) or a pharmaceutically acceptable salt, solvate, clathrate, or prodrug thereof or a pharmaceutical composition comprising an effective amount of a compound of formula (I) or a pharmaceutically acceptable salt, solvate, clathrate, or prodrug thereof.

In a further aspect, this invention features methods of treating or preventing a disorder associated with excessive bone resorption by osteoclasts in a subject in need thereof. The method includes administering to a subject (e.g., a human or an animal) in need thereof an effective amount of one or more compounds of formula (I) or a pharmaceutically acceptable salt, solvate, clathrate, or prodrug thereof, or a pharmaceutical composition having an effective amount of one or more compounds of formula (I) or a pharmaceutically acceptable salt, solvate, clathrate, or prodrug thereof. The method can also include the step of identifying that the subject is in need of treatment of diseases or disorders described above. The identification can be in the judgment of a subject or a health professional and can be subjective (e.g., opinion) or objective (e.g., measurable by a test or a diagnostic method).

Since the function of IL-12 is induction of INF-γ expression from T and NK cells which promotes the development of $T_H 1$ T lymphocyte type, the compounds of the invention can be used to inhibit the production of $T_H 1$ cells. Therefore, in another aspect, the invention features a method of inhibiting the production and/or development of $T_H 1$ cells in a subject by administering to the subject an effective amount of a compound of any of the formulae herein, or a pharmaceutically acceptable salt, solvate, clathrate, hydrate, polymorph, or prodrug thereof.

In another aspect, the invention provides a method of treating an IL-12 overproduction-related disorder, comprising administering to a subject in need thereof a therapeutically effective amount of a compound of any of the formulae herein or a pharmaceutically acceptable salt, solvate, clathrate, hydrate, polymorph, or prodrug thereof. IL-12 overproduction disorders include, but are not limited to multiple sclerosis, sepsis, myasthenia gravis, autoimmune neuropathies, Guillain-Barré syndrome, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, psoriatic arthritis, dermatitis herpetiformis, pemphigus vulgaris, vitiligo, Crohn's disease, ulcerative colitis, interstitial pulmonary fibrosis, myelofibrosis, hepatic fibrosis, myocarditis, thyroditis, primary biliary cirrhosis, autoimmune hepatitis, Type 1 or immune-mediated diabetes mellitus, Grave's disease, Hashimoto's thyroiditis, autoimmune oophoritis and orchitis, autoimmune disease of the adrenal gland; rheumatoid arthritis, juvenile rheumatoid arthritis, systemic lupus erythematosus, scleroderma, polymyositis, dermatomyositis, spondyloarthropathies, ankylosing spondylitis, Sjogren's syndrome and graft-versus-host disease.

In another aspect, the invention provides a method of inhibiting the production of IL-12 and/or inhibiting the production of a cytokine that stimulates or facilitates the production of IL-12 (e.g., IL-23 and IL-27) in a subject. The method includes administering to the subject a compound of any of the formulae herein or a pharmaceutically acceptable salt, solvate, clathrate, hydrate, polymorph, or prodrug thereof.

Although the mechanism is not yet understood, compounds of the invention have been found to inhibit the formation of osteoclasts (see co-owned PCT Application Number US04/17064 filed on May 28, 2004, published as WO2005/000404, the entire teachings of which are incorporated herein by reference). Osteoclasts are unique multinucleated cells within bone that are responsible for bone degradation and resorption. These are the only cells in the body known to be capable of this function. The regulation of osteoclastic formation and activity is only partly understood but it is known that excessive bone resorption by osteoclasts contributes to the pathology of many human diseases associated with excessive bone loss. Thus, in one aspect, the invention provides a method of treating or preventing disorders associated with excessive bone loss, comprising administering to a subject in need thereof a therapeutically effective amount of a compound of any of the formulae herein or pharmaceutically acceptable salt, solvate, clathrate, hydrate, polymorph, or prodrug thereof. Disorders associated with excessive bone loss include, but are not limited to periodontal disease, non-malignant bone disorders, osteoporosis, Paget's disease of bone, osteogenesis imperfecta, fibrous dysplasia, and primary hyperparathyroidism, estrogen deficiency, inflammatory bone loss, bone malignancy, arthritis, osteopetrosis, hypercalcemia of malignancy (HCM), osteolytic bone lesions of multiple myeloma and osteolytic bone metastases of breast cancer, and metastatic cancers.

In another aspect, the invention provides a method for inhibiting osteoclast formation in vitro or in vivo, comprising contacting a pre-osteoclast cell with an effective amount of a compound of any of the formulae herein or pharmaceutically acceptable salt, solvate, clathrate, hydrate, polymorph, or prodrug thereof.

In another aspect, the invention provides a method of treating or preventing a disorder associated with excessive bone resorption by osteoclasts in a subject in need thereof, comprising administering to the subject an effective amount of a compound of any of the formulae herein or pharmaceutically acceptable salt, solvate, clathrate, hydrate, polymorph, or prodrug thereof. The method includes administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

Other embodiments include the compounds, intermediates, or a pharmaceutically acceptable salt, solvate, clatharate, hydrate, polymorph, or prodrug thereof delineated herein, or compositions including them; as well as their methods of use for treatment or prevention of disease, inhibition of IL-12, or modulation of IL-12 mediated disease.

Another embodiment is a method of making a compound of any of the formulae herein using any one, or combination of, reactions delineated herein. The method can include the use of one or more intermediates or chemical reagents delineated herein.

As used herein, the term "effective amount" refers to an amount of a compound of this invention which is sufficient to reduce or ameliorate the severity, duration, progression, or onset of an inflammatory disorder, immune diseases, or bone loss disease, prevent the advancement of an inflammatory disorder, immune diseases, or bone loss disease, cause the regression of an inflammatory disorder, immune diseases, or bone loss disease, prevent the recurrence, development, onset or progression of a symptom associated with an inflammatory disorder, immune diseases, or bone loss disease, or enhance or improve the prophylactic or therapeutic effect(s) of another therapy. In certain preferred embodiments, treatment according to the invention provides a reduction in or prevention of at least one symptom or manifestation of an IL-12-, IL-23-, or IL-27-related disorder (e.g., inflammatory disorder, immune diseases, or bone loss disease), as determined in vivo or in vitro of at least about 10%, more preferably 20%, 30%, 40%, 50%, 60%, 70%, 80%, 90%, 95%, 98% or 99%.

The interrelationship of dosages for animals and humans (based on milligrams per meter squared of body surface) is described in Freireich et al., (1966) Cancer Chemother Rep 50: 219. Body surface area may be approximately determined from height and weight of the patient. See, e.g., Scientific Tables, Geigy Pharmaceuticals, Ardley, N.Y., 1970, 537. An effective amount of the pyridine compound of this invention can range from about 0.001 mg/kg to about 1000 mg/kg, more preferably 0.01 mg/kg to about 100 mg/kg, more preferably 0.1 mg/kg to about 10 mg/kg; or any range in which the low end of the range is any amount between 0.001 mg/kg and 900 mg/kg and the upper end of the range is any amount between 0.1 mg/kg and 1000 mg/kg (e.g., 0.005 mg/kg and 200 mg/kg, 0.5 mg/kg and 20 mg/kg). Effective doses will also vary, as recognized by those skilled in the art, depending on the diseases treated, route of administration, excipient usage, and the possibility of co-usage with other therapeutic treatments such as use of other agents.

To practice a method of the present invention, a heterocyclic compound, as a component of a pharmaceutical composition, can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, for example, a sterile injectable aqueous or oleaginous suspension, can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A heterocyclic compound of this invention can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the compounds of this invention, or one or more solubilizing agents, can be utilized as pharmaceutical excipients for delivery of the heterocyclic compounds. Examples of other carriers include colloidal silicon dioxide, magnesium stearate, cellulose, sodium lauryl sulfate, and D&C Yellow #10.

As used herein, the terms "animal", "subject" and "patient", include, but are not limited to, a cow, monkey, horse, sheep, pig, chicken, turkey, quail, cat, dog, mouse, rat, rabbit, guinea pig and human (preferably, a human).

In certain embodiments, pharmaceutical compositions and dosage forms of the invention comprise one or more active ingredients in relative amounts and formulated in such a way that a given pharmaceutical composition or dosage form inhibits the uptake of calcium. Preferred pharmaceutical compositions and dosage forms comprise a compound of formula (I), or a pharmaceutically acceptable prodrug, salt, solvate, or clathrate thereof, optionally in combination with one or more additional active agents.

The methods for treating or preventing disorders associated with excessive bone loss in a patient in need thereof can further comprise administering to the patient being administered a compound of this invention, an effective amount of one or more other therapeutic agents. Such therapeutic agents may include other therapeutic agents such as those conventionally used to prevent or treat disorders associated with excessive bone resorption or symptoms thereof. For example, such other agents include anti-resorptive agents for example progestins, polyphosphonates, bisphosphonate(s), estrogen agonists/antagonists, estrogen (such as Premarin®), estrogen/progestin combinations, and estrogen derivatives (such as estrone, estriol or $17\alpha,17\beta$-ethynyl estradiol).

In such combination therapy treatment, both the compounds of this invention and the other drug agent(s) are administered to mammals (e.g., humans, male or female) by conventional methods. The agents may be administered in a single dosage form or in separate dosage forms. Effective amounts of the other therapeutic agents are well known to those skilled in the art. However, it is well within the skilled artisan's purview to determine the other therapeutic agent's optimal effective-amount range. In one embodiment of the invention where another therapeutic agent is administered to an animal, the effective amount of the compound of this invention is less than its effective amount would be where the other therapeutic agent is not administered. In another embodiment, the effective amount of the conventional agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, dthynodiol diacetate, etonogestrel, flurogestone acetate, gestaclone, gestodene, gestonorone caproate, gestrinone, haloprogesterone, hydroxyprogesterone, caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenpropionate, progesterone, quingestanol acetate, quingestrone, and tigestol. Preferred progestins are medroxyprogestrone, norethindrone and norethynodrel.

Exemplary bone resorption inhibiting polyphosphonates include polyphosphonates of the type disclosed in U.S. Pat. No. 3,683,080. Preferred polyphosphonates are geminal dipolyphosphonates (also referred to as bis-phosphonates). Tiludronate disodium is an especially preferred polyphosphonate. Ibandronic acid is an especially preferred polyphosphonate. Alendronate is an especially preferred polyphosphonate. Zoledronic acid is an especially preferred polyphosphonate. Other preferred polyphosphonates are 6-amino-1-hydroxy-hexylidene-biphosphonic acid and 1-hydroxy-3(methylpentylamino)-propylidene-bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonic acid, N(2-hydroxyethyl)amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the compounds of this invention may be combined with a mammalian estrogen agonist/antagonist. Any estrogen agonist/antagonist may be used for this purpose. The term estrogen agonist/antagonist refers to compounds which bind with the estrogen receptor, inhibit bone turnover and/or prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue; and blocking the actions of estrogen in one or more tissues. Such activities are readily determined by those skilled in the art of standard assays including estrogen receptor binding assays, standard bone histomorphometric and densitometer methods, and E. F Eriksen et al., Bone Histomorphometry, Raven Press, New York, pp. 1-74 (1994); S. J. Grier et. al., The Use of Dual-Energy X-Ray Absorptiometry In Animals, Inv. Radiol. 31(1): 50-62 (1996); Wahner H. W. and Fogelman I., The Evaluation of Osteoporosis: Dual Energy X-Ray Absorptiometry in Clinical Practice., Martin Dunitz Ltd., London, pp. 1-296 (1994)). A variety of these compounds are described and referenced below.

A preferred estrogen agonist/antagonist is droloxifene: (phenol, 3-(1-(4-(2-(dimethylamino)ethoxy)phenyl)-2-phenyl-1-butenyl)-, (E)-) and related compounds which are disclosed in U.S. Pat. No. 5,047,431. Another preferred estrogen agonist/antagonist is 3-(4-(1,2-diphenyl-but-1-enyl)-phenyl)-acrylic acid, which is disclosed in Wilson et al., Endocrinology 138: 3901-11 (1997). Another preferred estrogen agonist/antagonist is tamoxifen: (ethanamine, 2-(-4-(1,2-diphenyl-1-butenyl)phenoxy)-N,N-dimethyl, (Z)-2-, 2-hydroxy-1,2,3-propanetricarboxylate(1:1)) and related compounds which are disclosed in U.S. Pat. No. 4,536,516. Another related compound is 4-hydroxy tamoxifen which is disclosed in U.S. Pat. No. 4,623,660.

A preferred estrogen agonist/antagonist is raloxifene: (methanone, (6-hydroxy-2-(4-hydroxyphenyl)benzo[b]thien-3-yl)(4-(2-(1-piperidinyl)ethoxy)phenyl)hydrochloride) which is disclosed in U.S. Pat. No. 4,418,068. Another preferred estrogen agonist/antagonist is toremifene: (ethanamine, 2-(4-(4-chloro-1,2-diphenyl-1-butenyl)phenoxy)-N,N-dimethyl-, (Z)-, 2-hydroxy-1,2,3-propanetricarboxylate (1:1) which is disclosed in U.S. Pat. No. 4,996,225. Another preferred estrogen agonist/antagonist is centchroman: 1-(2-((4-(-methoxy-2,2,dimethyl-3-phenyl-chroman-4-yl)-phenoxy)-ethyl)-pyrrolidine, which is disclosed in U.S. Pat. No. 3,822,287. Also preferred is levormeloxifene. Another preferred estrogen agonist/antagonist is idoxifene: (E)-1-(2-(4-(1-(4-iodo-phenyl)-2-phenyl-but-1-enyl)-phenoxy)-ethyl)-pyrrolidinone, which is disclosed in U.S. Pat. No. 4,839,155. Another preferred estrogen agonist/antagonist is 2-(4-methoxy-phenyl)-3-[4-(2-piperidin-1-yl-ethoxy)-phenoxy]-benzo[b]thiophen-6-ol which is disclosed in U.S. Pat. No. 5,488,058. Another preferred estrogen agonist/antagonist is 6-(4-hydroxy-phenyl)-5-(4-(2-piperidin-1-yl-ethoxy)-benzyl)-naphthalen-2-ol which is disclosed in U.S. Pat. No. 5,484,795. Another preferred estrogen agonist/antagonist is (4-(2-(2-aza-bicyclo[2.2.1]hept-2-yl)-ethoxy)-phenyl)-(6-hydroxy-2-(4-hydroxy-phenyl)-benzo[b]thiophen-3-yl)-methanone which is disclosed, along with methods of preparation, in PCT publication no. WO 95/10513 assigned to Pfizer Inc. Other preferred estrogen agonist/antagonists include compounds as described in U.S. Pat. No. 5,552,412. Especially preferred compounds described therein are: cis-6-(4-fluoro-phenyl)-5-(4-(2-piperidin-1-yl-ethoxy)-phenyl)-5,6,7,8-tetrahydro-naphthalene-2-ol; (−)-cis-6-phenyl-5-(4-(2-pyrrolidin-1-yl-ethoxy)-phenyl)-5,6,7,8-tetrahydro-naphthalene-2-ol; cis-6-phenyl-5-(4-(2-pyrrolidin-1-yl-ethoxy)-phenyl)-5,6,7,8-tetrahydro-naphthalene-2-ol; cis-1-(6'-pyrrolodinoethoxy-3'-pyridyl)-2-phenyl-6-hydroxy-1,2,3,4-tetrahydronaphthalene; 1-(4'-pyrrolidinoethoxyphenyl)-2-(4"-fluorophenyl)-6-hydroxy-1,2,3,4-tetrahydroisoquinoline; cis-6-(4-hydroxyphenyl)-5-(4-(2-piperidin-1-yl-ethoxy)-phenyl)-5,6,7,8-tetrahydro-naphthalene-2-ol; and 1-(4'-pyrrolidinolethoxyphenyl)-2-phenyl-6-hydroxy-1,2,3,4-tetrahydroisoquinoline. Other estrogen agonist/antagonists are described in U.S. Pat. No. 4,133,814. U.S. Pat. No. 4,133,814 discloses derivatives of 2-phenyl-3-aroyl-benzothiophene and 2-phenyl-3-aroylbenzothiophene-1-oxide.

Those skilled in the art will recognize that other bone anabolic agents, also referred to as bone mass augmenting agents, may be used in conjunction with the compounds of this invention. A bone mass augmenting agent is a compound that augments bone mass to a level which is above the bone fracture threshold as detailed in the World Health Organization Study World Health Organization, "Assessment of Fracture Risk and its Application to Screening for Postmenopausal Osteoporosis (1994). Report of a WHO Study Group. World Health Organization Technical Series 843." Any prostaglandin, or prostaglandin agonist/antagonist may be used in combination with the compounds of this invention. Those skilled in the art will recognize that IGF-1, sodium fluoride, parathyroid hormone (PTH), active fragments of parathyroid hormone, growth hormone or growth hormone secretagogues may also be used. The following paragraphs describes in greater detail exemplary compounds that may be administered in combination with compounds of this invention Prostaglandins: The term prostaglandin refers to compounds which are analogs of the natural prostaglandins $PGD_1$, $PGD_2$, $PGE_2$, $PGE_1$ and $PGF_2$ which are useful in the treatment of osteoporosis and other disorders associated with excessive osteoclastic bone resorption. These compounds bind to the prostaglandins receptors. Such binding is readily determined by those skilled in the art of standard assays (e.g., S. An et al., Cloning and Expression of the $EP_2$ Subtype of Human Receptors for Prostaglandin $E_2$ Biochemical and Biophysical Research Communications, 197(1): 263-270 (1993)).

Prostaglandins are alicyclic compounds related to the basic compound prostanoic acid. The carbon atoms of the basic prostaglandin are numbered sequentially from the carboxylic carbon atom through the cyclopentyl ring to the terminal carbon atom on the adjacent side chain. Normally the adjacent side chains are in the trans orientation. The presence of an oxo group at C-9 of the cyclopentyl moiety is indicative of a prostaglandin within the E class while $PGE_2$ contains a trans unsaturated double bond at the $C_{13}$-$C_{14}$ and a cis double bond at the $C_5$-$C_6$ position.

A variety of prostaglandins are described and referenced below. However, other prostaglandins will be known to those skilled in the art. Exemplary prostaglandins are disclosed in U.S. Pat. Nos. 4,171,331 and 3,927,197. Norrdin et al., The Role of Prostaglandins in Bone in Vivo, Prostaglandins Leukotriene Essential Fatty Acids 41: 139-150 (1990) is a review of bone anabolic prostaglandins. Any prostaglandin agonist/antagonist may be used in combination with the compounds of this invention. The term prostaglandin agonist/antagonist refers to compounds which bind to prostaglandin receptors (eg., An S. et al., Cloning and Expression of the $EP_2$ Subtype of Human Receptors for Prostaglandin $E_2$, Biochemical and Biophysical Research Communications 197(1): 263-70 (1993)) and mimic the action of prostaglandin in vivo (e.g., stimulate bone formation and increase bone mass). Such actions are readily determined by those skilled in the art of standard assays. Eriksen E. F. et al., Bone Histomorphometry, Raven Press, New York, 1994, pp. 1-74; S. J. Grier et al., The Use of Dual-Energy X-Ray Absorptiometry In Animals, Inv. Radiol. 31(1): 50-62 (1996); H. W. Wahner and I. Fogelman, The Evaluation of Osteoporosis: Dual Energy X-Ray Absorptiometry in Clinical Practice, Martin Dunitz Ltd. London, pp. 1-296 (1994). A number of these compounds are described and reference below. However, other prostaglandin agonists/antagonists will be known to those skilled in the art. Exemplary prostaglandin agonists/antagonists are disclosed as follows. U.S. Pat. No. 3,932,389 discloses 2-descarboxy-2-(tetrazol-5-yl)-11-desoxy-15-substituted-omega-pentanorpros taglandins useful for bone formation activity. U.S. Pat. No. 4,018,892, discloses 16-aryl-13,14-dihydro-$PGE_2$ p-biphenyl esters useful for bone formation activity. U.S. Pat. No. 4,219,483, discloses 2,3,6-substituted-4-pyrones useful for bone formation activity. U.S. Pat. No. 4,132,847, discloses 2,3,6-substituted-4-pyrones useful for bone formation activity. U.S. Pat. No. 4,000,309, discloses 16-aryl-13,14-dihydro-$PGE_2$ p-biphenyl esters useful for bone formation activity. U.S. Pat. No. 3,982,016, discloses 16-aryl-13,14-dihydro-$PGE_2$ p-biphenyl esters useful for bone formation activity. U.S. Pat. No. 4,621,100, discloses substituted cyclopentanes useful for bone formation activity. U.S. Pat. No. 5,216,183, discloses cyclopentanones useful for bone formation activity.

Sodium fluoride may be used in combination with the compounds of this invention. The term sodium fluoride refers to sodium fluoride in all its forms (e.g., slow release sodium fluoride, sustained release sodium fluoride). Sustained release sodium fluoride is disclosed in U.S. Pat. No. 4,904,478. The activity of sodium fluoride is readily determined by those skilled in the art of biological protocols.

Bone morphogenetic protein may be used in combination with the compounds of this invention (e.g., see Ono et al., Promotion of the Osteogenetic Activity of Recombinant Human Bone Morphogenetic Protein by Prostaglandin $E_1$, Bone 19(6): 581-588 (1996)).

Any parathyroid hormone (PTH) may be used in combination with the compound of this invention. The term parathyroid hormone refers to parathyroid hormone, fragments or metabolites thereof and structural analogs thereof which can stimulate bone formation and increase bone mass. Also included are parathyroid hormone related peptides and active fragments and analogs of parathyroid related peptides (see PCT publication No. WO 94/01460). Such bone anabolic functional activity is readily determined by those skilled in the art of standard assays. A variety of these compounds are described and referenced below. However, other parathyroid hormone will be known to those skilled in the art. Exemplary parathyroid hormones are disclosed in the following references. "Human Parathyroid Peptide Treatment of Vertebral Osteoporosis", Osteoporosis Int., 3, (Supp 1): 199-203. "PTH 1-34 Treatment of Osteoporosis with Added Hormone Replacement Therapy: Biochemical, Kinetic and Histological Responses" Osteoporosis Int. 1: 162-170.

Any growth hormone or growth hormone secretagogue may be used in combination with the compounds of this invention. The term growth hormone secretagogue refers to a compound which stimulates the release of growth hormone or mimics the action of growth hormone (e.g., increases bone formation leading to increased bone mass). Such actions are readily determined by those skilled in the art of standard assays well known to those of skill in the art. A variety of these compounds are disclosed in the following published PCT patent applications: WO 95/14666; WO 95/13069; WO 94/19367; WO 94/13696; and WO 95/34311. However, other growth hormones or growth hormone secretagogues will be known to those skilled in the art. In particular, a preferred growth hormone secretagogue is N-[1(R)-[1,2-Dihydro-1-methanesulfonylspiro[3H-indole-3,4'-piperidin]-1'-yl)carbonyl]-2-(phenylmethyloxy)ethyl]-2-amino-2-methylpropanamide: MK-667. Other preferred growth hormone secretagogues include 2-amino-N-(2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide or its L-tartaric acid salt; 2-amino-N-(1-(R)-benzyloxymethyl-2-(3a-(R)-(4-fluoro-benzyl)-2-methyl-3-oxo-2,3,3a,4,6,7-hexahydro-pyrazolo[4,3-c]pyridin-5-yl)-2-oxo-ethyl) isobutyramide; 2-amino-N-(2-(3a-(R)-benzyl-3-oxo-2,3,3a,4,6,7-hexahydro-pyrazolo[4,3-c]pyridin-5-yl)-1-(R) benzyloxymethyl-2-oxo-ethyl)isobutyramide; and 2-amino-N-(1-(2,4-difluoro-benzyloxymethyl)-2-oxo-2-(3-oxo-3a-pyridin-2-ylmethyl-2-(2,2,2-trifluoro-ethyl)-2,3,3a,4,6,7-hexahydro-pyrazolo[4,3-c]pyridin-5-yl)-ethyl)-2-methyl-propionamide.

The other therapeutic agent can be a steroid or a non-steroidal anti-inflammatory agent. Useful non-steroidal anti-inflammatory agents, include, but are not limited to, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam; salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone and pharmaceutically acceptable salts thereof and mixtures thereof. For a more detailed description of the NSAIDs, see Paul A. Insel, *Analgesic-Antipyretic and Antiinflammatory Agents and Drugs Employed in the Treatment of Gout*, in Goodman & Gilman's *The Pharmacological Basis of Therapeutics* 617-57 (Perry B. Molinhoff and Raymond W. Ruddon eds., $9^{th}$ ed 1996) and Glen R. Hanson,

*Analgesic, Antipyretic and Anti-Inflammatory Drugs in Remington: The Science and Practice of Pharmacy Vol II* 1196-1221 (A. R. Gennaro ed. 19th ed. 1995) which are hereby incorporated by reference in their entireties.

For arthritis, inflammation-mediated bone loss and other disorders that have an inflammatory component, preferred conventional treatments for use in combination therapy with the compounds and compositions of this invention include (without limitation) naproxen sodium (Anaprox® and Anaprox® DS, Roche), flurbiprofen (Ansaid®; Pharmacia), diclofenac sodium+misoprostil (Arthrotec®, Searle), valdecoxib (Bextra®, Pharmacia), diclofenac potassium (Cataflam® and Voltaren®, Novartis), celecoxib (Celebrex®, Pharmacia), sulindac (Clinoril®, Merck), oxaprozin (Daypro®, Pharmacia), salsalate (Disalcid®, 3M), diflunisal (Dolobid®, Merck), naproxen sodium (EC Naprosyn®, Roche), piroxicam (Feldene®, Pfizer), indomethacin (Indocin® and Indocin SR®, Merck), etodolac (Lodine® and Lodine XL®, Wyeth), meloxicam (Mobic®, Boehringer Ingelheim), ibuprofen (Motrin®, Pharmacia), naproxen (Naprelan®, Elan), naproxen (Naprosyn®, Roche), ketoprofen (Orudis® and Oruvail®, Wyeth), nabumetone (Relafen®, SmithKline), tolmetin sodium (Tolectin®, McNeil), choline magnesium trisalicylate (Trilisate®, Purdue Fredrick), and rofecoxib (Vioxx®, Merck).

In any case where pain in a component of the target disorder, the other therapeutic agent can be an analgesic. Useful analgesics include, but are not limited to, phenacetin, butacetin, acetaminophen, nefopam, acetoamidoquinone, and mixtures thereof.

For use against osteoporosis, Paget's disease and other disorders associated with bone deterioration, preferred conventional agents that may be used in combination with compounds and compositions of this invention include (without limitation) bisphosphonates (such as etidronate (Didronel®, Procter & Gamble), pamidronate (Aredia®, Novartis), and alendronate (Fosamax®, Merck)), tiludronate (Skelid®, Sanofi-Synthelabo, Inc.), risedronate (Actonel®, Procter & Gamble/Aventis), calcitonin (Miacalcin®), estrogens (Climara®, Estrace®, Estraderm®, Estratab®, Ogen®, Ortho-Est®, Vivelle®, Premarin®, and others) estrogens and progestins (Activella™, FemHrt®, Premphase®, Prempro®, and others), parathyroid hormone and portions thereof, such as teriparatide (Forteo®, Eli Lilly and Co.), selective estrogen receptor modulators (SERMs) (such as raloxifene (Evista®)) and treatments currently under investigation (such as other parathyroid hormones, sodium fluoride, vitamin D metabolites, and other bisphosphonates and selective estrogen receptor modulators).

Any method of the present invention can comprise administering an effective amount of a composition or pharmaceutical composition comprising at least one compound of this invention to a cell, tissue, organ, animal or patient in need of such modulation, treatment or therapy. Such a method can optionally further comprise co-administration or combination therapy for treating an IL-12 production related disorder, wherein the administering further comprises administering before, concurrently with, and/or after the compound of this invention, at least one additional active agent selected from a TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine or a cytokine antagonistm. Suitable dosages are well known in the art. See, e.g., Wells et al., eds., Pharmacotherapy Handbook, 2.sup.nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

TNF antagonists suitable for compositions, combination therapy, co-administration, devices and/or methods of the present invention include, but are not limited to, anti-TNF antibodies (such as, Remicade (Infliximab) or Humira (adalimumab)) for example, or, antigen-binding fragments thereof, and receptor molecules which bind specifically to TNF (such as, for example, Enbrel (Etanercept)); compounds which prevent and/or inhibit TNF synthesis, TNF release or its action on target cells, such as thalidomide, tenidap, phosphodiesterase inhibitors (e.g, pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

For clarification, a "tumor necrosis factor antibody," "TNF antibody," "TNF antibody," or fragment and the like decreases, blocks, inhibits, abrogates or interferes with TNF activity in vitro, in situ and/or preferably in vivo. For example, a suitable TNF human antibody of the present invention can bind TNFa and includes anti-TNF antibodies, antigen-binding fragments thereof, and specified mutants or domains thereof that bind specifically to TNFa. A suitable TNF antibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

The foregoing and other useful combination therapies will be understood and appreciated by those of skill in the art. Potential advantages of such combination therapies include the ability to use less of each of the individual active ingredients to minimize toxic side effects, synergistic improvements in efficacy, improved ease of administration or use and/or reduced overall expense of compound preparation or formulation.

The biological activities of a heterocyclic compound can be evaluated by a number of cell-based assays. One of such assays can be conducted using cells from human peripheral blood mononuclear cells (PBMC) or human monocytic cell line (THP-1). The cells are stimulated with a combination of human interferon-γ (IFNγ) and lipopolysaccharide or a combination of IFNγ and *Staphylococcus aureus* Cowan I in the presence of a test compound. The level of inhibition of IL-12 production can be measured by determining the amount of p70 by using a sandwich ELISA assay with anti-human IL-12 antibodies. $IC_{50}$ of the test compound can then be determined. Specifically, PBMC or THP-1 cells are incubated with the test compound. Cell viability was assessed using the bioreduction of MTS [3-(4,5-dimethylthiazol-2-yl)-5-(3-carboxymethoxyphenyl)-2-(4-sulfophenyl)-2H-tetrazolium] (Promega, Madison, Wis.).

A heterocyclic compound can also be evaluated by animal studies. For example, one of such studies involves the ability of a test compound to treat adjuvant arthritis (i.e., a IL-12 overproduction related disorder) in rats.

Without further elaboration, it is believed that the above description has adequately enabled the present invention. The following specific embodiments are, therefore, to be construed as merely illustrative, and not limitative of the remainder of the disclosure in any way whatsoever. All of the references and publications cited herein are hereby incorporated by reference in their entirety.

The compounds described above can be prepared by methods well known in the art, as well as by the synthetic routes disclosed herein. For example, certain compounds of the invention can be prepared by using a 2,4-dichloro-pyrimidine-6-carboxylate ester (e.g., compound A in Scheme I below) as a starting material.

Compound A and related compounds can be obtained by known methods; alternatively, compound A and related compounds can be prepared according to the following representative procedure:

Picolinic acid is added to an excess of $SOCl_2$, followed by addition of a catalytic amount of NaBr and the mixture is heated at reflux for about 16 to about 30 hours. Excess $SOCl_2$ is distilled off, and the residue is added to an excess of an alcohol, such as ethanol, over a period of 30 minutes, so that the ethanol is mildly refluxing due to the exothermic reaction. The mixture is cooled to room temperature and may be filtered through celite to remove suspended material. The ethanol is removed by distillation and the residue is poured slowly into cold aqueous basic solution, such as sodium carbonate solution. The product is extracted into an organic solvent and dried over a drying agent, such as magnesium sulfate or sodium sulfate; the product, a 4-chloro-pyridine-2-carboxylic acid ester (e.g., the ethyl ester), can be used in the next step without further purification.

To a 4-chloro-pyridine-2-carboxylic acid ester is added about 0.8 to about 1.5 equivalents with respect to the picolinic acid starting material of m-chloro-peroxybenzoic acid (mCPBA) in portions over a period of about a one to about three hour period. The solution is stirred without heating or cooling for about 1 day to about 3 days. The solid formed during reaction is removed by filtration, and the solution is neutralized with cold aqueous basic solution, such as aqueous sodium carbonate solution. The organic layer is separated and the aqueous layer is extracted with an organic solvent. The combined organic layers are dried over a drying agent, such as potassium carbonate, and concentrated. The residue is purified by stirring in hexane at room temperature for about 1 hour to about 10 hours. The precipitated solid is collected by filtration, washed with hexane, and dried, yielding a 4-chloropicolinic acid ester N-oxide.

A 4-chloropicolinic acid ester N-oxide is added to excess phosphorus oxychloride at about −20° C. to about 10° C. and stirred for one hour. The solution is then heated to about 70° C. to about 120° C. for about 1 hour to about six hours. Excess $POCl_3$ is removed in vacuo, and the residue is dissolved in an organic solvent, washed with cold sodium bicarbonate solution, and extracted with an organic solvent. Removal of the solvent gives a 4,6-dichloropicolinic acid ester (e.g., compound A).

It will be appreciated that, in the above procedure, different oxidants may be substituted for mCPBA (e.g., oxone) and substituted picolinic acid compounds can be used to provide identical or analogous materials. Thus, in one aspect, the invention provides a method for preparing a 4,6-dichloropicolinic acid ester. The method includes the steps of exposing a 4-chloropicolinic acid ester (e.g., a lower alkyl ester) to an oxidant (e.g., mCPBA, Oxone, and the like) to form a 4-chloropicolinic acid ester N-oxide, and exposing the 4-chloropicolinic acid ester N-oxide to phosphorous oxychloride, under conditions such that a 4,6-dichloropicolinic acid ester is formed.

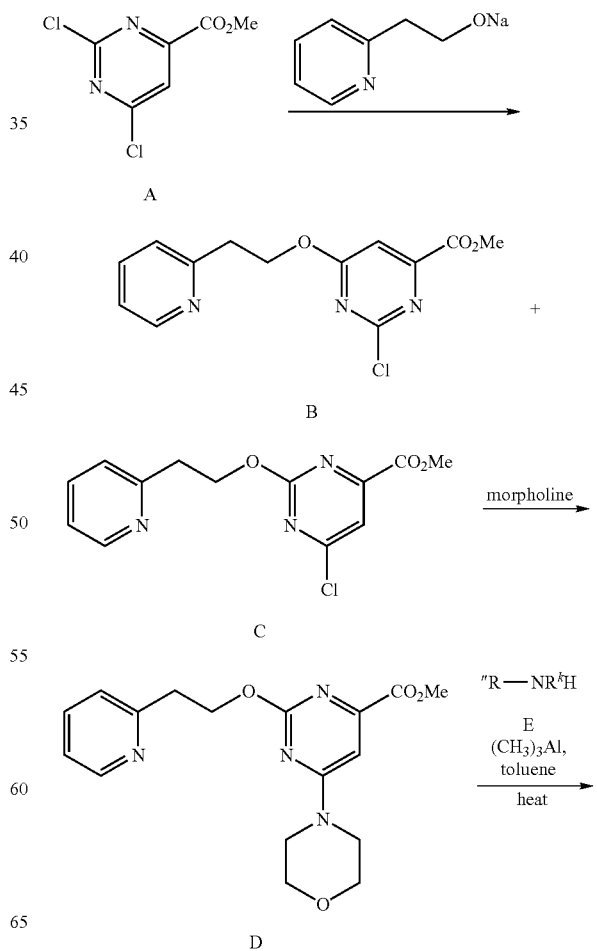

-continued

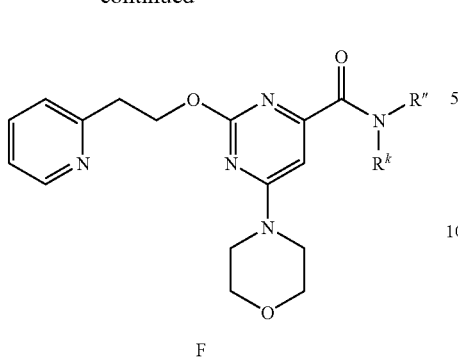

F

As shown in Scheme I, the two chloro groups of compound A can be displaced by various substitutes. More specifically, a first chloro group (e.g., at position 2 or 4) can react with, e.g., a metal alkoxide (e.g., sodium, potassium alkoxide), prepared from an alcohol with a base (e.g., NaH, KH). For example, exposure of compound A to the sodium salt of 2-pyridine ethanol (e.g., via 2-pyridine ethanol and NaH) affords a mixture of the isomeric pyrimidine ethers B and C. The remaining chloro group (e.g., at the 2 or 4 position) can be replaced with a nucleophile, e.g., a cyclic amine. For example, treatment of the B/C isomer mixture with morpholine provides, after chromatography compound D. The amide linkage can be formed by adding a solution of trimethylaluminum to a solution of compound D and an amine represented by compound E. The reaction mixture is then microwaved at 120° C. for 5-7 minutes. Flash column chromatography purification typically affords about 65-75% of compound F.

Alternatively, compounds having a urea linkage can be formed according to Scheme II below.

Scheme II

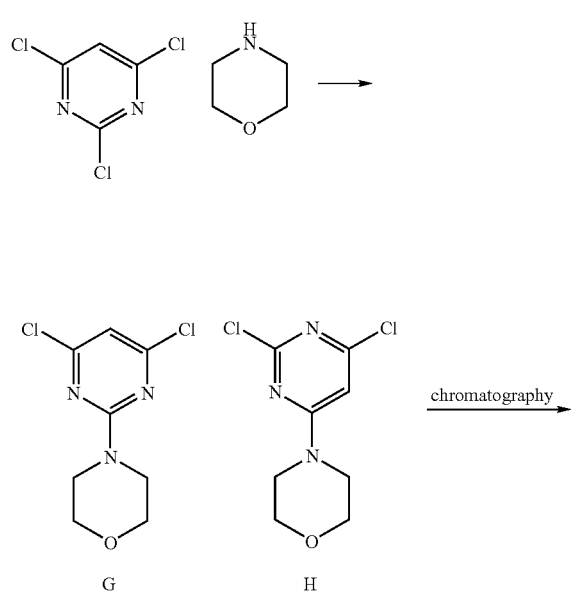

G  H

-continued

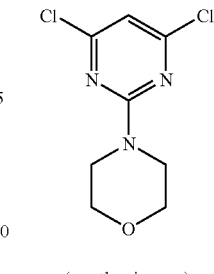

(or other isomer)
J 1) hydrazine
2) NaNO₂
3) H₂, Pd/C
4) R₁—NCO
NaH

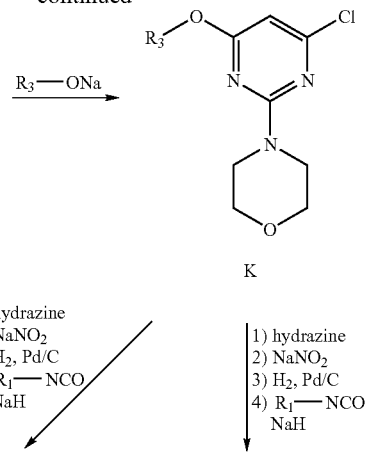

K 1) hydrazine
2) NaNO₂
3) H₂, Pd/C
4) R₁—NCO
NaH

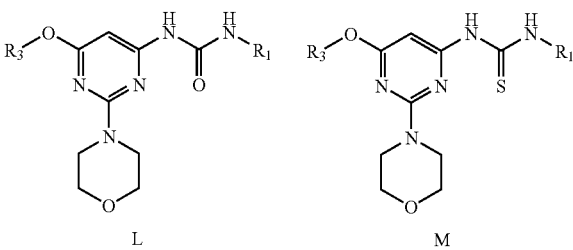

L  M

For example, a pyrimidine compound can be prepared by using 2,4,6-trichloro-pyrimidine as a starting material. The three chloro groups can be displaced by various substitutes. More specifically, a first chloro group (e.g., at position 6) can react with, e.g., morpholine, to form a morpholinyl pyrimidine (compounds G and H). 2-Aryl and 2-alkylpyrimidine dichloro compounds can also be prepared by reacting an amidine with a malonic ester followed by treatment with phosphorous oxychloride. A second chloro group can be replaced by reacting with a nucleophile, such as an alcohol in the presence of base, e.g., sodium hydride to form compound K. In other examples, a compound of formula (I), wherein Y is $CH_2$ can be prepared by reacting the pyrimidine chloride with a Grignard reagent, an organotin reagent, an organocopper reagent, an organoboric acid, or an organozinc reagent in the presence of an organopalladium compound as a catalyst. Isomeric forms may be produced. The desired isomeric product can be separated from others by, e.g., high performance liquid chromatography. A third chloro group can undergo a displacement reaction with hydrazine. The hydrazine group converted to an azido group by treatment with sodium nitrite, followed by treatment with palladium on carbon under hydrogen gas to convert the azido group to an amine. Finally, amine group is created with an isocyanate to form a urea linker (compound L) or an isothiocyanate to form a thiourea linker (compound M).

In another embodiment, certain urea compounds can be prepared according to the procedure shown in Scheme III, below.

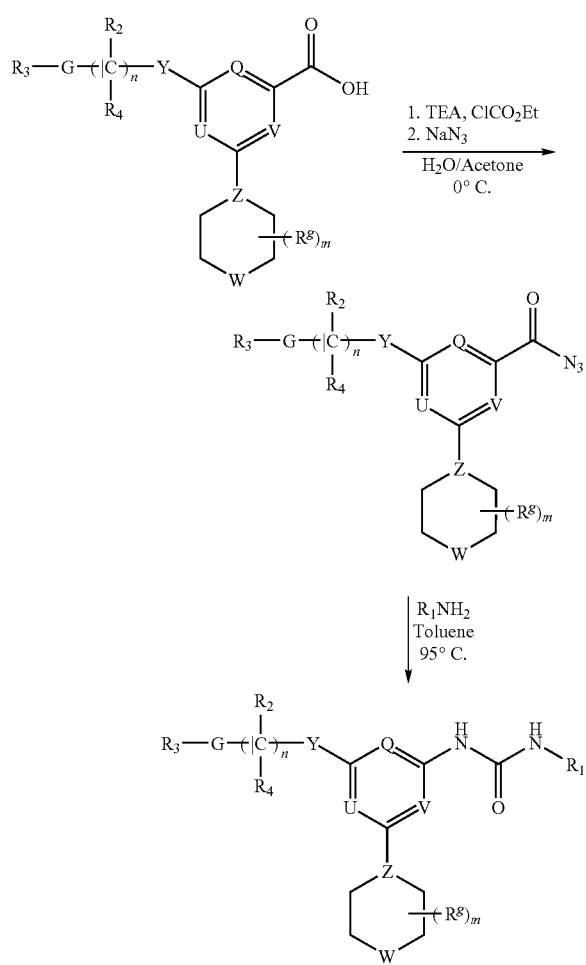

Scheme III

As shown in Scheme III, a carboxylic acid can be converted to an acyl azide by treatment with sodium azide. The acyl azide can undergo Curtius rearrangement and reaction with an amine to form a urea compound of the invention.

Thus, in another aspect, the invention provides a method for preparing a urea-containing compound according to the invention. The method includes the steps of (a) contacting a heteroaryl carboxylic acid (e.g., of the formula shown in Scheme III) with an azide-containing reagent (e.g., sodium azide or trimethylsilyl azide) under conditions such that an acyl azide is formed, (b) contacting the acyl azide with an amine compound under conditions such that a urea compound of the invention is formed. In preferred embodiments, the acyl azide compound is heated during or prior to the step of contacting with the amine compound; without wishing to be bound by theory, it is believed that the acyl azide is converted into an intermediate isocyanate compound which then reacts with the amine compound to form the urea compound of the invention.

If preferred, other types of linkages can be prepared by similar reactions. Sensitive moieties on a pyrimidinyl intermediate and a nucleophile can be protected prior to coupling. The chemicals used in the above-described synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the heterocyclic compounds. In addition, various synthetic steps may be performed in an alternate sequence or order to give the desired compounds. Synthetic chemistry transformations and protecting group methodologies (protection and deprotection) useful in synthesizing applicable heterocyclic compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Correspondingly, pyridine, pyridinyl and triazinyl compounds described herein can be made according to methods know in the art, including those in the aforementioned treatises. The pyridinyl and triazinyl compounds can be made using analogous synthetic procedures and reagents as described for the pyrimidinyl compounds. It is recognized by one of ordinary skill that pyrimidines demonstrate reactivity intermediate relative to that of pyridines and triazines, therefore reaction conditions (e.g., temperature, reaction time, etc.) may be adjusted accordingly, which is routine for one of ordinary skill Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

Nucleophilic agents are known in the art and are described in the chemical texts and treatises referred to herein. The chemicals used in the aforementioned methods may include, for example, solvents, reagents, catalysts, protecting group and deprotecting group reagents and the like. The methods described above may also additionally include steps, either before or after the steps described specifically herein, to add or remove suitable protecting groups in order to ultimately allow synthesis of the compound of the formulae described herein. The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, crystallization, chromatography). Other embodiments relate to the intermediate compounds delineated herein, and their use in the methods (e.g., treatment, synthesis) delineated herein.

A heterocyclic compound thus obtained can be further purified by flash column chromatography, high performance liquid chromatography, or crystallization.

Example 1

Synthesis of Compound 1

A. Preparation of 4,6-dichloropicolinic acid ethyl ester

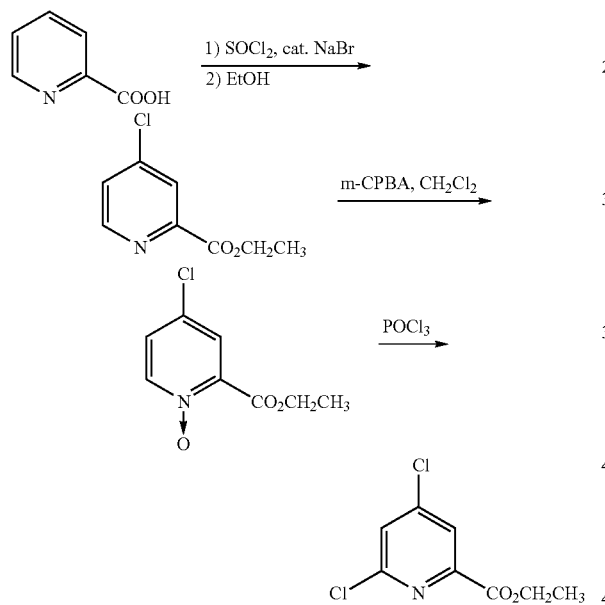

Picolinic acid (50 g, 0.4 mol) was added to 120 mL SOCl$_2$, followed by addition of NaBr (0.83 g, 0.008 mol, 0.02 equiv.) and the mixture was heated at reflux for 24 hours. Excess SOCl$_2$ was distilled off, and the residue was added to 200 mL ethanol over a period of 30 minutes, so that the ethanol was mildly refluxing due to the exothermic reaction. The mixture was cooled to room temperature and filtered through celite to remove the cloudy yellow substance. The ethanol was removed by distillation and the residue was poured slowly into cold sodium carbonate solution. The product was extracted with methylene chloride (3×150 mL) and dried over magnesium sulfate; the light brown solution is used in the next step without further purification.

To the light brown solution was added m-chloro-peroxybenzoic acid (mCPBA) in four portions (90 g, 77% pure, 0.4 mol, 1.0 equiv) over a period of two hours. The solution was stirred without heating or cooling for 2 days. The solid formed during reaction was removed by filtration, and the solution was neutralized with cold aqueous sodium carbonate solution. The organic layer was separated and the aqueous layer was extracted with methylene chloride (3×100 mL). The combined organic layers were dried over potassium carbonate and concentrated. The light brown viscous residue was treated with hexane and stirred at room temperature for 6 hours. The precipitated solid was collected by filtration, washed with hexane, and dried, yielding 4-chloropicolinic acid ethyl ester N-oxide as a light brown solid (25.1 g, 31% from picolinic acid).

4-Chloropicolinic acid ethyl ester N-oxide (1.6 g, 8 mmol) was added to 4 mL of phosphorus oxychloride at 0° C. and stirred at 0° C. for one hour. The solution was then heated at 100° C. for four hours. Excess POCl$_3$ was removed in vacuo, and the residue was dissolved in ethyl acetate, washed with cold sodium bicarbonate solution, and extracted with ethyl acetate. Removal of the solvent gave 4,6-dichloropicolinic acid ethyl ester (compound A) as an off-white solid (1.12 g, 64%). The methyl ester can be made by an analogous procedure.

B. Preparation of Compound 1 (2-Morpholin-4-yl-6-(2-morpholin-4-yl-ethoxy)-pyrimidine-4-carboxylic acid (2,3-dimethyl-1H-indol-5-yl)-amide)

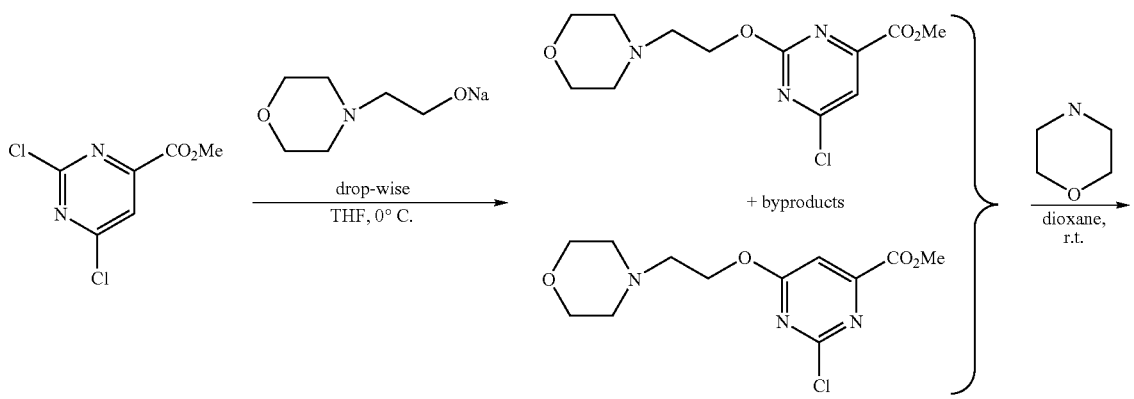

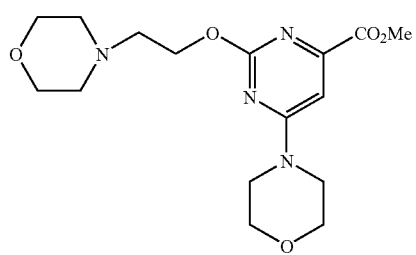

+ byproducts

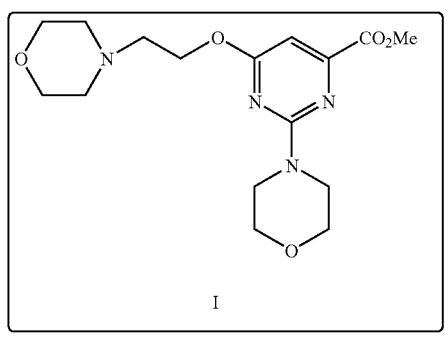

I

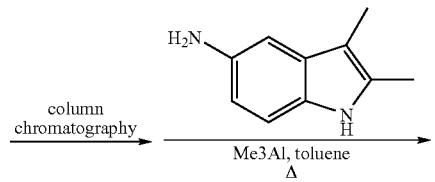

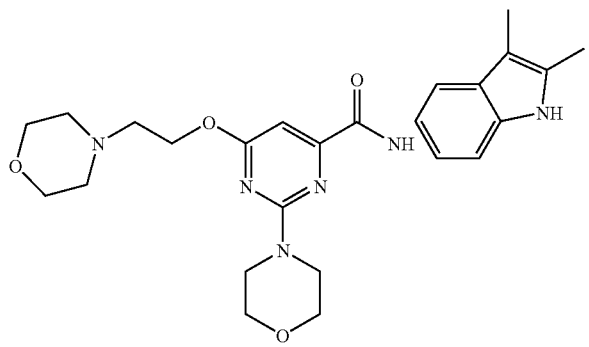

To a stirred solution of 4-(2-hydroxyethyl)morpholine (3.67 g, 28 mmol) in anhydrous THF (61 mL) cooled with ice, was added sodium hydride, 60% dispersion in mineral oil, (1.17 g, 29.2 mmol) in three portions under nitrogen purge. Ice-bath was removed and a mixture was stirred at room temperature for 20-30 minutes, cooled back to 0° C. and added drop-wise (using syringe or dropping funnel) under nitrogen purge to a solution of methyl 2,4-dichloropyrimidine carboxylate (5.26 g, 25.4 mmol) in anhydrous THF (53 mL) at 0° C. A resulted solution was stirred 30 minutes at 0° C., followed by 30 minutes at room temperature. It was then quenched carefully with ice-water (115 mL) and diluted with ethyl acetate (115 mL). Organic layer was separated, water layer extracted once with ethyl acetate, combined ethyl acetate extracts, washed with brine and dried over anhydrous sodium sulfate. Ethyl acetate was removed, a residue, about 6.2 g, containing two mono-substituted isomers, traces of starting material and byproducts, including some di-substituted product (most of which left in water layer), was dissolved in anhydrous 1,4-dioxane (25 mL) and treated with morpholine (~2.2 eq, 3.94 g) with stirring. Reaction was completed within 10 minutes, solvent removed, and residue separated between ethyl acetate and water. Water layer was extracted once with ethyl acetate, combined organic solutions washed with brine, and dried over anhydrous sodium sulfate.

A desired product was separated from less polar by-products and more polar isomer by column chromatography on silica gel, with gradient eluation with hexane-ethyl acetate (1:2), ethyl acetate and dichloromethane-acetone-methanol (3:1:01) mixture, to afford 2-morpholin-4-yl-6-(2-morpholin-4-yl-ethoxy)-pyrimidine-4-carboxylic acid methyl ester (I) (5 g, 25%, for two steps).

To a stirred mixture of compound (I) (1.02 g, 2.9 mmol) and 5-amino-2,3-dimethylindole (488 mg, 3.04 mmol) in toluene (6.9 mL) that was heated briefly until components partly dissolved and cooled to ambient temperature, was added 2 M solution of trimethylaluminum in toluene (2.32 mL, 1.6 eq) drop-wise under nitrogen purge. Reaction mixture was stirred until bubbling (gas evolution) completed, and then heated at 115° C. (oil bath) for 15 minutes. To a cooled reaction mixture chloroform and 1 N NaOH were added, chloroform layer was separated, washed twice with water, brine and dried over anhydrous sodium sulfate. Flash column chromatography on silica gel (eluent dichloromethane-acetone-methanol (3:1:01)) and recrystallization from chloroform-ethyl acetate mixture afforded target amide, 2-Morpholin-4-yl-6-(2-morpholin-4-yl-ethoxy)-pyrimidine-4-carboxylic acid (2,3-dimethyl-1H-indol-5-yl)-amide, as a pale yellow solid (1.1 g, 79%).

Example 2

Synthesis of Compound 80 (6-Morpholin-4-yl-2-(2-morpholin-4-yl-ethoxy)-pyrimidine-4-carboxylic acid N'-m-tolyl-hydrazide)

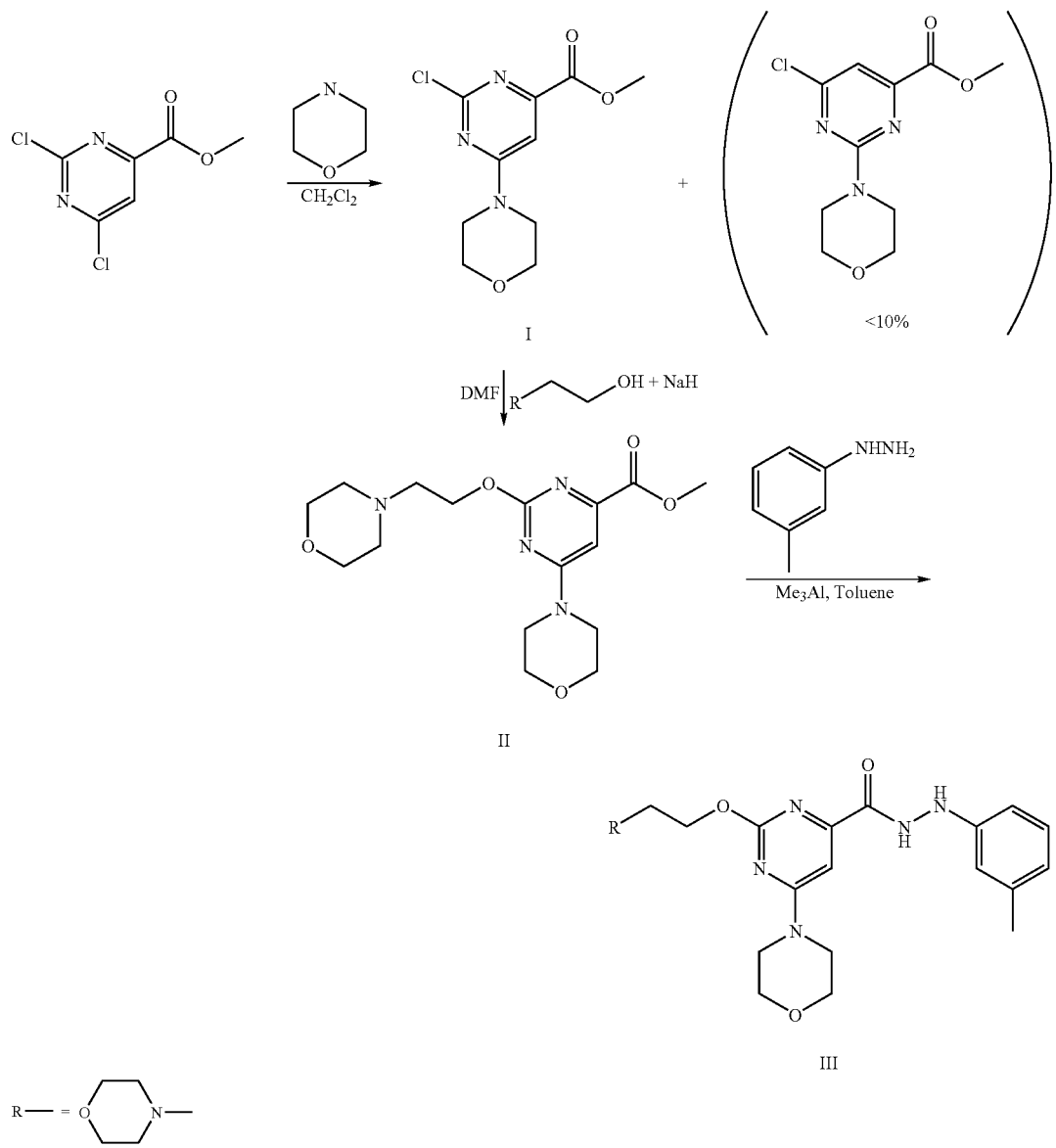

To a stirred solution of methyl 2,4-dichloropyrimidine-6-carboxylate (4.62 g, 22.3 mmol) in dichloromethane was added a solution of morpholine (3.9 mL, 44.6 mmol) at −78° C. under nitrogen purge, and the resulted solution was allowed to warm up to room temperature. Dichloromethane and water were added, and the organic phase was separated, washed with water, brine and dried over anhydrous sodium sulfate. Recrystallization from ethyl acetate afforded around 5 g (86%) of a major isomer, product (I).

To a stirred solution of 4-(2-hydroxyethyl)-morpholine (1.44 g, 11 mmol) in 10 mL of anhydrous DMF at ambient temperature was added sodium hydride, 60% dispersion in mineral oil, (0.46 g, 11.5 mmol) portion-wise under nitrogen purge. A resultant mixture was stirred for 15 minutes, cooled to 0° C., and a solid product (I) (2.7 g, 10.5 mmol) was added to the mixture. A reaction mixture was allowed to warm to ambient temperature and stirred at that temperature for 40 min. Water and ethyl acetate were added to the reaction mixture, organic layer separated, water layer extracted with ethyl acetate, and combined organic solutions were washed with brine and dried over anhydrous sodium sulfate. 6-Morpholin-4-yl-2-(2-morpholin-4-yl-ethoxy)-pyrimidine-4-carboxylic acid methyl ester, product (II) (2.59 g, 70%) was isolated by column chromatography (eluent dichloromethane:acetone:methanol, 3:1:0.25).

To a stirred mixture of product (II) (0.71 g, 2 mmol) and m-tolylhydrazine (0.256 g, 2.1 mmol) in toluene, 4.5 mL, a 2M solution of trimethylaluminum in toluene (1.6 mL) was added drop-wise under nitrogen purge. A resulted solution was stirred until gas evolution completed and then microwaved at 120° C. for 5 minutes. To the reaction mixture were added 1N NaOH solution and dichloromethane, organic layer separated, washed with water, brine and dried over anhydrous sodium sulfate. Column chromatography purification using gradient elution (hexane:ethyl acetate, 1:3; ethyl acetate; ethyl acetate:dichloromethane:methanol, 75:24:1) afforded the title compound (III) (1.07 g, 60%) 6-Morpholin-4-yl-2-(2-morpholin-4-yl-ethoxy)-pyrimidine-4-carboxylic acid N'-m-tolyl-hydrazide as a light-yellow solid.

Example 3

Synthesis of Compound 10 (1-[6-(2-Methylamino-ethoxy)-2-morpholin-4-yl-pyrimidin-4-yl]-3-m-tolyl-urea)

2-Morpholino-4,6-dichloropyrimidine (6.5 g; 27.8 mmol) was dissolved in dimethyl formamide (30 mL), and chilled in an ice bath. In a separate flask, 4-(2-hydroxyethyl)-morpholine was dissolved in dimethyl formamide (20 mL), to which was added sodium hydride (800 mg; 33.2 mmol). The alkoxide solution was added to the pyrimidine solution, and it was stirred for two hours. The solution was allowed to warm to room temperature, and tert-butoxycarbonyl anhydride (9.0 g; 41.3 mmol) was added. After stirring overnight, the solution was poured into ethyl acetate (200 mL) which was then washed with water (3×200 mL). The organic layer was dried over magnesium sulfate, evaporated, and purified by column chromatography to give [2-(6-chloro-2-morpholin-4-yl-pyrimidin-4-yloxy)-ethyl]-methyl-carbamic acid tert-butyl ester (5.6 g).

[2-(6-chloro-2-morpholin-4-yl-pyrimidin-4-yloxy)-ethyl]-methyl-carbamic acid tert-butyl ester (5.6 g) was dissolved in dioxane (100 mL) and hydrazine (6 mL) was added. The solution was heated to reflux for one hour, at which point the solvent was evaporated. The solid was dissolved in dichloromethane (200 mL) and washed with 10% sodium carbonate (10 mL). The organic layer was dried over magnesium sulfate and evaporated to give [2-(6-hydrazino-2-morpholin-4-yl-pyrimidin-4-yloxy)-ethyl]-methyl-carbamic acid tert-butyl ester, which was used without purification in the next reaction.

[2-(6-hydrazino-2-morpholin-4-yl-pyrimidin-4-yloxy)-ethyl]-methyl-carbamic acid tert-butyl ester was dissolved in glacial acetic acid (30 mL). To this solution was added a solution of sodium nitrite (1.3 g) in water (4 mL). The reaction was stirred for ten minutes, and poured into ethyl acetate (100 mL). The organic layer was then washed with water (100 mL) and 10% sodium carbonate (2×100 mL). The organic layer was dried over magnesium sulfate and evaporated to give [2-(6-azido-2-morpholin-4-yl-pyrimidin-4-yloxy)-ethyl]-methyl-carbamic acid tert-butyl ester, which was used without purification in the next reaction.

[2-(6-azido-2-morpholin-4-yl-pyrimidin-4-yloxy)-ethyl]-methyl-carbamic acid tert-butyl ester was dissolved in a mixture of tetrahydrofuran (200 mL) and methanol (20 mL). To the solution was added 10% palladium on carbon (2 g) and the reaction was stirred under an atmosphere of hydrogen for 24 hours. The reaction was then filtered through celite and evaporated to give [2-(6-amino-2-morpholin-4-yl-pyrimidin-4-yloxy)-ethyl]-methyl-carbamic acid tert-butyl ester (5.0 g).

Methyl-{2-[2-morpholin-4-yl-6-(3-m-tolyl-ureido)-pyrimidin-4-yloxy]-ethyl}-carbamic acid tert-butyl ester was synthesized in an analogous fashion to compound 14 (vida supra) except that [2-(6-amino-2-morpholin-4-yl-pyrimidin-4-yloxy)-ethyl]-methyl-carbamic acid tert-butyl ester was used as the starting material and the appropriate isocyanate was used.

Methyl-{2-[2-morpholin-4-yl-6-(3-m-tolyl-ureido)-pyrimidin-4-yloxy]-ethyl}-carbamic acid tert-butyl ester (1.23 g) was dissolved in dichloromethane (30 mL) and to this mixture was added trifluoroacetic acid (30 mL). The solution was stirred for one hour, and then quenched with sufficient 10% sodium carbonate solution to raise the pH of the aqueous layer above seven. The organic layer was separated, dried over magnesium sulfate, and concentrated to approximately 5 mL volume. The resulting precipitate was collected to give Compound 10 (580 mg).

Example 4

Synthesis of Compound 11 (1-[6-(2-Hydroxy-2-methyl-propoxy)-2-morpholin-4-yl-pyrimidin-4-yl]-3-m-tolyl-urea)

2-Morpholino-4,6-dichloropyrimidine (2.34 g; 10 mmol) and ethyl glycolate (1.3 g; 12 mmol) were dissolved in tetrahydrofuran (100 mL), and chilled in an ice bath. To the solution was added sodium hydride (300 mg; 12 mmol), and it was stirred overnight at ambient temperature. The solvents were evaporated, and the solid was dissolved in ethyl acetate (200 mL) which was then washed with water (2×100 mL). The organic layer was dried over magnesium sulfate, and evaporated to give (6-chloro-2-morpholin-4-yl-pyrimidin-4-yloxy)-acetic acid ethyl ester (3.16 g).

(6-Chloro-2-morpholin-4-yl-pyrimidin-4-yloxy)-acetic acid ethyl ester (3.16 g) was dissolved in tetrahydrofuran (100 mL) and chilled in an ice bath. To the solution was added a 1.4M solution of methyl magnesium bromide in ether (21.5 mL) and it was stirred for one hour. The solvents were evaporated, and the solid was dissolved in ethyl acetate (200 mL) which was then washed with water (2×100 mL). The organic layer was separated, dried over magnesium sulfate, and purified by column chromatography to give 1-(6-chloro-2-morpholin-4-yl-pyrimidin-4-yloxy)-2-methyl-propan-2-ol (2.58 g).

1-(6-chloro-2-morpholin-4-yl-pyrimidin-4-yloxy)-2-methyl-propan-2-ol (2.58 g) was dissolved in dioxane (50 mL) and hydrazine (3 mL) was added. The solution was heated to reflux for one hour, at which point the solvent was evaporated. The solid was dissolved in dichloromethane (200 mL) and washed with 10% sodium carbonate (10 mL). The organic layer was dried over magnesium sulfate and evaporated to give 1-(6-hydrazino-2-morpholin-4-yl-pyrimidin-4-yloxy)-2-methyl-propan-2-ol, which was used without purification in the next reaction.

1-(6-hydrazino-2-morpholin-4-yl-pyrimidin-4-yloxy)-2-methyl-propan-2-ol was dissolved in glacial acetic acid (30 mL). To this solution was added a solution of sodium nitrite (700 mg) in water (4 mL). The reaction was stirred for ten minutes, and poured into ethyl acetate (100 mL). The organic layer was then washed with water (100 mL) and 10% sodium carbonate (2×100 mL). The organic layer was dried over magnesium sulfate and evaporated to give 1-(6-Azido-2-morpholin-4-yl-pyrimidin-4-yloxy)-2-methyl-propan-2-ol, which was used without purification in the next reaction.

1-(6-azido-2-morpholin-4-yl-pyrimidin-4-yloxy)-2-methyl-propan-2-ol was dissolved in a mixture of tetrahydrofuran (200 mL) and methanol (20 mL). To the solution was added 10% palladium on carbon (2 g) and the reaction was stirred under an atmosphere of hydrogen for 24 hours. The reaction was then filtered through celite and evaporated to give 1-(6-amino-2-morpholin-4-yl-pyrimidin-4-yloxy)-2-methyl-propan-2-ol (2.0 g).

1-(6-amino-2-morpholin-4-yl-pyrimidin-4-yloxy)-2-methyl-propan-2-ol (1.03 g; 3.8 mmol) and imidazole (500 mg; 8 mmol) were dissolved in dimethyl formamide (16 mL). To this solution was added tert-butyldimethylsilyl chloride (1.2 g; 8 mmol), and it was stirred for 72 hours. The solution was poured into ethyl acetate (100 mL) which was then washed with water (3×200 mL). The organic layer was separated, dried over magnesium sulfate, and purified by column chromatography to give 642-(tert-butyl-dimethyl-silanyloxy)-2-methyl-propoxyl-2-morpholin-4-yl-pyrimidin-4-ylamine (500 mg).

1-{6-[2-(tert-Butyl-dimethyl-silanyloxy)-2-methyl-propoxy]-2-morpholin-4-yl-pyrimidin-4-yl}-3-m-tolyl-urea was synthesized in an analogous fashion to compound 14 (vida supra), except that 6-[2-(tert-butyl-dimethyl-silanyloxy)-2-methyl-propoxy]-2-morpholin-4-yl-pyrimidin-4-ylamine was used as the starting material and the appropriate isocyanate was used.

1-{6-[2-(tert-Butyl-dimethyl-silanyloxy)-2-methyl-propoxy]-2-morpholin-4-yl-pyrimidin-4-yl}-3-m-tolyl-urea (30 mg) was dissolved in a 1.0 M solution of tetrabutylammonium fluoride in tetrahydrofuran (2 mL), and the solution was stirred overnight. The solvents were evaporated, and the solid was dissolved in ethyl acetate (20 mL) which was then washed with water (2×10 mL). The organic layer was separated, dried over magnesium sulfate, and purified by column chromatography to give Compound 11 (18 mg).

Example 5

Synthesis of Compound 12 (1-[6-Morpholin-4-yl-2-(2-morpholin-4-yl-ethoxy)pyrimidin-4-yl]-3-p-tolyl-thiourea)

4-[2-(4-Chloro-6-(morpholin-4-yl)-pyrimidin-2-yloxy)-ethyl]-morpholine was synthesized in an analogous fashion to (6-chloro-2-morpholin-4-yl-pyrimidin-4-yloxy)-acetic acid ethyl ester, except that 4-(2-hydroxyethyl)-morpholine was used instead of ethyl glycolate, and 6-morpholino-2,4-dichloropyrimidine was used instead of 2-morpholino-4,6-dichloropyrimidine. Column chromatography was necessary to separate the isomers.

6-Morpholin-4-yl-2-(2-morpholin-4-yl-ethoxy)-pyrimidin-4-ylamine was synthesized in an analogous fashion to 1-(6-amino-2-morpholin-4-yl-pyrimidin-4-yloxy)-2-methyl-propan-2-ol, except that 4-[2-(4-Chloro-6-(morpholin-4-yl)-pyrimidin-2-yloxy)-ethyl]-morpholine was used as the precursor.

6-Morpholin-4-yl-2-(2-morpholin-4-yl-ethoxy)-pyrimidin-4-ylamine (1.24 g; 4 mmol) and p-tolyl isocyanate (750 mg; 5 mmol) were dissolved in dimethyl formamide (6 mL), and to the solution was added sodium hydride (200 mg; 8 mmol). After stirring overnight, the solution was poured into ethyl acetate (20 mL) which was then washed with water (3×20 mL). The organic layer was separated, dried over magnesium sulfate, and purified by column chromatography to give Compound 12 (630 mg).

Example 6

Synthesis of Compound 14 (1-[2-Morpholin-4-yl-6-(2-morpholin-4-yl-ethoxy)pyrimidin-4-yl]-3-phenyl-urea)

4-[2-(6-Chloro-2-(morpholin-4-yl)-pyrimidin-4-yloxy)-ethyl]-morpholine was synthesized in an analogous fashion to (6-chloro-2-morpholin-4-yl-pyrimidin-4-yloxy)-acetic acid ethyl ester, except that 4-(2-hydroxyethyl)-morpholine was used instead of ethyl glycolate.

2-Morpholin-4-yl-6-(2-morpholin-4-yl-ethoxy)-pyrimidin-4-ylamine was synthesized in an analogous fashion to 1-(6-amino-2-morpholin-4-yl-pyrimidin-4-yloxy)-2-methyl-propan-2-ol, except that 4-[2-(6-chloro-2-(morpholin-4-yl)-pyrimidin-4-yloxy)-ethyl]-morpholine was used as the precursor.

2-Morpholin-4-yl-6-(2-morpholin-4-yl-ethoxy)-pyrimidin-4-ylamine (206 g; 4 mmol) and phenyl isocyanate (750 mg; 5 mmol) were dissolved in dimethyl formamide (6 mL), and to the solution was added sodium hydride (200 mg; 8 mmol). After stirring overnight, the solution was poured into ethyl acetate (20 mL) which was then washed with water (3×20 mL). The organic layer was separated, dried over magnesium sulfate, and purified by column chromatography to give Compound 14 (630 mg).

Example 7

Synthesis of Compound 9 (1-[2-Morpholin-4-yl-6-(2-morpholin-4-yl-ethoxy)-pyrimidin-4-yl]-3-m-tolyl-urea)

Compound 9 was synthesized in an analogous fashion to Compound 14, except that m-tolyl isocyanate was used instead of phenyl isocyanate.

Example 8

Synthesis of Compound 13 (1-(2-Bromo-4-methyl-phenyl)-3-[6-morpholin-4-yl-2-(2-morpholin-4-yl-ethoxy)-pyrimidin-4-yl]-thiourea)

Compound 13 was synthesized in an analogous fashion to compound 14, except that 3-bromo-p-tolyl isocyanate was used instead of phenyl isocyanate.

Example 9

Synthesis of Compound 15 (1-[2-Morpholin-4-yl-6-(2-morpholin-4-yl-ethoxy)-pyrimidin-4-yl]-3-p-tolyl-urea)

Compound 15 was synthesized in an analogous fashion to compound 14, except that p-tolyl isocyanate was used instead of phenyl isocyanate.

Example 10

Synthesis of Compound 16 (1-(3-Methoxy-phenyl)-3-[2-morpholin-4-yl-6-(2-morpholin-4-yl-ethoxy)-pyrimidin-4-yl]-urea)

Compound 16 was synthesized in an analogous fashion to compound 14, except that 3-methoxyphenyl isocyanate was used instead of phenyl isocyanate.

Example 11

Synthesis of Compound 17 (1-(4-Chloro-phenyl)-3-[2-morpholin-4-yl-6-(2-morpholin-4-yl-ethoxy)-pyrimidin-4-yl]-urea)

Compound 17 was synthesized in an analogous fashion to compound 14, except that p-chlorophenyl isocyanate was used instead of phenyl isocyanate.

Example 12

Synthesis of Compound 18 (1-(2-Methoxy-phenyl)-3-[2-morpholin-4-yl-6-(2-morpholin-4-yl-ethoxy)-pyrimidin-4-yl]-urea)

Compound 18 was synthesized in an analogous fashion to compound 14, except that 2-methoxyphenyl isocyanate was used instead of phenyl isocyanate.

Example 13

Synthesis of Compound 19 (1-Benzyl-3-[2-morpholin-4-yl-6-(2-morpholin-4-yl-ethoxy)-pyrimidin-4-yl]-urea)

Compound 19 was synthesized in an analogous fashion to Compound 14, except that benzyl isocyanate was used instead of phenyl isocyanate.

Example 14

Synthesis of Compound 323 (1-(2,3-Dimethyl-1H-indol-5-yl)-3-[2-morpholin-4-yl-6-(2-morpholin-4-yl-ethoxy)-pyrimidin-4-yl]-urea)

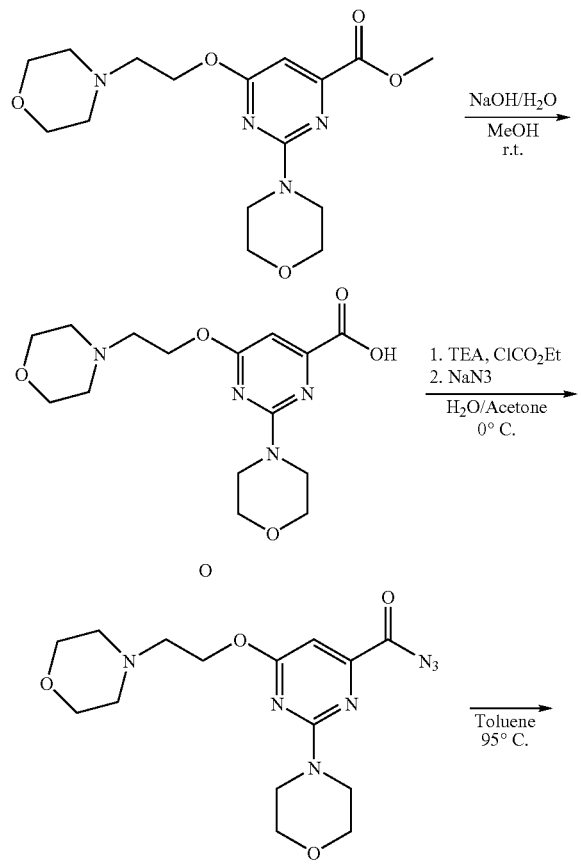

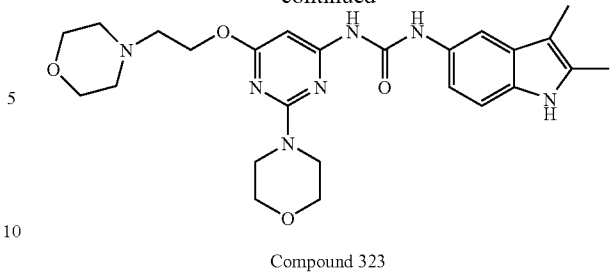

Compound 323

To a suspension of 2-morpholin-4-yl-6-(2-morpholin-4-yl-ethoxy)-pyrimidine-4-carboxylic acid methyl ester (2.4 g, 6.68 mmol) in methanol, 5 mL, was added a solution of sodium hydroxide (0.3 g, 7.43 mmol) in water (1 mL), and a resulted solution was stirred at ambient temperature until TLC showed that starting material was consumed. The reaction mixture was neutralized with 37% HCl (0.58 mL, 7.43 mmol). The majority of the solvent was removed under reduced pressure to give a precipitated product which was filtered out, washed 2×10 mL 95% ethanol and vacuum-dried. Crude 2-morpholin-4-yl-6-(2-morpholin-4-yl-ethoxy)-pyrimidine-4-carboxylic acid (O), 2.67 g, contained NaCl, and was used for the next step without further purification.

$^1$H NMR (DMSO-d$_6$): δ 6.51 (s, 1H), 4.44 (t, J=5.7 Hz, 2H), 3.72 (m, 4H), 3.65 (m, 4H), 3.57 (m, 8H), 2.71 (t, J=5.7 Hz, 2H).

To a suspension of compound O (2.2 g, ~6.5 mmol) in water (6 mL)/acetone (3 mL) mixture at 0° C. were added consecutively triethylamine (1.1 mL, 7.9 mmol) in acetone (5 mL) and ethyl chloroformate (0.9 mL, 11.6 mmol) in acetone (5 mL), and a resulted solution was stirred at that temperature for 30 minutes. A solution of sodium azide (0.7 g, 10.8 mmol) in water (2.5 mL) was added to the reaction mixture causing evolution of gas and formation of thick suspension that was stirred at 0° C. for 1 hour. Ice-water (15 mL) was to the suspension, and the yellow solid was filtered out, washed with water (2×10 mL), then with ether (10 mL) and dried to give 2-morpholin-4-yl-6-(2-morpholin-4-yl-ethoxy)-pyrimidine-4-carbonyl azide (P), 2 g (84.7%).

$^1$H NMR (CDCl$_3$): δ 6.71 (s, 1H), 4.56 (t, J=5.7 Hz, 2H), 3.81, 3.74 (m, 12H), 2.77 (t, J=5.7 Hz, 2H), 2.55 (m, 4H); ESMS clcd for C$_{15}$H$_{21}$N$_7$O$_4$: 363.17; Found: 364.1 (M+1)$^+$.

To a stirred solution of 5-amino-2,3-dimethylindole (292 mg, 1.82 mmol) in toluene (10 mL) at 95° C., compound P (0.6 g, 1.65 mmol) was added in 5 portions within 15 minutes. The reaction mixture was heated for 10 more minutes then cooled down. The precipitated urea was filtered out, washed with ethyl acetate, 2×10 mL to give a crude 1-(2,3-Dimethyl-1H-indol-5-yl)-3-[2-morpholin-4-yl-6-(2-morpholin-4-ethoxy)-pyrimidin-4-yl]-urea (compound 323), 0.61 g (75%) of >85% purity. Re-crystallization from dichloromethane-methanol mixture gave Compound 323 of a higher purity.

$^1$H NMR (CDCl$_3$): δ 10.57 (s, 1H), 9.81 (s, 1H), 9.19 (s, 1H), 7.48 (s, 1H), 7.14 (d, J=8.4 Hz, 1H), 6.97 (d, J=7.0 Hz, 1H), 6.20 (s, 1H), 4.35 (m, 2H), 3.68, 3.56 (m, 12H), 2.64 (m, 2H), 2.44 (m, 4H), 2.28 (s, 3H), 2.11 (s, 3H); ESMS clcd for C$_{25}$H$_{33}$N$_7$O$_4$: 495.26; Found: 496.2 (M+1)$^+$.

Example 15

ESMS of Synthesized Compounds

The ESMS was calculated and measured for each of the compounds synthesized.

TABLE 1

| COMPOUND | CMPD NO. | CALCULATED ESMS | MEASURED ESMS (M + 1) |
|---|---|---|---|
| 2-Morpholin-4-yl-6-(2-morpholin-4-yl-ethoxy)-pyrimidine-4-carboxylic acid (2,3-dimethyl-1H-indol-5-yl)-amide | 1 | 480.25 | 481.2 |
| 2-Morpholin-4-yl-6-(2-pyridin-2-yl-ethoxy)-pyrimidine-4-carboxylic acid (2,3-dimethyl-1H-indol-5-yl)-amide | 2 | 472.22 | 473.2 |
| [6-(2,3-Dimethyl-1H-indol-5-ylcarbamoyl)-2-morpholin-4-yl-pyrimidin-4-yloxy]-acetic acid ethyl ester | 3 | 453.20 | 454.1 |
| 2-Morpholin-4-yl-6-(2-pyridin-2-yl-ethoxy)-pyrimidine-4-carboxylic acid (1H-indol-5-yl)-amide | 4 | 444.19 | 445.1 |
| 2-Morpholin-4-yl-6-(2-pyridin-2-yl-ethoxy)-pyrimidine-4-carboxylic acid m-tolylamide | 5 | 419.20 | 420.2 |
| 1-[2-Morpholin-4-yl-6-(2-morpholin-4-yl-ethoxy)-pyrimidin-4-yl]-3-m-tolyl-urea | 9 | 442 | 443.1 |
| 1-[6-(2-Methylamino-ethoxy)-2-morpholin-4-yl-pyrimidin-4-yl]-3-m-tolyl-urea | 10 | 386 | 387.1 |
| 1-[6-(2-Hydroxy-2-methyl-propoxy)-2-morpholin-4-yl-pyrimidin-4-yl]-3-m-tolyl-urea | 11 | 401 | 402.1 |
| 1-[6-Morpholin-4-yl-2-(2-morpholin-4-yl-ethoxy)-pyrimidin-4-yl]-3-p-tolyl-thiourea | 12 | 458 | 459.1 |
| 1-(2-Bromo-4-methyl-phenyl)-3-[6-morpholin-4-yl-2-(2-morpholin-4-yl-ethoxy)-pyrimidin-4-yl]-thiourea | 13 | 536 | 537.0 |
| 1-[2-Morpholin-4-yl-6-(2-morpholin-4-yl-ethoxy)-pyrimidin-4-yl]-3-phenyl-urea | 14 | 428 | 429.0 |
| 1-[2-Morpholin-4-yl-6-(2-morpholin-4-yl-ethoxy)-pyrimidin-4-yl]-3-p-tolyl-urea | 15 | 442 | 443.0 |
| 1-(3-Methoxy-phenyl)-3-[2-morpholin-4-yl-6-(2-morpholin-4-yl-ethoxy)-pyrimidin-4-yl]-urea | 16 | 458 | 459.1 |
| 1-(4-Chloro-phenyl)-3-[2-morpholin-4-yl-6-(2-morpholin-4-yl-ethoxy)-pyrimidin-4-yl]-urea | 17 | 462 | 463.0 |
| 1-(2-Methoxy-phenyl)-3-[2-morpholin-4-yl-6-(2-morpholin-4-yl-ethoxy)-pyrimidin-4-yl]-urea | 18 | 458 | 459.1 |
| 1-Benzyl-3-[2-morpholin-4-yl-6-(2-morpholin-4-yl-ethoxy)-pyrimidin-4-yl]-urea | 19 | 442 | 443.1 |
| [6-(2.3-Dimethyl-1H-indol-5-ylcarbamoyl)-2-morpholin-4-yl-pyrimidin-4-yloxy]-acetic acid ethyl ester | 20 | 453.20 | 454.1 |
| 2-Morpholin-4-yl-6-[2-(2-oxo-oxazolidin-3-yl)-ethoxy]-pyrimidine-4-carboxylic acid (2,3-dimethyl-1H-indol-5-yl)-amide | 21 | 480.21 | 481.0 |
| 2,6-Di-morpholin-4-yl-pyrimidine-4-carboxylic acid (2,3-dimethyl-1H-indol-5-yl)-amide | 22 | 436.22 | 437.1 |
| 2-Morpholin-4-yl-6-(2-morpholin-4-yl-ethoxy)-pyrimidine-4-carboxylic acid (3,4-dimethyl-phenyl)-amide | 23 | 441.24 | 442.1 |
| 2-Morpholin-4-yl-6-(2-morpholin-4-yl-ethoxy)-pyrimidine-4-carboxylic acid (1,2,3-trimethyl-1H-indol-5-yl)-amide | 24 | 494.26 | 495.2 |
| 2-Morpholin-4-yl-6-(2-morpholin-4-yl-ethoxy)-pyrimidine-4-carboxylic acid (3-carbamoyl-phenyl)-amide | 25 | 456.21 | 457 |
| 2-Morpholin-4-yl-6-(2-morpholin-4-yl-ethoxy)-pyrimidine-4-carboxylic acid (3-dimethylamino-phenyl)-amide | 26 | 456.25 | 457.1 |
| 2-Morpholin-4-yl-6-[2-(4-oxy-morpholin-4-yl)-ethoxy]-pyrimidine-4-carboxylic acid (2,3-dimethyl-1H-indol-5-yl)-amide | 27 | 496.24 | 497.1 |
| 6-Methoxy-2-morpholin-4-yl-pyrimidine-4-carboxylic acid (2,3-dimethyl-1H-indol-5-yl)-amide | 28 | 381.18 | 382.0 |
| 6-Morpholin-4-yl-4-(2-morpholin-4-yl-ethoxy)-pyridine-2-carboxylic acid (2,3-dimethyl-1H-indol-5-yl)-amide | 29 | 479.25 | 480.2 |
| 4,6-Di-morpholin-4-yl-pyridine-2-carboxylic acid (2,3-dimethyl-1H-indol-5-yl)-amide | 30 | 435.23 | 436.2 |
| 2-Morpholin-4-yl-6-(2-morpholin-4-yl-ethoxy)-pyrimidine-4-carboxylic acid methyl-(1,2,3-trimethyl-1H-indol-5-yl)-amide | 31 | 508.28 | 509.2 |
| 2-Morpholin-4-yl-6-(2-pyridin-2-yl-ethoxy)-pyrimidine-4-carboxylic acid (6-methyl-benzothiazol-2-yl)-amide | 32 | 476.16 | 477.1 |
| 2-Morpholin-4-yl-6-(2-pyridin-2-yl-ethoxy)-pyrimidine-4-carboxylic acid (9-ethyl-9H-carbazol-2-yl)-amide | 33 | 522.24 | 523.3 |

TABLE 1-continued

| COMPOUND | CMPD NO. | CALCULATED ESMS | MEASURED ESMS (M + 1) |
|---|---|---|---|
| 2-Morpholin-4-yl-6-(2-pyridin-2-yl-ethoxy)-pyrimidine-4-carboxylic acid (6-methyl-pyridin-2-yl)-amide | 34 | 420.19 | 421.2 |
| 2-Morpholin-4-yl-6-(2-pyridin-2-yl-ethoxy)-pyrimidine-4-carboxylic acid (4-methyl-pyridin-2-yl)-amide | 35 | 420.19 | 421.2 |
| 2-Morpholin-4-yl-6-(2-pyridin-2-yl-ethoxy)-pyrimidine-4-carboxylic acid benzothiazol-6-ylamide | 36 | 462.15 | 463.1 |
| 2-Morpholin-4-yl-6-(2-pyridin-2-yl-ethoxy)-pyrimidine-4-carboxylic acid naphthalen-2-ylamide | 37 | 455.20 | 456.1 |
| 2-Morpholin-4-yl-6-(2-pyridin-2-yl-ethoxy)-pyrimidine-4-carboxylic acid quinolin-6-ylamide | 38 | 456.19 | 457.2 |
| 2-Morpholin-4-yl-6-(2-pyridin-2-yl-ethoxy)-pyrimidine-4-carboxylic acid quinolin-5-ylamide | 39 | 456.19 | 457.2 |
| 2-Morpholin-4-yl-6-(2-morpholin-4-yl-ethoxy)-pyrimidine-4-carboxylic acid indan-5-ylamide | 40 | 453.24 | 454.1 |
| 2-Morpholin-4-yl-6-(2-morpholin-4-yl-ethoxy)-pyrimidine-4-carboxylic acid (2,3-dimethyl-1H-indol-7-yl)-amide | 41 | 480.25 | 481.3 |
| 2-Morpholin-4-yl-6-(2-piperidin-1-yl-ethoxy)-pyrimidine-4-carboxylic acid (2,3-dimethyl-1H-indol-5-yl)-amide | 42 | 478.27 | 479.1 |
| 2-Morpholin-4-yl-6-[2-(2-oxo-oxazolidin-3-yl)-ethoxy]-pyrimidine-4-carboxylic acid (3-carbamoyl-phenyl)-amide | 43 | 456.18 | 457.0 |
| 2-Morpholin-4-yl-6-[2-(2-oxo-oxazolidin-3-yl)-ethoxy]-pyrimidine-4-carboxylic acid m-tolylamide | 44 | 427.19 | 428.0 |
| 2-Morpholin-4-yl-6-(2-morpholin-4-yl-ethoxy)-pyrimidine-4-carboxylic acid (5-thiophen-2-yl-1H-pyrazol-3-yl)-amide | 45 | 485.18 | 486.0 |
| 2-Morpholin-4-yl-6-(2-morpholin-4-yl-ethoxy)-pyrimidine-4-carboxylic acid (3-ethyl-phenyl)-amide | 46 | 441.24 | 442.1 |
| 2-Morpholin-4-yl-6-(2-morpholin-4-yl-ethoxy)-pyrimidine-4-carboxylic acid (3-bromo-phenyl)-amide | 47 | 491.12 | 492.0 |
| 2-Morpholin-4-yl-6-(2-morpholin-4-yl-ethoxy)-pyrimidine-4-carboxylic acid (5-methyl-isoxazol-3-yl)-amide | 48 | 418.0 | 419.0 |
| 2-Morpholin-4-yl-6-(2-morpholin-4-yl-ethoxy)-pyrimidine-4-carboxylic acid (2-acetylamino-phenyl)-amide | 49 | 470.23 | 471.1 |
| 2-Morpholin-4-yl-6-(2-morpholin-4-yl-ethoxy)-pyrimidine-4-carboxylic acid (3-sulfamoyl-phenyl)-amide | 50 | 492.18 | 493.0 |
| 2,6-Di-morpholin-4-yl-pyrimidine-4-carboxylic acid (3,4-dimethyl-phenyl)-amide | 51 | 397.21 | 398.0 |
| 2,6-Di-morpholin-4-yl-pyrimidine-4-carboxylic acid (3-carbamoyl-phenyl)-amide | 52 | 412.19 | 413.0 |
| 2-Morpholin-4-yl-6-(2-morpholin-4-yl-ethoxy)-pyrimidine-4-carboxylic acid (3-dimethylcarbamoyl-phenyl)-amide | 53 | 484.24 | 485.1 |
| Indol-1-yl-[2-morpholin-4-yl-6-(2-morpholin-4-yl-ethoxy)-pyrimidin-4-yl]-methanone | 54 | 437.21 | 438.1 |
| (3,4-Dihydro-1H-isoquinolin-2-yl)-[2-morpholin-4-yl-6-(2-morpholin-4-yl-ethoxy)-pyrimidin-4-yl]-methanone | 55 | 453.24 | 453.1 |
| 2-Morpholin-4-yl-6-(2-morpholin-4-yl-ethoxy)-pyrimidine-4-carboxylic acid m-tolylamide | 56 | 427.22 | 428.1 |
| 2-Morpholin-4-yl-6-(2-morpholin-4-yl-ethoxy)-pyrimidine-4-carboxylic acid (4-dimethylamino-phenyl)-amide | 57 | 456.25 | 457.1 |
| 2-Morpholin-4-yl-6-(2-morpholin-4-yl-ethoxy)-pyrimidine-4-carboxylic acid [3-(pyrrolidine-1-carbonyl)-phenyl]-amide | 58 | 510.26 | 511.2 |
| 2-Morpholin-4-yl-6-(2-morpholin-4-yl-ethoxy)-pyrimidine-4-carboxylic acid (1,3-dioxo-2,3-dihydro-1H-isoindol-5-yl)-amide | 59 | 482.19 | 483.0 |
| 2-Morpholin-4-yl-6-(2-morpholin-4-yl-ethoxy)-pyrimidine-4-carboxylic acid (2-methoxy-5-methyl-phenyl)-amide | 60 | 457.23 | 458.1 |
| 2-Morpholin-4-yl-6-(2-morpholin-4-yl-ethoxy)-pyrimidine-4-carboxylic acid (3-hydroxy-phenyl)-amide | 61 | 429.20 | 430.0 |
| 6-Morpholin-4-yl-2-(2-pyridin-2-yl-ethoxy)-pyrimidine-4-carboxylic acid m-tolylamide | 62 | 419.20 | 420.2 |

TABLE 1-continued

| COMPOUND | CMPD NO. | CALCULATED ESMS | MEASURED ESMS (M + 1) |
|---|---|---|---|
| 6-Morpholin-4-yl-2-(2-pyridin-2-yl-ethoxy)-pyrimidine-4-carboxylic acid (2,3-dimethyl-1H-indol-5-yl)-amide | 63 | 472.22 | 473.2 |
| 6-Morpholin-4-yl-2-(2-pyridin-2-yl-ethoxy)-pyrimidine-4-carboxylic acid (6-methyl-benzothiazol-2-yl)-amide | 64 | 476.16 | 477.2 |
| 2-[2-(3,4-Dimethoxy-phenyl)-ethoxy]-6-morpholin-4-yl-N-m-tolyl-isonicotinamide | 65 | 477.23 | 478.1 |
| N-(2,3-Dimethyl-1H-indol-5-yl)-2-morpholin-4-yl-6-(2-morpholin-4-yl-ethoxy)-isonicotinamide | 66 | 479.25 | 480.2 |
| 1-[2-Morpholin-4-yl-6-(2-pyridin-2-yl-ethoxy)-pyrimidin-4-yl]-3-m-tolyl-urea | 67 | 434.21 | 435.2 |
| 1-[6-Morpholin-4-yl-2-(2-pyridin-2-yl-ethoxy)-pyrimidin-4-yl]-3-m-tolyl-urea | 68 | 434.21 | 435.1 |
| 1-Methyl-3-[6-morpholin-4-yl-2-(2-pyridin-2-yl-ethoxy)-pyrimidin-4-yl]-1-m-tolyl-urea | 69 | 448.22 | 449.5 |
| 1-(4,6-Di-morpholin-4-yl-pyridin-2-yl)-3-m-tolyl-urea | 70 | 397.21 | 398.1 |
| 1-[4-Morpholin-4-yl-6-(2-pyridin-2-yl-ethoxy)-pyrimidin-2-yl]-3-m-tolyl-urea | 71 | 434.21 | 435.1 |
| 2-Morpholin-4-yl-6-(2-pyridin-2-yl-ethoxy)-pyrimidine-4-carboxylic acid 1H-indol-5-yl ester | 72 | 445.18 | 446.1 |
| 1H-Indole-5-carboxylic acid [2-morpholin-4-yl-6-(2-pyridin-2-yl-ethoxy)-pyrimidin-4-yl]-amide | 73 | 444.19 | 445.1 |
| 1H-Indole-5-carboxylic acid [6-morpholin-4-yl-2-(2-pyridin-2-yl-ethoxy)-pyrimidin-4-yl]-amide | 74 | 444.19 | 445.1 |
| 3-Methyl-N-[4-morpholin-4-yl-6-(2-pyridin-2-yl-ethoxy)-pyrimidin-2-yl]-benzamide | 75 | 419.20 | 420.1 |
| N-[4-Morpholin-4-yl-6-(2-pyridin-2-yl-ethoxy)-pyrimidin-2-yl]-isonicotinamide | 76 | 406.18 | 407.1 |
| 5-Methyl-isoxazole-3-carboxylic acid-[4-morpholin-4-yl-6-(2-pyridin-2-yl-ethoxy)-pyrimidin-2-yl]-amide | 77 | 410.17 | 411.1 |
| 6-Morpholin-4-yl-2-(2-pyridin-2-yl-ethoxy)-pyrimidine-4-carboxylic acid N'-m-tolyl-hydrazide | 78 | 434.21 | 435.4 |
| 2-Morpholin-4-yl-6-(2-pyridin-2-yl-ethoxy)-pyrimidine-4-carboxylic acid N'-m-tolyl-hydrazide | 79 | 434.21 | 435.4 |
| 6-Morpholin-4-yl-2-(2-morpholin-4-yl-ethoxy)-pyrimidine-4-carboxylic acid N'-m-tolyl-hydrazide | 80 | 442.23 | 443.1 |
| 6-Morpholin-4-yl-2-(2-morpholin-4-yl-ethoxy)-pyrimidine-4-carboxylic acid N'-(3,4-dimethyl-phenyl)-hydrazide | 81 | 456.25 | 457.2 |
| 2-Morpholin-4-yl-6-(2-morpholin-4-yl-ethoxy)-isonicotinic acid N'-m-tolyl-hydrazide | 82 | 441.24 | 442.2 |
| [2-Morpholin-4-yl-6-(2-pyridin-2-yl-ethoxy)-pyrimidin-4-yl]-carbamic acid m-tolyl ester | 83 | 435.19 | 436.1 |
| (2,3-Dimethyl-1H-indol-5-yl)-[2-morpholin-4-yl-6-(2-pyridin-2-yl-ethoxy)-pyrimidin-4-ylmethyl]-amine | 84 | 458.24 | 459.2 |
| N-[2-Morpholin-4-yl-6-(2-pyridin-2-yl-ethoxy)-pyrimidin-4-yl]-N'-m-tolyl-oxalamide | 85 | 462.20 | 463.1 |
| N-(3-Hydroxy-phenyl)-N'-[2-morpholin-4-yl-6-(2-pyridin-2-yl-ethoxy)-pyrimidin-4-yl]-oxalamide | 86 | 464.18 | 465.1 |
| N-(3-Hydroxy-phenyl)-N'-[6-morpholin-4-yl-2-(2-pyridin-2-yl-ethoxy)-pyrimidin-4-yl]-oxalamide | 87 | 464.18 | 465.1 |
| [6-Morpholin-4-yl-2-(2-pyridin-2-yl-ethoxy)-pyrimidin-4-yl]-carbamic acid m-tolyl ester | 88 | 435.48 | 436.1 |
| 2-Morpholin-4-yl-6-(2-morpholin-4-yl-2-oxo-ethylamino)-pyrimidine-4-carboxylic acid (2,3-dimethyl-1H-indol-5-yl)-amide | 89 | 493 | 494.2 |
| 2-Morpholin-4-yl-6-(4-pyridin-2-yl-piperazin-1-yl)-pyrimidine-4-carboxylic acid (2,3-dimethyl-1H-indol-5-yl)-amide | 90 | 512 | 513.3 |
| 6-[Bis-(2-hydroxy-ethyl)-amino]-2-morpholin-4-yl-pyrimidine-4-carboxylic acid (2,3-dimethyl-1H-indol-5-yl)-amide | 91 | 454 | 455.3 |
| 6-Dibutylamino-2-morpholin-4-yl-pyrimidine-4-carboxylic acid (2,3-dimethyl-1H-indol-5-yl)-amide | 92 | 478 | 479.3 |
| 6-Diethylamino-2-morpholin-4-yl-pyrimidine-4-carboxylic acid (2,3-dimethyl-1H-indol-5-yl)-amide | 93 | 422 | 423.2 |
| 6-[4-(2-Hydroxy-ethyl)-piperazin-1-yl]-2-morpholin-4-yl-pyrimidine-4-carboxylic acid (2,3-dimethyl-1H-indol-5-yl)-amide | 94 | 479 | 480.2 |
| 6-(2-Dimethylamino-ethylamino)-2-morpholin-4-yl-pyrimidine-4-carboxylic acid (2,3-dimethyl-1H-indol-5-yl)-amide | 95 | 437 | 438.3 |

TABLE 1-continued

| COMPOUND | CMPD NO. | CALCULATED ESMS | MEASURED ESMS (M + 1) |
|---|---|---|---|
| [6-(2,3-Dimethyl-1H-indol-5-ylcarbamoyl)-2-morpholin-4-yl-pyrimidin-4-ylamino]-acetic acid | 96 | 424 | |
| [6-(2,3-Dimethyl-1H-indol-5-ylcarbamoyl)-2-morpholin-4-yl-pyrimidin-4-ylamino]-acetic acid methyl ester | 97 | 438 | |
| 6-{[(2-Methoxy-ethylcarbamoyl)-methyl]-amino}-2-morpholin-4-yl-pyrimidine-4-carboxylic acid (2,3-dimethyl-1H-indol-5-yl)-amide | 98 | 481 | 482.2 |
| 6-[2-(4-Carbamoyl-piperidin-1-yl)-2-oxo-ethylamino]-2-morpholin-4-yl-pyrimidine-4-carboxylic acid (2,3-dimethyl-1H-indol-5-yl)-amide | 99 | 534 | 535.2 |
| 6-[2-(4-Hydroxy-piperidin-1-yl)-2-oxo-ethylamino]-2-morpholin-4-yl-pyrimidine-4-carboxylic acid (2,3-dimethyl-1H-indol-5-yl)-amide | 100 | 507 | 508.3 |
| 6-({[(2-Hydroxy-ethyl)-methyl-carbamoyl]-methyl}-amino)-2-morpholin-4-yl-pyrimidine-4-carboxylic acid (2,3-dimethyl-1H-indol-5-yl)-amide | 101 | 481 | 482.2 |
| 6-[2-(4-Acetyl-piperazin-1-yl)-2-oxo-ethylamino]-2-morpholin-4-yl-pyrimidine-4-carboxylic acid (2,3-dimethyl-1H-indol-5-yl)-amide | 102 | 534 | 535.2 |
| 6-[2-(3,4-Dihydro-1H-isoquinolin-2-yl)-2-oxo-ethylamino]-2-morpholin-4-yl-pyrimidine-4-carboxylic acid (2,3-dimethyl-1H-indol-5-yl)-amide | 103 | 539 | 540.3 |
| 6-(Carbamoylmethyl-amino)-2-morpholin-4-yl-pyrimidine-4-carboxylic acid (2,3-dimethyl-1H-indol-5-yl)-amide | 104 | 423 | 424.2 |
| 6-(Ethylcarbamoylmethyl-amino)-2-morpholin-4-yl-pyrimidine-4-carboxylic acid (2,3-dimethyl-1H-indol-5-yl)-amide | 105 | 451 | 452.2 |
| 6-[2-(4-Methyl-piperazin-1-yl)-2-oxo-ethylamino]-2-morpholin-4-yl-pyrimidine-4-carboxylic acid (2,3-dimethyl-1H-indol-5-yl)-amide | 106 | 506 | 507.2 |
| 6-{[(Butyl-methyl-carbamoyl)-methyl]-amino}-2-morpholin-4-yl-pyrimidine-4-carboxylic acid (2,3-dimethyl-1H-indol-5-yl)-amide | 107 | 493 | 494.2 |
| 2-Morpholin-4-yl-6-(2-oxo-2-pyrrolidin-1-yl-ethylamino)-pyrimidine-4-carboxylic acid (2,3-dimethyl-1H-indol-5-yl)-amide | 108 | 477 | 478.3 |
| 2-Morpholin-4-yl-6-(2-oxo-2-piperidin-1-yl-ethylamino)-pyrimidine-4-carboxylic acid (2,3-dimethyl-1H-indol-5-yl)-amide | 109 | 491 | 492.3 |
| 6-(Cyclopentylcarbamoylmethyl-amino)-2-morpholin-4-yl-pyrimidine-4-carboxylic acid (2,3-dimethyl-1H-indol-5-yl)-amide | 110 | 491 | 492.3 |
| 2-Morpholin-4-yl-6-[(m-tolylcarbamoyl-methyl)-amino]-pyrimidine-4-carboxylic acid (2,3-dimethyl-1H-indol-5-yl)-amide | 111 | 513 | 514.2 |
| 6-(Dimethylcarbamoylmethyl-amino)-2-morpholin-4-yl-pyrimidine-4-carboxylic acid (2,3-dimethyl-1H-indol-5-yl)-amide | 112 | 451 | 452.2 |
| 6-[Methyl-(2-oxo-2-piperidin-1-yl-ethyl)-amino]-2-morpholin-4-yl-pyrimidine-4-carboxylic acid (2,3-dimethyl-1H-indol-5-yl)-amide | 113 | 492 | |
| 6-[Methyl-(2-morpholin-4-yl-2-oxo-ethyl)-amino]-2-morpholin-4-yl-pyrimidine-4-carboxylic acid (2,3-dimethyl-1H-indol-5-yl)-amide | 114 | 507 | |
| 2-Morpholin-4-yl-6-(2-oxo-2-piperidin-1-yl-ethoxy)-pyrimidine-4-carboxylic acid (3-pyrazol-1-yl-phenyl)-amide | 115 | 490 | |
| 6-[Methyl-(2-oxo-2-piperidin-1-yl-ethyl)-amino]-2-morpholin-4-yl-pyrimidine-4-carboxylic acid (3-dimethylamino-phenyl)-amide | 116 | 468 | |
| 6-(Carbamoylmethyl-methyl-amino)-2-morpholin-4-yl-pyrimidine-4-carboxylic acid (2,3-dimethyl-1H-indol-5-yl)-amide | 117 | 437 | |
| 1-(3-Bromo-phenyl)-3-[6-morpholin-4-yl-2-(2-morpholin-4-yl-ethoxy)-pyrimidin-4-yl]-urea | 118 | 506 | 507.0 |
| 1-(3,4-Dichloro-phenyl)-3-[6-morpholin-4-yl-2-(2-morpholin-4-yl-ethoxy)-pyrimidin-4-yl]-urea | 119 | 496 | 497.0 |
| 1-Indan-5-yl-3-[6-morpholin-4-yl-2-(2-morpholin-4-yl-ethoxy)-pyrimidin-4-yl]-urea | 120 | 468 | 469.4 |
| 1-[6-Morpholin-4-yl-2-(2-morpholin-4-yl-ethoxy)-pyrimidin-4-yl]-3-(3-trifluoromethyl-phenyl)-urea | 121 | 496 | 497.1 |
| 1-(3,4-Dimethyl-phenyl)-3-[6-morpholin-4-yl-2-(2-morpholin-4-yl-ethoxy)-pyrimidin-4-yl]-urea | 122 | 456 | 457.1 |
| 1-Benzo[1,3]dioxol-5-yl-3-[6-morpholin-4-yl-2-(2-morpholin-4-yl-ethoxy)-pyrimidin-4-yl]-urea | 123 | 472 | 473.3 |

TABLE 1-continued

| COMPOUND | CMPD NO. | CALCULATED ESMS | MEASURED ESMS (M + 1) |
|---|---|---|---|
| 1-[6-Morpholin-4-yl-2-(2-morpholin-4-yl-ethoxy)-pyrimidin-4-yl]-3-naphthalen-2-yl-urea | 124 | 478 | 479.3 |
| 1-(3-Fluoro-phenyl)-3-[2-morpholin-4-yl-6-(2-morpholin-4-yl-ethoxy)-pyrimidin-4-yl]-urea | 125 | 446 | 447.3 |
| 1-(3-Chloro-phenyl)-3-[2-morpholin-4-yl-6-(2-morpholin-4-yl-ethoxy)-pyrimidin-4-yl]-urea | 126 | 462 | 463.3 |
| 1-(3-Cyano-phenyl)-3-[2-morpholin-4-yl-6-(2-morpholin-4-yl-ethoxy)-pyrimidin-4-yl]-urea | 127 | 453 | 454.3 |
| 1-[2-Morpholin-4-yl-6-(2-morpholin-4-yl-ethoxy)-pyrimidin-4-yl]-3-(3-nitro-phenyl)-urea | 128 | 473 | 474.2 |
| 1-(2-Bromo-phenyl)-3-[2-morpholin-4-yl-6-(2-morpholin-4-yl-ethoxy)-pyrimidin-4-yl]-urea | 129 | 506 | 507.2 |
| 1-(3-Iodo-phenyl)-3-[2-morpholin-4-yl-6-(2-morpholin-4-yl-ethoxy)-pyrimidin-4-yl]-urea | 130 | 554 | 555.2 |
| 1-(3-Ethyl-phenyl)-3-[2-morpholin-4-yl-6-(2-morpholin-4-yl-ethoxy)-pyrimidin-4-yl]-urea | 131 | 456 | 457.3 |
| 1-(2-Chloro-phenyl)-3-[2-morpholin-4-yl-6-(2-morpholin-4-yl-ethoxy)-pyrimidin-4-yl]-urea | 132 | 462 | 463.3 |
| 1-(3-Methyl-2-oxo-2,3-dihydro-benzothiazol-6-yl)-3-[2-morpholin-4-yl-6-(2-morpholin-4-yl-ethoxy)-pyrimidin-4-yl]-urea | 133 | 515 | 516.2 |
| 1-(3-Methyl-2-oxo-2,3-dihydro-benzooxazol-6-yl)-3-[2-morpholin-4-yl-6-(2-morpholin-4-yl-ethoxy)-pyrimidin-4-yl]-urea | 134 | 499 | 500.3 |
| 1-(6-Chloro-benzooxazol-2-yl)-3-[2-morpholin-4-yl-6-(2-morpholin-4-yl-ethoxy)-pyrimidin-4-yl]-urea | 135 | 503 | 504.1 |
| 1-(2-Methyl-quinolin-6-yl)-3-[2-morpholin-4-yl-6-(2-morpholin-4-yl-ethoxy)-pyrimidin-4-yl]-urea | 136 | 493 | 494.3 |
| 1-(1H-Indol-5-yl)-3-[2-morpholin-4-yl-6-(2-morpholin-4-yl-ethoxy)-pyrimidin-4-yl]-urea | 137 | 467 | 468.2 |
| 1-(5-Hydroxy-naphthalen-1-yl)-3-[2-morpholin-4-yl-6-(2-morpholin-4-yl-ethoxy)-pyrimidin-4-yl]-urea | 138 | 494 | 495.2 |
| 1-(6-Chloro-benzothiazol-2-yl)-3-[2-morpholin-4-yl-6-(2-morpholin-4-yl-ethoxy)-pyrimidin-4-yl]-urea | 139 | 519 | 520.2 |
| 1-[2-Morpholin-4-yl-6-(2-morpholin-4-yl-ethoxy)-pyrimidin-4-yl]-3-quinolin-5-yl-urea | 140 | 479 | 480 |
| 1-(5-Cyclopropyl-[1,3,4]thiadiazol-2-yl)-3-[2-morpholin-4-yl-6-(2-morpholin-4-yl-ethoxy)-pyrimidin-4-yl]-urea | 141 | 476 | 477.2 |
| 1-[2-Morpholin-4-yl-6-(2-morpholin-4-yl-ethoxy)-pyrimidin-4-yl]-3-(4-p-tolyl-thiazol-2-yl)-urea | 142 | 525 | 526.2 |
| 1-(4-Hydroxy-phenyl)-3-[2-morpholin-4-yl-6-(2-morpholin-4-yl-ethoxy)-pyrimidin-4-yl]-urea | 143 | 444 | 445.2 |
| 1-(5-Furan-2-yl-2H-pyrazol-3-yl)-3-[2-morpholin-4-yl-6-(2-morpholin-4-yl-ethoxy)-pyrimidin-4-yl]-urea | 144 | 484 | 485.2 |
| 4,6-Di-morpholin-4-yl-pyridine-2-carboxylic acid (2,3-dimethyl-1H-indol-5-yl)-amide; compound with methanesulfonic acid | 145 | 531.22 | 436.2 |
| 6-Morpholin-4-yl-4-(2-morpholin-4-yl-ethoxy)-pyridine-2-carboxylic acid (1,2,3-trimethyl-1H-indol-5-yl)-amide | 146 | 493.27 | 494.1 |
| 4,6-Di-morpholin-4-yl-pyridine-2-carboxylic acid (1,2,3-trimethyl-1H-indol-5-yl)-amide | 147 | 449.24 | 450.1 |
| 6-Morpholin-4-yl-4-(2-morpholin-4-yl-ethoxy)-pyridine-2-carboxylic acid (2,3-dimethyl-1H-indol-5-yl)-amide; compound with methanesulfonic acid | 148 | 575.24 | 480.2 |
| 2-Morpholin-4-yl-6-(2-morpholin-4-yl-ethoxy)-pyrimidine-4-carboxylic acid (2-chloro-pyridin-4-yl)-amide | 149 | 448.16 | 449.1 |
| 2-Morpholin-4-yl-6-(2-morpholin-4-yl-ethoxy)-pyrimidine-4-carboxylic acid (5-carbamoyl-pyridin-2-yl)-amide | 150 | 457.21 | 458.2 |
| 2-Morpholin-4-yl-6-(2-morpholin-4-yl-ethoxy)-pyrimidine-4-carboxylic acid (2-pyrrolidin-1-yl-pyridin-4-yl)-amide | 151 | 483.26 | 484.1 |
| 2-Morpholin-4-yl-6-(2-morpholin-4-yl-ethoxy)-pyrimidine-4-carboxylic acid (3-acetyl-phenyl)-amide | 152 | 455.22 | 456.1 |
| (E)-N-(3-(1-(2,2-dimethylhydrazono)ethyl)phenyl)-2-morpholino-6-(2-morpholinoethoxy)pyrimidine-4-carboxamide | 153 | 497.28 | 498.2 |

TABLE 1-continued

| COMPOUND | CMPD NO. | CALCULATED ESMS | MEASURED ESMS (M + 1) |
|---|---|---|---|
| (E)-N-(3-(1-(methoxyimino)ethyl)phenyl)-2-morpholino-6-(2-morpholinoethoxy)pyrimidine-4-carboxamide | 154 | 484.24 | 485.1 |
| 6-Morpholin-4-yl-4-(2-morpholin-4-yl-ethoxy)-pyridine-2-carboxylic acid (3-dimethylamino-phenyl)-amide | 155 | 455.25 | 456.1 |
| 6-[(2-Methoxy-ethyl)-methyl-amino]-4-morpholin-4-yl-pyridine-2-carboxylic acid (2,3-dimethyl-1H-indol-5-yl)-amide | 156 | 437.24 | 438.1 |
| 6-[(2-Methoxy-ethyl)-methyl-amino]-4-morpholin-4-yl-pyridine-2-carboxylic acid (3-dimethylamino-phenyl)-amide | 157 | 413.24 | 414.1 |
| 4-[(2-Methoxy-ethyl)-methyl-amino]-6-morpholin-4-yl-pyridine-2-carboxylic acid (2,3-dimethyl-1H-indol-5-yl)-amide | 158 | 437.24 | 438.1 |
| 4-[(2-Methoxy-ethyl)-methyl-amino]-6-morpholin-4-yl-pyridine-2-carboxylic acid (3-dimethylamino-phenyl)-amide | 159 | 413.24 | 414.1 |
| 4-Methoxyamino-6-morpholin-4-yl-pyridine-2-carboxylic acid (3-dimethylamino-phenyl)-amide | 160 | 371.20 | 372.1 |
| 4-Methoxyamino-6-morpholin-4-yl-pyridine-2-carboxylic acid (2,3-dimethyl-1H-indol-5-yl)-amide | 161 | 395.20 | 396.1 |
| 6-[(2-Methoxy-ethyl)-methyl-amino]-2-morpholin-4-yl-pyrimidine-4-carboxylic acid (2-dimethylamino-ethyl)-amide | 162 | 366.24 | 367.1 |
| 2-Morpholin-4-yl-6-(2-morpholin-4-yl-ethoxy)-pyrimidine-4-carboxylic acid (5-cyclopropyl-[1,3,4]thiadiazol-2-yl)-amide | 163 | 461.18 | 462.0 |
| 6-[(2-Methoxy-ethyl)-methyl-amino]-2-morpholin-4-yl-pyrimidine-4-carboxylic acid (3-diethylaminomethyl-4-hydroxy-phenyl)-amide | 164 | 472.28 | 473.1 |
| 6-[(2-Methoxy-ethyl)-methyl-amino]-2-morpholin-4-yl-pyrimidine-4-carboxylic acid (4-acetylamino-phenyl)-amide | 165 | 428.22 | 429.1 |
| 6-[(2-Methoxy-ethyl)-methyl-amino]-2-morpholin-4-yl-pyrimidine-4-carboxylic acid [3-(acetyl-methyl-amino)-phenyl]-amide | 166 | 442.23 | 443.1 |
| (E)-N-(3-(1-(2,2-dimethylhydrazono)ethyl)phenyl)-6-((2-methoxyethyl)(methyl)amino)-2-morpholinopyrimidine-4-carboxamide | 167 | 455.26 | 456.1 |
| 6-Morpholin-4-yl-pyridine-2-carboxylic acid (2,3-dimethyl-1H-indol-5-yl)-amide | 168 | 350.17 | 351.2 |
| 4-(4-Acetyl-piperazin-1-yl)-6-morpholin-4-yl-pyridine-2-carboxylic acid (2,3-dimethyl-1H-indol-5-yl)-amide | 169 | 476.25 | 477.1 |
| 2-Morpholin-4-yl-6-(2-morpholin-4-yl-ethoxy)-pyrimidine-4-carboxylic acid [3-(2-methyl-pyrimidin-4-yl)-phenyl]-amide | 170 | 505.24 | 506.1 |
| 4-Hydroxy-6'-morpholin-4-yl-3,4,5,6-tetrahydro-2H-[1,4']bipyridinyl-2'-carboxylic acid (2,3-dimethyl-1H-indol-5-yl)-amide | 171 | 449.24 | 450.1 |
| 6-(1,4-Dioxa-8-aza-spiro[4.5]dec-8-yl)-2-morpholin-4-yl-pyrimidine-4-carboxylic acid (2,3-dimethyl-1H-indol-5-yl)-amide | 172 | 492.25 | 493.1 |
| 6-(4-Hydroxy-piperidin-1-yl)-2-morpholin-4-yl-pyrimidine-4-carboxylic acid (2,3-dimethyl-1H-indol-5-yl)-amide | 173 | 450.24 | 451.1 |
| 4-Hydroxy-6'-morpholin-4-yl-3,4,5,6-tetrahydro-2H-[1,4']bipyridinyl-2'-carboxylic acid (3-ethyl-1H-indol-5-yl)-amide | 174 | 449.24 | 450.1 |
| 6-(1,4-Dioxa-8-aza-spiro[4.5]dec-8-yl)-2-morpholin-4-yl-pyrimidine-4-carboxylic acid (3-ethyl-1H-indol-5-yl)-amide | 175 | 492.25 | 493.1 |
| 2'-(2,3-Dimethyl-1H-indol-5-ylcarbamoyl)-6'-morpholin-4-yl-3,4,5,6-tetrahydro-2H-[1,4']bipyridinyl-4-carboxylic acid ethyl ester | 176 | 505.27 | 506.1 |
| 6-(4-Hydroxy-piperidin-1-yl)-2-morpholin-4-yl-pyrimidine-4-carboxylic acid (3-ethyl-2-methyl-1H-indol-5-yl)-amide | 177 | 464.25 | 465.1 |
| 6-(4-Methyl-piperidin-1-yl)-2-morpholin-4-yl-pyrimidine-4-carboxylic acid (3-ethyl-1H-indol-5-yl)-amide | 178 | 448.26 | 449.1 |
| 2-Morpholin-4-yl-6-piperidin-1-yl-pyrimidine-4-carboxylic acid (3-ethyl-1H-indol-5-yl)-amide | 179 | 434.24 | 435.1 |
| 6-(1,4-Dioxa-8-aza-spiro[4.5]dec-8-yl)-2-morpholin-4-yl-pyrimidine-4-carboxylic acid (3-ethyl-2-methyl-1H-indol-5-yl)-amide | 180 | 506.26 | 507.1 |

TABLE 1-continued

| COMPOUND | CMPD NO. | CALCULATED ESMS | MEASURED ESMS (M + 1) |
|---|---|---|---|
| 4-(4-Acetyl-piperazin-1-yl)-6-morpholin-4-yl-pyridine-2-carboxylic acid (3-ethyl-1H-indol-5-yl)-amide | 181 | 476.25 | 477.1 |
| 6'-Morpholin-4-yl-3,4,5,6-tetrahydro-2H-[1,4']bipyridinyl-2'-carboxylic acid (2,3-dimethyl-1H-indol-5-yl)-amide | 182 | 433.25 | 434.1 |
| 6-(4-Carbamoyl-piperidin-1-yl)-2-morpholin-4-yl-pyrimidine-4-carboxylic acid (3-ethyl-2-methyl-1H-indol-5-yl)-amide | 183 | 491.26 | 492.1 |
| 6-(4-Hydroxy-piperidin-1-yl)-2-morpholin-4-yl-pyrimidine-4-carboxylic acid (6,7,8,9-tetrahydro-5H-carbazol-3-yl)-amide | 184 | 476.25 | 477.1 |
| 4-Hydroxy-6'-morpholin-4-yl-3,4,5,6-tetrahydro-2H-[1,4']bipyridinyl-2'-carboxylic acid (6,7,8,9-tetrahydro-5H-carbazol-3-yl)-amide; compound with methanesulfonic acid | 185 | 571.25 | 476.2 |
| 4-Hydroxy-6'-morpholin-4-yl-3,4,5,6-tetrahydro-2H-[1,4']bipyridinyl-2'-carboxylic acid (6,7,8,9-tetrahydro-5H-carbazol-3-yl)-amide | 186 | 475.26 | 476.1 |
| 6-(4-Hydroxy-piperidin-1-yl)-2-morpholin-4-yl-pyrimidine-4-carboxylic acid (3-methyl-1H-indol-5-yl)-amide | 187 | 436.22 | 437.1 |
| 6-(4-Hydroxy-piperidin-1-yl)-2-morpholin-4-yl-pyrimidine-4-carboxylic acid (6,7,8,9-tetrahydro-5H-carbazol-3-yl)-amide; compound with methanesulfonic acid | 188 | 572.24 | 477.3 |
| N-(2,3-dimethyl-1H-indol-5-yl)-6-((2-hydroxyethyl)(methyl)amino)-2-morpholinopyrimidine-4-carboxamide | 189 | 424.22 | 425.2 |
| 2-morpholino-6-(2-morpholinoethylamino)-N-(2-(trifluoromethyl)-1H-benzo[d]imidazol-5-yl)pyrimidine-4-carboxamide | 190 | 520.22 | 521.3 |
| 2-morpholino-6-(2-morpholinoethylamino)-N-(4-(trifluoromethyl)phenyl)pyrimidine-4-carboxamide | 191 | 480.21 | 481.3 |
| 2-morpholino-6-(2-morpholinoethylamino)-N-(2-oxo-4-(trifluoromethyl)-2H-chromen-7-yl)pyrimidine-4-carboxamide | 192 | 548.2 | 549.3 |
| N-(2,3-dimethyl-1H-indol-5-yl)-6-(methoxy(methyl)amino)-2-morpholinopyrimidine-4-carboxamide | 193 | 410.21 | 411.2 |
| N-(2,3-dimethyl-1H-indol-5-yl)-6-(2-hydroxyethylamino)-2-morpholinopyrimidine-4-carboxamide | 194 | 410.21 | 411.2 |
| N-(2,3-dimethyl-1H-indol-5-yl)-6-(methoxy(2-morpholinoethyl)amino)-2-morpholinopyrimidine-4-carboxamide | 195 | 509.28 | 510.3 |
| N-(3-(dimethylamino)phenyl)-6-(methoxyamino)-2-morpholinopyrimidine-4-carboxamide | 196 | 372.19 | 373.2 |
| 2-morpholino-6-(2-morpholinoethoxy)-N-(2-oxoindolin-5-yl)pyrimidine-4-carboxamide | 197 | 468.21 | 469.1 |
| N-(3-(3,3-diethylureido)phenyl)-2-morpholino-6-(2-morpholinoethoxy)pyrimidine-4-carboxamide | 198 | 527.29 | 528.2 |
| 2-morpholino-6-(2-morpholinoethoxy)-N-(3-oxo-3,4-dihydro-2H-benzo[b][1,4]oxazin-6-yl)pyrimidine-4-carboxamide | 199 | 484.21 | 485.2 |
| N-(2,3-dihydrobenzo[b][1,4]dioxin-6-yl)-6-((2-methoxyethyl)(methyl)amino)-2-morpholinopyrimidine-4-carboxamide | 200 | 429.2 | 430.2 |
| N-(4-tert-butylthiazol-2-yl)-6-((2-methoxyethyl)(methyl)amino)-2-morpholinopyrimidine-4-carboxamide | 201 | 434.21 | 435.2 |
| 6-((2-methoxyethyl)(methyl)amino)-N-(2-methylquinolin-6-yl)-2-morpholinopyrimidine-4-carboxamide | 202 | 436.22 | 437.2 |
| N-(5,6-dimethylbenzo[d]thiazol-2-yl)-6-((2-methoxyethyl)(methyl)amino)-2-morpholinopyrimidine-4-carboxamide | 203 | 456.19 | 457.2 |
| N-(2,5-diethoxy-4-morpholinophenyl)-6-((2-methoxyethyl)(methyl)amino)-2-morpholinopyrimidine-4-carboxamide | 204 | 544.3 | 545.3 |
| N-(3-isopropylphenyl)-6-((2-methoxyethyl)(methyl)amino)-2-morpholinopyrimidine-4-carboxamide | 205 | 413.24 | 414.2 |
| N-(1-acetylindolin-5-yl)-6-((2-methoxyethyl)(methyl)amino)-2-morpholinopyrimidine-4-carboxamide | 206 | 454.23 | 455.2 |

TABLE 1-continued

| COMPOUND | CMPD NO. | CALCULATED ESMS | MEASURED ESMS (M + 1) |
|---|---|---|---|
| 6-((2-methoxyethyl)(methyl)amino)-N-(3-(3-methyl-1,2,4-oxadiazol-5-yl)phenyl)-2-morpholinopyrimidine-4-carboxamide | 207 | 453.21 | 454.2 |
| 6-((2-methoxyethyl)(methyl)amino)-N-(3-(4-methyl-4H-1,2,4-triazol-3-yl)phenyl)-2-morpholinopyrimidine-4-carboxamide | 208 | 452.23 | 453.1 |
| 6-((2-methoxyethyl)(methyl)amino)-2-morpholino-N-(3-(trifluoromethyl)phenyl)pyrimidine-4-carboxamide | 209 | 439.18 | 440.2 |
| N-(benzo[d][1,3]dioxol-5-yl)-6-((2-methoxyethyl)(methyl)amino)-2-morpholinopyrimidine-4-carboxamide | 210 | 415.19 | 416.2 |
| 6-((2-methoxyethyl)(methyl)amino)-N-(1-methylindolin-6-yl)-2-morpholinopyrimidine-4-carboxamide | 211 | 426.24 | 427.2 |
| N-(5-(dimethylamino)-2-fluorophenyl)-6-((2-methoxyethyl)(methyl)amino)-2-morpholinopyrimidine-4-carboxamide | 212 | 432.23 | 433.2 |
| N-(3-isopropylphenyl)-2-morpholino-6-(2-morpholinoethoxy)pyrimidine-4-carboxamide | 213 | 455.25 | 456.2 |
| N-(1-methylindolin-6-yl)-2-morpholino-6-(2-morpholinoethoxy)pyrimidine-4-carboxamide | 214 | 468.25 | 469.2 |
| N-(3-(dimethylamino)-4-fluorophenyl)-6-((2-methoxyethyl)(methyl)amino)-2-morpholinopyrimidine-4-carboxamide | 215 | 432.23 | 433.2 |
| N-(1-methyl-1H-indazol-6-yl)-2-morpholino-6-(2-morpholinoethoxy)pyrimidine-4-carboxamide | 216 | 467.23 | 468.2 |
| 6-((2-methoxyethyl)(methyl)amino)-N-(1-methyl-1H-indazol-6-yl)-2-morpholinopyrimidine-4-carboxamide | 217 | 425.22 | 426.2 |
| N-(3-methyl-2-oxo-2,3-dihydrobenzo[d]oxazol-5-yl)-2-morpholino-6-(2-morpholinoethoxy)pyrimidine-4-carboxamide | 218 | 484.21 | 485.2 |
| 2-morpholino-6-(2-morpholinoethoxy)-N-(1,3,3-trimethyl-2-oxoindolin-5-yl)pyrimidine-4-carboxamide | 219 | 510.26 | 511.2 |
| N-(1-ethyl-1H-indol-6-yl)-2-morpholino-6-(2-morpholinoethoxy)pyrimidine-4-carboxamide | 220 | 480.25 | 481.2 |
| N-(1-ethylindolin-6-yl)-2-morpholino-6-(2-morpholinoethoxy)pyrimidine-4-carboxamide | 221 | 482.26 | 483.3 |
| 2-Morpholin-4-yl-6-[2-(2-oxo-oxazolidin-3-yl)-ethoxy]-pyrimidine-4-carboxylic acid (3-ethyl-2-methyl-1H-indol-5-yl)-amide | 222 | 494.23 | 495.2 |
| 2-Morpholin-4-yl-6-[2-(2-oxo-oxazolidin-3-yl)-ethoxy]-pyrimidine-4-carboxylic acid (6,7,8,9-tetrahydro-5H-carbazol-3-yl)-amide | 223 | 506.23 | 507.2 |
| 2-Morpholin-4-yl-6-(2-(2,2,3,3,5,5,6,6-octadeuteromorpholin-4-yl-ethoxy)-pyrimidine-4-carboxylic acid (6,7,8,9-tetrahydro-5H-carbazol-3-yl)-amide | 224 | 514.31 | 515.3 |
| 6-[(2-Methoxy-ethyl)-methyl-amino]-2-morpholin-4-yl-pyrimidine-4-carboxylic acid (5-tert-butyl-2-hydroxy-phenyl)-amide | 225 | 443.25 | 444.2 |
| 6-[(2-Methoxy-ethyl)-methyl-amino]-2-morpholin-4-yl-pyrimidine-4-carboxylic acid [3-(3-hydroxy-3-methyl-but-1-ynyl)-phenyl]-amide | 226 | 453.24 | 454.1 |
| 6-[(2-Methoxy-ethyl)-methyl-amino]-2-morpholin-4-yl-pyrimidine-4-carboxylic acid [5-(4-chloro-phenyl)-2-methyl-2H-pyrazol-3-yl]-amide | 227 | 485.19 | 486.2 |
| 6-[(2-Methoxy-ethyl)-methyl-amino]-2-morpholin-4-yl-pyrimidine-4-carboxylic acid (5-tert-butyl-isoxazol-3-yl)-amide | 228 | 418.23 | 419.2 |
| 6-[(2-Methoxy-ethyl)-methyl-amino]-2-morpholin-4-yl-pyrimidine-4-carboxylic acid (4-isopropyl-3-methyl-phenyl)-amide | 229 | 427.26 | 428.2 |
| 6-[(2-Methoxy-ethyl)-methyl-amino]-2-morpholin-4-yl-pyrimidine-4-carboxylic acid (4-bromo-3-methyl-phenyl)-amide | 230 | 463.12 | 464.1 |
| 6-[(2-Methoxy-ethyl)-methyl-amino]-2-morpholin-4-yl-pyrimidine-4-carboxylic acid (3-methanesulfonyl-phenyl)-amide | 231 | 449.17 | 449.2 |
| 6-[(2-Methoxy-ethyl)-methyl-amino]-2-morpholin-4-yl-pyrimidine-4-carboxylic acid (3-benzoyl-phenyl)-amide | 232 | 475.22 | 476.2 |
| 6-[(2-Methoxy-ethyl)-methyl-amino]-2-morpholin-4-yl-pyrimidine-4-carboxylic acid (2-p-tolyl-ethyl)-amide | 233 | 413.24 | 414.2 |

TABLE 1-continued

| COMPOUND | CMPD NO. | CALCULATED ESMS | MEASURED ESMS (M + 1) |
|---|---|---|---|
| 6-[(2-Methoxy-ethyl)-methyl-amino]-2-morpholin-4-yl-pyrimidine-4-carboxylic acid (3-carbamoyl-4-morpholin-4-yl-phenyl)-amide | 234 | 499.25 | 500.2 |
| 6-[(2-Methoxy-ethyl)-methyl-amino]-2-morpholin-4-yl-pyrimidine-4-carboxylic acid [3-(4-bromo-1-methyl-1H-pyrazol-3-yl)-phenyl]-amide | 235 | 529.14 | 530.2 |
| 6-[(2-Methoxy-ethyl)-methyl-amino]-2-morpholin-4-yl-pyrimidine-4-carboxylic acid (5-tert-butyl-[1,3,4]thiadiazol-2-yl)-amide | 236 | 435.21 | 436.2 |
| 6-[(2-Methoxy-ethyl)-methyl-amino]-2-morpholin-4-yl-pyrimidine-4-carboxylic acid (5-methyl-isoxazol-3-yl)-amide | 237 | 376.19 | 377.2 |
| 6-[(2-Methoxy-ethyl)-methyl-amino]-2-morpholin-4-yl-pyrimidine-4-carboxylic acid (4,6-dimethyl-pyridin-2-yl)-amide | 238 | 400.22 | 401.2 |
| 6-[(2-Methoxy-ethyl)-methyl-amino]-2-morpholin-4-yl-pyrimidine-4-carboxylic acid (3-methyl-isothiazol-5-yl)-amide | 239 | 392.16 | 393.2 |
| 6-[(2-Methoxy-ethyl)-methyl-amino]-2-morpholin-4-yl-pyrimidine-4-carboxylic acid (4,6-dimethyl-pyrimidin-2-yl)-amide | 240 | 401.22 | 402.2 |
| 6-[(2-Methoxy-ethyl)-methyl-amino]-2-morpholin-4-yl-pyrimidine-4-carboxylic acid (2,3-dimethyl-quinoxalin-6-yl)-amide | 241 | 451.23 | 452.2 |
| 6-[(2-Methoxy-ethyl)-methyl-amino]-2-morpholin-4-yl-pyrimidine-4-carboxylic acid (3-quinoxalin-2-yl-phenyl)-amide | 242 | 499.23 | 500.2 |
| 6-[(2-Methoxy-ethyl)-methyl-amino]-2-morpholin-4-yl-pyrimidine-4-carboxylic acid (5,7-bis-trifluoromethyl-[1,8]naphthyridin-2-yl)-amide | 243 | 559.18 | 560.2 |
| 6-[(2-Methoxy-ethyl)-methyl-amino]-2-morpholin-4-yl-pyrimidine-4-carboxylic acid (3-trifluoromethoxy-phenyl)-amide | 244 | 455.18 | 456.1 |
| 6-[(2-Methoxy-ethyl)-methyl-amino]-2-morpholin-4-yl-pyrimidine-4-carboxylic acid [3-(2-methyl-thiazol-4-yl)-phenyl]-amide | 245 | 468.19 | 469.1 |
| N-(2,3-dimethyl-1H-indol-5-yl)-2-morpholino-6-(2-(piperazin-1-yl)ethoxy)pyrimidine-4-carboxamide | 246 | 479.26 | 480.2 |
| N-(2,3-dimethyl-1H-indol-5-yl)-6-(methylamino)-2-morpholino-pyrimidine-4-carboxamide | 247 | 380.20 | 381.2 |
| N-(2,3-dimethyl-1H-indol-5-yl)-6-(dimethylamino)-2-morpholino-pyrimidine-4-carboxamide | 248 | 394.21 | 395.2 |
| N-(2,3-dimethyl-1H-indol-5-yl)-6-(2-(methylsulfonyl)ethoxy)-2-morpholinopyrimidine-4-carboxamide | 249 | 473.17 | 474.1 |
| 6-(2-cyanoethoxy)-N-(2,3-dimethyl-1H-indol-5-yl)-2-morpholinopyrimidine-4-carboxamide | 250 | 420.19 | 421.2 |
| N-(2,3-dimethyl-1H-indol-5-yl)-6-(4-methylpiperazin-1-yl)-2-morpholinopyrimidine-4-carboxamide | 251 | 449.25 | 450.2 |
| N-(2,3-dimethyl-1H-indol-5-yl)-6-(2-methoxyethylamino)-2-morpholinopyrimidine-4-carboxamide | 252 | 424.22 | 425.2 |
| N-(2,3-dimethyl-1H-indol-5-yl)-6-methyl-2-morpholinopyrimidine-4-carboxamide | 253 | 365.19 | 366.2 |
| N-(2,3-dimethyl-1H-indol-5-yl)-6-hydroxy-2-morpholinopyrimidine-4-carboxamide | 254 | 367.16 | 368.1 |
| N-(2,3-dimethyl-1H-indol-5-yl)-6-(2,3-dimethyl-1H-indol-5-ylamino)-2-morpholinopyrimidine-4-carboxamide | 255 | 509.25 | 510.2 |
| 6-(2-(diethylamino)-2-oxoethoxy)-N-(2,3-dimethyl-1H-indol-5-yl)-2-morpholinopyrimidine-4-carboxamide | 256 | 480.25 | 481.2 |
| 6-(4-acetylpiperazin-1-yl)-N-(2,3-dimethyl-1H-indol-5-yl)-2-morpholinopyrimidine-4-carboxamide | 257 | 477.25 | 478.2 |
| 6-(bis(2-methoxyethyl)amino)-N-(2,3-dimethyl-1H-indol-5-yl)-2-morpholinopyrimidine-4-carboxamide | 258 | 482.26 | 483.2 |
| N-(2,3-dimethyl-1H-indol-5-yl)-2-morpholino-6-(morpholinomethyl)pyrimidine-4-carboxamide | 259 | 450.24 | 451.2 |
| (S)-6-(3-acetamidopyrrolidin-1-yl)-N-(3-methyl-1H-indol-5-yl)-2-morpholinopyrimidine-4-carboxamide | 260 | 463.23 | 464.2 |
| 6-(4-acetylpiperazin-1-yl)-N-(3-methyl-1H-indol-5-yl)-2-morpholinopyrimidine-4-carboxamide | 261 | 463.23 | 464.2 |

TABLE 1-continued

| COMPOUND | CMPD NO. | CALCULATED ESMS | MEASURED ESMS (M + 1) |
|---|---|---|---|
| 6-(4-acetylpiperazin-1-yl)-2-morpholino-N-(2,3,4,9-tetrahydro-1H-carbazol-6-yl)pyrimidine-4-carboxamide | 262 | 503.26 | 504.2 |
| 1-(2,3-dimethyl-1H-indol-5-yl)-3-(6-methyl-2-morpholinopyrimidin-4-yl)urea | 263 | 380.20 | 381.2 |
| 1-(6-(4-acetylpiperazin-1-yl)-2-morpholinopyrimidin-4-yl)-3-(2,3-dimethyl-1H-indol-5-yl)urea | 264 | 492.26 | 493.2 |
| 1-(2,3-dimethyl-1H-indol-5-yl)-3-(6-((2-methoxyethyl)(methyl)amino)-2-morpholinopyrimidin-4-yl)urea | 265 | 453.25 | 454.2 |
| 1-(6-(4-acetylpiperazin-1-yl)-2-morpholinopyrimidin-4-yl)-3-(3-ethyl-2-methyl-1H-indol-5-yl)urea | 266 | 506.28 | 507.2 |
| 1-(3-ethyl-2-methyl-1H-indol-5-yl)-3-(6-methyl-2-morpholinopyrimidin-4-yl)urea | 267 | 394.21 | 395.2 |
| 1-(2,3-dimethyl-1H-indol-5-yl)-3-(2-morpholino-6-(4-(pyridin-2-yl)piperazin-1-yl)pyrimidin-4-yl)urea | 268 | 527.28 | 528.2 |
| 1-(3-ethyl-2-methyl-1H-indol-5-yl)-3-(2-morpholino-6-(4-(pyridin-2-yl)piperazin-1-yl)pyrimidin-4-yl)urea | 269 | 541.29 | 542.3 |
| 1-(3-ethyl-2-methyl-1H-indol-5-yl)-3-(2-morpholino-6-(2-morpholinoethylamino)pyrimidin-4-yl)urea | 270 | 508.29 | 509.2 |
| 2-Morpholin-4-yl-6-(2-morpholin-4-yl-ethoxy)-pyrimidine-4-carboxylic acid (5-methyl-2-nitro-phenyl)-amide | 271 | 472.21 | 473.1 |
| 2-Morpholin-4-yl-6-(2-morpholin-4-yl-ethoxy)-pyrimidine-4-carboxylic acid (2-amino-5-methyl-phenyl)-amide | 272 | 442.23 | 443.0 |
| 6-(2-Amino-ethoxy)-2-morpholin-4-yl-pyrimidine-4-carboxylic acid (2,3-dimethyl-1H-indol-5-yl)-amide | 273 | 410.21 | 411.0 |
| 2-Morpholin-4-yl-6-(2-morpholin-4-yl-ethoxy)-pyrimidine-4-carboxylic acid (2-methyl-1,3-dioxo-2,3-dihydro-1H-isoindol-5-yl)-amide | 274 | 496.21 | 497.3 |
| 2-Morpholin-4-yl-6-(2-morpholin-4-yl-ethoxy)-pyrimidine-4-carboxylic acid (1H-indol-6-yl)-amide | 275 | 452.22 | 453.3 |
| 2-Morpholin-4-yl-6-(2-morpholin-4-yl-ethoxy)-pyrimidine-4-carboxylic acid (3-nitro-phenyl)-amide | 276 | 458.19 | 459.3 |
| 2-Morpholin-4-yl-6-(2-morpholin-4-yl-ethoxy)-pyrimidine-4-carboxylic acid (3-amino-phenyl)-amide | 277 | 428.22 | 429.2 |
| 2-Morpholin-4-yl-6-(2-morpholin-4-yl-ethoxy)-pyrimidine-4-carboxylic acid (3-pyrrolidin-1-yl-phenyl)-amide | 278 | 482.26 | 483.3 |
| 2-Morpholin-4-yl-6-(2-morpholin-4-yl-ethoxy)-pyrimidine-4-carboxylic acid (3-methoxy-phenyl)-amide | 279 | 443.22 | 444.2 |
| 2-Morpholin-4-yl-6-(2-morpholin-4-yl-ethoxy)-pyrimidine-4-carboxylic acid (3-methylamino-phenyl)-amide | 280 | 442.23 | 443.3 |
| 2-(2,6-Dimethyl-morpholin-4-yl)-6-morpholin-4-yl-pyrimidine-4-carboxylic acid (2,3-dimethyl-1H-indol-5-yl)-amide | 281 | 464.25 | 465.3 |
| 2-Morpholin-4-yl-6-(2-morpholin-4-yl-ethoxy)-pyrimidine-4-carboxylic acid (3,5-dimethyl-phenyl)-amide | 282 | 441.24 | 442.3 |
| 2,6-Di-morpholin-4-yl-pyrimidine-4-carboxylic acid (1,2,3-trimethyl-1H-indol-5-yl)-amide | 283 | 450.24 | 451.3 |
| 2-Morpholin-4-yl-6-(2-morpholin-4-yl-ethoxy)-pyrimidine-4-carboxylic acid (4-phenylamino-phenyl)-amide | 284 | 504.25 | 505.3 |
| 2-Morpholin-4-yl-6-(2-morpholin-4-yl-ethoxy)-pyrimidine-4-carboxylic acid (3-pyrrol-1-yl-phenyl)-amide | 285 | 478.23 | 479.3 |
| 6-(2-Methylamino-ethoxy)-2-morpholin-4-yl-pyrimidine-4-carboxylic acid (1,2,3-trimethyl-1H-indol-5-yl)-amide | 286 | 438.24 | 439.3 |
| 2-Morpholin-4-yl-6-(2-morpholin-4-yl-ethoxy)-pyrimidine-4-carboxylic acid (3-chloro-phenyl)-amide | 287 | 447.17 | 448.3 |
| 2-Morpholin-4-yl-6-(2-morpholin-4-yl-ethoxy)-pyrimidine-4-carboxylic acid (4-dimethylamino-3-methyl-phenyl)-amide | 288 | 470.26 | 471.3 |

TABLE 1-continued

| COMPOUND | CMPD NO. | CALCULATED ESMS | MEASURED ESMS (M + 1) |
|---|---|---|---|
| 2-Morpholin-4-yl-6-(2-morpholin-4-yl-ethoxy)-pyrimidine-4-carboxylic acid (3-methyl-4-methylamino-phenyl)-amide | 289 | 456.25 | 457.2 |
| 2-Morpholin-4-yl-6-(2-morpholin-4-yl-ethoxy)-pyrimidine-4-carboxylic acid (3-dimethylamino-4-methyl-phenyl)-amide | 290 | 470.26 | 471.3 |
| 2-Morpholin-4-yl-6-(2-morpholin-4-yl-ethoxy)-pyrimidine-4-carboxylic acid (4-methyl-3-methylamino-phenyl)-amide | 291 | 456.25 | 457.2 |
| 2-Morpholin-4-yl-6-(2-morpholin-4-yl-ethoxy)-pyrimidine-4-carboxylic acid pyridin-3-ylamide | 292 | 414.20 | 415.1 |
| 2-Morpholin-4-yl-6-(2-morpholin-4-yl-ethoxy)-pyrimidine-4-carboxylic acid (5-morpholin-4-yl-4H-[1,2,4]triazol-3-yl)-amide | 293 | 489.24 | 490.3 |
| {2-[6-(2,3-Dimethyl-1H-indol-5-ylcarbamoyl)-2-morpholin-4-yl-pyrimidin-4-yloxy]-ethyl}-carbamic acid methyl ester | 294 | 468.21 | 469.3 |
| 2-Morpholin-4-yl-6-(2-morpholin-4-yl-ethoxy)-pyrimidine-4-carboxylic acid (3-morpholin-4-yl-phenyl)-amide | 295 | 498.26 | 499.3 |
| 2-Morpholin-4-yl-6-(2-morpholin-4-yl-ethoxy)-pyrimidine-4-carboxylic acid (1,2,3,4-tetrahydro-quinolin-7-yl)-amide | 296 | 468.25 | 469.2 |
| 2-Morpholin-4-yl-6-(2-morpholin-4-yl-ethoxy)-pyrimidine-4-carboxylic acid (6-methyl-pyridin-3-yl)-amide | 297 | 428.22 | 429.2 |
| 6-[(2-Hydroxy-ethyl)-methyl-amino]-2-morpholin-4-yl-pyrimidine-4-carboxylic acid m-tolylamide | 298 | 371.20 | 372.2 |
| 2-Morpholin-4-yl-6-(2-morpholin-4-yl-ethoxy)-pyrimidine-4-carboxylic acid (2-methyl-1,2,3,4-tetrahydro-quinolin-7-yl)-amide | 299 | 482.26 | 483.2 |
| 2-Morpholin-4-yl-6-(2-morpholin-4-yl-ethoxy)-pyrimidine-4-carboxylic acid (3-diethylamino-phenyl)-amide | 300 | 484.28 | 485.2 |
| 6-(2-Methoxy-ethoxy)-2-morpholin-4-yl-pyrimidine-4-carboxylic acid (2,3-dimethyl-1H-indol-5-yl)-amide | 301 | 425.21 | 426.2 |
| 6-[(2-Methoxy-ethyl)-methyl-amino]-2-morpholin-4-yl-pyrimidine-4-carboxylic acid (3-dimethylamino-phenyl)-amide | 302 | 414.24 | 415.2 |
| 6-[(2-Hydroxy-ethyl)-methyl-amino]-2-morpholin-4-yl-pyrimidine-4-carboxylic acid (3-dimethylamino-phenyl)-amide | 303 | 400.22 | 401.2 |
| 6-[(2-Hydroxy-ethyl)-methyl-amino]-2-morpholin-4-yl-pyrimidine-4-carboxylic acid (3-pyrrol-1-yl-phenyl)-amide | 304 | 422.21 | 423.2 |
| 2-Morpholin-4-yl-6-(2-morpholin-4-yl-ethoxy)-pyrimidine-4-carboxylic acid (3-imidazol-1-yl-phenyl)-amide | 305 | 479.23 | 480.2 |
| 2,6-Di-morpholin-4-yl-pyrimidine-4-carboxylic acid (3-dimethylamino-phenyl)-amide | 306 | 412.22 | 413.2 |
| 6-(2-Hydroxy-ethoxy)-2-morpholin-4-yl-pyrimidine-4-carboxylic acid (2,3-dimethyl-1H-indol-5-yl)-amide | 307 | 411.19 | 412.2 |
| 2-Morpholin-4-yl-6-(2-morpholin-4-yl-ethoxy)-pyrimidine-4-carboxylic acid [3-(isopropyl-methyl-amino)-phenyl]-amide | 308 | 484.28 | 485.2 |
| 6-(2-Hydroxy-ethoxy)-2-morpholin-4-yl-pyrimidine-4-carboxylic acid (3-dimethylamino-phenyl)-amide | 309 | 387.19 | 388.2 |
| 6-[(2-Hydroxy-ethyl)-methyl-amino]-2-morpholin-4-yl-pyrimidine-4-carboxylic acid (3-pyrrolidin-1-yl-phenyl)-amide | 310 | 426.24 | 427.2 |
| 6-[(2-Methoxy-ethyl)-methyl-amino]-2-morpholin-4-yl-pyrimidine-4-carboxylic acid (3-pyrazol-1-yl-phenyl)-amide | 311 | 437.22 | 438.2 |
| 2-Morpholin-4-yl-6-(2-morpholin-4-yl-ethoxy)-pyrimidine-4-carboxylic acid [3-(ethyl-methyl-amino)-phenyl]-amide | 312 | 470.26 | 471.3 |
| 2-Morpholin-4-yl-6-(2-morpholin-4-yl-ethoxy)-pyrimidine-4-carboxylic acid (3-pyrazol-1-yl-phenyl)-amide | 313 | 479.23 | 480.3 |
| 6-(2-Hydroxy-2-methyl-propoxy)-2-morpholin-4-yl-pyrimidine-4-carboxylic acid (2,3-dimethyl-1H-indol-5-yl)-amide | 314 | 439.22 | 440.2 |

TABLE 1-continued

| COMPOUND | CMPD NO. | CALCULATED ESMS | MEASURED ESMS (M + 1) |
|---|---|---|---|
| 6-[(2-Hydroxy-ethyl)-methyl-amino]-2-morpholin-4-yl-pyrimidine-4-carboxylic acid (3-pyrazol-1-yl-phenyl)-amide | 315 | 423.20 | 424.1 |
| [6-(2,3-Dimethyl-1H-indol-5-ylcarbamoyl)-2-morpholin-4-yl-pyrimidin-4-yloxy]-acetic acid tert-butyl ester | 316 | 481.23 | 482.2 |
| 2-Morpholin-4-yl-6-(2-morpholin-4-yl-ethoxy)-pyrimidine-4-carboxylic acid (1-methyl-1,2,3,4-tetrahydro-quinolin-7-yl)-amide | 317 | 482.26 | 483.1 |
| 2-Morpholin-4-yl-6-(2-morpholin-4-yl-ethoxy)-pyrimidine-4-carboxylic acid (1-methyl-1,2,3,4-tetrahydro-quinolin-6-yl)-amide | 318 | 482.26 | 483.1 |
| 6-Methyl-2-morpholin-4-yl-pyrimidine-4-carboxylic acid (1-hydroxy-2,3-dimethyl-1H-indol-5-yl)-amide | 319 | 381.18 | 382.1 |
| 2-Morpholin-4-yl-6-(2-morpholin-4-yl-ethoxy)-pyrimidine-4-carboxylic acid (1-hydroxy-2,3-dimethyl-1H-indol-5-yl)-amide | 320 | 496.24 | 497.2 |
| 2-Morpholin-4-yl-6-(2-morpholin-4-yl-ethoxy)-pyrimidine-4-carboxylic acid (1,2-dimethyl-1,2,3,4-tetrahydro-quinolin-7-yl)-amide | 321 | 496.28 | 497.2 |
| 2-Morpholin-4-yl-6-[2-(1-oxy-pyridin-2-yl)-ethoxy]-pyrimidine-4-carboxylic acid (6,7,8,9-tetrahydro-5H-carbazol-3-yl)-amide | 322 | 514.23 | fragments 394.2 (M1 + 1) and 122.0 (M2 + 1); M1 + M2 = 514.2 |
| 1-(2,3-Dimethyl-1H-indol-5-yl)-3-[2-morpholin-4-yl-6-(2-morpholin-4-yl-ethoxy)-pyrimidin-4-yl]-urea | 323 | 495.26 | 496.2 |
| 1-(3-Amino-phenyl)-3-[2-morpholin-4-yl-6-(2-morpholin-4-yl-ethoxy)-pyrimidin-4-yl]-urea | 324 | 443.23 | 444.2 |
| 1-[2-Morpholin-4-yl-6-(2-morpholin-4-yl-ethoxy)-pyrimidin-4-yl]-3-(6,7,8,9-tetrahydro-5H-carbazol-3-yl)-urea | 325 | 521.28 | 522.3 |
| 1-{6-[(2-Hydroxy-ethyl)-methyl-amino]-2-morpholin-4-yl-pyrimidin-4-yl}-3-(6,7,8,9-tetrahydro-5H-carbazol-3-yl)-urea | 326 | 465.25 | 466.2 |
| 1-[2-Morpholin-4-yl-6-(2-morpholin-4-yl-ethoxy)-pyrimidin-4-yl]-3-(3-pyrazol-1-yl-phenyl)-urea | 327 | 494.24 | 495.2 |
| 1-(3-Imidazol-1-yl-phenyl)-3-[2-morpholin-4-yl-6-(2-morpholin-4-yl-ethoxy)-pyrimidin-4-yl]-urea | 328 | 494.24 | 495.2 |
| 1-(4-Isopropyl-3-methyl-phenyl)-3-[2-morpholin-4-yl-6-(2-morpholin-4-yl-ethoxy)-pyrimidin-4-yl]-urea | 329 | 484.28 | 485.3 |
| 1-(3-Isopropyl-phenyl)-3-[2-morpholin-4-yl-6-(2-morpholin-4-yl-ethoxy)-pyrimidin-4-yl]-urea | 330 | 470.26 | 471.3 |

Example 16

In Vitro Assays

Reagents. *Staphylococcus aureus* Cowan I (SAC) was obtained from Calbiochem (La Jolla, Calif.), and lipopolysaccharide (LPS, *Serratia marscencens*) was obtained from Sigma (St. Louis, Mo.). Human and mouse recombinant IFNγ were purchased from Boehringer Mannheim (Mannheim, Germany) and Pharmingen (San Diego, Calif.), respectively.

Human In Vitro Assay. Human PBMC were isolated by centrifugation using Ficoll-Paque (Pharmacia Biotech, Uppsala, Sweden) and prepared in RPMI medium supplemented with 10% fetal calf serum (FCS), 100 U/mL penicillin, and 100 μg/mL streptomycin. PBMC were plated in wells of a 96-well plate at a concentration of $5 \times 10^5$ cells/well, and primed by adding IFNγ (30 U/mL) for 22 h and stimulated by adding LPS (1 μg/mL), or by adding IFNγ (100 U/mL) and then stimulated by adding SAC (0.01%). A test pyrimidine compound was dissolved in DMSO, and added to wells of the 96-well plate. The final DMSO concentration was adjusted to 0.25% in all cultures, including the compound-free control.

Human THP-1 cells were plated in wells, primed by adding IFNγ (100 U/mL) for 22 h and stimulated by adding SAC (0.025%) in the presence of different concentrations of the pyrimidine compound. Cell-free supernatants were taken 18 h later for measurement of cytokines. Cell viability was assessed using the bioreduction of MTS. Cell survival was estimated by determining the ratio of the absorbance in compound-treated groups versus compound-free control.

The supernatant was assayed for the amount of IL-12p40, IL-12p70, or IL-10 by using a sandwich ELISA with anti-human antibodies, i.e., a Human IL-12 p40 ELISA kit from R&D Systems (Berkeley, Calif.), and a Human IL-12 p70 or IL-10 ELISA kit from Endogen (Cambridge, Mass.). Assays were based on the manufacturer's instructions.

Murine In Vitro Assay. Balb/c mice (Taconic, Germantown, N.Y.) were immunized with *Mycobacterium tuberculosis* H37Ra (Difco, Detroit, Mich.). The splenocytes were harvested 5 days and prepared in RPMI medium supplemented with 10% FCS and antibiotics in a flat bottom 96-well plate with $1 \times 10^6$ cells/well. The splenocytes were then stimulated with a combination of IFNγ (60 ng/mL) and SAC (0.025%) (LPS (20 μg/mL can be used instead of SAC)) in the presence of a test compound. Cell-free supernatants were taken 24 h later for the measurement of cytokines. The preparation of compound and the assessment of cell viability were carried out as described above. Compound 273 was tested and found to have an $IC_{50}$ of 1248 nM for IL-12 in the murine assay. Mouse IL-12 p'70, IL-10, IL-1β, and TNFα are measured using ELISA kits from Endogen, according to the manufacturer's instructions.

The biological activities of pyrimidine compounds were tested on human PBMC or THP-1 cells. Representative results are shown in Table 2.

TABLE 2

Representative in vitro IC50 data

| $IC_{50}$ Range | Compounds |
|---|---|
| <1 µM | 1, 2, 4, 5, 9, 10, 21, 22, 23, 24, 25, 26, 27, 29, 30, 51, 67, 78, 80, 81, 84, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 121, 125, 126, 127, 130, 131, 132, 135, 136, 137, 139, 143, 145, 146, 147, 148, 150, 151, 153, 154, 155, 156, 158, 159, 160, 161, 167, 168, 169, 171, 172, 173, 174, 175, 176, 177, 178, 179, 180, 181, 182, 183, 184, 185, 186, 187, 188, 189, 193, 194, 195, 196, 205, 211, 214, 215, 218, 219, 220, 221, 222, 223, 245, 246, 247, 248, 250, 251, 252, 253, 254, 255, 256, 257, 258, 259, 260, 261, 262, 263, 264, 265, 266, 267, 268, 269, 270, 271, 273, 275, 277, 278, 280, 281, 282, 283, 285, 286, 290, 291, 294, 295, 298, 301, 302, 303, 304, 307, 309, 310, 311, 312, 313, 314, 315, 316, 317, 319, 320, 322, 323, 324, 325, 326, 329, 330 |
| ≧1 µM | 11, 12, 31, 32, 33, 34, 35, 36, 37, 38, 39, 40, 41, 42, 43, 44, 45, 46, 47, 48, 49, 50, 52, 53, 54, 55, 56, 57, 62, 63, 64, 65, 66, 68, 69, 71, 72, 73, 74, 75, 76, 77, 79, 82, 83, 85, 86, 87, 88, 119, 120, 122, 123, 124, 128, 129, 133, 134, 138, 140, 141, 142, 144, 149, 152, 157, 162, 163, 164, 165, 166, 170, 190, 191, 192, 197, 198, 199, 200, 201, 202, 203, 204, 206, 207, 208, 209, 210, 212, 213, 216, 217, 225, 226, 227, 228, 229, 230, 231, 232, 233, 234, 235, 236, 237, 238, 239, 240, 241, 242, 243, 244, 249, 272, 274, 276, 279, 284, 287, 288, 289, 292, 293, 296, 297, 299, 300, 305, 308, 318, 321, 327, 328 |

Example 17

In Vivo Assays

A. Adjuvant Arthritis

Treatment of adjuvant arthritis in rats: Adjuvant arthritis (AA) was induced in female Lewis rats by the intracutaneous injection (base of the tail) of 0.1 mL of a 10 mg/mL bacterial suspension made from ground, heat-killed *Mycobacterium tuberculosis* (MTB) H37Ra suspended in incomplete Freund's adjuvant. Rats were given Compound 1 or vehicle orally once a day for 7 days (day 7-14), starting day 7 after mycobacterium induction. The development of polyarthritis was monitored daily by macroscopic inspection and assignment of an arthritis index to each animal, during the critical period (days 10 to 25 post-immunization).

The intensity of polyarthritis was scored according to the following scheme: (a) Grade each paw from 0 to 3 based on erythema, swelling, and deformity of the joints: 0 for no erythema or swelling; 0.5 if swelling is detectable in at least one joint; 1 for mild swelling and erythema; 2 for swelling and erythema of both tarsus and carpus; and 3 for ankylosis and bony deformity. Maximum score for all 4 paws was thus 12. (b) Grade for other parts of the body: for each ear, 0.5 for redness and another 0.5 if knots are present; 1 for connective tissue swelling (saddle nose); and 1 for the presence of knots or kinks in the tail. The highest possible arthritic index was 16.

Experiments with the AA model were repeated four times. Oral administration of Compound 1 reproducibly reduced the arthritic score and delayed the development of polyarthritis in a dose-dependent manner. The arthritis score used in this model was a reflection of the inflammatory state of the structures monitored and the results therefore show the ability of the test compound to provide relief for this aspect of the pathology. As shown in FIG. 1, administration of Compound 1 to a rat after *Mycobacterium tuberculosis* (MTB) challenge resulted in a decrease in arthritic index compared to the administration of a vehicle control.

B. Crohn's Disease: Dinitrobenzene Sulfonic Acid-Induced Inflammatory Bowel Syndrome Model in Rats Wistar derived male or female rats weighing 200±20 g and fasted for 24 hours are used. Distal colitis is induced by intra-colonic instillation of 2,4-dinitrobenzene sulfonic acid (DNBS, 25 mg in 0.5 mL ethanol 30%) after which air (2 mL) is gently injected through the cannula to ensure that the solution remained in the colon. A test compound and/or vehicle is administered orally 24 and 2 hours before DNBS instillation and then daily for 5 days. One control group is similarly treated with vehicle alone while the other is treated with vehicle plus DNBS. The animals are sacrificed 24 hours after the final dose of test compound administration and each colon is removed and weighed. Colon-to-body weight ratio is then calculated for each animal according to the formula: Colon (g)/BW×100. The "Net" increase in ratio of Vehicle-control+ DNBS group relative to Vehicle-control group is used as a base for comparison with test substance treated groups and expressed as "% Deduction."

C. Crohn's Disease: $CD4^+CD45Rb^{high}$ T Cell-Reconstituted SCID Colitis Model Mice:

Spleen cells are prepared from normal female BALB/c mice. For cell purification, the following anti-mouse antibodies are used to label non-$CD4^+$ T cells: B220 (RA3-6B2), CD11b (M1/70), and CD8α (53-6.72). All antibodies are obtained from BioSource (Camarillo, Calif.). M450 anti-rat IgG-coated magnetic beads (Dynal, Oslo, Norway) are used to bind the antibodies and negative selection is accomplished using an MPC-1 magnetic concentrator. The enriched CD4+ cells are then labeled for cell sorting with FITC-conjugated CD45RB (16A, Pharmingen, San Diego, Calif.) and PE-conjugated CD4 (CT-CD4, Caltag, Burlingame, Calif.). CD4+ CD45RB$^{high}$ cells are operationally defined as the upper 40% of CD45RB-staining CD4+ cells and sorted under sterile conditions by flow cytometry. Harvested cells are resuspended at 4×10$^6$/mL in PBS and injected 100 μL intraperitoneally into female C.B-17 SCID mice. Pyridine compounds of this invention and/or vehicle is orally administered once a day, 5 days per week, starting the day following the transfer. The transplanted SCID mice are weighed weekly and their clinical condition was monitored.

Colon tissue samples are fixed in 10% buffered formalin and embedded in paraffin. Sections (4 μm) collected from ascending, transverse, and descending colon are cut and stained with hematoxylin and eosin. The severity of colitis is determined based on histological examination of the distal colon sections, whereby the extent of colonic inflammation is graded on a scale of 0-3 in each of four criteria: crypt elongation, cell infiltration, depletion of goblet cells, and the number of crypt abscesses.

LP lymphocytes are isolated from freshly obtained colonic specimens. After removal of payer's patches, the colon is washed in Ca/Mg-free HBSS, cut into 0.5 cm pieces and incubated twice in HBSS containing EDTA (0.75 mM), DTT (1 mM), and antibiotics (amphotericin 2.5 μg/mL, gentamicin 50 μg/mL from Sigma) at 37° C. for 15 min. Next, the tissue is digested further in RPMI containing 0.5 mg/mL collagenase D, 0.01 mg/mL DNase I (Boehringer Manheim), and antibiotics at 37° C. LP cells are then layered on a 40-100% Percoll gradient (Pharmacia, Uppsala, Sweden), and lymphocyte-enriched populations are isolated from the cells at the 40-100% interface.

To measure cytokine production, 48-well plates are coated with 10 μg/mL murine anti-CD3ε antibody (145-2C11) in carbonate buffer (PH 9.6) overnight at 4° C. 5×10$^5$ LP cells are then cultured in 0.5 ml of complete medium in precoated wells in the presence of 1 μg/mL soluble anti-CD28 antibody (37.51). Purified antibodies are obtained from Pharmingen. Culture supernatants are removed after 48 h and assayed for cytokine production. Murine IFNγ is measured using an ELISA kit from Endogen (Cambridge, Mass.), according to the manufacturer's instructions.

Example 18

Osteoclast Formation

Human peripheral blood mononuclear cells (PBMC) are isolated from healthy donor blood. The cells are seeded in multi-well plates at 7.5×10$^5$ cells/ml in RPMI 1640 medium including 10% FBS. Osteoclast formation is induced with 20 ng/ml of recombinant human receptor activator of NF-kB-ligand (RANKL) and 10 ng/ml of human M-CSF in the presence of various doses of test compounds. After 48 hours of culture, RANKL and M-CSF is replenished and further cultured for 2 days. Then, the cultured cells are stained for tartrate-resistant acid phosphatase (TRAP). Osteoclasts are identified as TRAP-positive cells with more than 3 nuclei.

Total cell viability is assessed by CCK-8 assay (Dojindo, Gaithersburg, Md.) with 24 hour incubation.

Other Embodiments

All of the features, specific embodiments and particular substituents disclosed herein may be combined in any combination. Each feature, embodiment or substituent disclosed in this specification may be replaced by an alternative feature, embodiment or substituent serving the same, equivalent, or similar purpose. In the case of chemical compounds, specific values can be combined in any combination resulting in a stable structure. Furthermore, specific values (whether preferred or not) for substituents in one type of chemical structure may be combined with values for other substituents (whether preferred or not) in the same or different type of chemical structure. Thus, unless expressly stated otherwise, each feature, embodiment or substituent disclosed is only an example of a generic series of equivalent or similar features feature, embodiments or substituents.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to a heterocyclic compound described in the specification also can be made, screened for their inhibiting IL-12 activities, and used to practice this invention. Thus, other embodiments are also within the claims.

The contents of all patents, patent applications, and publications cited throughout this specification are hereby incorporated herein by reference in their entirety.

What is claimed is:
1. A method for treating an interleukin-12 overproduction-related disorder, comprising administering to a subject in need thereof an effective amount of a compound of formula (I):

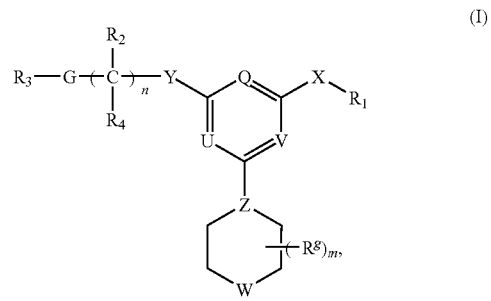

or a pharmaceutically acceptable salt thereof, wherein:
X is represented by a formula selected from the group consisting of:

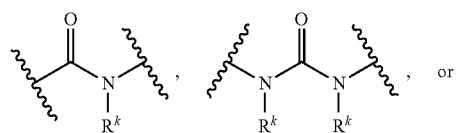

-continued

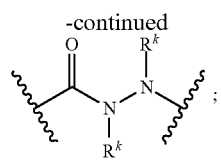

and

R, for each occurrence, is independently H, an optionally substituted alkyl, an optionally substituted cycloalkyl, an optionally substituted cyclyl, an optionally substituted heterocycloalkyl, an optionally substituted heterocyclyl, an optionally substituted aryl, an optionally substituted heteroaryl, an optionally substituted aralkyl, an optionally substituted heteroaralkyl, —C(O)R$^e$, —OR$^k$, —SR$^k$, —NR$^h$R$^j$, hydroxylalkyl, nitro, cyano, haloalkyl, aminoalkyl, or —S(O)$_2$R$^e$;

R$_1$ is R'-L'-R";

R' is an optionally substituted cycloalkyl, an optionally substituted cyclyl, an optionally substituted heterocycloalkyl, an optionally substituted aryl, an optionally substituted heteroaryl, an optionally substituted aralkyl, an optionally substituted heteroaralkyl, or absent;

L' is O, S(O)$_p$, N(R$^k$), N(R$^k$)C(O), C(O)N(R$^k$), C(O)O, or OC(O), or absent; and R" is H, an optionally substituted alkyl, an optionally substituted cycloalkyl, an optionally substituted cyclyl, an optionally substituted heterocycloalkyl, an optionally substituted heterocyclyl, an optionally substituted aryl, an optionally substituted heteroaryl, an optionally substituted aralkyl, an optionally substituted heteroaralkyl, N(R$^k$)(CH$_2$)$_n$R$^g$, —OR$^k$, —SR$^k$, —NR$^h$R$^j$, hydroxylalkyl, —C(O)R$^e$, —C(S)R$^e$, —C(NR)R$^e$, halo, haloalkyl, aminoalkyl, mercaptoalkyl, cyano, nitro, —S(O)R$^e$, —S(O)$_2$R$^e$, —P(O)R$^e$R$^e$, —P(S)R$^e$R$^e$, or an optionally substituted alkylcarbonylalkyl;

Q is CR$^g$, V and U are N;

R$_3$ is R$^g$, —C(O)R$^e$, —OC(O)R$^e$, —SC(O)R$^e$, —NR$^k$C(O)R$^e$, —C(S)R$^e$, —OC(S)R$^e$, —SC(S)R$^e$, —NR$^k$C(S)R$^e$, —C(NR)R$^e$, —OC(NR)R$^e$, —SC(NR)R$^e$, —NR$^k$C(NR)R$^e$, —S(O)$_2$R$^e$, —S(O)R$^e$, —NR$^k$S(O)$_2$R$^e$, —OS(O)$_2$R$^e$, —OP(O)R$^e$R$^e$, or —P(O)R$^e$R$^e$;

R$_2$ and R$_4$ are, independently, H, an optionally substituted alkyl, an optionally substituted alkylcarbonyl, —OR$^k$, —SR$^k$, —NR$^h$R$^j$, hydroxylalkyl, —C(O)R$^e$, —OC(O)R$^e$, —SC(O)R$^e$, —NR$^k$C(O)R$^e$, —C(S)R$^e$, —OC(S)R$^e$, —SC(S)R$^e$, —NR$^k$C(S)R$^e$, —C(NR)R$^e$, —OC(NR)R$^e$, —SC(NR)R$^e$, —NR$^k$C(NR)R$^e$, —SO$_2$R$^e$, —S(O)R$^e$, —NR$^k$SO$_2$R$^e$, —OS(O)$_2$R$^e$, —OP(O)R$^e$R$^e$, —P(O)R$^e$R$^e$, halo, haloalkyl, aminoalkyl, mercaptoalkyl, cyano, nitro, nitroso, azide, an optionally substituted alkylcarbonylalkyl, an optionally substituted cyclyl, an optionally substituted cycloalkyl, an optionally substituted heterocyclyl, an optionally substituted heterocycloalkyl, an optionally substituted aryl, an optionally substituted aralkyl, an optionally substituted heteroaryl, an optionally substituted heteroaralkyl, or isothionitro; or R$_2$ and R$_4$ taken together are =O, =S, or =NR;

R$^e$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —OR$^k$, —SR$^k$, —NR$^h$R$^j$, hydroxylalkyl, alkylcarbonylalkyl, mercaptoalkyl, aminoalkyl, sulfonylalkyl, sulfonylaryl, or thioalkoxy;

R$^d$ and R$^e$, together with the nitrogen to which they are attached, form an optionally substituted heterocycloalkyl, an optionally substituted heterocyclyl, and an optionally substituted heteroaryl;

R$^g$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —OR$^k$, —SR$^k$, —NR$^h$R$^j$, hydroxylalkyl, alkylcarbonylalkyl, mercaptoalkyl, aminoalkyl, sulfonylalkyl, sulfonylaryl, thioalkoxy, —C(O)R$^e$, —OC(O)R$^e$, —SC(O)R$^e$, —NR$^k$C(O)R$^e$, —C(S)R$^e$, —OC(S)R$^e$, —SC(S)R$^e$, —NR$^k$C(S)R$^e$, —C(NR)R$^e$, —OC(NR)R$^e$, —SC(NR)R$^e$, —NR$^k$C(NR)R$^e$, —S(O)$_2$R$^e$, —S(O)R$^e$, —NR$^k$S(O)$_2$R$^e$, —OS(O)$_2$R$^e$, —OP(O)R$^e$R$^e$, —P(O)R$^e$R$^e$, halo, aminoalkyl, mercaptoalkyl, cyano, nitro, nitroso, or azide;

R$^h$ and R$^j$, for each occurrence, are independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl; or R$^h$ and R$^j$ taken together with the N to which they are attached is an optionally substituted heterocyclyl, an optionally substituted heterocycloalkyl, or an optionally substituted heteroaryl;

R$^k$, for each occurrence, is independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, or an optionally substituted heteroaryl;

G is absent;

Y is O, or CH$_2$;

m is 0, 1, 2, 3, or 4;

n is 0, 1, 2, 3, or 4;

p is 0, 1 or 2;

Z is N; and

W is O;

wherein said interleukin-12 overproduction-related disorder is selected from the group of periodontal disease, osteoporosis, Paget's disease of bone, osteogenesis imperfecta, fibrous dysplasia, primary hyperparathyroidism, estrogen deficiency, inflammatory bone loss, bone malignancy, arthritis, hypercalcemia of malignancy (HCM), osteolytic bone lesions of multiple myeloma, and osteolytic bone metastases of breast cancer.

2. A method for treating an interleukin-12 overproduction-related disorder, comprising administering to a subject in need thereof an effective amount of a compound selected from the group consisting of: 2-Morpholin-4-yl-6-(2-morpholin-4-yl-ethoxy)-pyrimidine-4-carboxylic acid (2,3-dimethyl-1H-indol-5-yl)-amide, 2-Morpholin-4-yl-6-(2-pyridin-2-yl-ethoxy)-pyrimidine-4-carboxylic acid (2,3-dimethyl- 1H-indol-5-yl)-amide, [6-(2,3-Dimethyl-1H-indol-5-ylcarbamoyl)-2-morpholin-4-yl-pyrimidin-4-yloxy]-acetic acid ethyl ester, 2-Morpholin-4-yl-6-(2-pyridin-2-yl-ethoxy)-pyrimidine-4-carboxylic acid (1H-indol-5-yl)-amide, 2-Morpholin-4-yl-6-(2-pyridin-2-yl-ethoxy)-pyrimidine-4-carboxylic acid m-tolylamide, 6-(2-Hydroxy-2-methyl-propoxy)-2-morpholin-4-yl-pyrimidine-4-carboxylic acid (2,3-dimethyl-1H-indol-5-yl)-amide, 2-Morpholin-4-yl-6-(2-morpholin-4-yl-ethoxy)-pyrimidine-4-carboxylic acid (6,7,8,9-tetrahydro-5H-carbazol-3-yl)-amide, 2-Morpholin-4-yl-6-(2-morpholin-4-yl-ethoxy)-pyrimidine-4-carboxylic acid (5-furan-2-yl-1H-pyrazol-3-yl)-amide, 1-[2-Morpholin-4-yl-6-(2-morpholin-4-yl-ethoxy)-pyrimidin-4-yl]-3-m-tolyl-urea, 1-[6-(2-Methylamino-ethoxy)-2-morpholin-4-yl-pyrimidin-4-yl]-3-m-tolyl-urea, 1-[6-(2-Hydroxy-2-methyl-propoxy)-2-morpholin-4-yl-pyrimidin-4-yl]-3-m-tolyl-urea, 1-[6-Morpholin-4-yl-2-(2-morpholin-4-yl-ethoxy)-pyrimidin-4-yl]-3-p-tolyl-thiourea, 1-(2-Bromo-4-methyl-phenyl)-3-[6-morpholin-4-yl-2-(2-morpholin-4-yl-ethoxy)-pyrimidin-4-yl]-thiourea, 1-[2-Morpholin-4-yl-6-(2-morpholin-4-yl-ethoxy)-pyrimidin-4-yl]-3-phenyl-urea, 1-[2-Morpholin-4-yl-6-(2-morpholin-4-yl-ethoxy)-pyrimidin-4-yl]-3-p-tolyl-urea, 1-(3-Methoxy-phenyl)-3-[2-morpholin-4-yl-6-(2-morpholin-4-yl-ethoxy)-pyrimidin-4-yl]-urea, 1-(4-Chloro-phenyl)-3-[2-morpholin-4-yl-6-(2-morpholin-4-yl-ethoxy)-pyrimidin-4-yl]-urea, 1-(2-Methoxy-phenyl)-3-[2-morpholin-4-yl-6-(2-morpholin-4-yl-ethoxy)-pyrimidin-4-yl]-urea, 1-Benzyl-3-[2-morpholin-4-yl-6-(2-morpholin-4-yl-ethoxy)-pyrimidin-4-yl]-urea, [6-(2,3-Dimethyl-1H-indol-5-ylcarbamoyl)-2-morpholin-4-yl-pyrimidin-4-yloxy]-acetic acid ethyl ester, 2-Morpholin-4-yl-6-[2-(2-oxo-oxazolidin-3-yl)-ethoxy]-pyrimidine-4-carboxylic acid (2,3-dimethyl-1H-indol-5-yl)-amide, 2,6-Di-morpholin-4-yl-pyrimidine-4-carboxylic acid (2,3-dimethyl-1H-indol-5-yl)-amide, 2-Morpholin-4-yl-6-(2-morpholin-4-yl-ethoxy)-pyrimidine-4-carboxylic acid (3,4-dimethyl-phenyl)-amide, 2-Morpholin-4-yl-6-(2-morpholin-4-yl-ethoxy)-pyrimidine-4-carboxylic acid (1,2,3-trimethyl-1H-indol-5-yl)-amide, 2-Morpholin-4-yl-6-(2-morpholin-4-yl-ethoxy)-pyrimidine-4-carboxylic acid (3-carbamoyl-phenyl)-amide, 2-Morpholin-4-yl-6-(2-morpholin-4-yl-ethoxy)-pyrimidine-4-carboxylic acid (3-dimethylamino-phenyl)-amide, 2-Morpholin-4-yl-6-[2-(4-oxy-morpholin-4-yl)-ethoxy]-pyrimidine-4-carboxylic acid (2,3-dimethyl-1H-indol-5-yl)-amide, 6-Methoxy-2-morpholin-4-yl-pyrimidine-4-carboxylic acid (2,3-dimethyl-1H-indol-5-yl)-amide, 6-Morpholin-4-yl-4-(2-morpholin-4-yl-ethoxy)-pyridine-2-carboxylic acid (2,3-dimethyl-1H-indol-5-yl)-amide, 4,6-Di-morpholin-4-yl-pyridine-2-carboxylic acid (2,3-dimethyl-1H-indol-5-yl)-amide, 2-Morpholin-4-yl-6-(2-morpholin-4-yl-ethoxy)-pyrimidine-4-carboxylic acid methyl-(1,2,3-trimethyl-1H-indol-5-yl)-amide, 2-Morpholin-4-yl-6-(2-pyridin-2-yl-ethoxy)-pyrimidine-4-carboxylic acid (6-methyl-benzothiazol-2-yl)-amide, 2-Morpholin-4-yl-6-(2-pyridin-2-yl-ethoxy)-pyrimidine-4-carboxylic acid (9-ethyl-9H-carbazol-2-yl)-amide, 2-Morpholin-4-yl-6-(2-pyridin-2-yl-ethoxy)-pyrimidine-4-carboxylic acid (6-methyl-pyridin-2-yl)-amide, 2-Morpholin-4-yl-6-(2-pyridin-2-yl-ethoxy)-pyrimidine-4-carboxylic acid (4-methyl-pyridin-2-yl)-amide, 2-Morpholin-4-yl-6-(2-pyridin-2-yl-ethoxy)-pyrimidine-4-carboxylic acid benzothiazol-6-ylamide, 2-Morpholin-4-yl-6-(2-pyridin-2-yl-ethoxy)-pyrimidine-4-carboxylic acid naphthalen-2-ylamide, 2-Morpholin-4-yl-6-(2-pyridin-2-yl-ethoxy)-pyrimidine-4-carboxylic acid quinolin-6-ylamide, 2-Morpholin-4-yl-6-(2-pyridin-2-yl-ethoxy)-pyrimidine-4-carboxylic acid quinolin-5-ylamide, 2-Morpholin-4-yl-6-(2-morpholin-4-yl-ethoxy)-pyrimidine-4-carboxylic acid indan-5-ylamide, 2-Morpholin-4-yl-6-(2-morpholin-4-yl-ethoxy)-pyrimidine-4-carboxylic acid (2,3-dimethyl-1H-indol-7-yl)-amide, 2-Morpholin-4-yl-6-(2-piperidin-1-yl-ethoxy)-pyrimidine-4-carboxylic acid (2,3-dimethyl-1H-indol-5-yl)-amide, 2-Morpholin-4-yl-6-[2-(2-oxo-oxazolidin-3-yl)-ethoxy]-pyrimidine-4-carboxylic acid (3-carbamoyl-phenyl)-amide, 2-Morpholin-4-yl-6-[2-(2-oxo-oxazolidin-3-yl)-ethoxy]-pyrimidine-4-carboxylic acid m-tolylamide, 2-Morpholin-4-yl-6-(2-morpholin-4-yl-ethoxy)-pyrimidine-4-carboxylic acid (5-thiophen-2-yl-1H-pyrazol-3-yl)-amide, 2-Morpholin-4-yl-6-(2-morpholin-4-yl-ethoxy)-pyrimidine-4-carboxylic acid (3-ethyl-phenyl)-amide, 2-Morpholin-4-yl-6-(2-morpholin-4-yl-ethoxy)-pyrimidine-4-carboxylic acid (3-bromo-phenyl)-amide, 2-Morpholin-4-yl-6-(2-morpholin-4-yl-ethoxy)-pyrimidine-4-carboxylic acid (5-methyl-isoxazol-3-yl)-amide, 2-Morpholin-4-yl-6-(2-morpholin-4-yl-ethoxy)-pyrimidine-4-carboxylic acid (2-acetylamino-phenyl)-amide, 2-Morpholin-4-yl-6-(2-morpholin-4-yl-ethoxy)-pyrimidine-4-carboxylic acid (3-sulfamoyl-phenyl)-amide, 2,6-Di-morpholin-4-yl-pyrimidine-4-carboxylic acid (3,4-dimethyl-phenyl)-amide, 2,6-Di-morpholin-4-yl-pyrimidine-4-carboxylic acid (3-carbamoyl-phenyl)-amide, 2-Morpholin-4-yl-6-(2-morpholin-4-yl-ethoxy)-pyrimidine-4-carboxylic acid (3-dimethylcarbamoyl-phenyl)-amide, Indol-1-yl-[2-morpholin-4-yl-6-(2-morpholin-4-yl-ethoxy)-pyrimidin-4-yl]-methanone, (3,4-Dihydro-1H-isoquinolin-2-yl)-[2-morpholin-4-yl-6-(2-morpholin-4-yl-ethoxy)-pyrimidin-4-yl]-methanone, 2-Morpholin-4-yl-6-(2-morpholin-4-yl-ethoxy)-pyrimidine-4-carboxylic acid m-tolylamide, 2-Morpholin-4-yl-6-(2-morpholin-4-yl-ethoxy)-pyrimidine-4-carboxylic acid (4-dimethylamino-phenyl)-amide, 2-Morpholin-4-yl-6-(2-morpholin-4-yl-ethoxy)-pyrimidine-4-carboxylic acid [3-(pyrrolidine-1-carbonyl)-phenyl]-amide, 2-Morpholin-4-yl-6-(2-morpholin-4-yl-ethoxy)-pyrimidine-4-carboxylic acid (1,3-dioxo-2,3-dihydro-1H-isoindol-5-yl)-amide, 2-Morpholin-4-yl-6-(2-morpholin-4-yl-ethoxy)-pyrimidine-4-carboxylic acid (2-methoxy-5-methyl-phenyl)-amide, 2-Morpholin-4-yl-6-(2-morpholin-4-yl-ethoxy)-pyrimidine-4-carboxylic acid (3-hydroxy-phenyl)-amide, 6-Morpholin-4-yl-2-(2-pyridin-2-yl-ethoxy)-pyrimidine-4-carboxylic acid m-tolylamide, 6-Morpholin-4-yl-2-(2-pyridin-2-yl-ethoxy)-pyrimidine-4-carboxylic acid (2,3-dimethyl-1H-indol-5-yl)-amide, 6-Morpholin-4-yl-2-(2-pyridin-2-yl-ethoxy)-pyrimidine-4-carboxylic acid (6-methyl-benzothiazol-2-yl)-amide, 2-[2-(3,4-Dimethoxy-phenyl)-ethoxy]-6-morpholin-4-yl-N-m-tolyl-isonicotinamide, N-(2,3-Dimethyl-1H-indol-5-yl)-2-morpholin-4-yl-6-(2-morpholin-4-yl-ethoxy)-isonicotinamide, 1-[2-Morpholin-4-yl-6-(2-pyridin-2-yl-ethoxy)-pyrimidin-4-yl]-3-m-tolyl-urea, 1-[6-Morpholin-4-yl-2-(2-pyridin-2-yl-ethoxy)-pyrimidin-4-yl]-3-m-tolyl-urea, 1-Methyl-3-[6-morpholin-4-yl-2-(2-pyridin-2-yl-ethoxy)-pyrimidin-4-yl]-1-m-tolyl-urea, 1-(4,6-Di-morpholin-4-yl-pyridin-2-yl)-3-m-tolyl-urea, 1-[4-Morpholin-4-yl-6-(2-pyridin-2-yl-ethoxy)-pyrimidin-2-yl]-3-m-tolyl-urea, 2-Morpholin-4-yl-6-(2-pyridin-2-yl-ethoxy)-pyrimidine-4-carboxylic acid 1H-indol-5-yl ester, 1H-Indole-5-carboxylic acid [2-morpholin-4-yl-6-(2-pyridin-2-yl-ethoxy)-pyrimidin-4-yl]-amide, 1H-Indole-5-carboxylic acid [6-morpholin-4-yl-2-(2-pyridin-2-yl-ethoxy)-pyrimidin-4-yl]-amide, 3-Methyl-N-[4-morpholin-4-yl-6-(2-pyridin-2-yl-ethoxy)-pyrimidin-2-yl]-benzamide, N-[4-Morpholin-4-yl-6-(2-pyridin-2-yl-ethoxy)-pyrimidin-2-yl]-isonicotinamide, 5-Methyl-isoxazole-3-carboxylic acid-p-morpholin-4-yl-6-(2-pyridin-2-yl-ethoxy)-pyrimidin-2-yl]-amide, 6-Morpholin-4-yl-2-(2-pyridin-2-yl-ethoxy)-pyrimidine-4-carboxylic acid N'-m-tolyl-hydrazide, 2-Morpholin-4-yl-6-(2-pyridin- 2-yl-ethoxy)-pyrimidine-4-carboxylic acid N'-m-tolyl-hydrazide, 6-Morpholin-4-yl-2-(2-morpholin-4-yl-ethoxy)-pyrimidine-4-carboxylic acid N'-m-tolyl-hydrazide, 6-Morpholin-4-yl-2-(2-morpholin-4-yl-ethoxy)-pyrimidine-4-carboxylic acid N'-(3,4-dimethyl-phenyl)-hydrazide, 2-Morpholin-4-yl-6-(2-morpholin-4-yl-ethoxy)-isonicotinic acid N'-m-tolyl-hydrazide, [2-Morpholin-4-yl-6-(2-pyridin-2-yl-ethoxy)-pyrimidin-4-yl]-carbamic acid m-tolyl ester, (2,3-Dimethyl-1H-indol-5-yl)-[2-morpholin-4-yl-6-(2-pyridin-2-yl-ethoxy)-pyrimidin-4-ylmethyl]-amine, N-[2-Morpholin-4-yl-6-(2-pyridin-2-yl-ethoxy)-pyrimidin-4-yl]-N'-m-tolyl-oxalamide, N-(3-Hydroxy-phenyl)-N'-[2-morpholin-4-yl-6-(2-pyridin-2-yl-ethoxy)-pyrimidin-4-yl]-oxalamide, N-(3-Hydroxy-phenyl)-N'-[6-morpholin-4-yl-2-(2-pyridin-2-yl-ethoxy)-pyrimidin-4-yl]-oxalamide, and [6-Morpholin-4-yl-2-(2-pyridin-2-yl-ethoxy)-pyrimidin-4-yl]-carbamic acid m-tolyl ester, or a pharmaceutically acceptable salt thereof, wherein said interleukin-12 overproduction-related disorder is selected from the group of periodontal disease, osteoporosis, Paget's disease of bone, osteogenesis imperfecta, fibrous dysplasia, primary hyperparathyroidism, estrogen deficiency, inflammatory bone loss, bone malignancy, arthritis, hypercalcemia of malignancy (HCM), osteolytic bone lesions of multiple myeloma, and osteolytic bone metastases of breast cancer.

3. A method for treating disorders associated with excessive bone loss, the method comprising administering to a subject in need thereof an effective amount of a compound of formula (I):

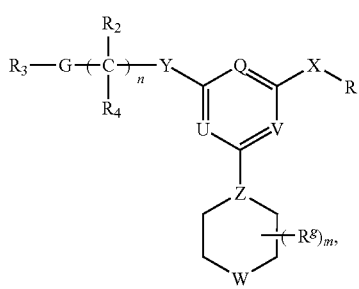

or a pharmaceutically acceptable salt thereof,
wherein:
X is represented by a formula selected from the group consisting of:

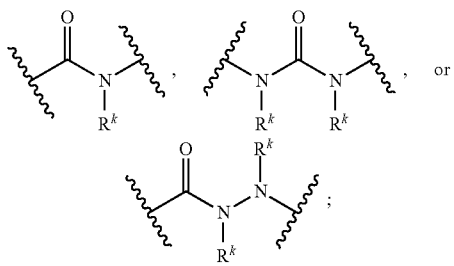

and
R, for each occurrence, is independently H, an optionally substituted alkyl, an optionally substituted cycloalkyl, an optionally substituted cyclyl, an optionally substituted heterocycloalkyl, an optionally substituted heterocyclyl, an optionally substituted aryl, an optionally substituted heteroaryl, an optionally substituted aralkyl, an optionally substituted heteroaralkyl, —C(O)R$^c$, —OR$^k$, —SR$^k$, —NR$^h$R$^j$, hydroxylalkyl, nitro, cyano, haloalkyl, aminoalkyl, or —S(O)$_2$R$^c$;

R$_1$ is R'-L'-R";

R' is an optionally substituted cycloalkyl, an optionally substituted cyclyl, an optionally substituted heterocloalkyl, an optionally substituted aryl, an optionally substituted heteroaryl, an optionally substituted aralkyl, an optionally substituted heteroaralkyl, or absent;

L' is O, S(O)$_p$, N(R$^k$), N(R$^k$)C(O), C(O)N(R$^k$), C(O)O, or OC(O), or absent; and R" is H, an optionally substituted alkyl, an optionally substituted cycloalkyl, an optionally substituted cyclyl, an optionally substituted heterocycloalkyl, an optionally substituted heterocyclyl, an optionally substituted aryl, an optionally substituted heteroaryl, an optionally substituted aralkyl, an optionally substituted heteroaralkyl, N(R$^k$)(CH$_2$)$_n$R$^g$, —OR$^k$, —SR$^k$, —NR$^h$R$^j$, hydroxylalkyl, —C(O)R$^c$, —C(S)R$^c$, —C(NR)R$^c$, halo, haloalkyl, aminoalkyl, mercaptoalkyl, cyano, nitro, —S(O)R$^c$, —S(O)$_2$R$^c$, —P(O)R$^c$R$^c$, —P(S)R$^c$R$^c$, or an optionally substituted alkylcarbonylalkyl;

Q is CR$^g$, V and U are N;

R$_3$ is R$^g$, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —S(O)$_2$R$^c$, —S(O)R$^c$, —NR$^k$S(O)$_2$R$^c$, —OS(O)$_2$R$^c$, —OP(O)R$^c$R$^c$, or —P(O)R$^c$R$^c$;

R$_2$ and R$_4$ are, independently, H, an optionally substituted alkyl, an optionally substituted alkylcarbonyl, —OR$^k$, —SR$^k$, —NR$^h$R$^j$, hydroxylalkyl, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —SO$_2$R$^c$, —S(O)R$^c$, —NR$^k$SO$_2$R$^c$, —OS(O)$_2$R$^c$, —OP(O)R$^c$R$^c$, —P(O)R$^c$R$^c$, halo, haloalkyl, aminoalkyl, mercaptoalkyl, cyano, nitro, nitroso, azide, an optionally substituted alkylcarbonylalkyl, an optionally substituted cyclyl, an optionally substituted cycloalkyl, an optionally substituted heterocyclyl, an optionally substituted heterocycloalkyl, an optionally substituted aryl, an optionally substituted heteroaryl, an optionally substituted aralkyl, an optionally substituted heteroaralkyl, or isothionitro; or R$_2$ and R$_4$ taken together are =O, =S, or =NR;

R$^c$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —OR$^k$, —SR$^k$, —NR$^h$R$^j$, hydroxylalkyl, alkylcarbonylalkyl, mercaptoalkyl, aminoalkyl, sulfonylalkyl, sulfonylaryl, or thioalkoxy;

R$^d$ and R$^e$, together with the nitrogen to which they are attached, form an optionally substituted heterocloalkyl, an optionally substituted heterocyclyl, and an optionally substituted heteroaryl;

R$^g$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —OR$^k$, —SR$^k$, —NR$^h$R$^j$, hydroxylalkyl, alkylcarbonylalkyl, mercaptoalkyl, aminoalkyl, sulfonylalkyl, sulfonylaryl, thioalkoxy, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —S(O)$_2$R$^c$, —S(O)R$^c$, —NR$^k$S(O)$_2$R$^c$, —OS(O)$_2$R$^c$, —OP(O)R$^c$R$^c$, —P(O)R$^c$R$^c$, halo, aminoalkyl, mercaptoalkyl, cyano, nitro, nitroso, or azide;

R$^h$ and R$^j$, for each occurrence, are independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl; or R$^h$ and R$^j$ taken together with the N to which they are attached is an optionally substituted heterocyclyl, an optionally substituted heterocycloalkyl, or an optionally substituted heteroaryl;

R$^k$, for each occurrence, is independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, or an optionally substituted heteroaryl;

G is absent;
Y is O, or CH$_2$;
m is 0, 1, 2, 3, or 4;
n is 0, 1, 2, 3, or 4;
p is 0, 1 or 2;
Z is N; and
W is O,
wherein said disorder is selected from the group of periodontal disease, osteoporosis, Paget's disease of bone, osteogenesis imperfecta, fibrous dysplasia, primary hyperparathyroidism, estrogen deficiency, inflammatory bone loss, bone malignancy, arthritis, hypercalcemia of malignancy (HCM), osteolytic bone lesions of multiple myeloma, and osteolytic bone metastases of breast cancer.

4. A method of treating a disorder associated with excessive bone resorption by osteoclasts in a subject in need thereof, the method comprising administering to the subject an effective amount of a compound of formula (I):

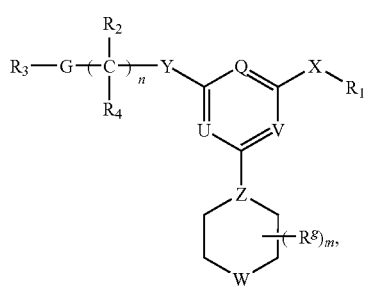

or a pharmaceutically acceptable salt thereof, wherein:
X is represented by a formula selected from the group consisting of:

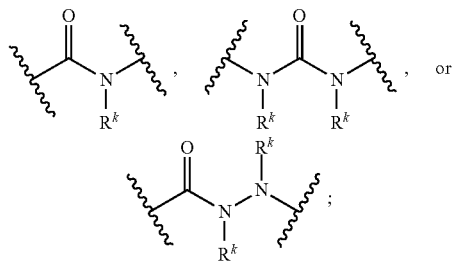

and

R, for each occurrence, is independently H, an optionally substituted alkyl, an optionally substituted cycloalkyl, an optionally substituted cyclyl, an optionally substituted heterocycloalkyl, an optionally substituted heterocyclyl, an optionally substituted aryl, an optionally substituted heteroaryl, an optionally substituted aralkyl, an optionally substituted heteroaralkyl, —C(O)R$^c$, —OR$^k$, —SR$^k$, —NR$^h$R$^j$, hydroxylalkyl, nitro, cyano, haloalkyl, aminoalkyl, or —S(O)$_2$R$^c$;

R$_1$ is R'-L'-R";
R' is an optionally substituted cycloalkyl, an optionally substituted cyclyl, an optionally substituted heterocycloalkyl, an optionally substituted aryl, an optionally substituted heteroaryl, an optionally substituted aralkyl, an optionally substituted heteroaralkyl, or absent;
L' is O, S(O)$_p$, N(R$^k$), N(R$^k$)C(O), C(O)N(R$^k$), C(O)O, or OC(O), or absent; and
R" is H, an optionally substituted alkyl, an optionally substituted cycloalkyl, an optionally substituted cyclyl, an optionally substituted heterocycloalkyl, an optionally substituted heterocyclyl, an optionally substituted aryl, an optionally substituted heteroaryl, an optionally substituted aralkyl, an optionally substituted heteroaralkyl, N(R$^k$)(CH$_2$)$_n$R$^g$, —OR$^k$, —SR$^k$, —NR$^h$R$^j$, hydroxylalkyl, —C(O)R$^c$, —C(S)R$^c$, —C(NR)R$^c$, halo, haloalkyl, aminoalkyl, mercaptoalkyl, cyano, nitro, —S(O)R$^c$, —S(O)$_2$R$^c$, —P(O)R$^c$R$^c$, —P(S)R$^c$R$^c$, or an optionally substituted alkylcarbonylalkyl;

Q is CR$^g$, V and U are N;
R$_3$ is R$^g$, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —S(O)$_2$R$^c$, —S(O)R$^c$, —NR$^k$S(O)$_2$R$^c$, —OS(O)$_2$R$^c$, —OP(O)R$^c$R$^c$, or —P(O)R$^c$R$^c$;

R$_2$ and R$_4$ are, independently, H, an optionally substituted alkyl, an optionally substituted alkylcarbonyl, —OR$^k$, —SR$^k$, —NR$^h$R$^j$, hydroxylalkyl, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —SO$_2$R$^c$, —S(O)R$^c$, —NR$^k$SO$_2$R$^c$, —OS(O)$_2$R$^c$, —OP(O)R$^c$R$^c$, —P(O)R$^c$R$^c$, halo, haloalkyl, aminoalkyl, mercaptoalkyl, cyano, nitro, nitroso, azide, an optionally substituted alkylcarbonylalkyl, an optionally substituted cyclyl, an optionally substituted cycloalkyl, an optionally substituted heterocyclyl, an optionally substituted heterocycloalkyl, an optionally substituted aryl, an optionally substituted aralkyl, an optionally substituted heteroaryl, an optionally substituted heteroaralkyl, or isothionitro; or $R_2$ and $R_4$ taken together are =O, =S, or =NR;

$R^c$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —$OR^k$, —$SR^k$, —$NR^hR^j$, hydroxylalkyl, alkylcarbonylalkyl, mercaptoalkyl, aminoalkyl, sulfonylalkyl, sulfonylaryl, or thioalkoxy;

$R^d$ and $R^e$, together with the nitrogen to which they are attached, form an optionally substituted heterocycloalkyl, an optionally substituted heterocyclyl, and an optionally substituted heteroaryl;

$R^g$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —$OR^k$, —$SR^k$, —$NR^hR^j$, hydroxylalkyl, alkylcarbonylalkyl, mercaptoalkyl, aminoalkyl, sulfonylalkyl, sulfonylaryl, thioalkoxy, —C(O)$R^c$, —OC(O)$R^c$, —SC(O)$R^c$, —$NR^k$C(O)$R^c$, —C(S)$R^c$, —OC(S)$R^c$, —SC(S)$R^c$, —$NR^k$C(S)$R^c$, —C(NR)$R^c$, —OC(NR)$R^c$, —SC(NR)$R^c$, —$NR^k$C(NR)$R^c$, —S(O)$_2R^c$, —S(O)$R^c$, —$NR^k$S(O)$_2R^c$, —OS(O)$_2R^c$, —OP(O)$R^cR^c$, —P(O)$R^cR^c$, halo, aminoalkyl, mercaptoalkyl, cyano, nitro, nitroso, or azide;

$R^h$ and $R^j$, for each occurrence, are independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl; or $R^h$ and $R^j$ taken together with the N to which they are attached is an optionally substituted heterocyclyl, an optionally substituted heterocycloalkyl, or an optionally substituted heteroaryl;

$R^k$, for each occurrence, is independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, or an optionally substituted heteroaryl;

G is absent;
Y is O, or $CH_2$;
m is 0, 1, 2, 3, or 4;
n is 0, 1, 2, 3, or 4;
p is 0, 1 or 2;
Z is N; and
W is O, wherein said disorder is selected from the group of periodontal disease, osteoporosis, Paget's disease of bone, osteogenesis imperfecta, fibrous dysplasia, primary hyperparathyroidism, estrogen deficiency, inflammatory bone loss, bone malignancy, arthritis, hypercalcemia of malignancy (HCM), osteolytic bone lesions of multiple myeloma, and osteolytic bone metastases of breast cancer.

5. A method of inhibiting IL-23 and/or IL-27 production in a subject, comprising administering to the subject an effective amount of a compound of formula (I):

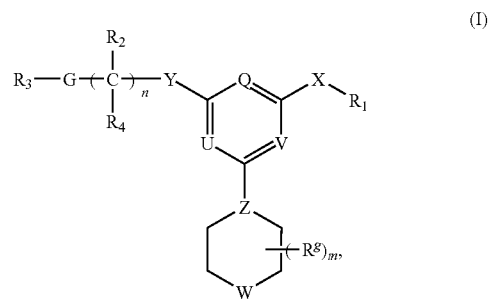

or a pharmaceutically acceptable salt thereof,
wherein:
X is represented by a formula selected from the group consisting of:

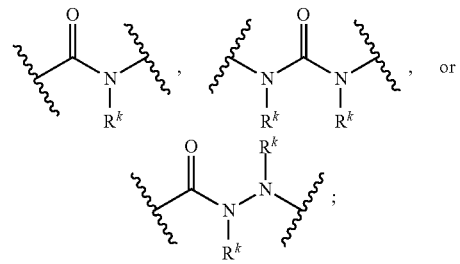

and
R, for each occurrence, is independently H, an optionally substituted alkyl, an optionally substituted cycloalkyl, an optionally substituted cyclyl, an optionally substituted heterocycloalkyl, an optionally substituted heterocyclyl, an optionally substituted aryl, an optionally substituted heteroaryl, an optionally substituted aralkyl, an optionally substituted heteroaralkyl, —C(O)$R^c$, —$OR^k$, —$SR^k$, —$NR^hR^j$, hydroxylalkyl, nitro, cyano, haloalkyl, aminoalkyl, or —S(O)$_2R^c$;

$R_1$ is R'-L'-R";
R' is an optionally substituted cycloalkyl, an optionally substituted cyclyl, an optionally substituted heterocycloalkyl, an optionally substituted aryl, an optionally substituted heteroaryl, an optionally substituted aralkyl, an optionally substituted heteroaralkyl, or absent;
L' is O, S(O)$_p$, N($R^k$), N($R^k$)C(O), C(O)N($R^k$), C(O)O, or OC(O), or absent; and
R" is H, an optionally substituted alkyl, an optionally substituted cycloalkyl, an optionally substituted cyclyl, an optionally substituted heterocycloalkyl, an optionally substituted heterocyclyl, an optionally substituted aryl, an optionally substituted heteroaryl, an optionally substituted aralkyl, an optionally substituted heteroaralkyl, N($R^k$)(CH$_2$)$_n$$R^g$, —$OR^k$, —$SR^k$, —$NR^hR^j$, hydroxylalkyl, —C(O)$R^c$, —C(S)$R^c$, —C(NR)$R^c$, halo, haloalkyl, aminoalkyl, mercaptoalkyl, cyano, nitro, —S(O)$R^c$, —S(O)$_2R^c$, —P(O)$R^cR^c$, —P(S)$R^cR^c$, or an optionally substituted alkylcarbonylalkyl;

Q is $CR^g$, V and U are N;

$R_3$ is $R^g$, —C(O)$R^c$, —OC(O)$R^c$, —SC(O)$R^c$, —$NR^k$C(O)$R^c$, —C(S)$R^c$, —OC(S)$R^c$, —SC(S)$R^c$, —$NR^k$C(S)$R^c$, —C(NR)$R^c$, —OC(NR)$R^c$, —SC(NR)$R^c$, —$NR^k$C(NR)$R^c$, —S(O)$_2R^c$, —S(O)$R^c$, —$NR^k$S(O)$_2R^c$, —OS(O)$_2R^c$, —OP(O)$R^cR^c$, or —P(O)$R^cR^c$;

$R_2$ and $R_4$ are, independently, H, an optionally substituted alkyl, an optionally substituted alkylcarbonyl, —$OR^k$, —$SR^k$, —$NR^hR^j$, hydroxylalkyl, —C(O)$R^c$, —OC(O)$R^c$, —SC(O)$R^c$, —$NR^k$C(O)$R^c$, —C(S)$R^c$, —OC(S)$R^c$, —SC(S)$R^c$, —$NR^k$C(S)$R^c$, —C(NR)$R^c$, —OC(NR)$R^c$, —SC(NR)$R^c$, —$NR^k$C(NR)$R^c$, —SO$_2R^c$, —S(O)$R^c$, —$NR^k$SO$_2R^c$, —OS(O)$_2R^c$, —OP(O)$R^cR^c$, —P(O)$R^cR^c$, halo, haloalkyl, aminoalkyl, mercaptoalkyl, cyano, nitro, nitroso, azide, an optionally substituted alkylcarbonylalkyl, an optionally substituted cyclyl, an optionally substituted cycloalkyl, an optionally substituted heterocyclyl, an optionally substituted heterocycloalkyl, an optionally substituted aryl, an optionally substituted aralkyl, an optionally substituted heteroaryl, an optionally substituted heteroaralkyl, or isothionitro; or $R_2$ and $R_4$ taken together are =O, =S, or =NR;

$R^c$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —$OR^k$, —$SR^k$, —$NR^hR^j$, hydroxylalkyl, alkylcarbonylalkyl, mercaptoalkyl, aminoalkyl, sulfonylalkyl, sulfonylaryl, or thioalkoxy;

$R^d$ and $R^e$, together with the nitrogen to which they are attached, form an optionally substituted heterocycloalkyl, an optionally substituted heterocyclyl, and an optionally substituted heteroaryl;

$R^g$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —$OR^k$, —$SR^k$, —$NR^hR^j$, hydroxylalkyl, alkylcarbonylalkyl, mercaptoalkyl, aminoalkyl, sulfonylalkyl, sulfonylaryl, thioalkoxy, —C(O)$R^c$, —OC(O)$R^c$, —SC(O)$R^c$, —$NR^k$C(O)$R^c$, —C(S)$R^c$, —OC(S)$R^c$, —SC(S)$R^c$, —$NR^k$C(S)$R^c$, —C(NR)$R^c$, —OC(NR)$R^c$, —SC(NR)$R^c$, —$NR^k$C(NR)$R^c$, —S(O)$_2R^c$, —S(O)$R^c$, —$NR^k$S(O)$_2R^c$, —OS(O)$_2R^c$, —OP(O)$R^cR^c$, —P(O)$R^cR^c$, halo, aminoalkyl, mercaptoalkyl, cyano, nitro, nitroso, or azide;

$R^h$ and $R^j$, for each occurrence, are independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl; or $R^h$ and $R^j$ taken together with the N to which they are attached is an optionally substituted heterocyclyl, an optionally substituted heterocycloalkyl, or an optionally substituted heteroaryl;

$R^k$, for each occurrence, is independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, or an optionally substituted heteroaryl;

G is absent;
Y is O, or $CH_2$;
m is 0, 1, 2, 3, or 4;
n is 0, 1, 2, 3, or 4;
p is 0, 1 or 2;
Z is N; and
W is O.

6. The method of claim 5, further comprising inhibiting the production of IL-12.

* * * * *